(12) United States Patent
Lifshitz-Liron et al.

(10) Patent No.: US 7,687,642 B2
(45) Date of Patent: Mar. 30, 2010

(54) FLUVASTATIN SODIUM CRYSTAL FORMS, PROCESSES FOR PREPARING THEM, COMPOSITIONS CONTAINING THEM AND METHODS OF USING THEM

(75) Inventors: Revital Lifshitz-Liron, Herzlia (IL); Tamas Koltai, Natanja (IL); Judith Aronhime, Rehovot (IL); Nurit Perlman, Kfar Saba (IL); Sharon Avhar-Maydan, Givataym (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 289 days.

(21) Appl. No.: 11/699,659

(22) Filed: Jan. 29, 2007

(65) Prior Publication Data

US 2008/0146817 A1 Jun. 19, 2008

Related U.S. Application Data

(63) Continuation of application No. 10/872,089, filed on Jun. 18, 2004, now Pat. No. 7,414,140.

(60) Provisional application No. 60/479,182, filed on Jun. 18, 2003, provisional application No. 60/483,099, filed on Jun. 30, 2003, provisional application No. 60/485,748, filed on Jul. 10, 2003, provisional application No. 60/493,793, filed on Aug. 11, 2003, provisional application No. 60/507,954, filed on Oct. 3, 2003, provisional application No. 60/545,466, filed on Feb. 19, 2004.

(51) Int. Cl.
C07D 209/12 (2006.01)

(52) U.S. Cl. ...................................... 548/494
(58) Field of Classification Search .................. 548/494
See application file for complete search history.

(56) References Cited

U.S. PATENT DOCUMENTS

| 4,231,938 A | 11/1980 | Monaghan et al. |
| 4,346,227 A | 8/1982 | Terahara et al. |
| 4,444,784 A | 4/1984 | Hoffman et al. |
| 4,739,073 A | 4/1988 | Kathawala |
| 5,003,080 A | 3/1991 | Butler et al. |
| 5,006,530 A | 4/1991 | Angerbauer et al. |
| 5,177,080 A | 1/1993 | Angerbauer et al. |
| 5,189,164 A | 2/1993 | Kapa et al. |
| 5,202,029 A | 4/1993 | Haytko et al. |
| 5,260,440 A | 11/1993 | Hirai et al. |
| 5,354,772 A | 10/1994 | Kathawala |
| 5,856,336 A | 1/1999 | Fujikawa et al. |
| 6,124,340 A * | 9/2000 | Horvath ....................... 514/419 |
| 6,696,479 B2 | 2/2004 | Van Der Schaaf et al. |
| 7,368,468 B2 | 5/2008 | Lifshitz-Liron et al. |
| 2003/0032666 A1 | 2/2003 | Van Der Schaaf et al. |
| 2005/0032884 A1 | 2/2005 | Lifshitz-Liron et al. |
| 2005/0038114 A1 | 2/2005 | Lifshitz-Liron et al. |
| 2005/0209259 A1 | 9/2005 | Huang et al. |

FOREIGN PATENT DOCUMENTS

| EP | 0 363 934 | 4/1990 |
| WO | WO 00/53566 | 9/2000 |
| WO | WO 02/36563 | 5/2002 |
| WO | WO 03/004455 | 1/2003 |
| WO | WO 03/013512 | 2/2003 |
| WO | WO 2006/030304 | 3/2006 |
| WO | WO 2006/038219 | 4/2006 |
| WO | WO 2006/109147 | 10/2006 |

OTHER PUBLICATIONS

Brittain, Polymorphism in Pharmaceutical Solids, Drugs and the Pharmaceutical Science; 1999, pp. 348-361, vol. 95.
Bhaskar, et al., "Enantioselective Synthesis Of Beta Hydroxy Delta Lactones: A New Approach To The Synthetic Congeners Of 3-Hydroxy-3-Methylglutaryl Coenzyme A Reductase Inhibitors", *J. Org. Chem.*, 1991, pp. 5752-5754, vol. 56, No. 20.
Evans, et al., "Reduction of Beta Hydroxy Ketones With Catecholborane. A Stereoselective Approach To The Synthesis Of Syn 1,3-Diols", *J. Org. Chem.*, 1990, p. 5190-5192.
Lipid Research Clinics Program, "The Lipid Research Clinics Coronary Primary Prevention Trial Results: I. Reduction In Incidence Of Coronary Heart Disease", *J.A.M.A.*, 1984, 351-74, vol. 251, No. 3.
Scandinavian Simvastatin Survival Study Group, "Randomised Trial Of Cholesterol Lowering In 4444 Patients With Coronary Heart Disease: The Scandinavian Survival Study (4s)", *The Lancet*, 1994, pp. 1383-1389, vol. 344.
Shao, et al., "Asymmetric Hydrogenation Of 3,5-Dioxoesters Catalyzed By Ru-Binap Complex: A Short Step Asymmetric Synthesis Of 6-Substituted 5,6-Dihydro-2-Pyronse", *Tetrahedron*, 1993, pp. 1997-2010, vol. 49, No. 10.
Tang, et al., Synthesis Of Carbon-14 Labeled Fluvatatin (Lescol®), *Journal of Labeled Compounds & Radiopharmaceuticals*, 1998, pp. 1-7, vol. XLI, No. 1.
Tempkin, et al., "Asymmetric Synthesis of 3,5-Dihydroxy-6(E)-heptenoate-containing HMG-CoA Reductase Inhibitors", *Tetrahedron*, 1997, pp. 10659-10670, vol. 53 (31).
Witztum, "Chapter 36: Drugs Used In The Treatment Of Hyperlipoproteinemias", *Goodman and Gilman's The Pharmacological Basis of Therapeutics*, 9th ed., 1996, pp. 875-897.

* cited by examiner

*Primary Examiner*—Rei-tsang Shiao
(74) *Attorney, Agent, or Firm*—Kenyon & Kenyon LLP

(57) ABSTRACT

Provided are crystalline forms of fluvastatin sodium and processes for their preparation.

21 Claims, 136 Drawing Sheets

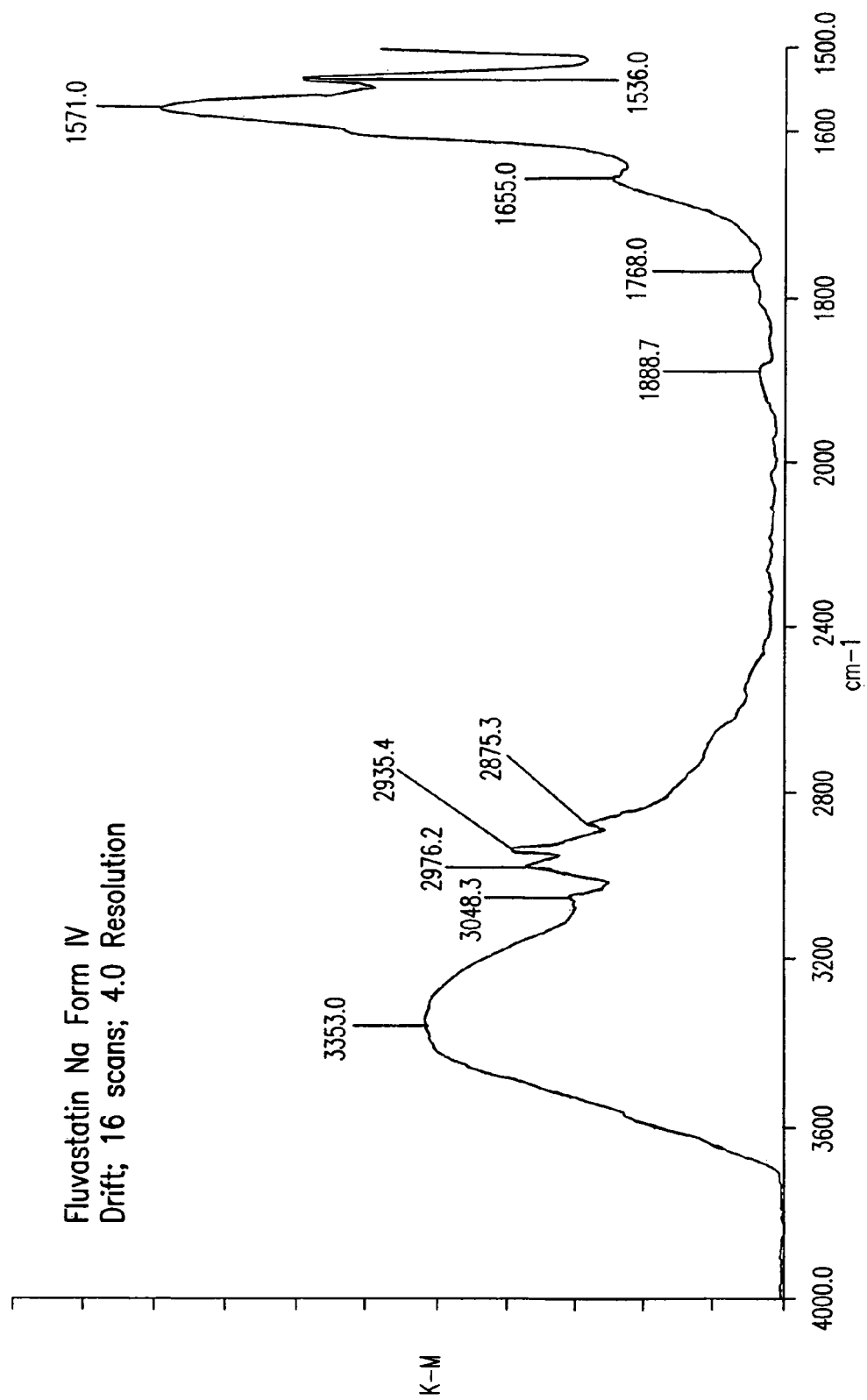

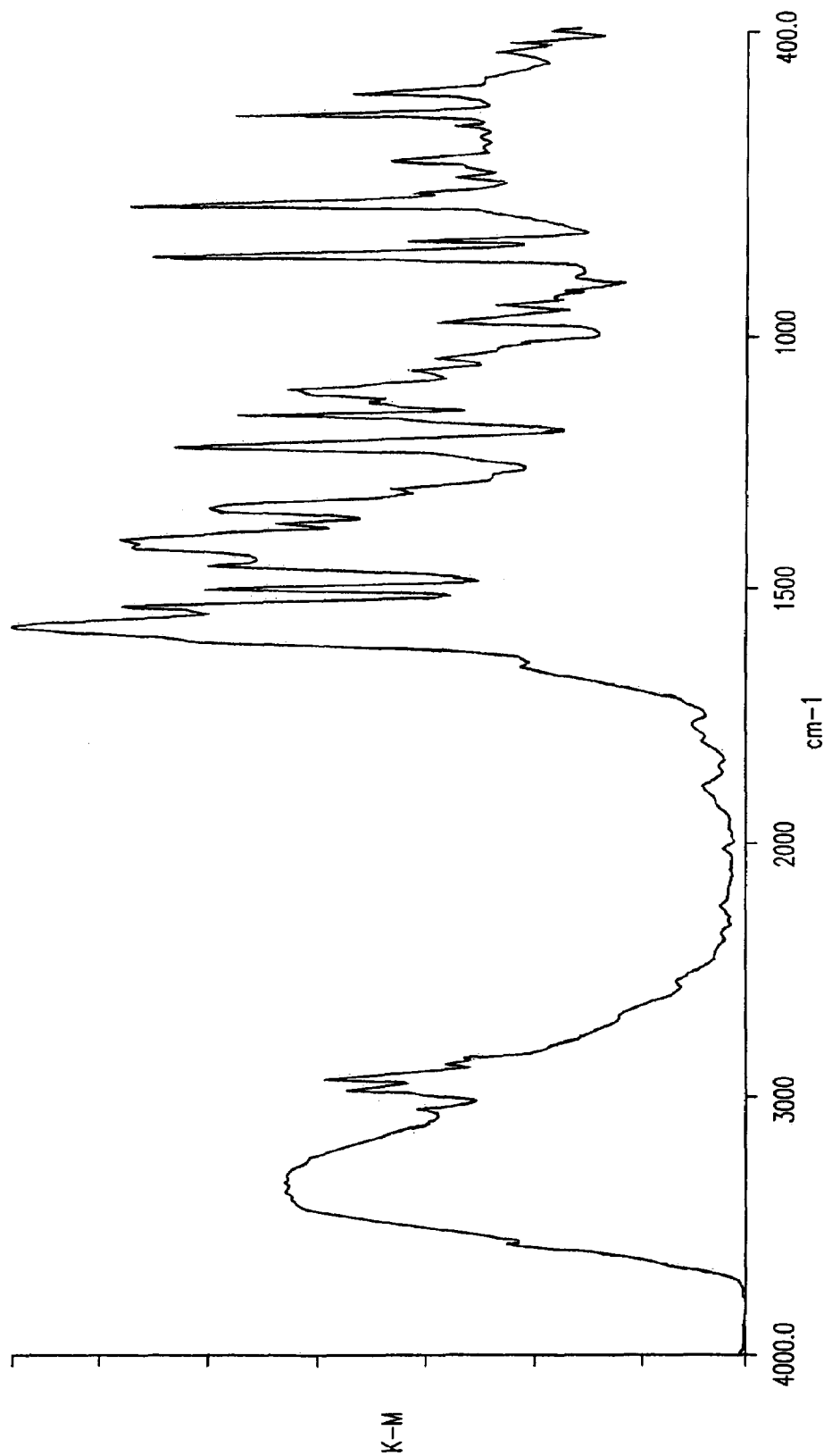

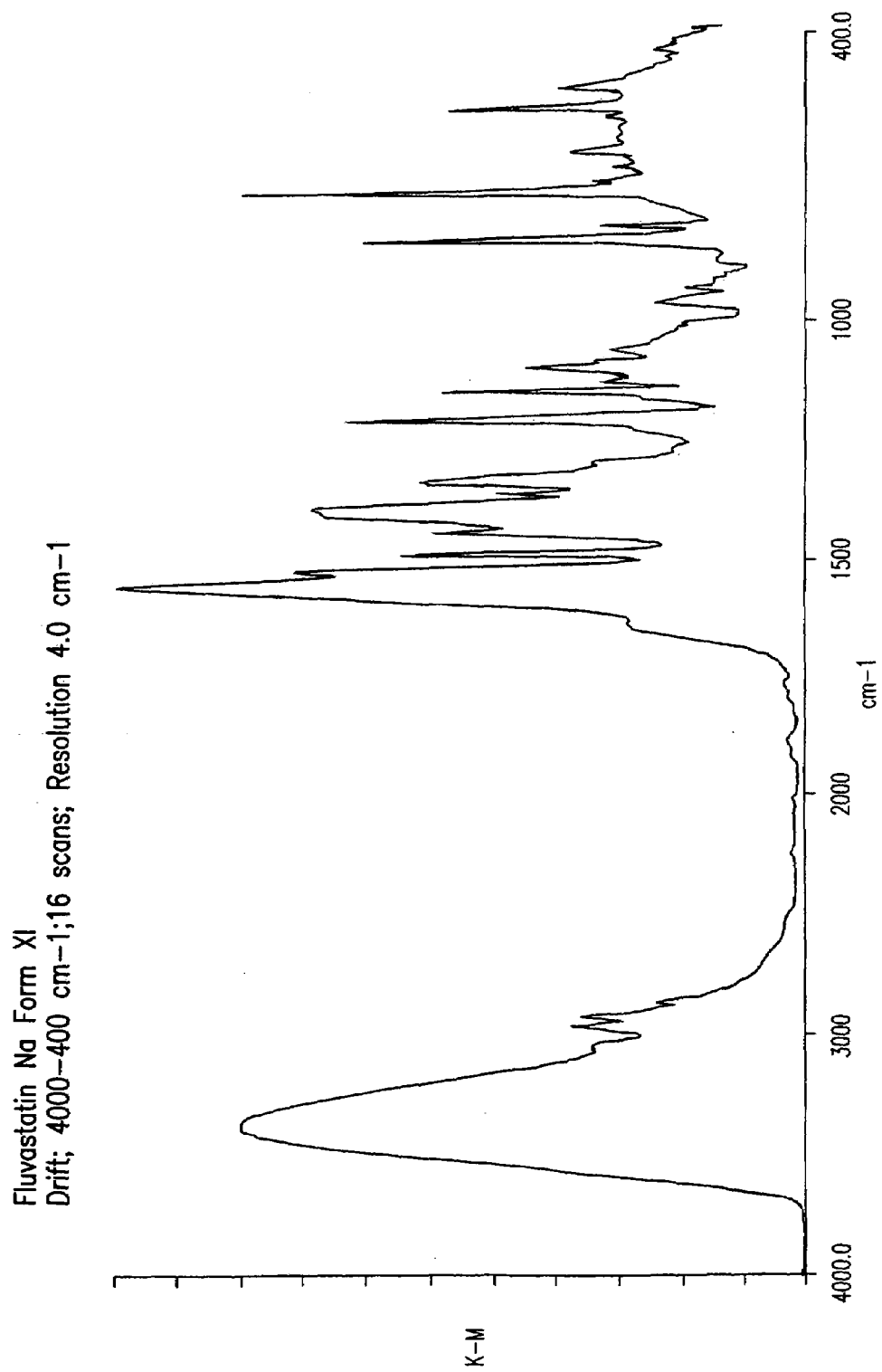

FLUVASTATIN SODIUM CRYSTAL FORMS, PROCESSES FOR PREPARING THEM, COMPOSITIONS CONTAINING THEM AND METHODS OF USING THEM

PRIORITY

This application is a continuation of U.S. application Ser. No.: 10/872,089 filed Jun. 18, 2004, now U.S. Pat. No. 7,414,140, which claims the benefit of U.S. Provisional Application Ser. Nos. 60/479,182 filed Jun. 18, 2003; 60/483,099 filed Jun. 30, 2003; 60/485,748 filed Jul. 10, 2003; 60/493,793 filed Aug. 11, 2003; 60/507,954 filed Oct. 3, 2003 and 60/545,466 filed Feb. 19, 2004, all of which are incorporated herein by reference.

FIELD OF THE INVENTION

The present invention relates to the antihypercholesterolemia and antilipidemia agent fluvastatin and, more particularly, to the solid state properties of its monosodium salt.

BACKGROUND OF THE INVENTION

Complications of cardiovascular disease, such as myocardial infarction, stroke, and peripheral vascular disease account for half of the deaths in the United States. A high level of low density lipoprotein (LDL) in the bloodstream has been linked to the formation of coronary lesions which obstruct the flow of blood and can rupture and promote thrombosis. Goodman and Gilman, *The Pharmacological Basis of Therapeutics* 879 (9th ed. 1996). Reducing plasma LDL levels has been shown to reduce the risk of clinical events in patients with cardiovascular disease and in patients who are free of cardiovascular disease but who have hypercholesterolemia. Scandinavian Simvastatin Survival Study Group, 1994; Lipid Research Clinics Program, 1984a, 1984b.

Statin drugs are currently the most therapeutically effective drugs available for reducing the level of LDL in the blood stream of a patient at risk for cardiovascular disease. This class of drugs includes, inter alia, compactin, lovastatin, simvastatin, pravastatin and fluvastatin. The mechanism of action of statin drugs has been elucidated in some detail. They disrupt the synthesis of cholesterol and other sterols in the liver by competitively inhibiting the 3-hydroxy-3-methyl-glutaryl-coenzyme A reductase enzyme ("HMG-CoA reductase"). HMG-CoA reductase catalyzes the conversion of HMG-CoA to mevalonate, which is the rate determining step in the biosynthesis of cholesterol. Consequently, its inhibition leads to a reduction in the rate of formation of cholesterol in the liver.

[R*,S*-(E)]-(±)-7-[3-(4-fluorophenyl)-1-(1-methylethyl)-1H-indol-2-yl]-3,5-dihydroxy-6-heptenoic acid is a statin drug. It is known by the trivial name fluvastatin and has the molecular formula (I):

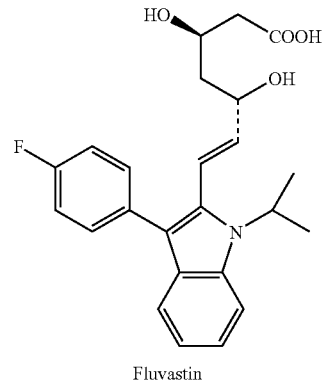

Fluvastin depicted in free acid form.

Fluvastatin is commercially available under the trade name Lescol®. Fluvastatin is supplied as a monosodium salt in capsules containing the equivalent of 20 and 40 mg of fluvastatin and in extended-release tablets containing the equivalent of 80 mg of fluvastatin. Fluvastatin and its sodium salt are described in U.S. Pat. No. 4,739,073. In Example 6(a) of the '073 patent, a methyl ester precursor of (±) fluvastatin was hydrolyzed with sodium hydroxide in methanol, which yielded, after evaporation of the methanol, crude fluvastatin sodium. In Example 6(b), the fluvastatin methyl ester was hydrolyzed with sodium hydroxide in ethanol. After evaporation of the ethanol, the residue was taken up in water and lyophilized. The lyophilized product had a melting point range of 194EC-197EC. In Example 8, the sodium salt was prepared by ring opening of fluvastatin lactone with sodium hydroxide in ethanol as described in Example 6(b). The product of Example 8 produced an infrared spectrum in a KBr pellet with bands at: 3413, 2978, 2936, 1572 and 1216 cm$^{-1}$.

According to U.S. Pat. No. 6,124,340, lyophilization of fluvastatin sodium as was performed in Examples 6(b) and 8 of the '073 patent yields solid fluvastatin sodium as a mixture of a crystalline form, designated as Form A, and amorphous material. The '340 patent sets forth the spectroscopic properties of another crystal form of fluvastatin sodium which is said to have low hygroscopicity and photostability. This other form is called Form B in the '340 patent. It is characterized by an infrared spectrum with bands at 3343, 2995, 1587, 1536, 1386, 1337, 1042 and 1014 cm$^{-1}$ and by the following powder X-ray diffraction peak positions and intensities.

| E22 | d (Å) | I/I$_O$(%) |
|---|---|---|
| 4.063 | 21.728 | 100 |
| 11.056 | 7.996 | 2.9 |
| 11.328 | 7.805 | 5.5 |
| 12.210 | 7.243 | 45.2 |
| 12.965 | 6.823 | 34.6 |
| 14.925 | 5.931 | 9.3 |
| 15.277 | 5.795 | 4.5 |
| 15.750 | 5.622 | 18.5 |
| 16.350 | 5.417 | 10.6 |
| 17.760 | 4.990 | 17.6 |
| 18.320 | 4.839 | 14.3 |

-continued

| E22 | d (Å) | I/I$_O$(%) |
|---|---|---|
| 18.875 | 4.698 | 11.3 |
| 19.396 | 4.573 | 7.0 |
| 19.701 | 4.503 | 13.4 |
| 20.395 | 4.351 | 13.5 |
| 21.329 | 4.163 | 8.5 |
| 21.785 | 4.076 | 15.9 |
| 22.610 | 3.929 | 7.5 |
| 23.868 | 3.725 | 5.4 |
| 24.281 | 3.663 | 3.6 |
| 24.463 | 3.636 | 3.6 |
| 25.446 | 3.498 | 5.6 |
| 25.655 | 3.470 | 3.6 |
| 26.357 | 3.379 | 3.3 |
| 27.040 | 3.295 | 2.8 |
| 28.747 | 3.103 | 3.4 |
| 29.940 | 2.982 | 2.8 |
| 32.165 | 2.781 | 1.6 |
| 35.173 | 2.549 | 1.0 |
| 37.131 | 2.419 | 1.3 |

Fluvastatin sodium Form A is said to have the following powder X-ray diffraction peak positions and intensities.

| E22 | d (Å) | I/I$_O$ (%) |
|---|---|---|
| 3.965 | 22.265 | 100 |
| 7.936 | 11.131 | 0.9 |
| 10.554 | 8.375 | 1.7 |
| 10.645 | 8.304 | 1.5 |
| 11.931 | 7.412 | 44.5 |
| 12.215 | 7.240 | 14.5 |
| 14.496 | 6.106 | 1.1 |
| 14.812 | 5.976 | 0.8 |
| 15.916 | 5.564 | 0.3 |
| 17.769 | 4.988 | 3.2 |
| 18.640 | 4.756 | 5.3 |
| 19.856 | 4.468 | 5.8 |
| 20.518 | 4.325 | 2.9 |
| 20.908 | 4.245 | 1.2 |
| 21.389 | 4.151 | 1.3 |
| 21.722 | 4.088 | 1.1 |
| 22.675 | 3.918 | 0.8 |
| 24.089 | 3.691 | 1.0 |
| 24.533 | 3.626 | 0.5 |
| 26.519 | 3.358 | 0.2 |
| 27.973 | 3.187 | 0.9 |
| 28.861 | 3.091 | |

U.S. Patent Application Publication No. 2003/0032666 reports the existence of four crystal forms of fluvastatin monosodium called Forms C, D, E and F. The water content of the forms ranges between 3 and 32%. The new crystal forms of fluvastatin sodium were obtained by storing the samples under atmospheres ranging between 20 and 90% relative humidity.

According to the '666 publication, the PXRD pattern of fluvastatin sodium Form C possesses characteristic peaks at the following d-values and qualitative intensities:

| d (Å) | Intensity |
|---|---|
| 23.8 | (vs) |
| 11.8 | (w) |
| 7.8 | (vs) |
| 7.6 | (vw) |
| 7.4 | (vw) |
| 6.4 | (vw) |

-continued

| d (Å) | Intensity |
|---|---|
| 6.1 | (vw) |
| 5.90 | (w) |
| 5.00 | (vw) |
| 4.88 | (w) |
| 4.73 | (m) |
| 4.56 | (w) |
| 4.40 | (vw) |
| 4.12 | (vw) |
| 4.03 | (vw) |
| 3.96 | (vw) |
| 3.50 | (vw) |
| 3.36 | (vw) |
| 2.93 | (vw) | wherein (vs)=very strong intensity; (s)=strong intensity; (m)=medium intensity; (w)=weak intensity; and (vw)=very weak intensity.

According to the '666 publication, the PXRD pattern of fluvastatin sodium Form D possesses characteristic peaks at the following d-values and qualitative intensities:

| d (Å) | Intensity |
|---|---|
| 24.6 | (vs) |
| 12.5 | (w) |
| 8.3 | (vs) |
| 7.4 | (vw) |
| 6.2 | (m) |
| 4.97 | (w) |
| 4.85 | (vw) |
| 4.52 | (vw) |
| 4.40 | (vw) |
| 4.14 | (vw) |
| 3.96 | (vw) |
| 3.41 | (vw) |
| 3.10 | (vw) |

According to the '666 publication, the PXRD pattern of fluvastatin sodium Form E possesses characteristic peaks at the following d-values and qualitative intensities:

| d (Å) | Intensity |
|---|---|
| 27.6 | (m) |
| 13.9 | (vw) |
| 9.2 | (m) |
| 8.5 | (vw) |
| 8.1 | (vw) |
| 7.4 | (vw) |
| 6.9 | (s) |
| 6.1 | (vw) |
| 4.98 | (m) |
| 4.77 | (m) |
| 4.63 | (m) |
| 4.15 | (w) |
| 4.03 | (w) |
| 3.97 | (vw) |
| 3.52 | (vw) |
| 3.33 | (vw) |
| 3.08 | (vw) |
| 2.99 | (vw) |

According to the '666 publication, the PXRD pattern of fluvastatin sodium Form F possesses characteristic peaks at the following d-values and qualitative intensities:

| d (Å) | Intensity |
|---|---|
| 29.6 | (w) |
| 14.8 | (vw) |
| 9.9 | (w) |
| 8.6 | (vw) |
| 8.3 | (vw) |
| 7.4 | (s) |
| 6.6 | (vw) |
| 6.2 | (vw) |
| 5.93 | (w) |
| 5.03 | (m) |
| 4.94 | (m) |
| 4.35 | (vw) |
| 4.23 | (w) |
| 3.98 | (vw) |
| 3.54 | (vw) |
| 2.98 | (vw) |

It also deserves mention that International Publication No. WO 02/36563 discloses crystal forms of enantiomerically pure [3R,5S] and [3S,5R] fluvastatin sodium.

The present invention also relates to fluvastatin sodium and the properties that it can exhibit in the condensed phase. The occurrence of different crystal forms (polymorphism) is a property of some molecules and molecular complexes. A single molecule, like the fluvastatin in formula (I) or a salt complex like fluvastatin sodium, may give rise to a variety of solids having distinct physical properties like melting point, X-ray diffraction pattern, infrared absorption fingerprint and NMR spectrum. The crystalline form may give rise to thermal behavior different from that of the amorphous material or another crystalline form. Thermal behavior is measured in the laboratory by such techniques as capillary melting point, thermogravimetric analysis ("TGA") and differential scanning calorimetry ("DSC") and can be used to distinguish some polymorphic forms from others. The differences in the physical properties of different crystalline forms result from the orientation and intermolecular interactions of adjacent molecules (complexes) in the bulk solid. Accordingly, polymorphs are distinct solids sharing the same molecular formula yet having distinct advantageous and/or disadvantageous physical properties compared to other forms in the polymorph family. These properties can be influenced by controlling the conditions under which the salt is obtained in solid form.

Exemplary solid state physical properties include the flowability of the milled solid. Flowability affects the ease with which the material is handled during processing into a pharmaceutical product. When particles of the powdered compound do not flow past each other easily, a formulation specialist must take that fact into account in developing a tablet or capsule formulation, which may necessitate the use of glidants such as colloidal silicon dioxide, talc, starch or tribasic calcium phosphate.

One of the most important physical properties of pharmaceutical polymorphs is their solubility in aqueous solution, particularly their solubility in the gastric juices of a patient. For example, where absorption through the gastrointestinal tract is slow, it is often desirable for a drug that is unstable to conditions in the patient's stomach or intestine to dissolve slowly so that it does not accumulate in a deleterious environment. On the other hand, the method is not advantageous where the effectiveness of a drug correlates with peak bloodstream levels of the drug, as in the case of statin drugs. With a statin drug, provided the drug is rapidly absorbed by the GI system, a more rapidly dissolving form is likely to exhibit increased effectiveness over a comparable amount of a more slowly dissolving form.

It is often the case that the most rapidly dissolving solid state of a compound is amorphous. Amorphous forms are often less stable than crystalline forms because they do not have many of the stabilizing intermolecular interactions that are present in crystalline forms. With an amorphous form, therefore, stabilizing intermolecular interactions do not have to be broken when the compound goes into solution, and so the dissolution rate is not retarded. Although they are more rapidly dissolving than crystalline forms, amorphous forms of a compound can have disadvantages. A compound, when it is in an amorphous state, is frequently more hygroscopic than a crystalline form of the same compound (although exceptions abound, such as when the crystal has wide channels that allow water to enter and leave the crystal in response to changes in moisture density outside the crystal). Water has been implicated in drug stability problems. For instance the decomposition of aspirin which leads to the characteristic smell of vinegar when an old bottle of aspirin is opened is a hydrolysis reaction catalyzed by water. It is thus prudent when selecting a solid state form of a compound that is to be used as a drug, and possibly stored for a long time between packaging and use, to select a form that has low permeability to water. In the case of fluvastatin monosodium, a crystalline form designated Form B has already been discovered that is purportedly less hygroscopic than the partially crystalline/partially amorphous form of the salt that is obtained by following procedures in U.S. Pat. No. 4,739,073.

Although six distinct crystalline forms of racemic fluvastatin sodium have been reported to date, and at least one of them is purported to be less hygroscopic that the solid state form originally reported by the discovers of the compound, the discovery of yet other crystalline forms of fluvastatin sodium is desirable. The discovery of new crystalline forms and solvates of a pharmaceutically useful compound provides a new opportunity to improve the performance characteristics of a pharmaceutical product by enlarging the repertoire of materials that a formulation scientist has available for designing. For example, new crystalline forms can be used to design a pharmaceutical dosage form of a drug with low hygroscopicity, a targeted release profile, consistent dosing (enabled by good flow of the tableting composition into the tableting die), or other desired characteristic. New polymorphic forms and solvates of fluvastatin have now been discovered.

SUMMARY OF THE INVENTION

In one aspect the present invention provides various polymorphic forms of fluvastatin sodium. The polymorphic forms are identified inter alia by various characteristic PXRD peaks.

In another aspect, the present invention provides processes for preparation of these polymorphic forms. These polymorphic forms are prepared by various processes as set out in the examples and the Detailed Description of the Invention.

In another aspect, the present invention provides for pharmaceutical formulations prepared from such polymorphic forms.

In another aspect, the present invention provides for treatment of hypercholesterolemia or hyperlipidemia in a mammal by administering the pharmaceutical compositions to the mammal.

These polymorphic forms are useful inter alia for preparation of pharmaceutical compositions of fluvastatin sodium, purification of fluvastatin since many are of high crystallinity, and/or as starting material for preparation of other polymorphic forms of fluvastatin sodium.

Figure 1:
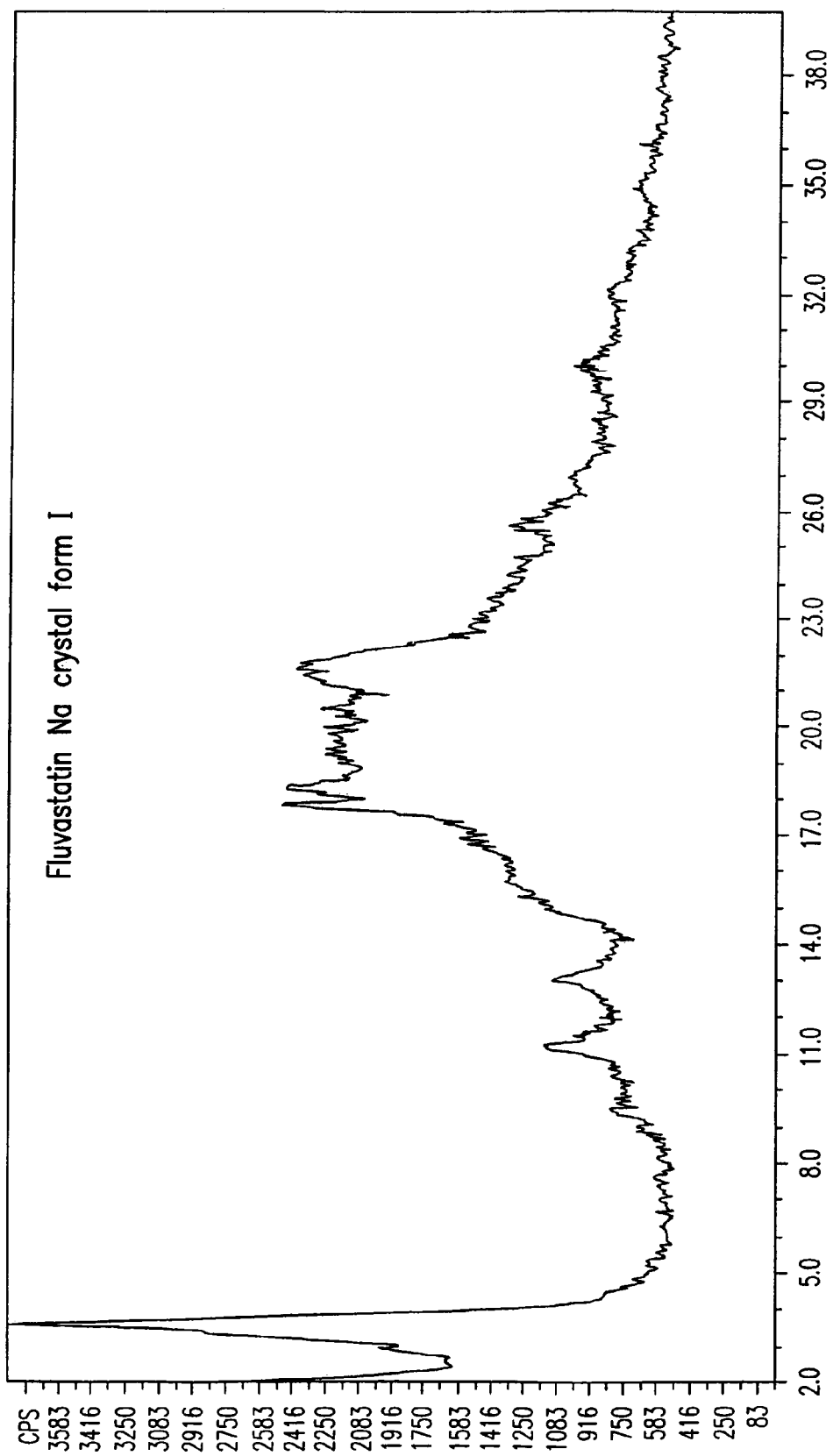
FIG. 1 depicts a powder X-ray diffractogram of fluvastatin sodium Form I.

The following numbered embodiments further summarize the present invention:

1. A crystalline form of fluvastatin sodium characterized by a PXRD pattern with peaks at 3.7, 11.3, 13.1, 17.9, 18.4 and 21.8±0.2 degrees two-theta.
2. The crystalline form of embodiment 1 wherein the crystalline form is characterized by a PXRD pattern substantially as depicted in FIG. 1.
3. The crystalline form of embodiment 1 wherein the crystalline form is fluvastatin sodium Form I.

Figure 2:
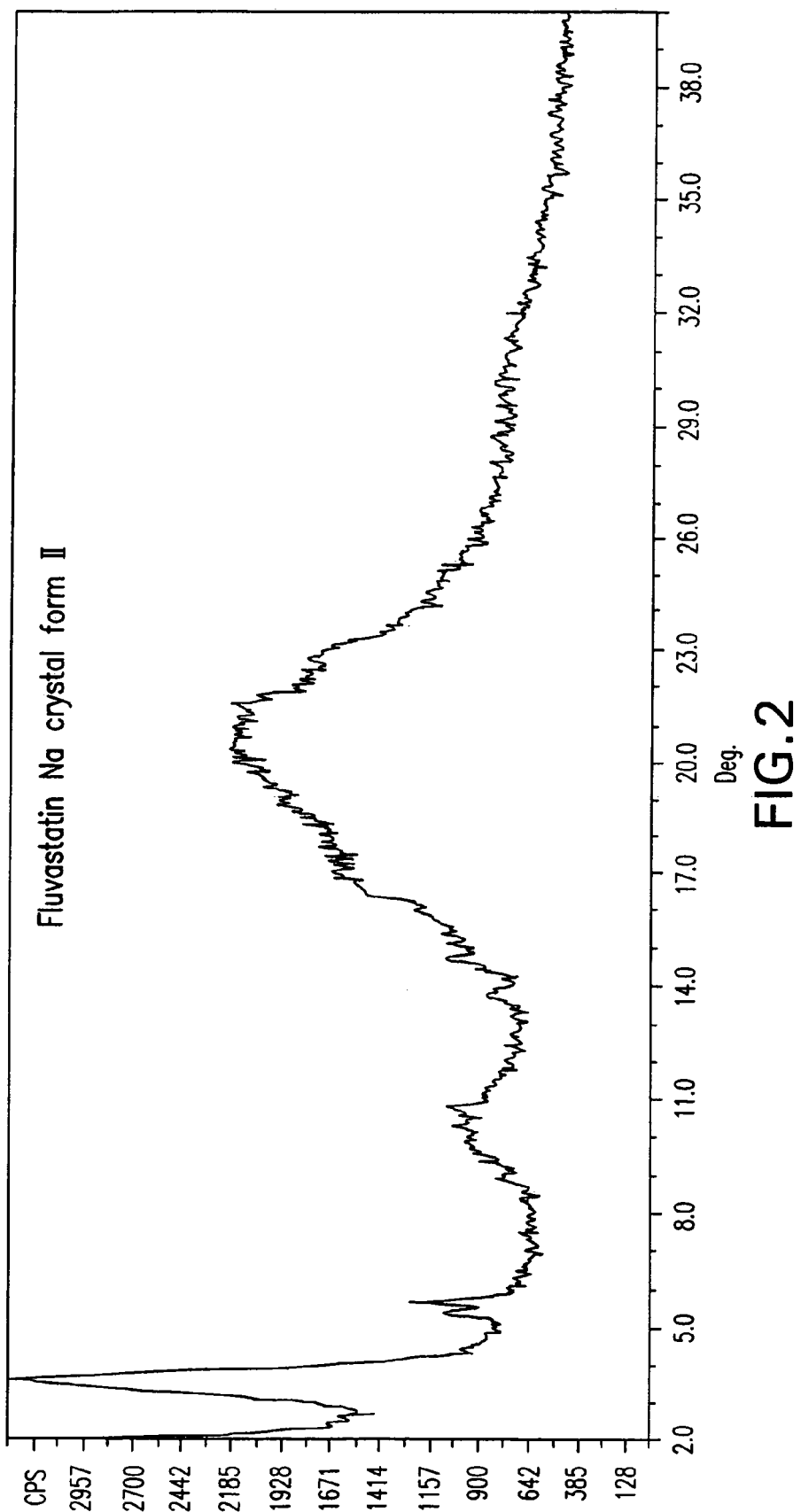
FIG. 2 depicts a powder X-ray diffractogram of fluvastatin sodium Form II.
Figure 3:
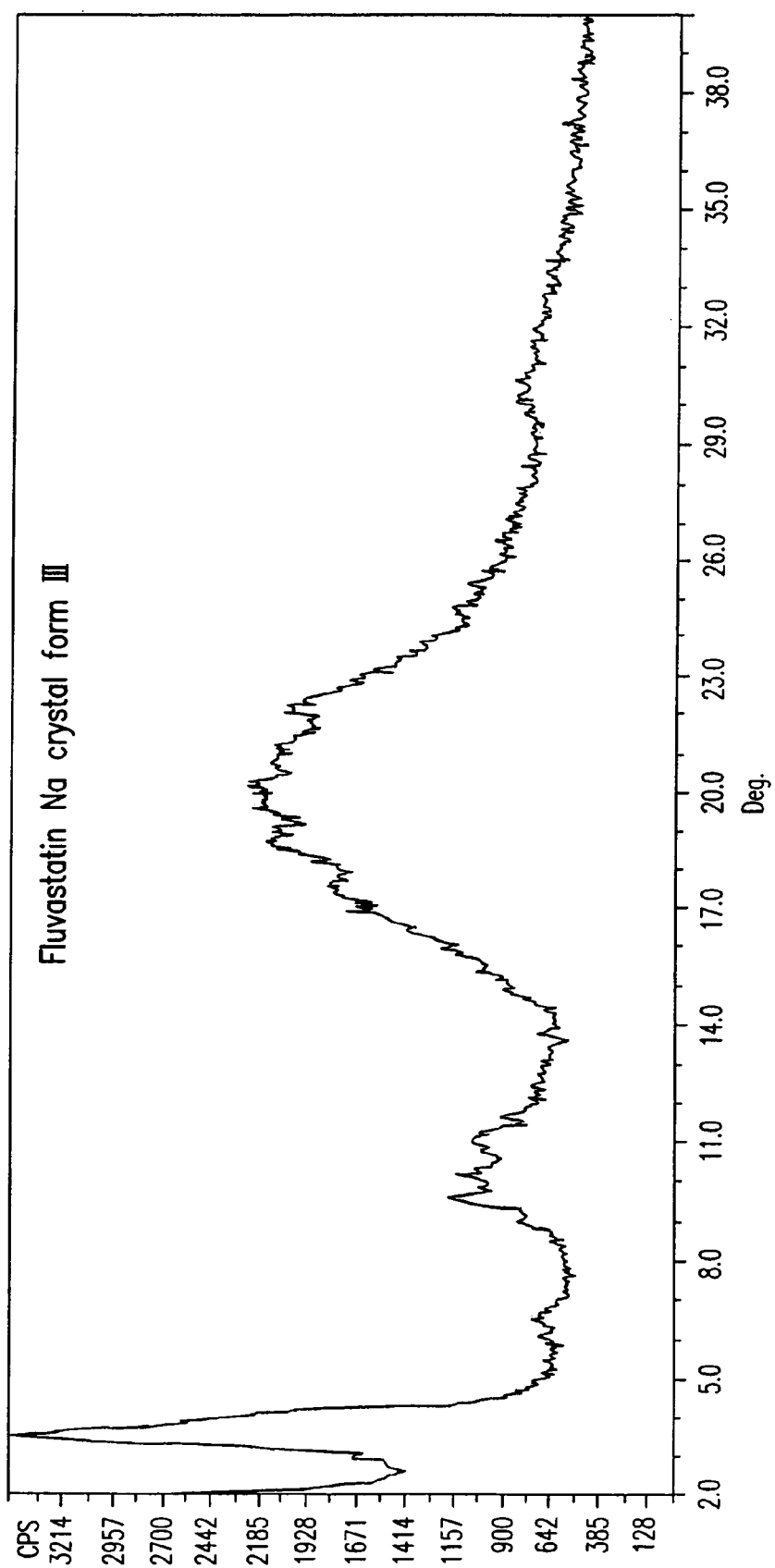
FIG. 3 depicts a powder X-ray diffractogram of fluvastatin sodium Form III.
Figure 4:
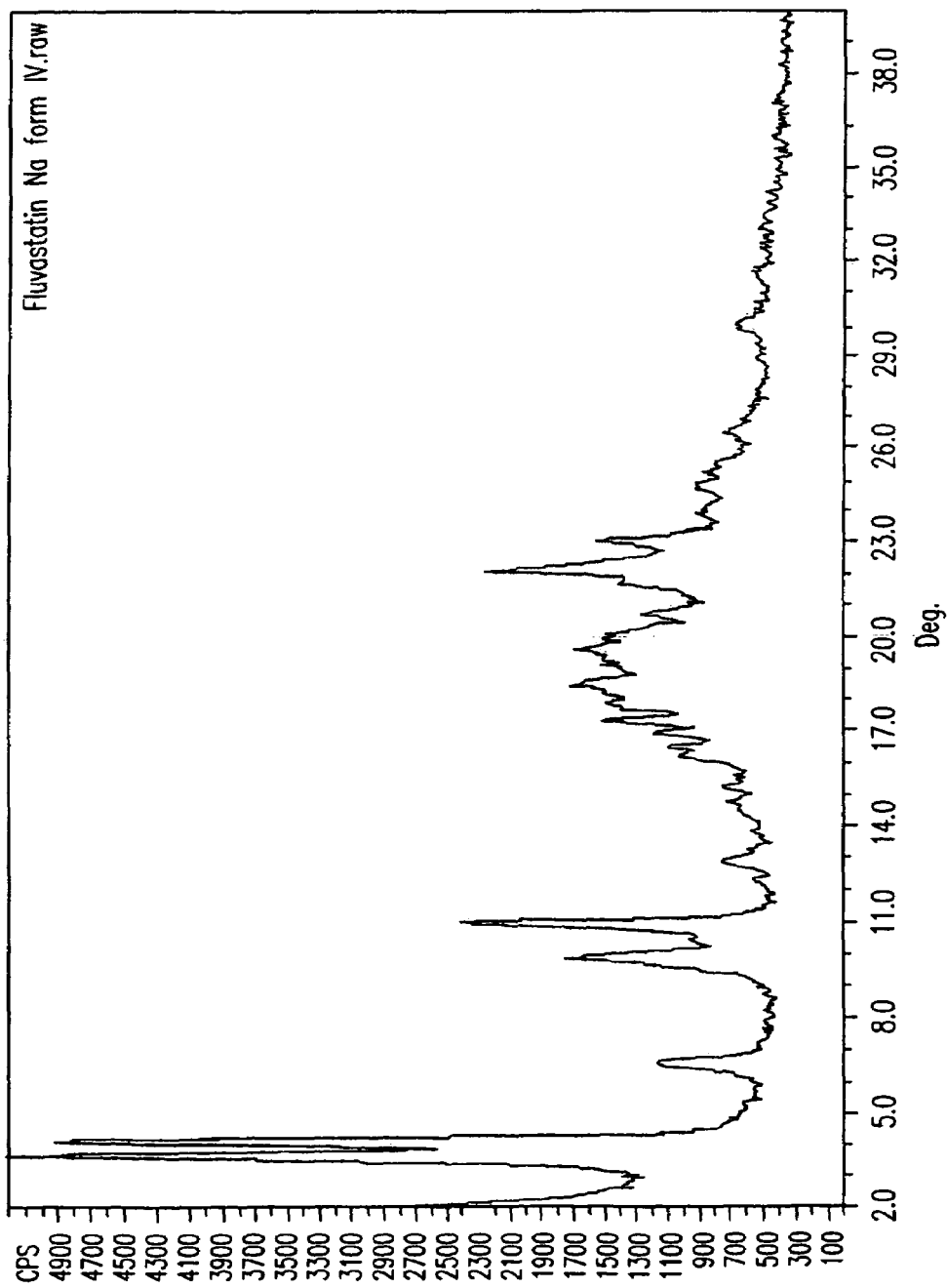
FIG. 4 depicts a powder X-ray diffractogram of fluvastatin sodium Form IV.
Figure 7:
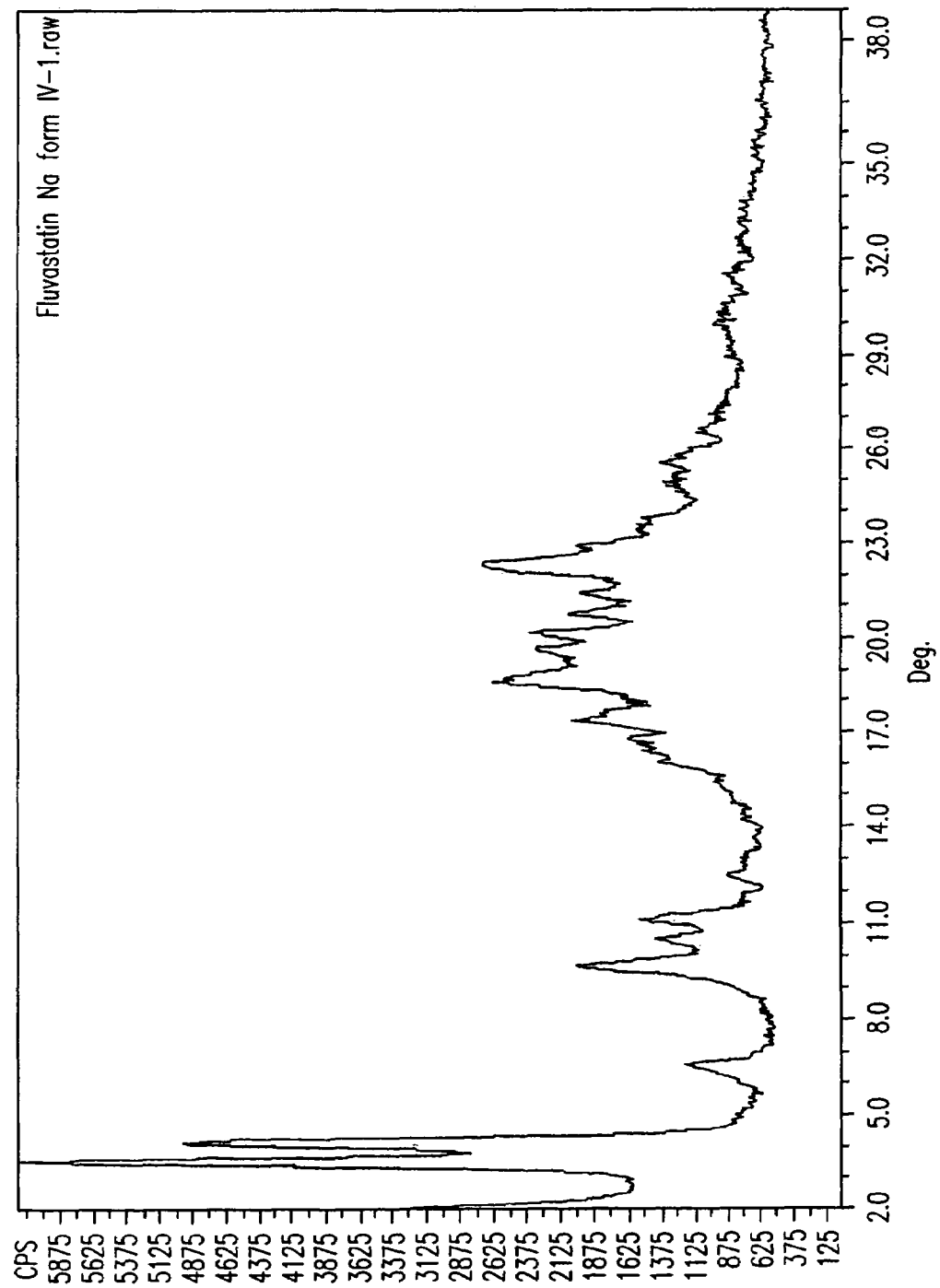
FIG. 7 depicts a powder X-ray diffractogram of fluvastatin sodium Form IV-1.
Figure 10:
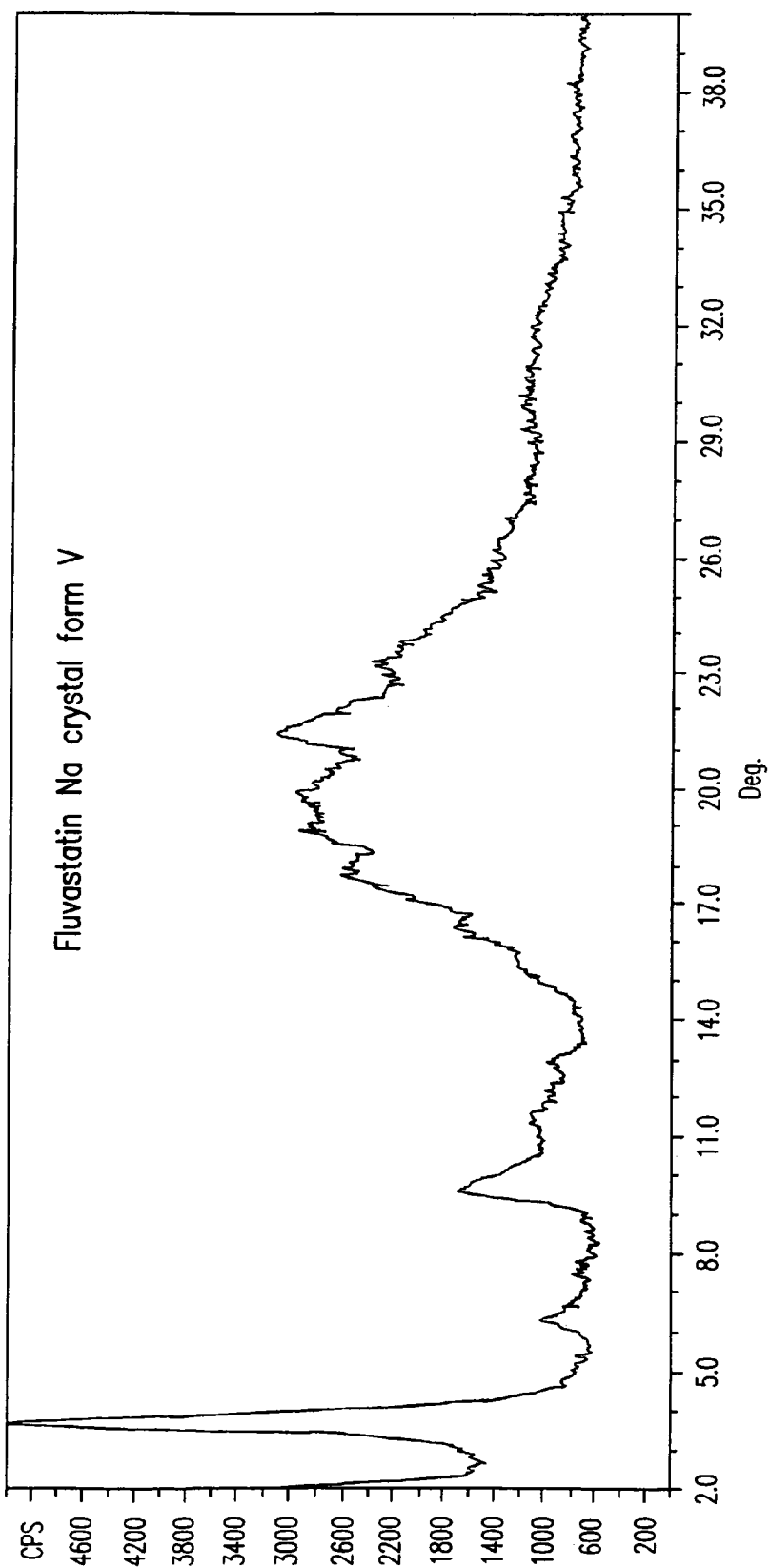
FIG. 10 depicts a powder X-ray diffractogram of fluvastatin sodium Form V.

4. A process for preparing crystalline fluvastatin sodium Form I comprising:
   a) contacting a lower alkyl ester of fluvastatin and sodium in a solvent selected from the group consisting of acetone and acetonitrile,
   b) precipitating fluvastatin sodium Form I from the solvent, and
   c) separating the solvent from Form I.
5. A process for preparing crystalline fluvastatin sodium Form I comprising:
   a) dissolving fluvastatin sodium in a solvent selected from acetone and mixtures of butan-2-ol and water,
   b) crystallizing Form I from the solvent, and
   c) separating the solvent from Form I.
6. A crystalline form of fluvastatin sodium characterized by a PXRD pattern with peaks at 3.6±0.2 degrees two-theta.
7. The crystalline form of embodiment 6 further characterized by peaks at 5.4, 5.7, 10.7 and 20.3±0.2 degrees two-theta.
8. The crystalline form of embodiment 7 wherein the crystalline form is characterized by a PXRD pattern substantially as depicted in FIG. 2.
9. The crystalline form of embodiment 7 wherein the crystalline form is fluvastatin sodium Form II.
10. A process for preparing crystalline fluvastatin sodium Form II comprising:
    a) dissolving solid fluvastatin sodium in a solvent selected from butan-1-ol and propan-2-ol,
    b) crystallizing Form II from the solvent, and
    c) separating the solvent from Form II.
11. A crystalline form of fluvastatin sodium characterized by a PXRD pattern with peaks at 3.5, 9.5, 10.1, 10.9 and 20.1±0.2 degrees two-theta.
12. The crystalline form of embodiment 11 wherein the crystalline form is characterized by a PXRD pattern substantially as depicted in FIG. 3.
13. The crystalline form of embodiment 11 wherein the crystalline form is fluvastatin sodium Form III.
14. A process for preparing crystalline fluvastatin sodium Form III comprising:
    a) dissolving fluvastatin sodium in a solvent selected from the group consisting of butan-1-ol, ethyl acetate and THF.
    b) slowly adding an anti-solvent selected from the group consisting of MTBE, hexanes and cyclohexane to the solvent to induce precipitation of Form III, and
    c) separating the solvent and anti-solvent from Form III.
15. A process for preparing crystalline fluvastatin sodium Form III comprising:
    a) dissolving amorphous fluvastatin sodium in refluxing ethanol.
    b) precipitating Form III from the ethanol, and
    c) separating the ethanol from the Form III.
16. A process for preparing crystalline fluvastatin sodium Form III comprising:
    a) suspending fluvastatin sodium Form XIV in refluxing ethanol for a period of time sufficient to effect the conversion to Form III,
    b) cooling the ethanol to ambient temperature, and
    c) separating the ethanol from the Form III.
17. A crystalline form of fluvastatin sodium characterized by a PXRD pattern with peaks at 3.6, 4.0, 9.8, 10.8 and 22.0±0.2 degrees two-theta.
18. The crystalline form of embodiment 17 wherein the crystalline form is characterized by a PXRD pattern substantially as depicted in FIG. 4.
19. The crystalline form of embodiment 17 wherein the crystalline form is fluvastatin sodium Form IV.
20. The fluvastatin sodium of embodiment 17 having a water content of about 4 percent by weight.
21. A process for preparing crystalline fluvastatin sodium Form IV comprising the steps of:
    a) dissolving fluvastatin sodium in solvent selected from the group consisting of THF, propan-2-ol, 1,4-dioxane and butan-1-ol to form a solution,
    b) refluxing the solution by heating the solvent, the heating being commenced either before or after dissolving the fluvastatin sodium,
    c) adding an organic anti-solvent to the refluxing solution to induce precipitation of fluvastatin sodium Form IV, and
    d) and separating the fluvastatin sodium Form IV from the solvent and anti-solvent.
22. The process of embodiment 20 where the anti-solvent is selected from the group consisting of chloroform, dichloromethane, 1,2-dichloroethane, diethyl ether, n-pentane, cyclohexane and methyl t-butyl ether.
23. A crystalline form of fluvastatin sodium characterized by a PXRD pattern with peaks at 3.6, 4.0, 9.6, 18.5 and 22.2±0.2 degrees two-theta.
24. The crystalline form of embodiment 23 further characterized by peaks at 6.6, 10.4, 11.0, 17.3, 19.5, 20.1, 20.7 and 21.3±0.2 degrees two-theta.
25. The crystalline form of embodiment 24 further characterized by a PXRD pattern substantially as depicted in FIG. 7.
26. The crystalline form of embodiment 23 wherein the crystalline form is fluvastatin sodium Form IV-1.
27. A process for preparing fluvastatin sodium Form IV-1 comprising the steps of:
    a) dissolving fluvastatin sodium in a solvent selected from the group consisting of THF, butan-2-ol and 1,4-dioxane to form a solution,
    b) refluxing the solution by heating the solvent the heating being commenced either before or after dissolving the fluvastatin sodium,
    c) adding an organic anti-solvent to the refluxing solution to induce precipitation of fluvastatin sodium Form IV-1, and
    d) separating the fluvastatin sodium Form IV-1 from the solvent and anti-solvent.
28. The process of embodiment 27 wherein the anti-solvent is selected from the group consisting of n-heptane, cyclohexane and MTBE.
29. Fluvastatin sodium Form IV-1 having a water content of from about 2 to about 3 weight percent.
30. A crystalline form of fluvastatin sodium characterized by a PXRD pattern with peaks at 3.8, 6.3, 9.5 and 21.2±0.2 degrees two-theta.
31. The crystalline form of embodiment 30 wherein the crystalline form is characterized by a PXRD pattern substantially as depicted in FIG. 10.
32. The crystalline form of embodiment 31 wherein the crystalline form is fluvastatin sodium Form V.
33. A process for preparing crystalline fluvastatin sodium Form V comprising:
    a) dissolving fluvastatin sodium in refluxing butan-1-ol,
    b) slowly adding heptane to the refluxing solution,
    c) precipitating Form V from the solution, and
    d) separating the butan-1-ol and heptane from the Form V.
34. A process for preparing crystalline fluvastatin sodium Form V comprising:
    a) dissolving fluvastatin sodium in a ternary solvent system of ethanol:ethyl acetate:propan-1-ol at reflux temperature,
    b) adding n-hexane to the solution, c) precipitating Form V from the solution,
d) separating the ethanol, ethyl acetate, propan-1-ol and n-hexane from the Form V.

35. A crystalline form of fluvastatin sodium characterized by a PXRD pattern with peaks at 3.7, 4.7, 5.7, 10.9, 12.2 and 19.9±0.2 degrees two-theta.

36. The crystalline form of embodiment 35 further characterized by peaks at 9.1, 9.6, 14.3 16.3, 16.9, 20.4 and 21.3±0.2 degrees two-theta.

Figure 11:
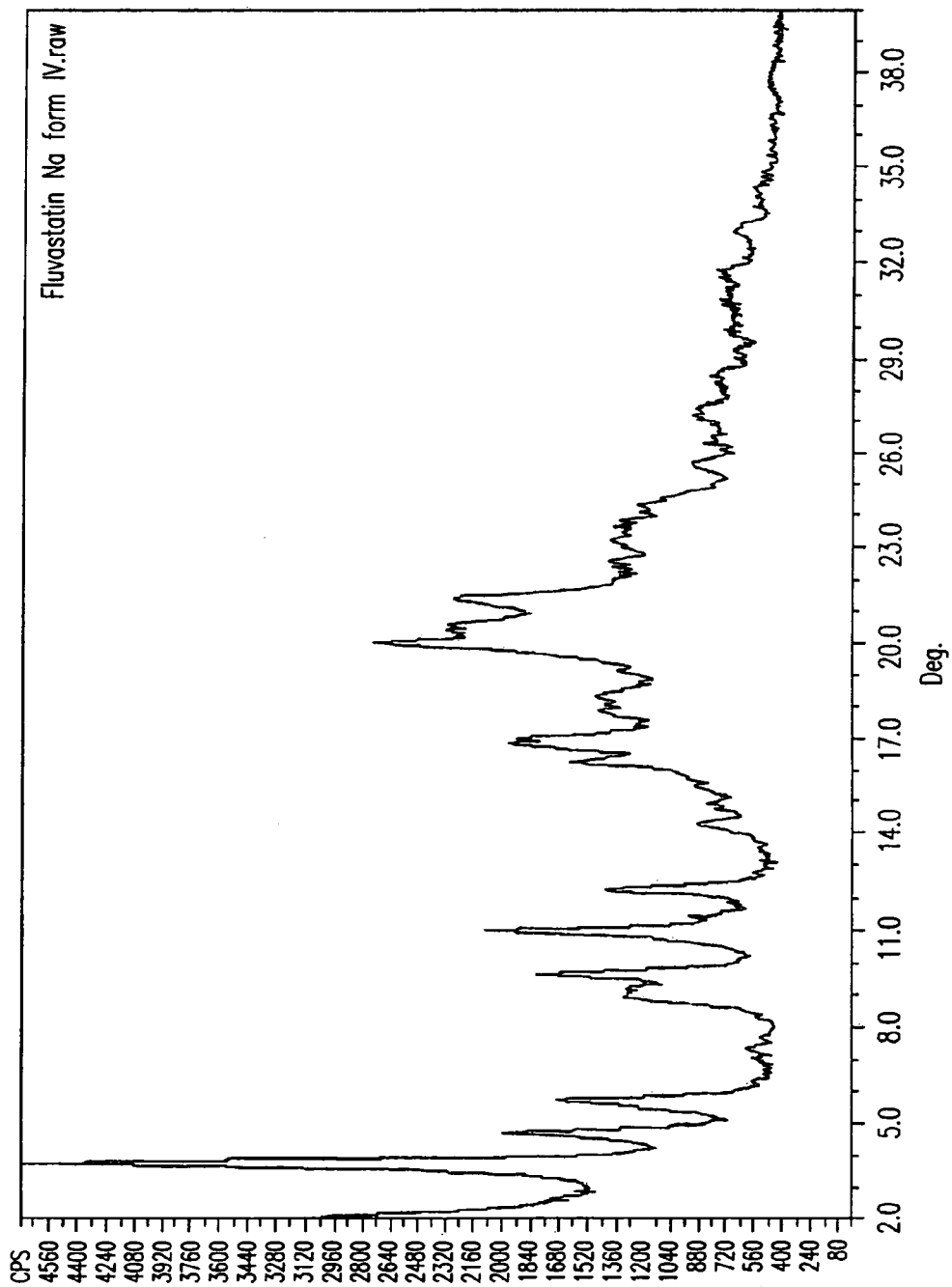
FIG. 11 depicts a powder X-ray diffractogram of fluvastatin sodium Form VI.

37. The crystalline form of embodiment 36 further characterized by a PXRD pattern substantially as depicted in FIG. 11.

38. The crystalline form of embodiment 35 wherein the crystalline form is fluvastatin sodium Form VI.

39. A process for preparing fluvastatin sodium Form VI comprising the steps of:
a) dissolving fluvastatin sodium in DMF at room temperature to form a solution,
b) adding an organic anti-solvent to the solution to induce precipitation of fluvastatin sodium Form VI, and
c) separating the fluvastatin sodium Form VI from the DMF and anti-solvent.

40. A process for preparing fluvastatin sodium Form VI comprising:
a) dissolving a lower alkyl ester of fluvastatin in a solution of about one molar equivalent of sodium hydroxide in a solvent system selected from the group consisting of methanol, ethanol and mixtures of methanol and water and butan-1-ol and water,
b) adding an anti-solvent selected from the group consisting of acetonitrile and acetone to the solution at elevated temperature, and
c) separating Form VI from the solvent system.

41. The process of embodiment 40 wherein the anti-solvent is selected from the group consisting of diethyl ether and hexanes.

42. Fluvastatin sodium Form VI having a water content of from about 5 to about 6 weight percent.

43. A crystalline form of fluvastatin sodium characterized by a PXRD pattern with peaks at 3.7, 4.3, 5.8, 8.6 and 20.7±0.2 degrees two-theta.

44. The crystalline form of embodiment 43 further characterized by peaks at 10.8, 12.3, 13.7, 15.8, 17.3, 19.4, 22.0, 23.9, 25.2, 26.2 and 27.6±0.2 degrees two-theta.

Figure 14:
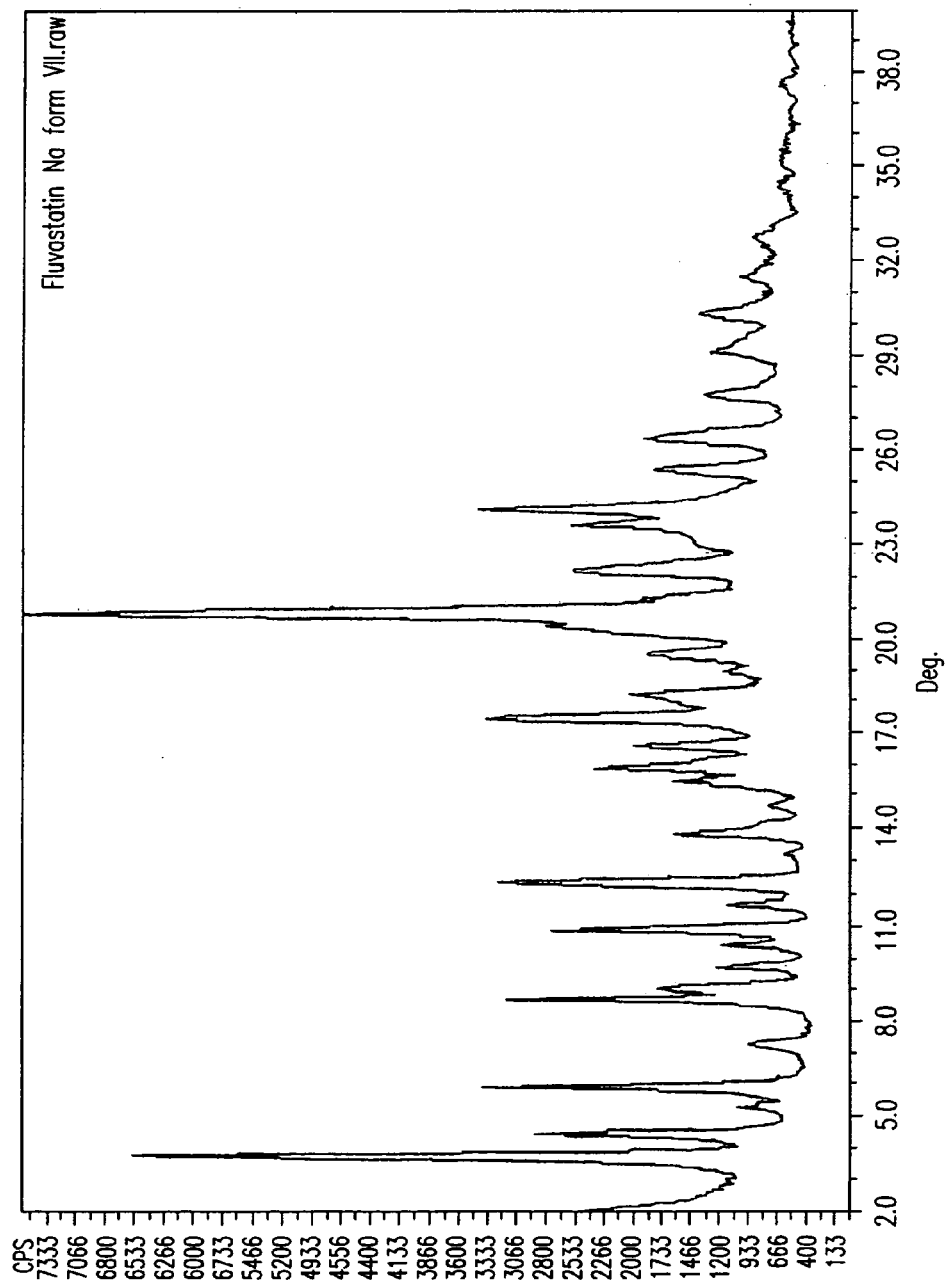
FIG. 14 depicts a powder X-ray diffractogram of fluvastatin sodium Form VII.

45. The crystalline form of embodiment 44 further characterized by a PXRD pattern substantially as depicted in FIG. 14.

46. The crystalline form of embodiment 43 wherein the crystalline form is fluvastatin sodium Form VII.

47. A process for preparing fluvastatin sodium Form VII comprising the steps of:
a) dissolving fluvastatin sodium in DMF at room temperature to form a solution,
b) adding an organic anti-solvent to induce precipitation of fluvastatin sodium Form VII from the solution, and
c) separating the fluvastatin sodium Form VII from the DMF and anti-solvent.

48. The process of embodiment 47 wherein the anti-solvent is selected from the group consisting of chloroform, MTBE, dichloromethane, cyclohexane and 1,2-dichloroethane.

49. A process for preparing fluvastatin sodium Form VII comprising the steps of:
a) dissolving a lower alkyl ester of fluvastatin in a solution of about one molar equivalent of sodium hydroxide in a solvent system selected from the group consisting of methanol, butan-1-ol and mixtures of butan-1-ol and propan-2-ol,
b) adding an anti-solvent selected from the group consisting of acetone, acetonitrile and methyl tert-butyl ether to induce precipitation of Form VII, and
c) separating the solvent system and anti-solvent from the Form VII.

50. A process for preparing fluvastatin sodium Form VII comprising the steps of:
a) dissolving a lower alkyl ester of fluvastatin in acetonitrile,
b) adding a solution of about one molar equivalent of sodium hydroxide in ethanol to induce precipitation of Form VII, and
c) separating the acetonitrile and ethanol from the Form VII.

51. Fluvastatin sodium Form VII having a water content of from about 1 to about 9 weight percent.

52. A crystalline form of fluvastatin sodium characterized by a PXRD pattern with peaks at 3.4, 10.0 and 19.7±0.2 degrees two-theta.

Figure 17:
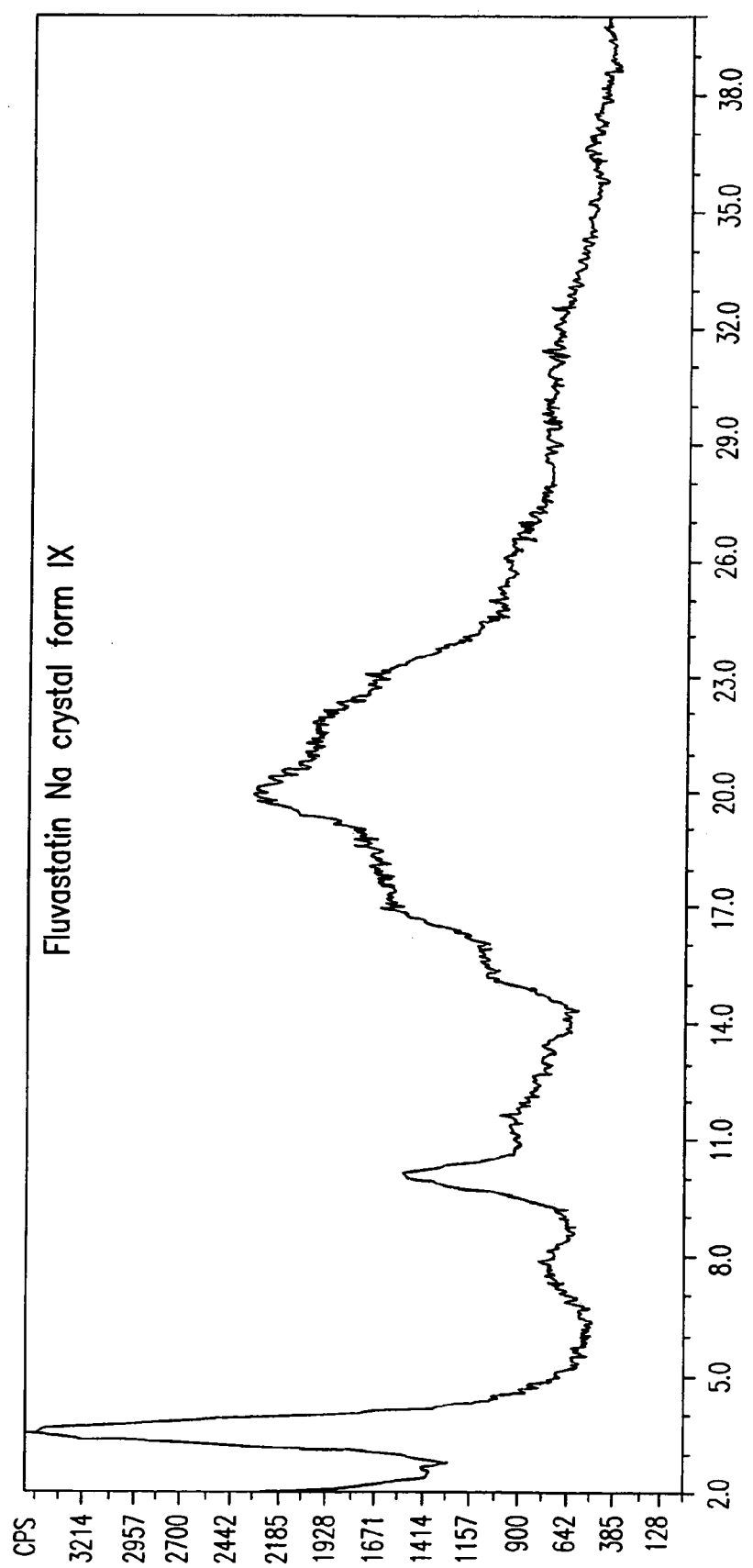
FIG. 17 depicts a powder X-ray diffractogram of fluvastatin sodium Form IX.

53. The crystalline form of embodiment 52 wherein the crystalline form is characterized by a PXRD pattern substantially as depicted in FIG. 17.

54. The crystalline form of embodiment 52 wherein the crystalline form is fluvastatin sodium Form IX.

55. A process for preparing crystalline fluvastatin sodium Form IX comprising:
a) dissolving fluvastatin sodium in 1,4-dioxane
b) adding dichloromethane to the solution to induce precipitation of Form IX, and
c) separating the 1,4-dioxane and dichloromethane from the Form IX.

56. A process for preparing crystalline fluvastatin sodium Form IX comprising:
a) dissolving fluvastatin sodium in ethanol,
b) adding ethyl acetate to the solution to induce precipitation of Form IX, and
c) separating the ethanol and ethyl acetate from Form IX.

57. A process for preparing crystalline fluvastatin sodium Form IX comprising:
a) dissolving fluvastatin sodium in a solvent system selected from the group consisting of diethyl ether, n-pentane and mixtures of ethanol and methanol,
b) adding hexanes to induce precipitation of Form IX, and
c) separating the solvent system from the Form IX.

58. A process for preparing crystalline fluvastatin sodium Form IX comprising:
a) suspending fluvastatin sodium Form B in refluxing ethyl acetate for a period of time sufficient to effect its conversion to Form IX, and
b) separating the ethyl acetate from the Form IX.

59. A process for preparing crystalline fluvastatin sodium Form IX comprising:
a) hydrolyzing a lower alkyl ester of fluvastatin with about one molar equivalent of sodium in ethanol at elevated temperature.
b) adding an excess of propan-2-ol with respect to the ethanol to the ethanol,
c) precipitating Form IX, and
d) separating the ethanol and propan-2-ol from the Form IX.

60. A crystalline form of fluvastatin sodium characterized by a PXRD pattern with peaks at 3.4, 6.6, 10.0, 13.2, 19.8±0.2 degrees two-theta.

Figure 18:
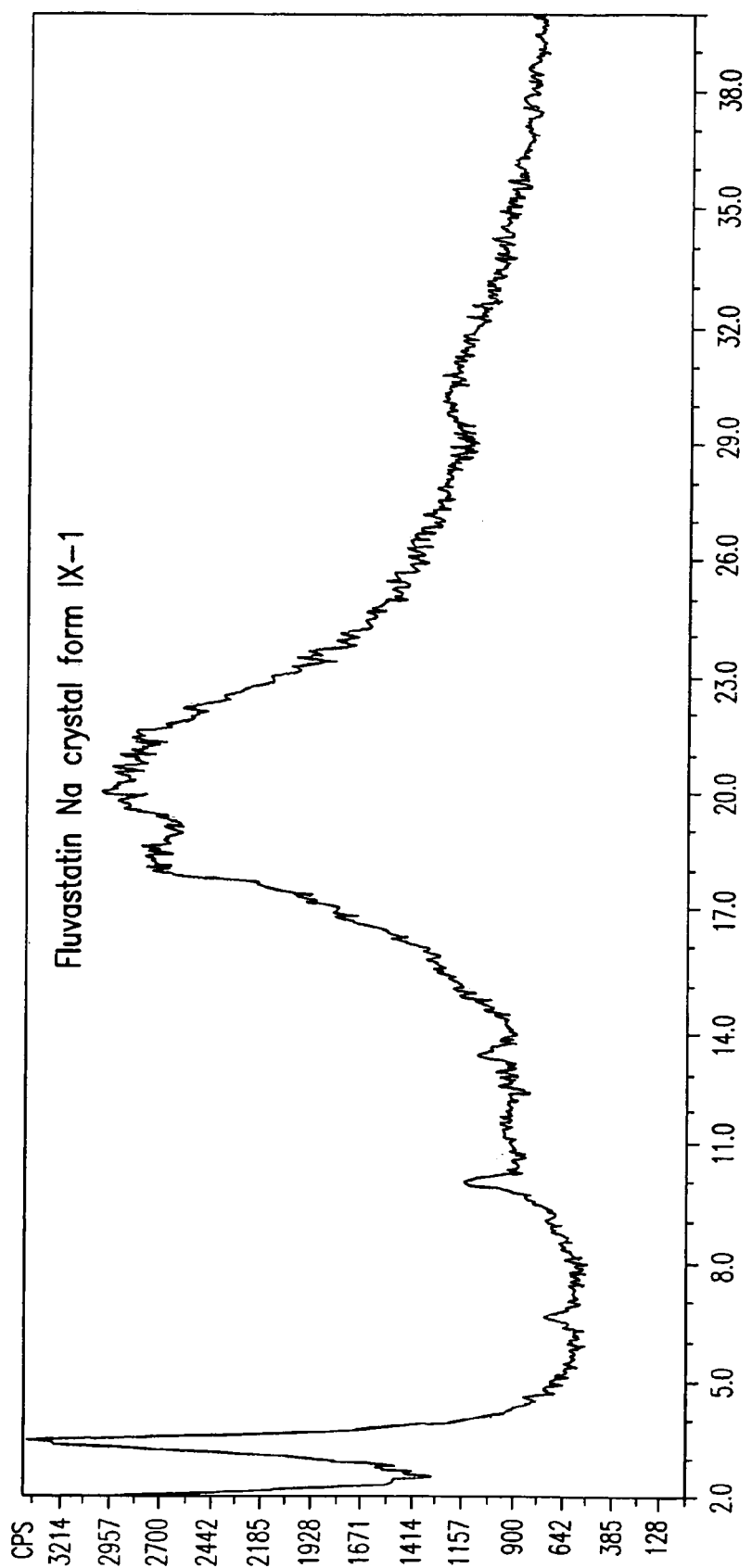
FIG. 18 depicts a powder X-ray diffractogram of fluvastatin sodium Form IX-1.

61. The crystalline form of embodiment 60 wherein the crystalline form is characterized by a PXRD pattern substantially as depicted in FIG. 18.

Figure 19:
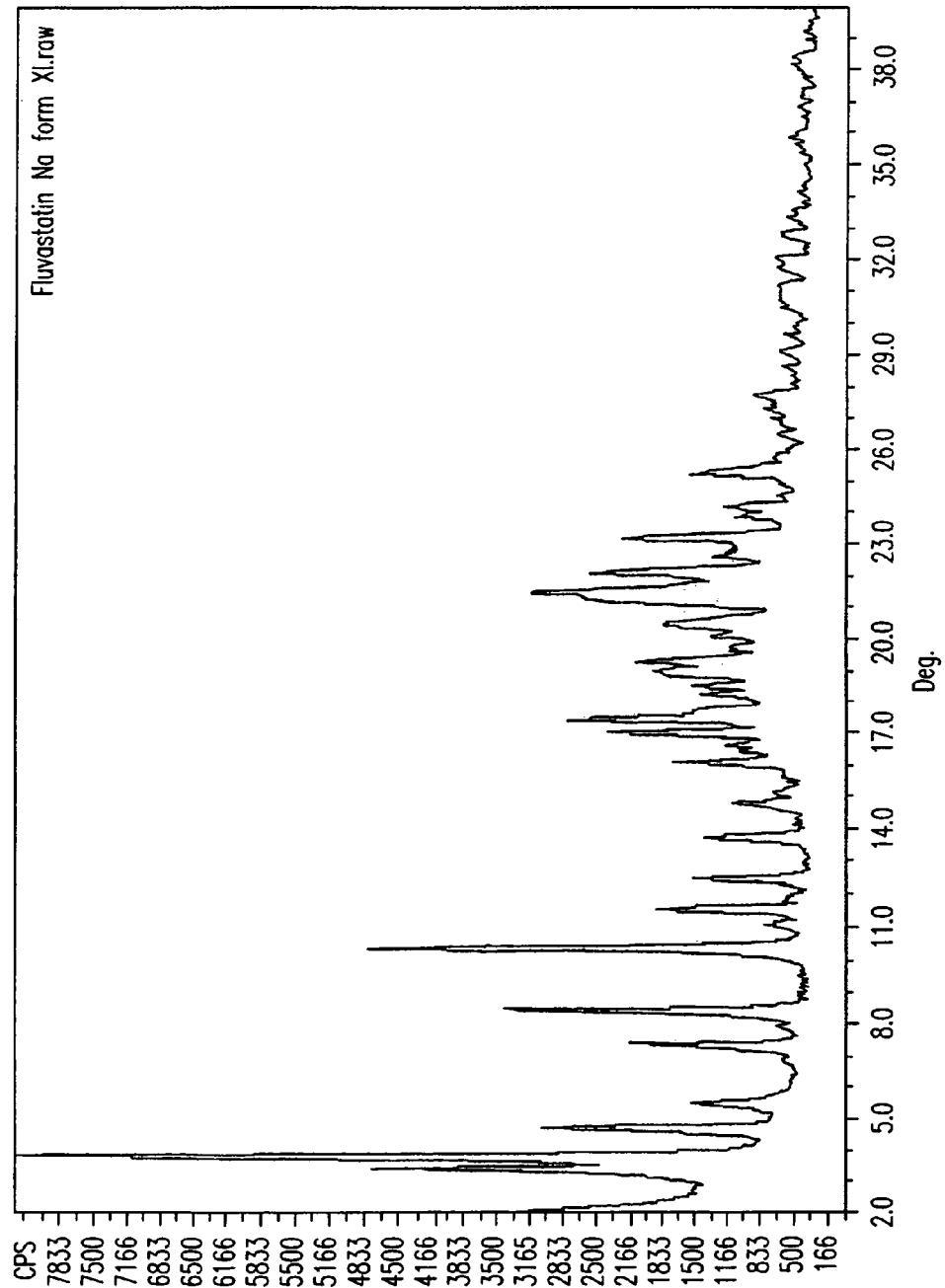
FIG. 19 depicts a powder X-ray diffractogram of fluvastatin sodium Form XI.
Figure 22:
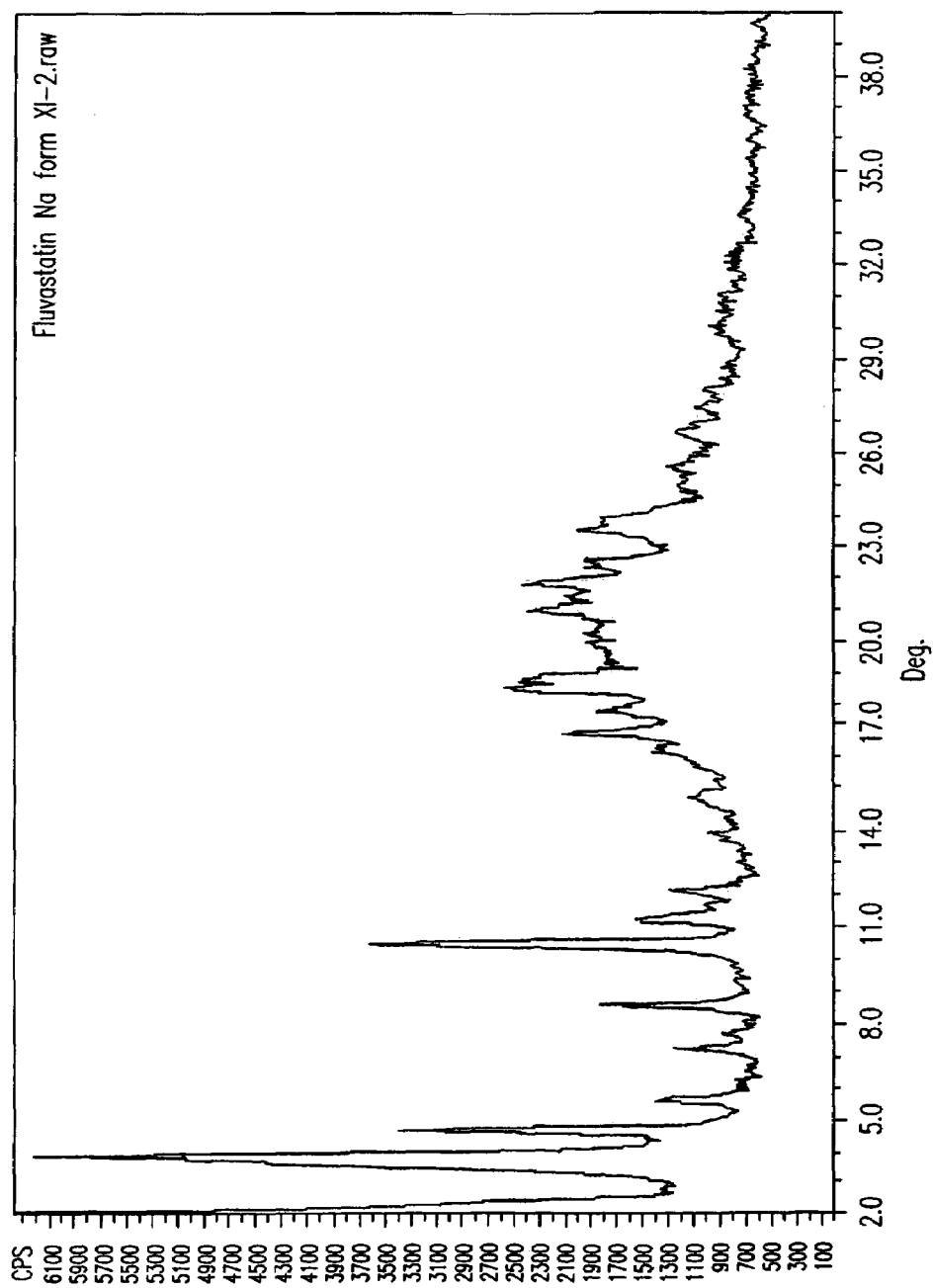
FIG. 22 depicts a powder X-ray diffractogram of fluvastatin sodium Form XI-2.
Figure 25:
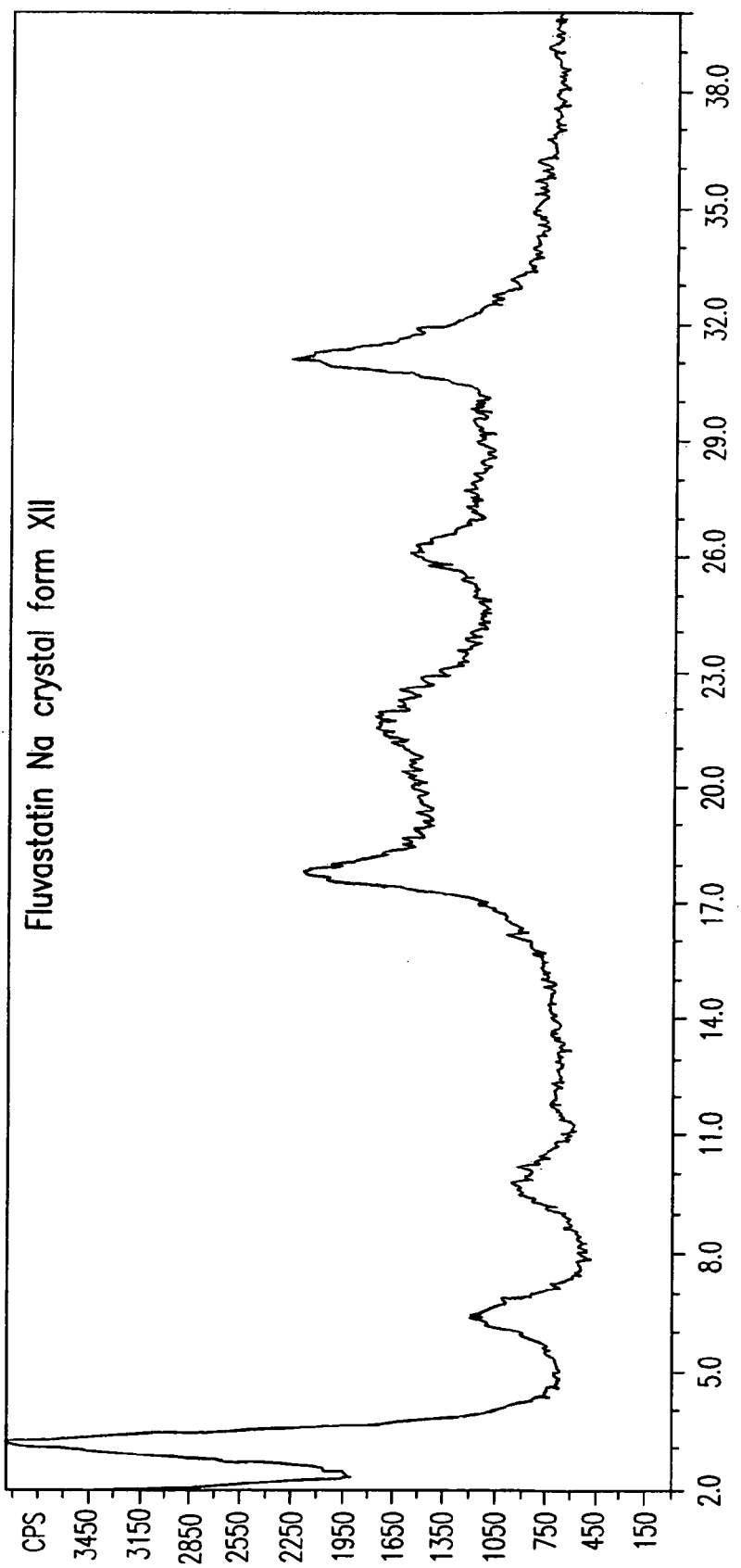
FIG. 25 depicts a powder X-ray diffractogram of fluvastatin sodium Form XII.
Figure 26:
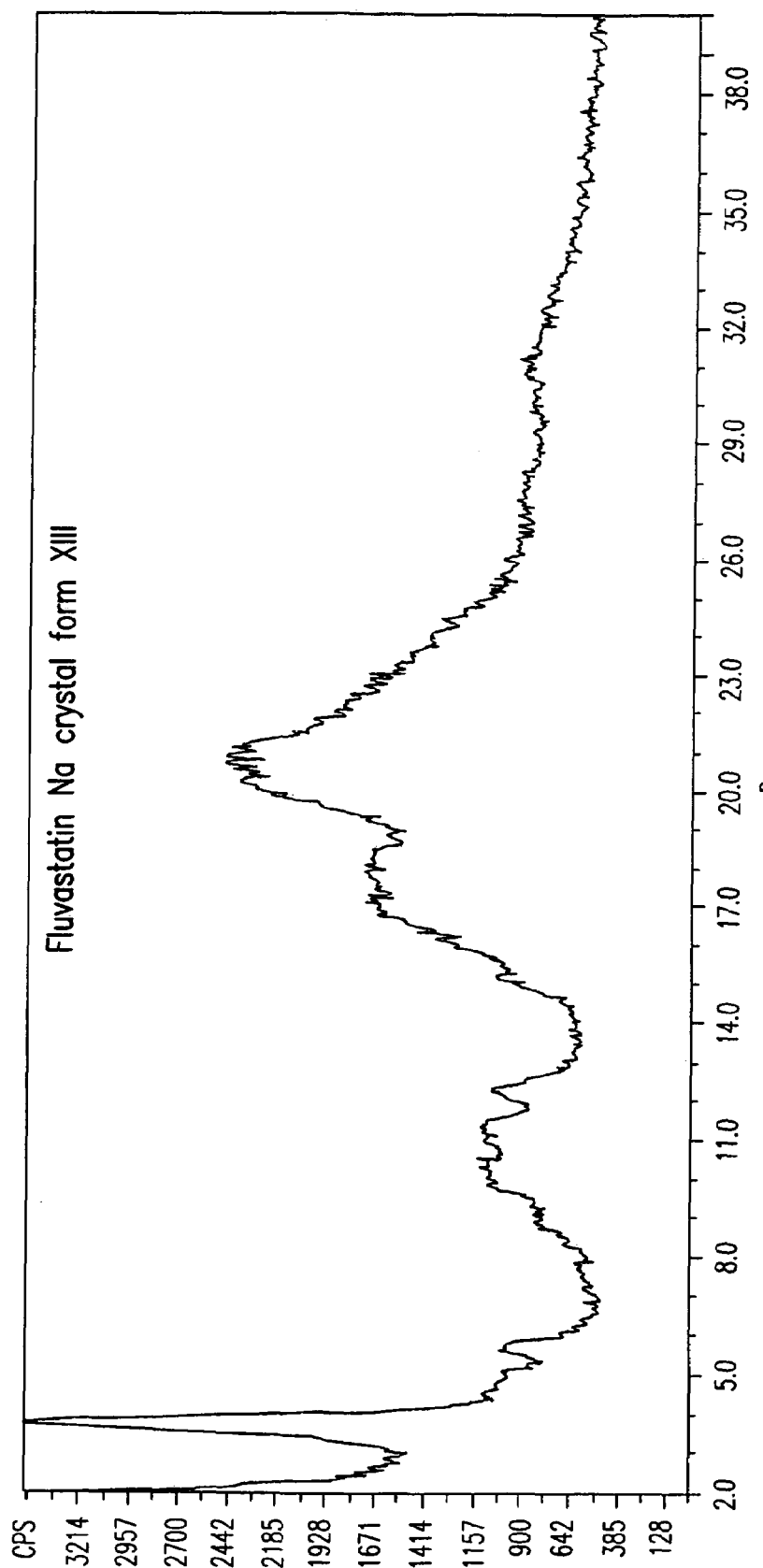
FIG. 26 depicts a powder X-ray diffractogram of fluvastatin sodium Form XIII.
Figure 27:
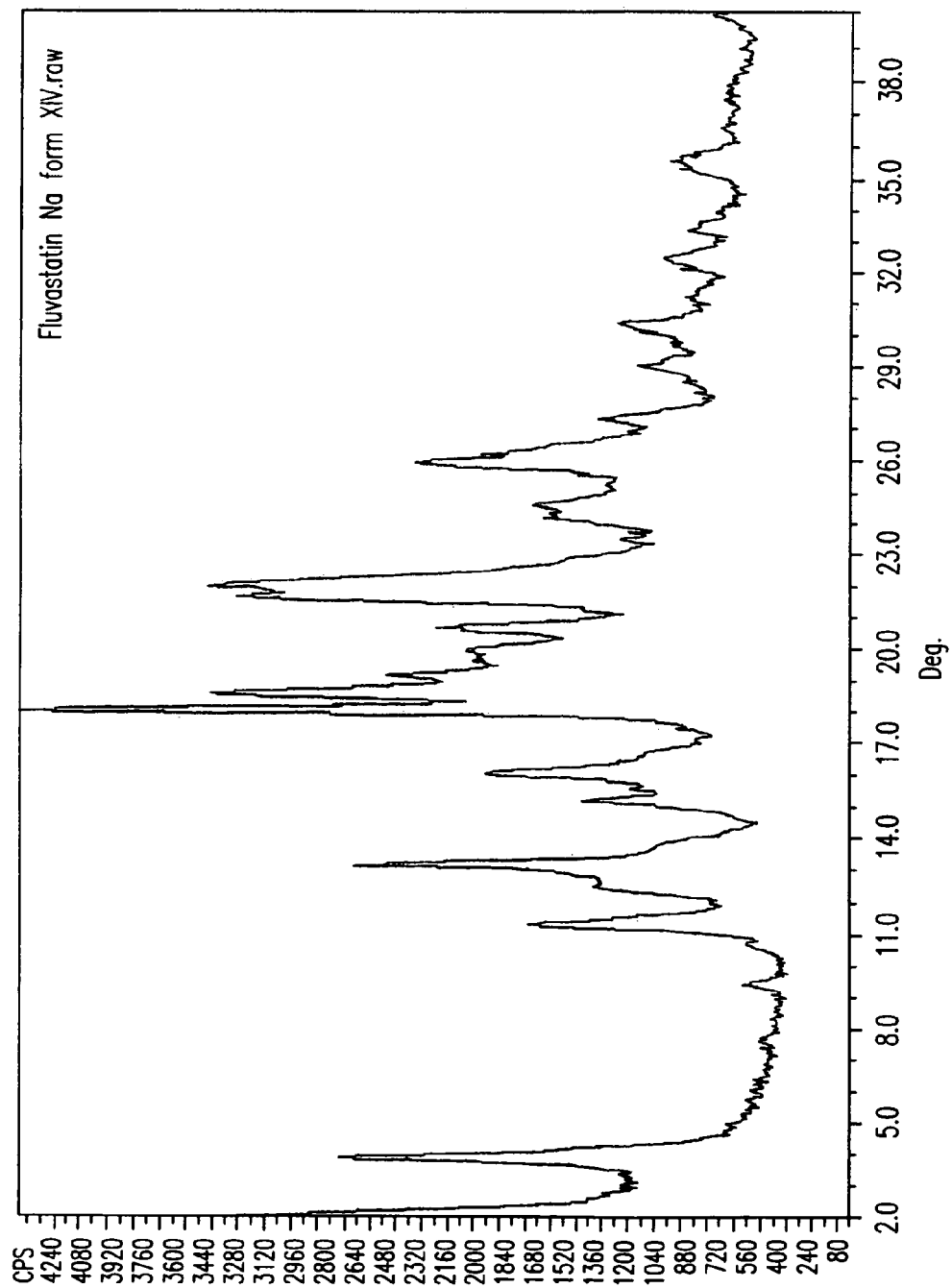
FIG. 27 depicts a powder X-ray diffractogram of fluvastatin sodium Form XIV.
Figure 28:
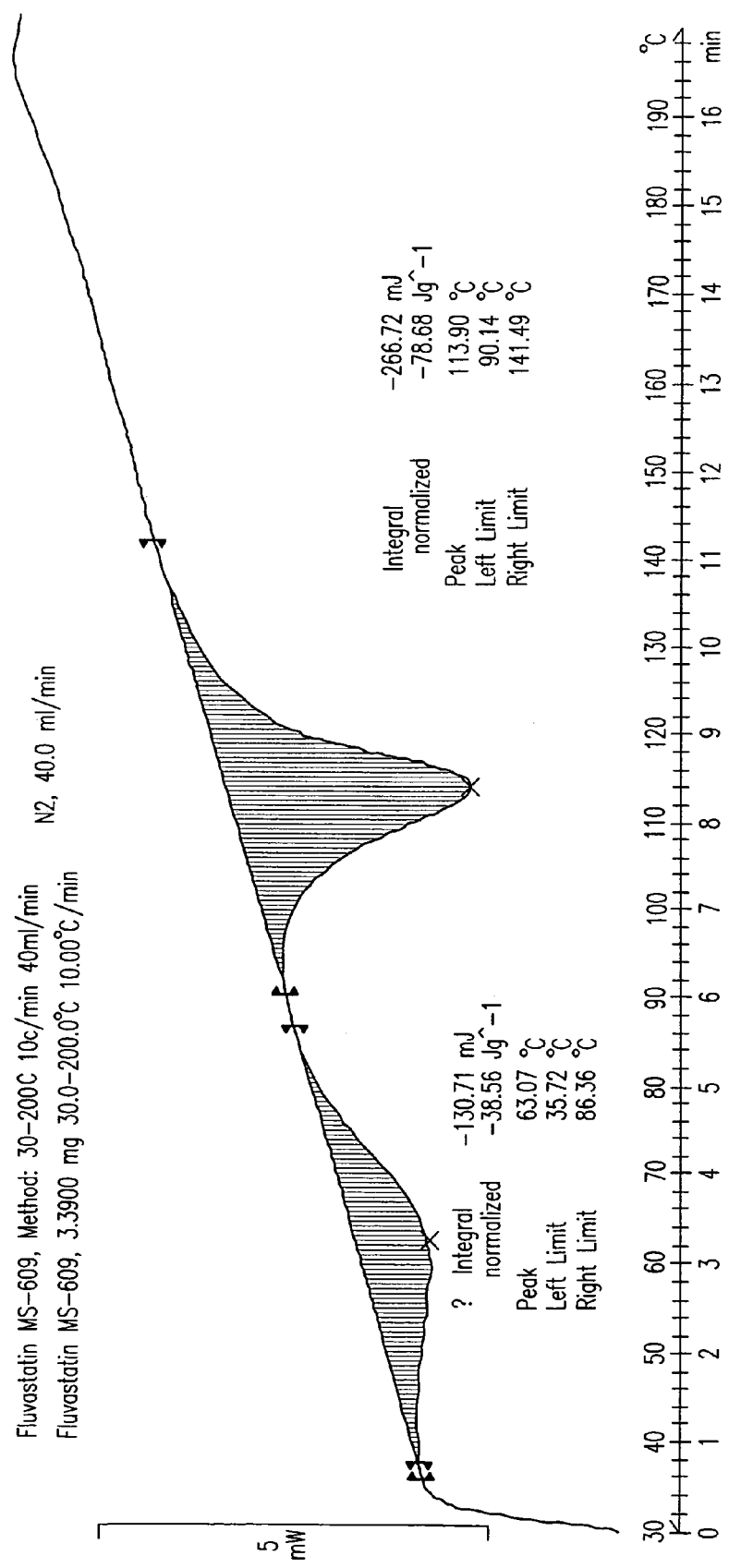
FIG. 28 depicts a DSC thermogram of fluvastatin sodium Form XIV.
Figure 29:
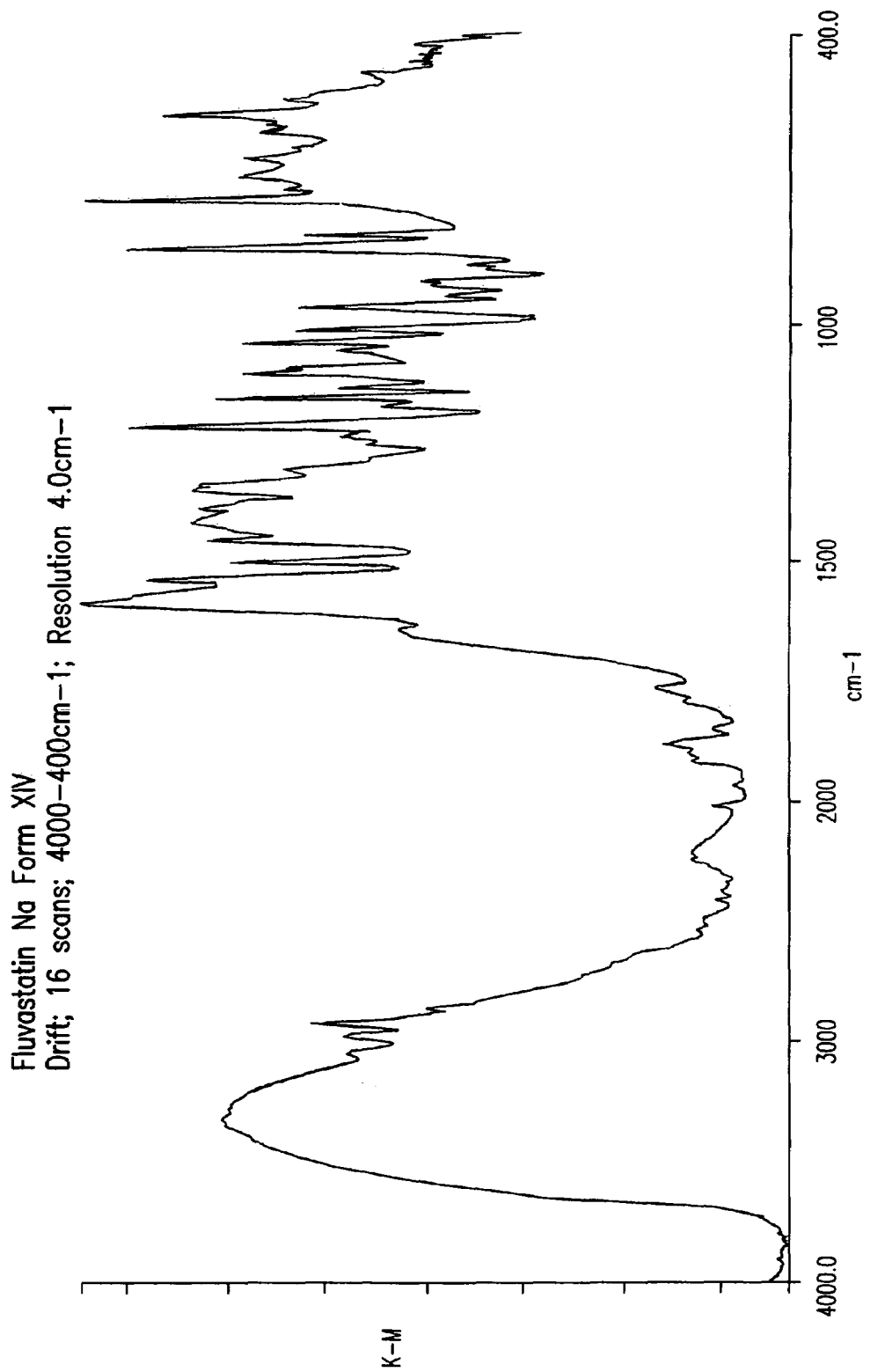
FIG. 29 depicts an IR spectrum of fluvastatin sodium Form XIV scanned from 4000 to 400 cm$^{-1}$, while FIG. 29a expands the 4000-1500 cm$^{-1}$ region of the spectrum and FIG. 29b expands the 1500-400 cm$^{-1}$ region of the spectrum.
Figure 29A:
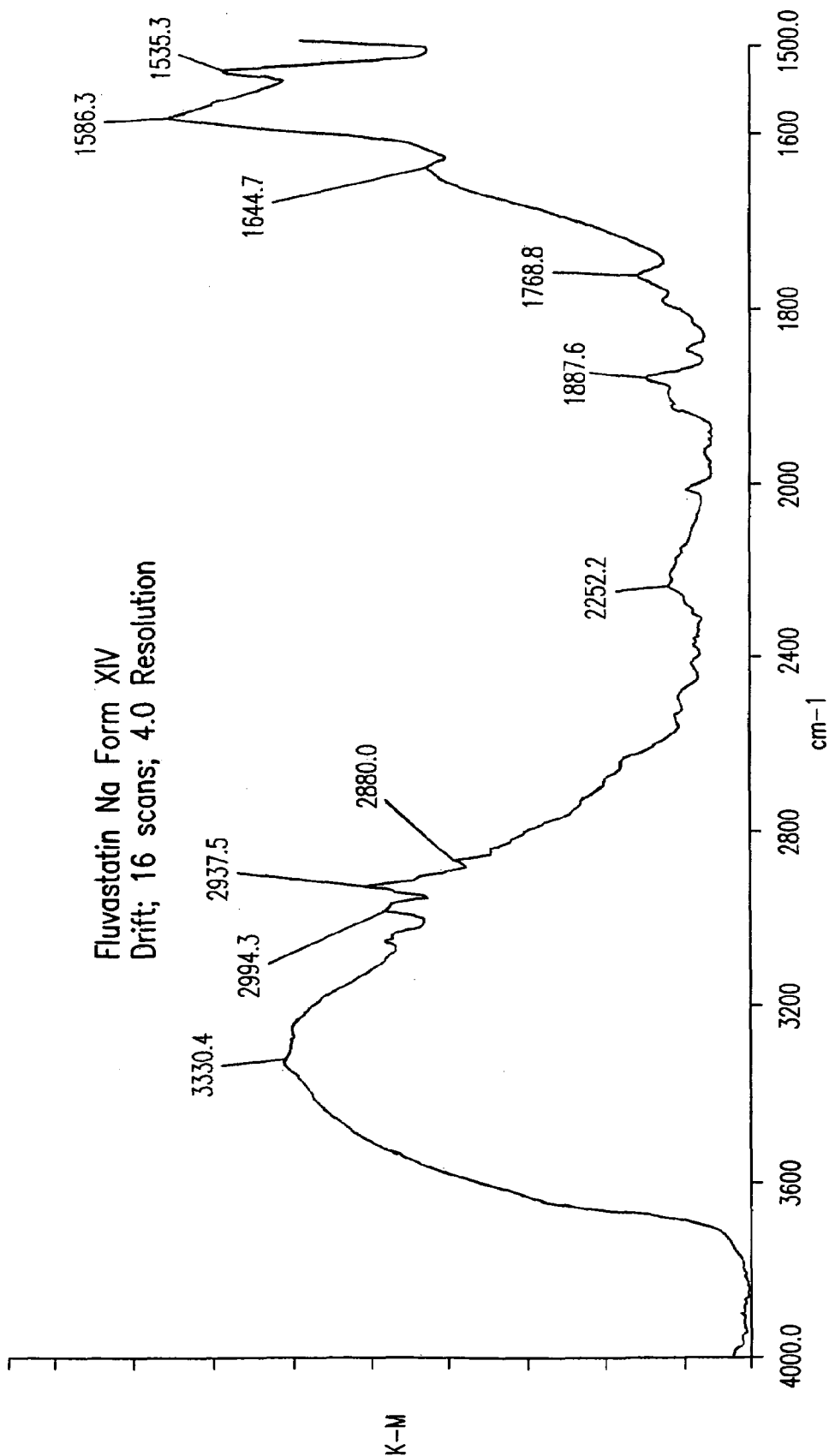
Figure 29B:
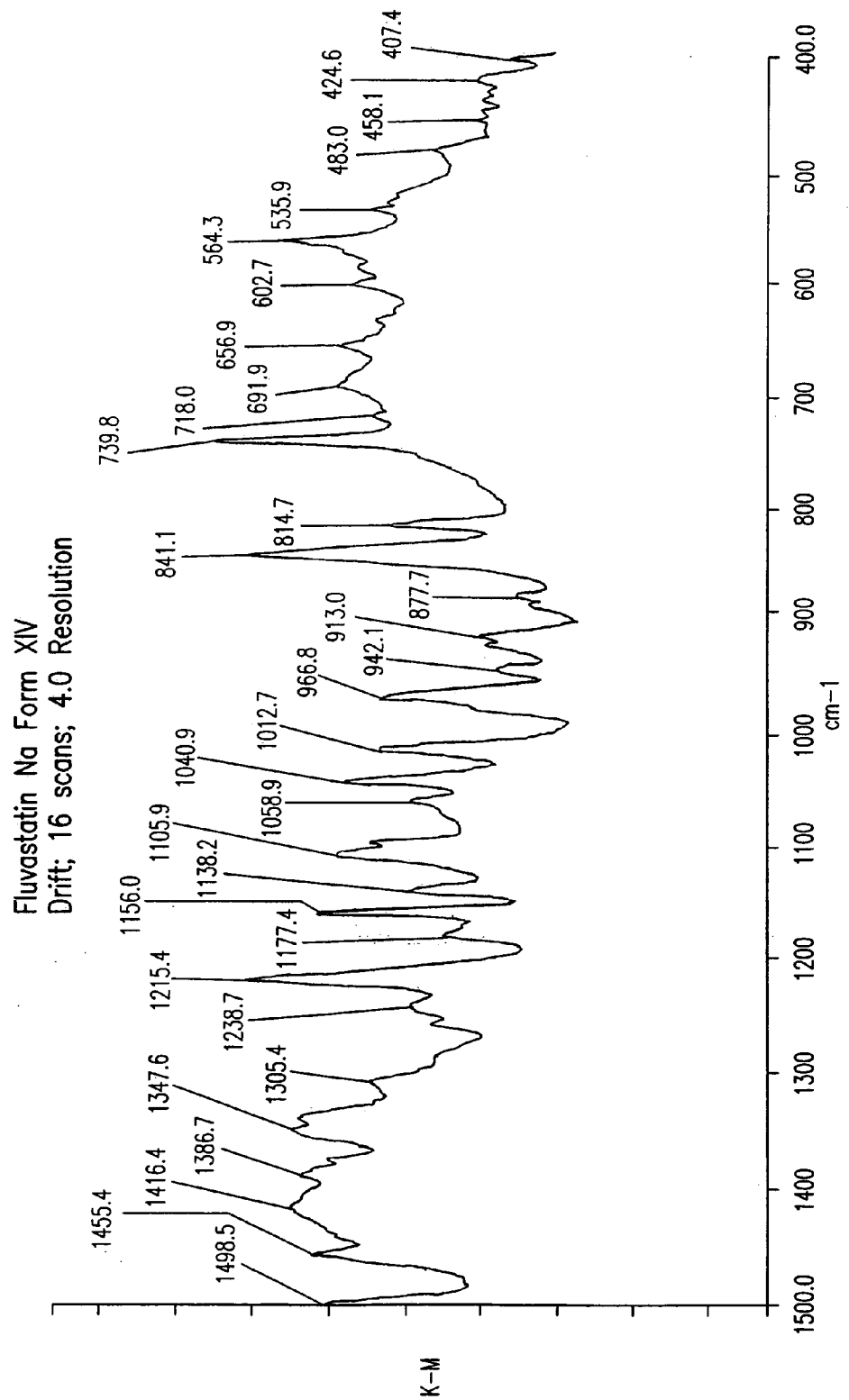
Figure 31:
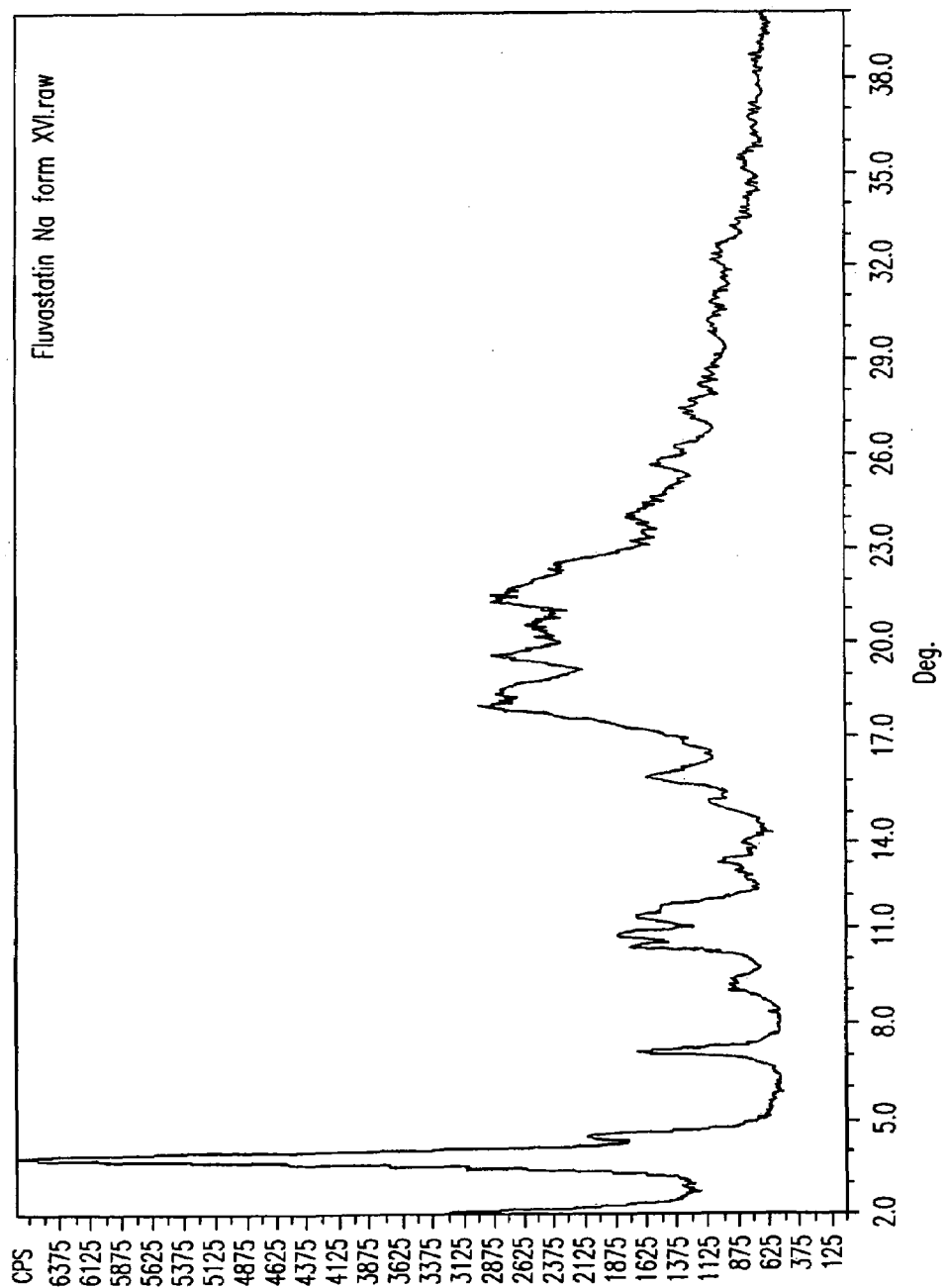
FIG. 31 depicts a powder X-ray diffractogram of fluvastatin sodium Form XVI.

62. The crystalline form of embodiment 60 wherein the crystalline form is fluvastatin sodium Form IX-1.
63. A process for preparing crystalline fluvastatin sodium Form IX-1 comprising:
   a) dissolving fluvastatin sodium in a solvent selected from the group consisting of butan-1-ol, ethyl acetate, isobutyl acetate, ethanol, toluene, tetrahydrofuran and methyl ethyl ketone,
   b) inducing precipitation of Form IX-1 by adding of an anti-solvent selected from the group consisting of n-pentane, diethyl ether, methyl tert-butyl ether, dichloromethane, hexanes and cyclohexane to the solvent, and
   c) separating the solvent and anti-solvent from the Form IX-1.
64. A crystalline form of fluvastatin sodium characterized by a PXRD pattern with peaks at 3.3, 3.8, 4.6, 8.3, 10.2 and 25.1±0.2 degrees two-theta.
65. The crystalline form of embodiment 64 further characterized by peaks at 7.2, 11.4, 12.4, 13.6, 16.0, 16.9, 17.4, 20.4, 21.3, 21.9 and 23.1±0.2 degrees two-theta.
66. The crystalline form of embodiment 65 further characterized by a PXRD pattern substantially as depicted in FIG. 19.
67. The crystalline form of embodiment 64 wherein the crystalline form is fluvastatin sodium Form XI.
68. A process for preparing fluvastatin sodium Form XI comprising the steps of:
   a) dissolving fluvastatin sodium in butan-2-ol to form a solution,
   b) refluxing the solution by heating the butan-2-ol, the heating being commenced either before or after dissolving the fluvastatin sodium,
   c) precipitating fluvastatin sodium Form XI from the solution, and
   d) separating the fluvastatin sodium Form XI from the butan-2-ol.
69. The process of embodiment 68 wherein precipitating is induced by adding an organic anti-solvent to the solution.
70. The process of embodiment 68 wherein the organic anti-solvent is selected from the group consisting of hexanes, n-pentane, methyl t-butyl ether, diethyl ether and chloroform.
71. Fluvastatin sodium Form XI having a water content of from about 1 to about 6 weight percent.
72. A crystalline form of fluvastatin sodium characterized by a PXRD pattern with peaks at 3.5, 3.8, 4.6, 10.4 and 18.5±0.2 degrees two-theta.
73. The crystalline form of embodiment 72 further characterized by peaks at 8.5, 11.2, 12.1, 16.4, 17.0, 17.7, 20.9, 21.2, 21.7, 22.2 and 23.6±0.2 degrees two-theta.
74. The crystalline form of embodiment 73 further characterized by a PXRD pattern substantially as depicted in FIG. 22.
75. The crystalline form of embodiment 72 wherein the crystalline form is fluvastatin sodium Form XI-2.
76. A process for preparing fluvastatin sodium Form XI-2 comprising the steps of:
   a) dissolving fluvastatin sodium in propan-1-ol to form a solution,
   b) refluxing the solution by heating the propan-1-ol, the heating being commenced either before or after dissolving the fluvastatin,
   c) adding an organic anti-solvent to the refluxing solution to induce precipitation of fluvastatin sodium Form XI-2, and
   d) and separating the fluvastatin sodium Form XI-2 from the propan-1-ol and anti-solvent.
77. The process of embodiment 76 wherein the anti-solvent is selected from the group consisting of hexanes, MTBE, and dichloromethane.
78. Fluvastatin sodium Form XI-2 having a water content of from about 2 to about 3%.
79. A crystalline form of fluvastatin sodium characterized by a PXRD pattern with peaks at 3.1, 6.5, 9.8, 17.6, 25.9 and 30.9±0.2 degrees two-theta.
80. The crystalline form of embodiment 79 wherein the crystalline form is characterized by a PXRD pattern substantially as depicted in FIG. 25.
81. The crystalline form of embodiment 79 wherein the crystalline form is fluvastatin sodium Form XII.
82. A process for preparing crystalline fluvastatin sodium Form XII comprising:
   a) dissolving fluvastatin sodium in butan-1-ol,
   b) inducing precipitation of Form XII by adding 1,4-dioxane to the butan-1-ol, and
   c) separating the 1,4-dioxane and butan-1-ol from the Form XII.
83. A crystalline form of fluvastatin sodium characterized by a PXRD pattern with peaks at 3.8, 5.6, 12.3 and 20.6±0.2 degrees two-theta.
84. The crystalline form of embodiment 83 wherein the crystalline form is characterized by a PXRD pattern substantially as depicted in FIG. 26.
85. The crystalline form of embodiment 83 wherein the crystalline form is fluvastatin sodium Form XIII.
86. A process for preparing crystalline fluvastatin sodium Form XIII comprising:
   a) suspending fluvastatin sodium Form B in acetonitrile at elevated temperature,
   b) cooling the suspension to induce precipitation of Form XIII, and
   c) separating the acetonitrile from the Form XIII.
87. A crystalline form of fluvastatin sodium characterized by a PXRD pattern with peaks at 3.8 and 7.0±0.2 degrees two-theta.
88. The crystalline form of embodiment 87 further characterized by peaks at 4.3, 10.2, 10.7, 11.2, 15.6, 17.8, 18.4 and 19.5±0.2 degrees two-theta.
89. The crystalline form of embodiment 88 further characterized by a PXRD pattern substantially as depicted in FIG. 31.
90. The crystalline form of embodiment 87 wherein the crystalline form is fluvastatin sodium Form XVI.
91. A process for preparing fluvastatin sodium Form XVI of any of embodiments—comprising the steps of:
   a) dissolving fluvastatin sodium in propan-2-ol to form a solution
   b) refluxing the solution by heating the propan-2-ol, the heating being commenced either before or after dissolving the fluvastatin sodium,
   c) adding dichloromethane to the refluxing solution to precipitate fluvastatin Form XVI, and
   d) separating the fluvastatin sodium Form XVI from the propan-2-ol.
92. Fluvastatin sodium Form XVI having a water content of from about 3 to about 4 weight percent.
93. A crystalline form of fluvastatin sodium characterized by a PXRD pattern with peaks at 3.5 (broad), 5.4, 5.8 and 13.8±0.2 degrees two-theta.
94. The crystalline form of embodiment 93 further characterized by peaks at 10.8, 14.8, 16.4, 19.4, 21.5 and 22.7±0.2 degrees two-theta.

Figure 34:
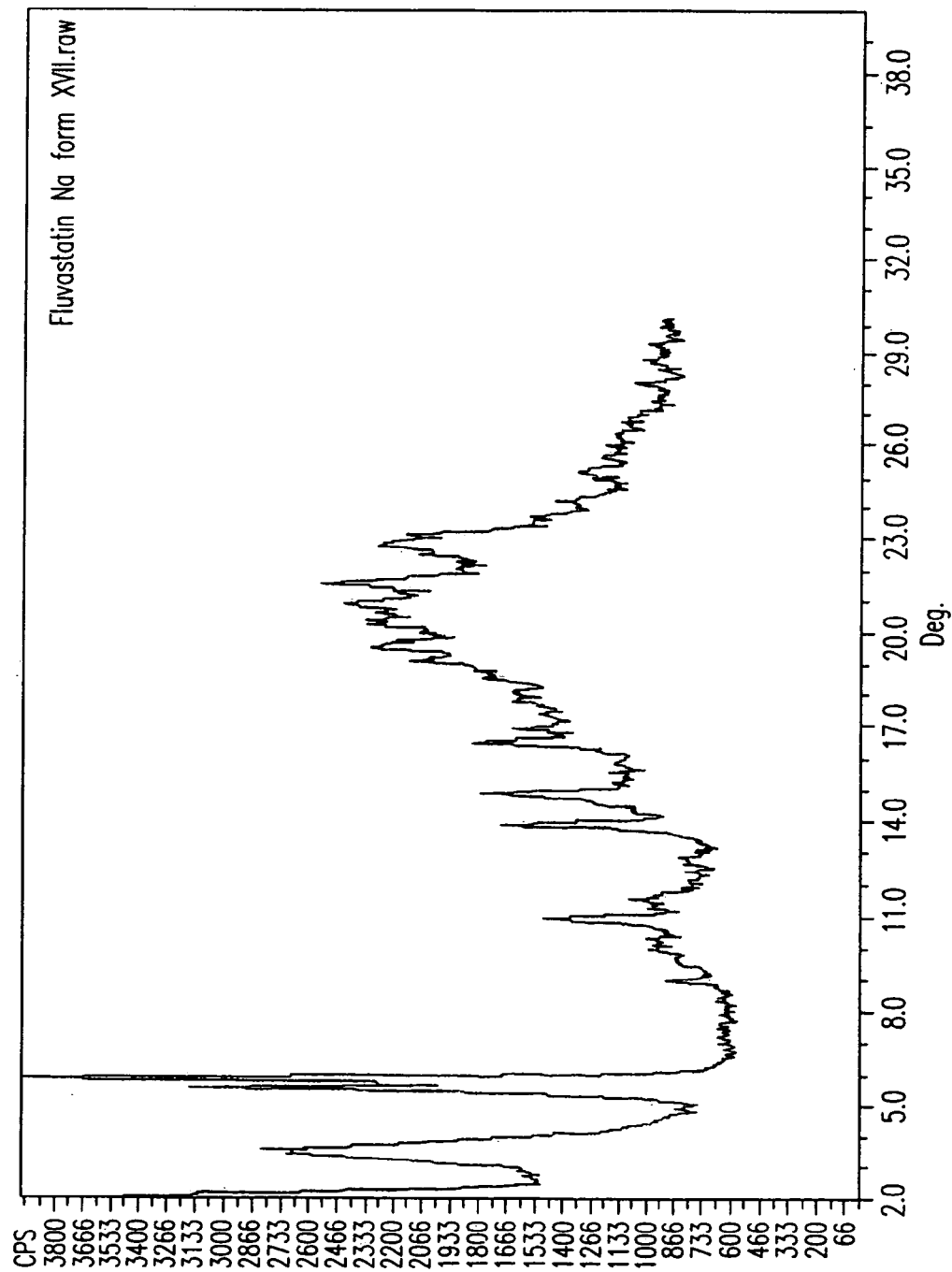
FIG. 34 depicts a powder X-ray diffractogram of fluvastatin sodium Form XVII.

95. The crystalline form of embodiment 94 further characterized by a PXRD pattern substantially as depicted in FIG. 34.

96. The crystalline form of embodiment 93 wherein the crystalline form is fluvastatin sodium Form XVII.

97. A process for preparing the fluvastatin sodium Form XVII of any of embodiments—comprising the steps of:
  a) dissolving fluvastatin sodium in propan-1-ol at elevated temperature,
  b) crystallizing fluvastatin sodium from the propan-1-ol at elevated temperature, and
  c) separating the fluvastatin sodium Form XVII from the propan-1-ol.

98. A crystalline form of fluvastatin sodium characterized by a PXRD pattern with peaks at 3.4, 8.4, 10.0 and 10.9±0.2 degrees two-theta.

99. The crystalline form of embodiment 98 further characterized by peaks at 11.7, 12.6, 15.8, 17.4, 18.0, 18.8, 20.0, 20.7 and 21.3±0.2 degrees two-theta.

Figure 36:
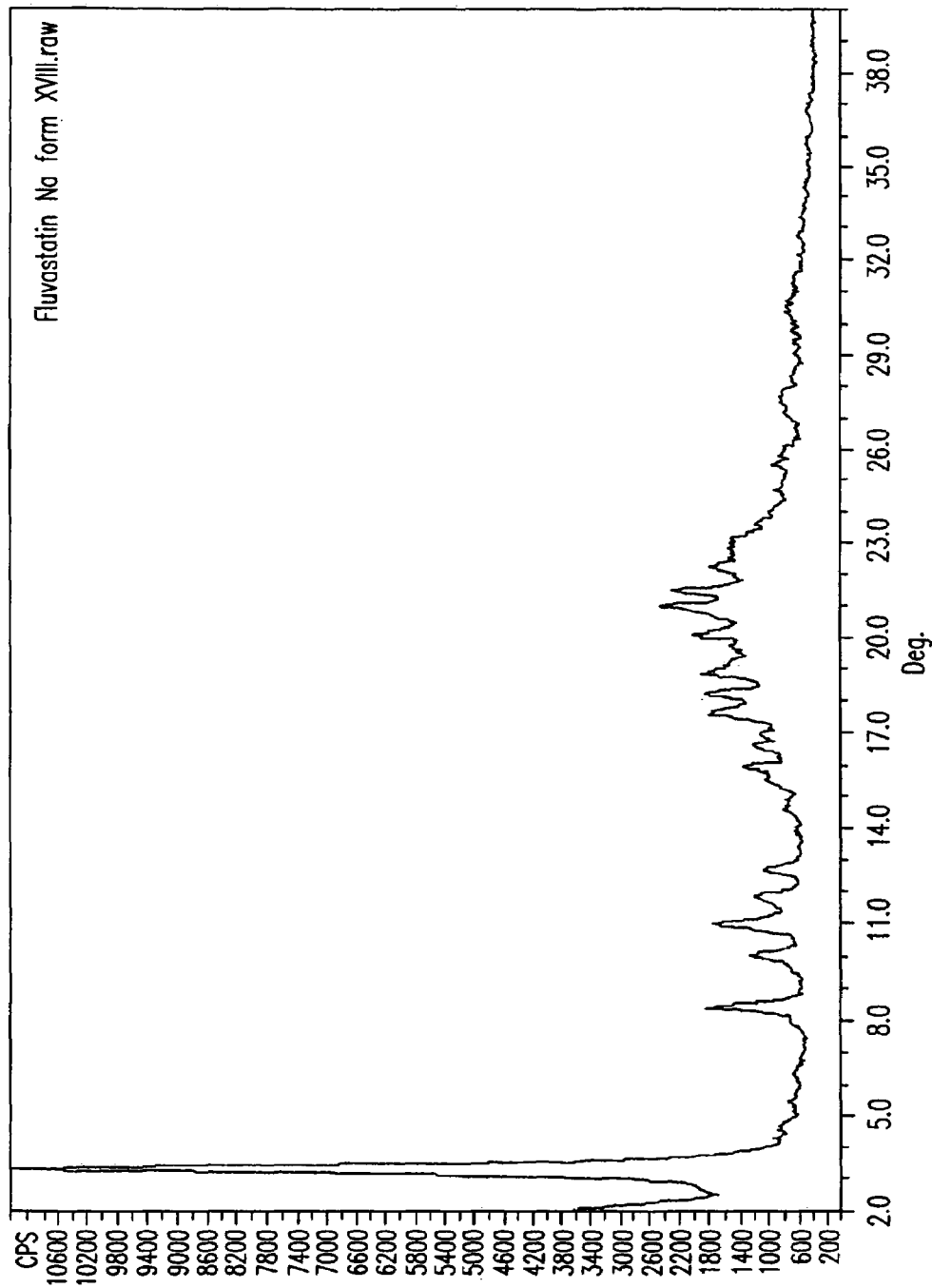
FIG. 36 depicts a powder X-ray diffractogram of fluvastatin sodium Form XVIII.

100. The crystalline form of embodiment 99 further characterized by a PXRD pattern substantially as depicted in FIG. 36.

101. The crystalline form of embodiment 98 wherein the crystalline form is fluvastatin sodium Form XVIII.

102. A process for preparing fluvastatin sodium Form XVIII comprising the steps of:
  a) forming a slurry of fluvastatin sodium in methylethylketone,
  b) refluxing the slurry for a period of time sufficient to substantially convert fluvastatin sodium to fluvastatin sodium Form XVIII, and
  c) separating the fluvastatin sodium Form XVIII from the slurry.

103. Fluvastatin sodium Form XVIII having a water content of about 4 weight percent.

104. A crystalline form of fluvastatin sodium characterized by a PXRD pattern with peaks at 3.4, 10.1, 13.5 and 18.0±0.2 degrees two-theta.

105. The crystalline form of embodiment 104 further characterized by peaks at 6.8, 20.1, 21.8 and 25.6±0.2 degrees two-theta.

Figure 39:
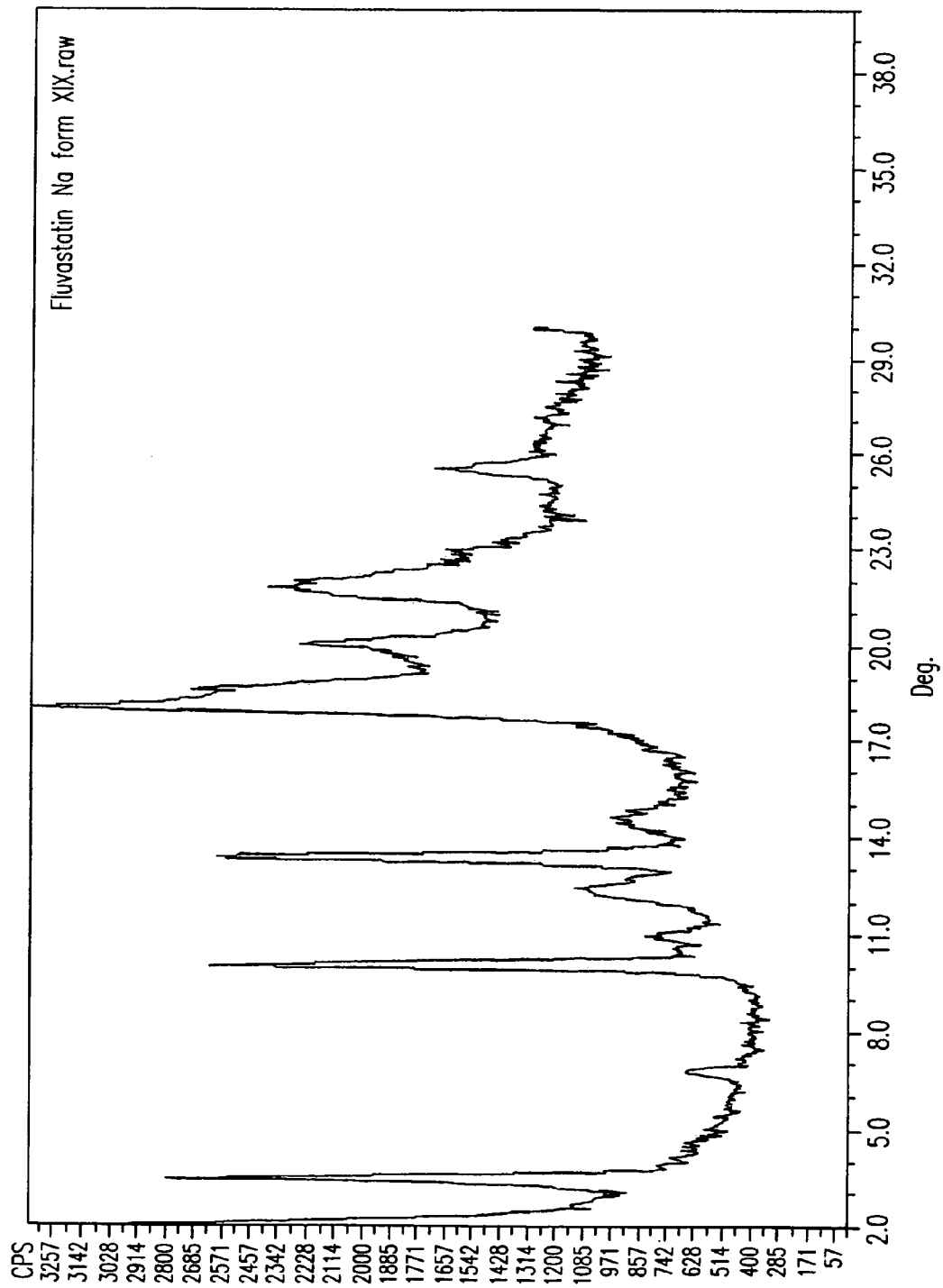
FIG. 39 depicts a powder X-ray diffractogram of fluvastatin sodium Form XIX.

106. The crystalline form of embodiment 105 further characterized by a PXRD pattern substantially as depicted in FIG. 39.

107. The crystalline form of embodiment 104 wherein the crystalline form is fluvastatin sodium Form XIX.

108. A process for preparing fluvastatin sodium Form XIX comprising the steps of:
  a) maintaining a crystalline form of fluvastatin sodium selected from the group consisting of Form XI, Form IV-1 and Form XVI under conditions of 60% relative humidity or higher for a period of time sufficient to effect conversion to fluvastatin sodium Form XIX, and
  b) removing the fluvastatin sodium Form XIX from the conditions of 60% relative humidity or higher.

109. Fluvastatin sodium Form XIX having a water content of from about 19 to about 28 weight percent.

110. A crystalline form of fluvastatin sodium characterized by a PXRD pattern with peaks at 3.5, 10.4, 11.9, 14.0, 22.5±0.2 degrees two-theta.

111. The crystalline form of embodiment 110 further characterized by peaks at 17.5, 17.8, 18.0, 18.3, 25.4±0.2 degrees two-theta.

Figure 42:
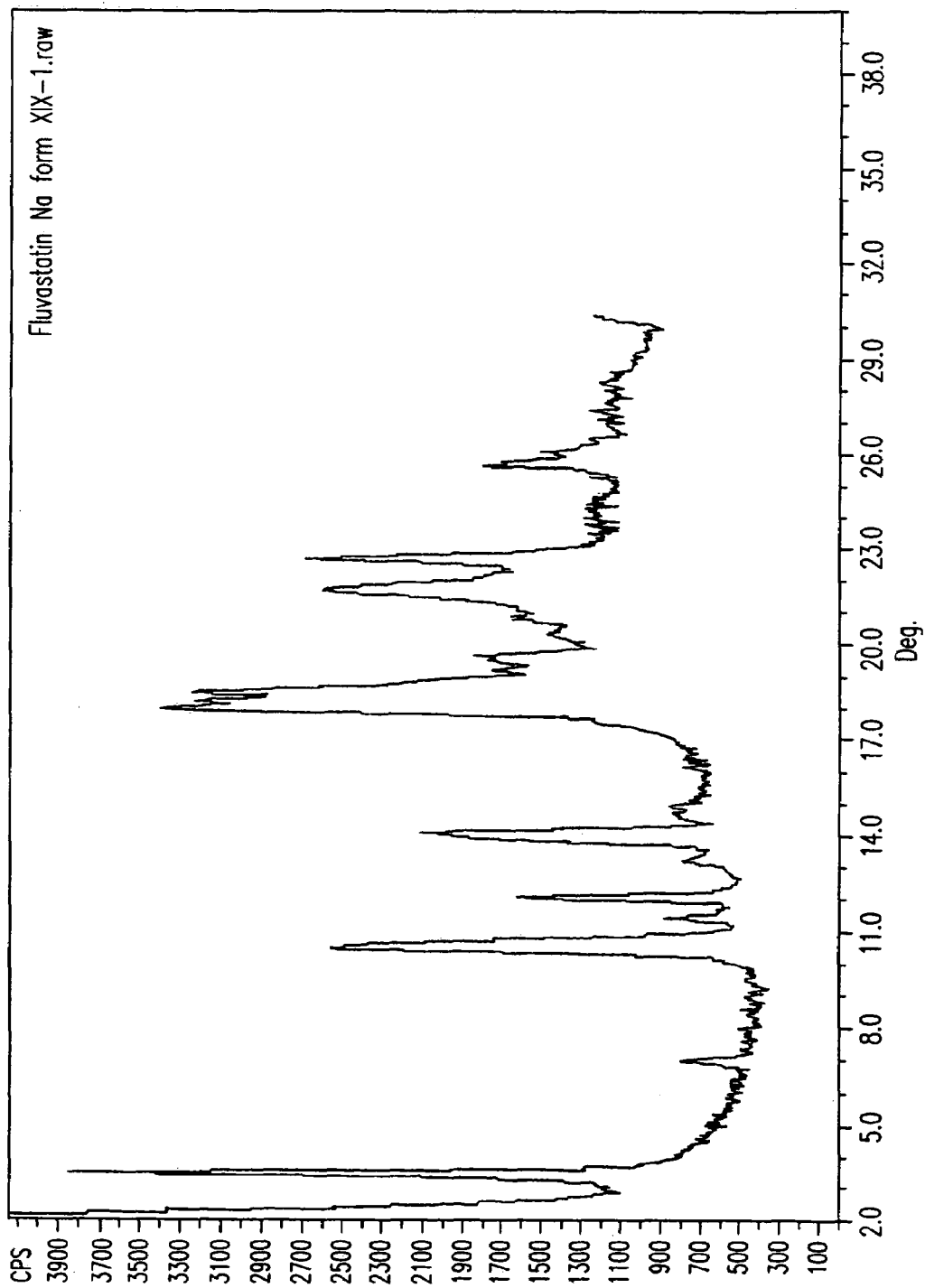
FIG. 42 depicts a powder X-ray diffractogram of fluvastatin sodium Form XIX-1.

112. The crystalline form of embodiment 111 further characterized by a PXRD pattern substantially as depicted in FIG. 42.

113. The crystalline form of embodiment 110 wherein the crystalline form is fluvastatin sodium Form XIX-1.

114. A process for preparing crystalline fluvastatin sodium Form XIX-1 comprising:
  a) forming a heterogeneous mixture of fluvastatin sodium Form XI and water
  b) maintaining the heterogeneous mixture to obtain Form XIX-1, and
  c) recovering fluvastatin sodium Form XIX-1 from the mixture.

115. A crystalline form of fluvastatin sodium characterized by a PXRD pattern with peaks at 3.5, 10.1, 13.5, 18.0 and 20.8±0.2 degrees two-theta 116. The crystalline form of embodiment 115 further characterized by peaks at 5.9 and 12.4±0.2 degrees two-theta.

Figure 43:
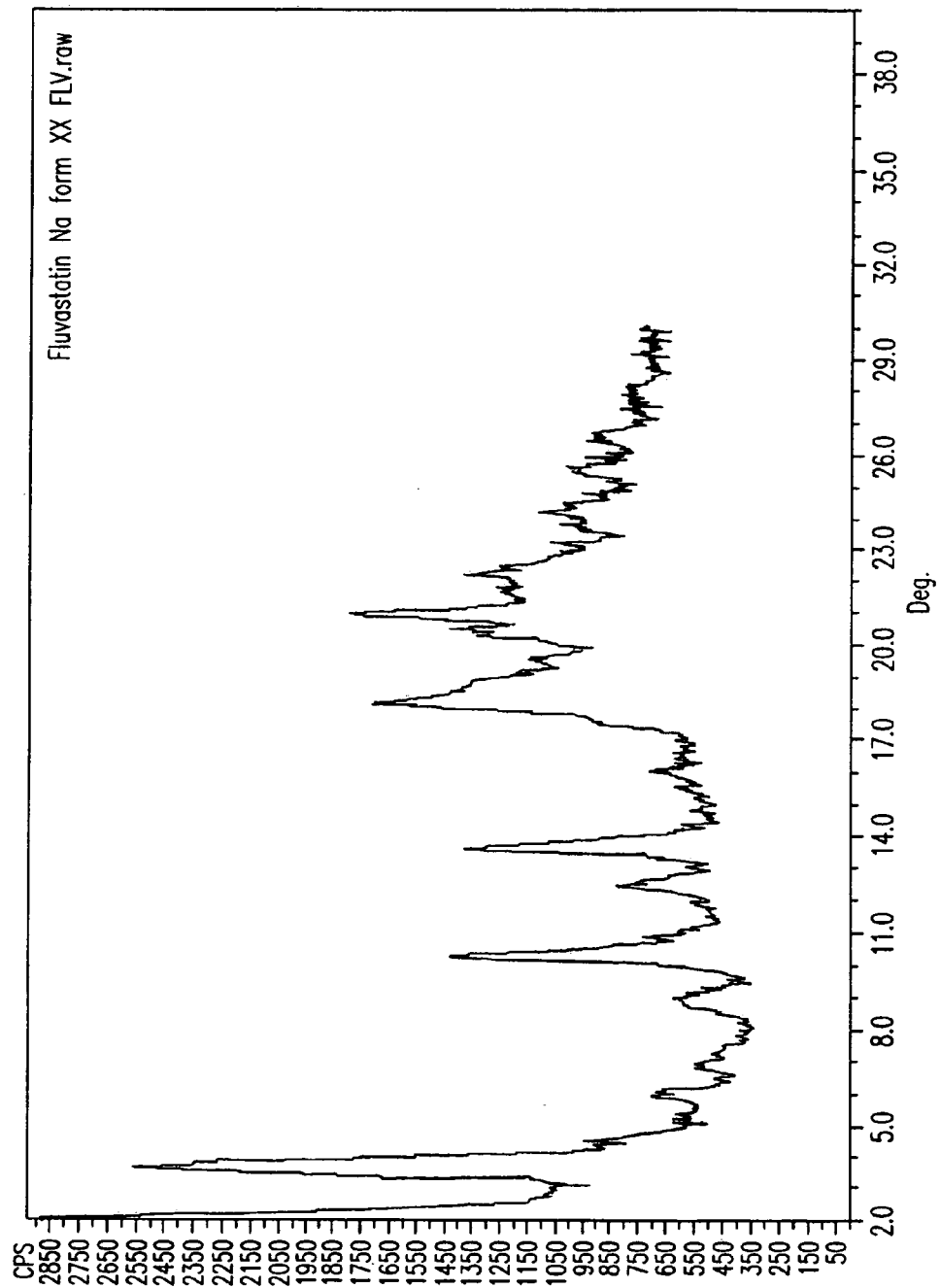
FIG. 43 depicts a powder X-ray diffractogram of fluvastatin sodium Form XX.

117. The crystalline form of embodiment 116 further characterized by a PXRD pattern substantially as depicted in FIG. 43.

118. The crystalline form of embodiment 115 wherein the crystalline form is fluvastatin sodium Form XX.

119. A process for preparing fluvastatin sodium Form XX comprising the steps of:
  a) maintaining fluvastatin sodium Form VII under conditions of 80% relative humidity for a period of time sufficient to effect conversion to fluvastatin sodium Form XX and
  b) removing the fluvastatin sodium Form XX from the conditions of 80% relative humidity.

120. Fluvastatin sodium Form XX having a water content of about 19 percent by weight.

121. A crystalline form of fluvastatin sodium characterized by a PXRD pattern with peaks at 3.2, 12.4, and 18.3±0.2 degrees two-theta.

122. The crystalline form of embodiment 121 further characterized by peaks at 6.4, 9.5, 15.6 and 21.4±0.2 degrees two-theta.

Figure 46:
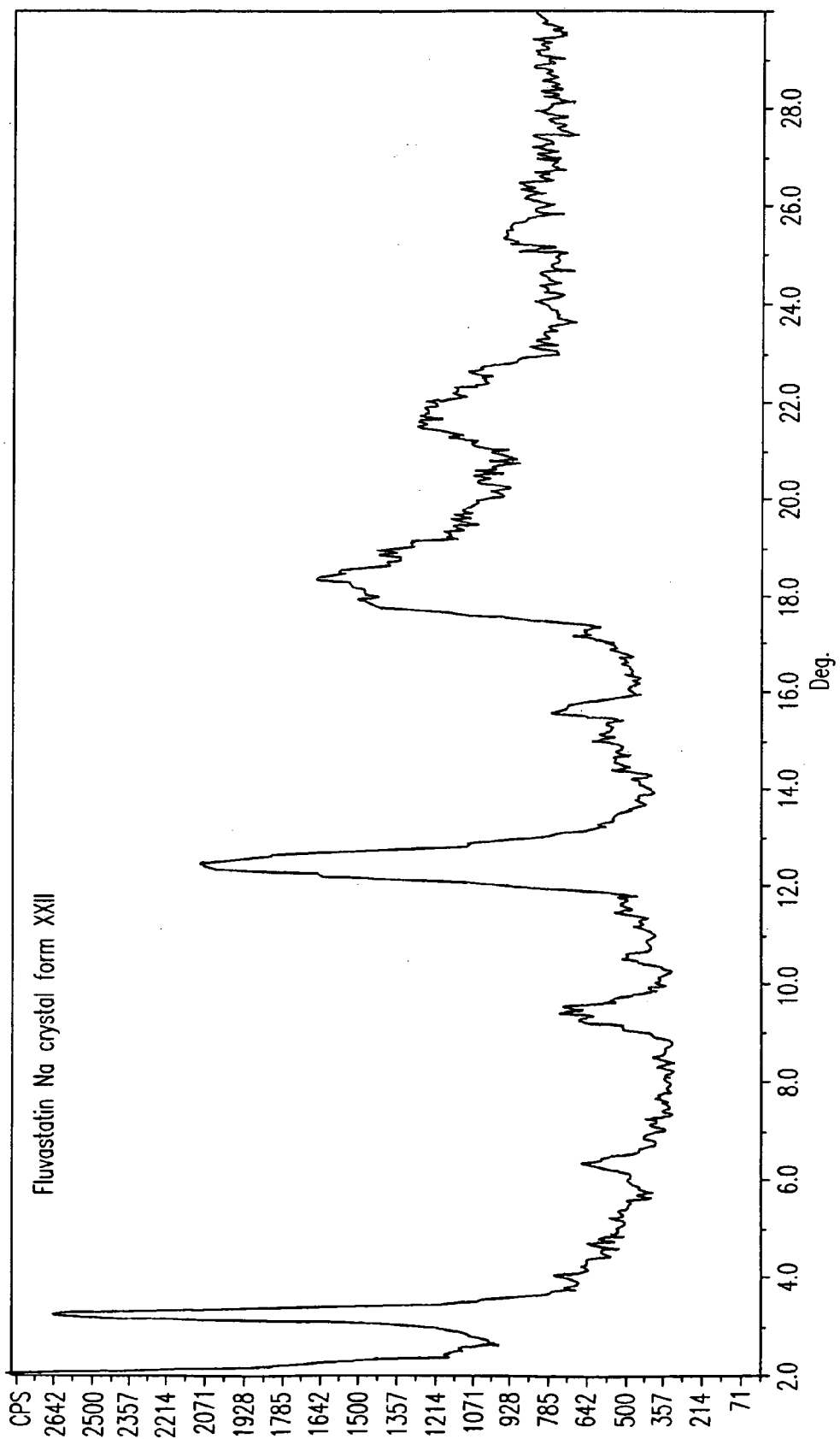
FIG. 46 depicts a powder X-ray diffractogram of fluvastatin sodium Form XXII.

123. The crystalline form of embodiment 122 wherein the crystalline form is characterized by a PXRD pattern substantially as depicted in FIG. 46.

124. The crystalline form of embodiment 121 wherein the crystalline form is fluvastatin sodium Form XXII.

125. A process for preparing crystalline fluvastatin sodium Form XXII comprising:
  a) contacting fluvastatin sodium Form XV with water vapor in a vessel containing an atmosphere of controlled elevated humidity relative to the atmosphere outside of the vessel for a period of time effective to convert the Form XV into Form XXII, and
  b) ceasing control of the humidity within the vessel or removing the Form XV from the vessel.

126. A crystalline form of fluvastatin sodium characterized by a PXRD pattern with peaks at 3.6, 4.0, 4.4, 17.1 and 19.3±0.2 degrees two-theta.

127. The crystalline form of embodiment 126 further characterized by peaks at 6.2, 7.2, 9.3, 10.2 and 18.6±0.2 degrees two-theta.

Figure 47:
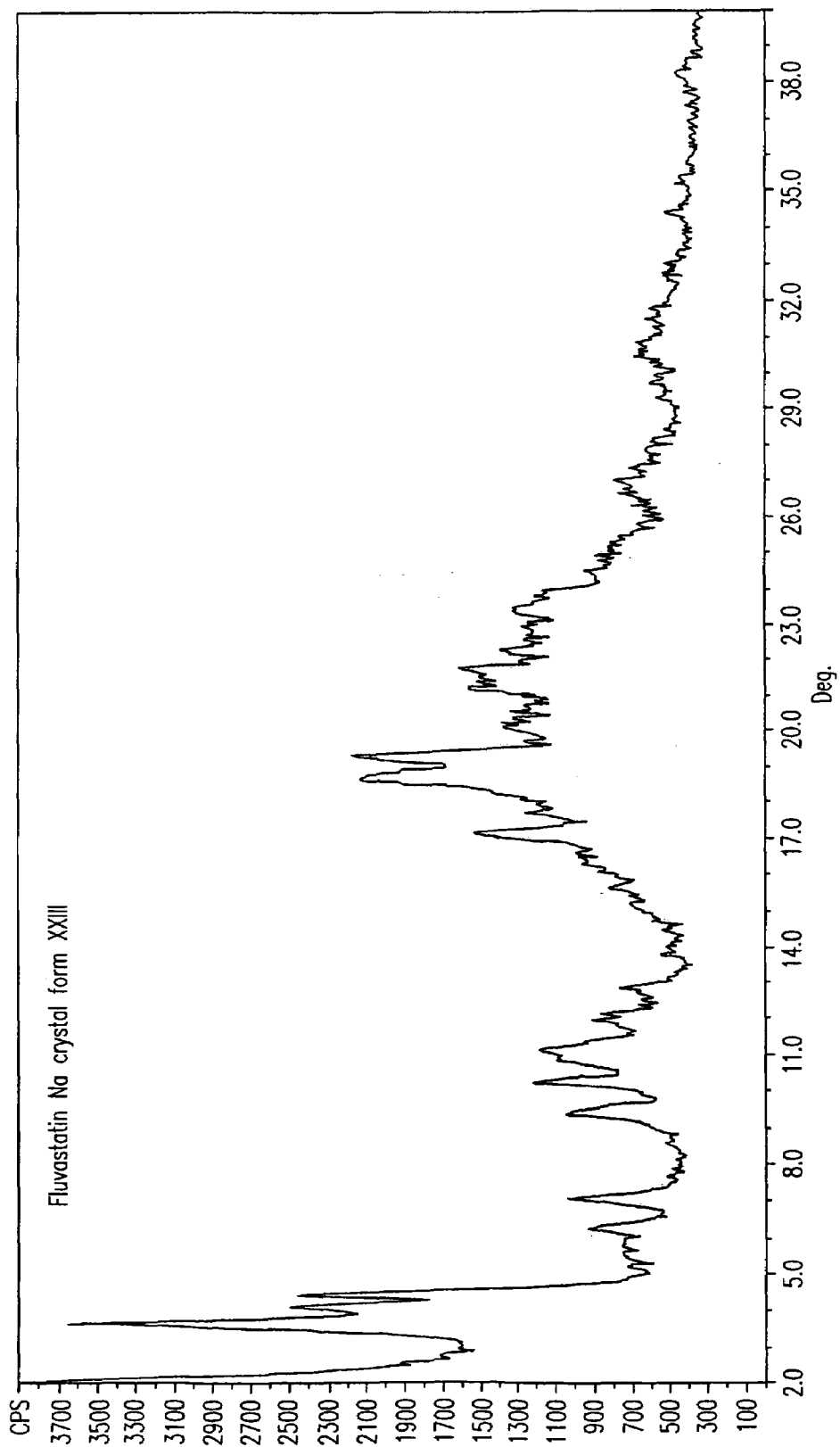
FIG. 47 depicts a powder X-ray diffractogram of fluvastatin sodium Form XXIII.

128. The crystalline form of embodiment 127 wherein the crystalline form is characterized by a PXRD pattern substantially as depicted in FIG. 47.

129. The crystalline form of embodiment 126 wherein the crystalline form is fluvastatin sodium Form XXIII.

130. A process for preparing crystalline fluvastatin sodium Form XXIII comprising:
  a) dissolving fluvastatin sodium in propan-1-ol at elevated temperature,
  b) precipitating Form XXIII from the propan-1-ol,
  c) separating the propan-1-ol from the Form XXIII.

Figure 48:
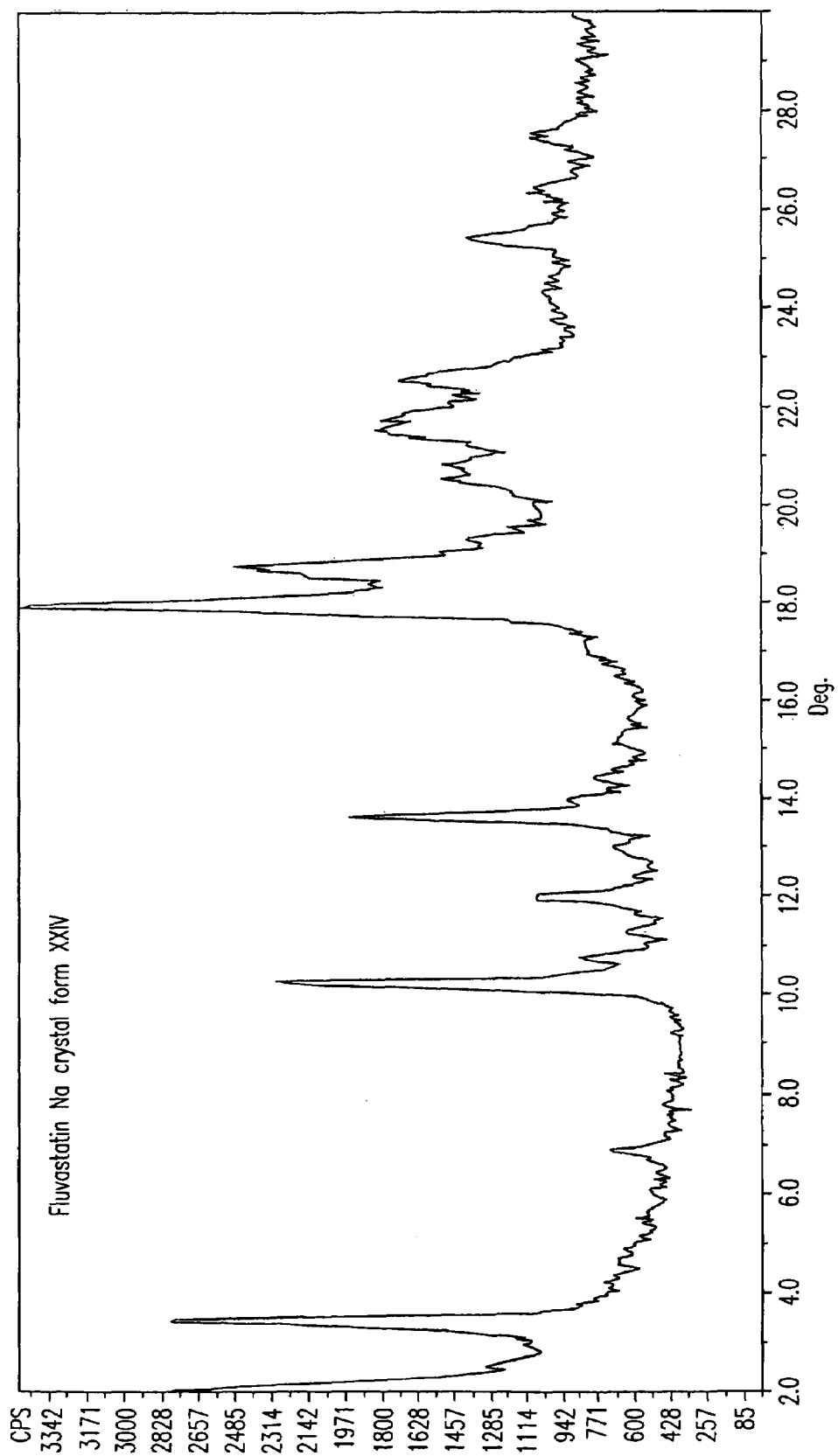
FIG. 48 depicts a powder X-ray diffractogram of fluvastatin sodium Form XXIV.
Figure 49:
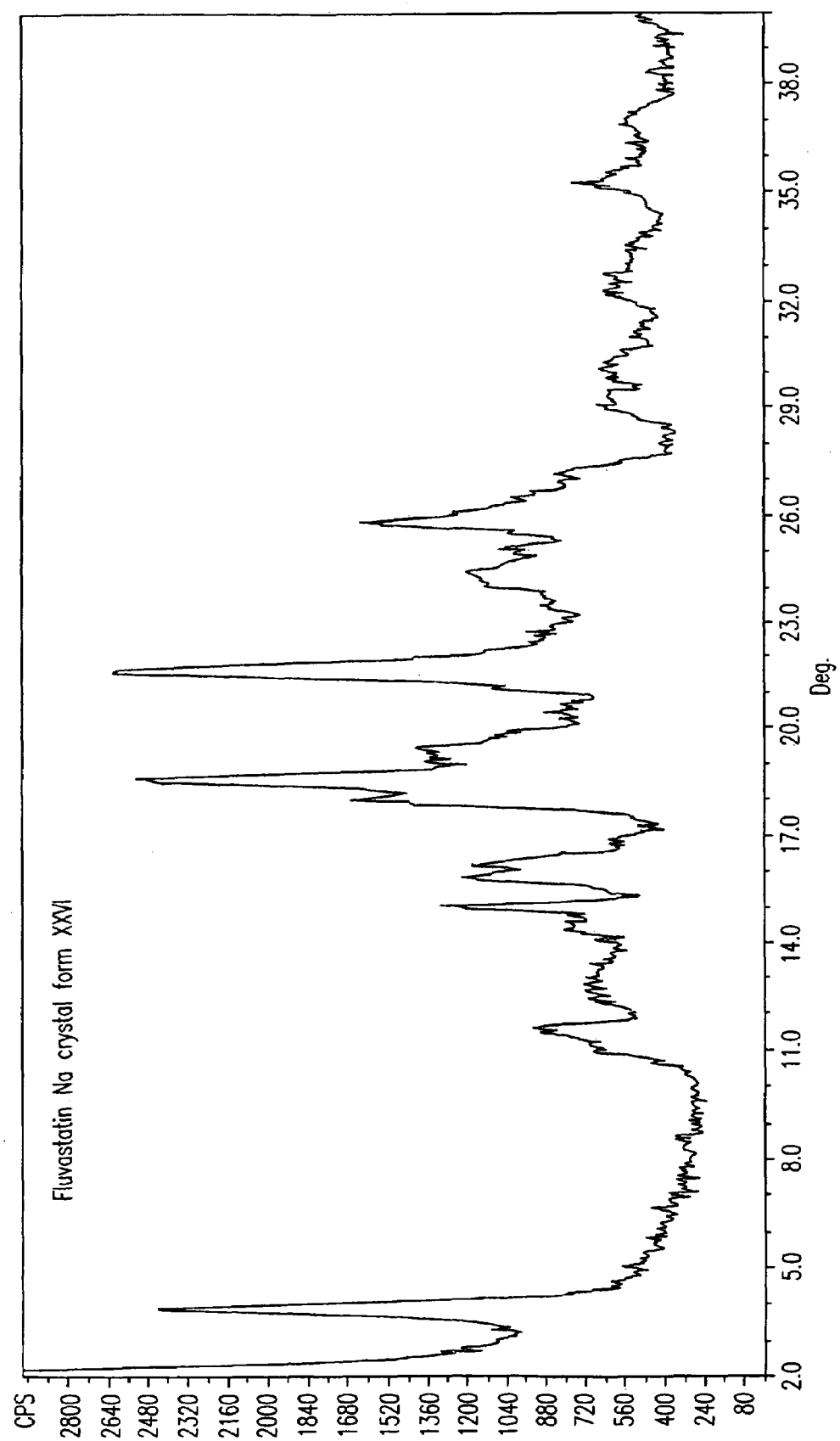
FIG. 49 depicts a powder X-ray diffractogram of fluvastatin sodium Form XXVI.
Figure 50:
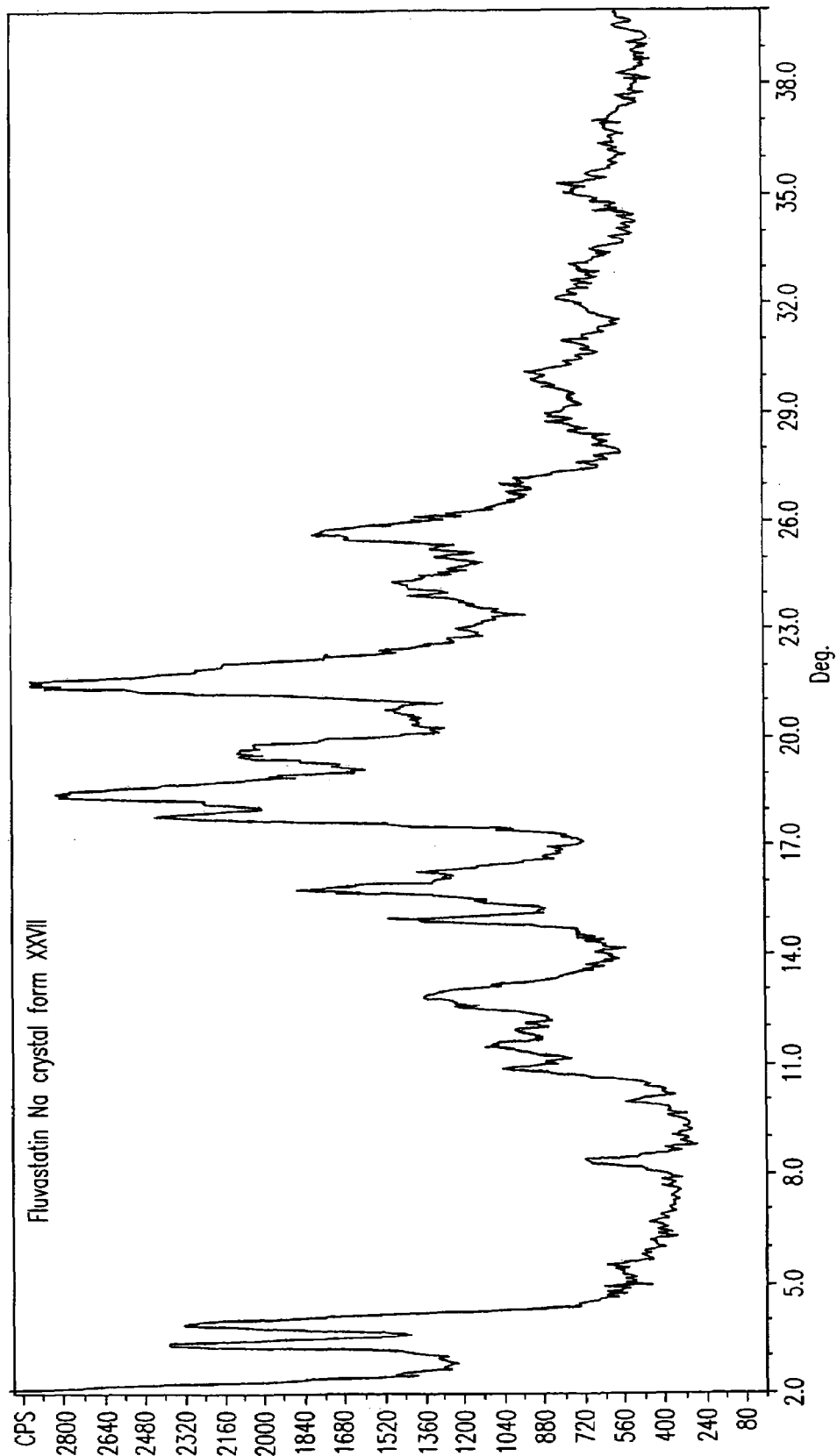
FIG. 50 depicts a powder X-ray diffractogram of fluvastatin sodium Form XXVII.
Figure 51:
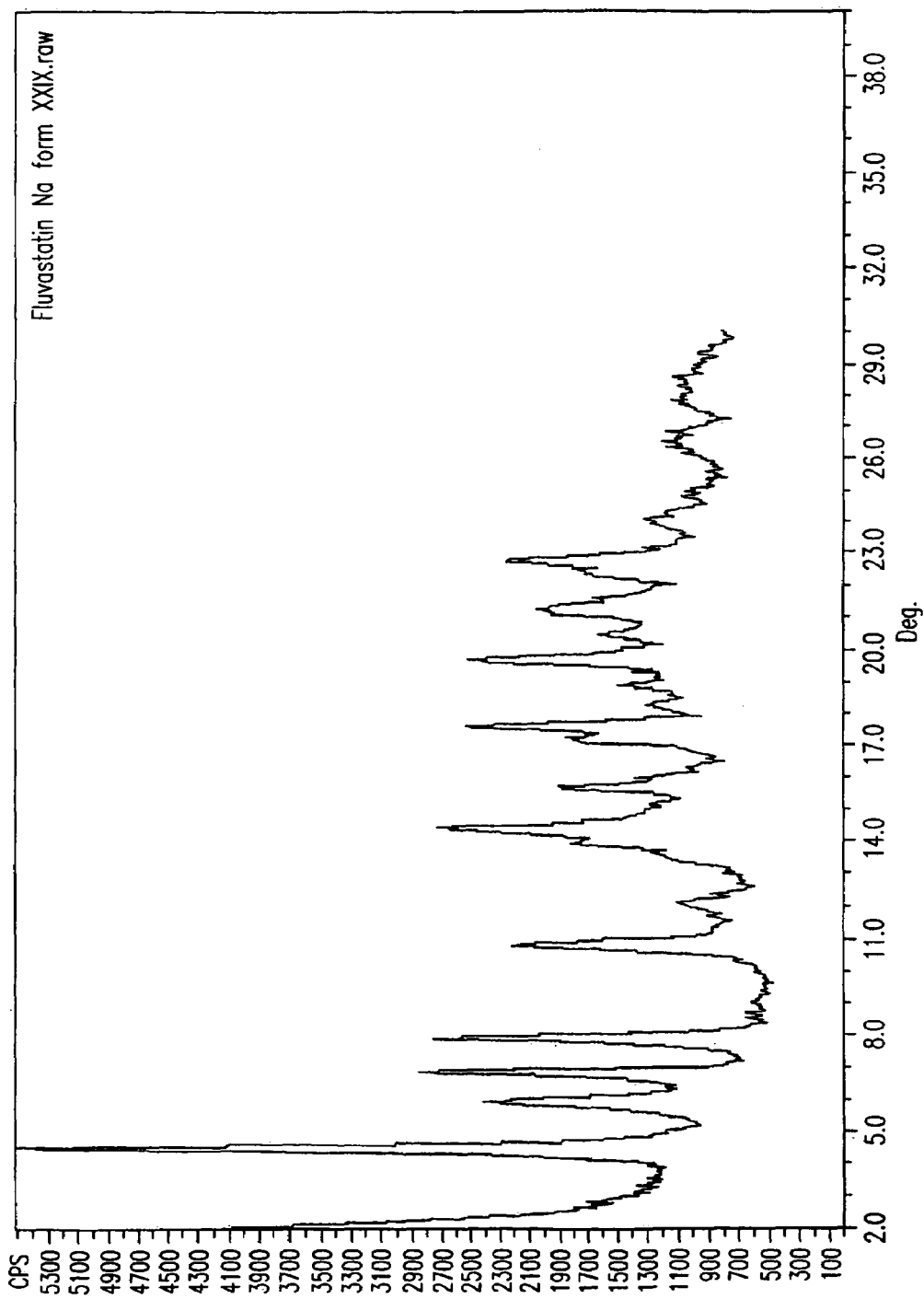
FIG. 51 depicts a powder X-ray diffractogram of fluvastatin sodium Form XXIX.
Figure 52:
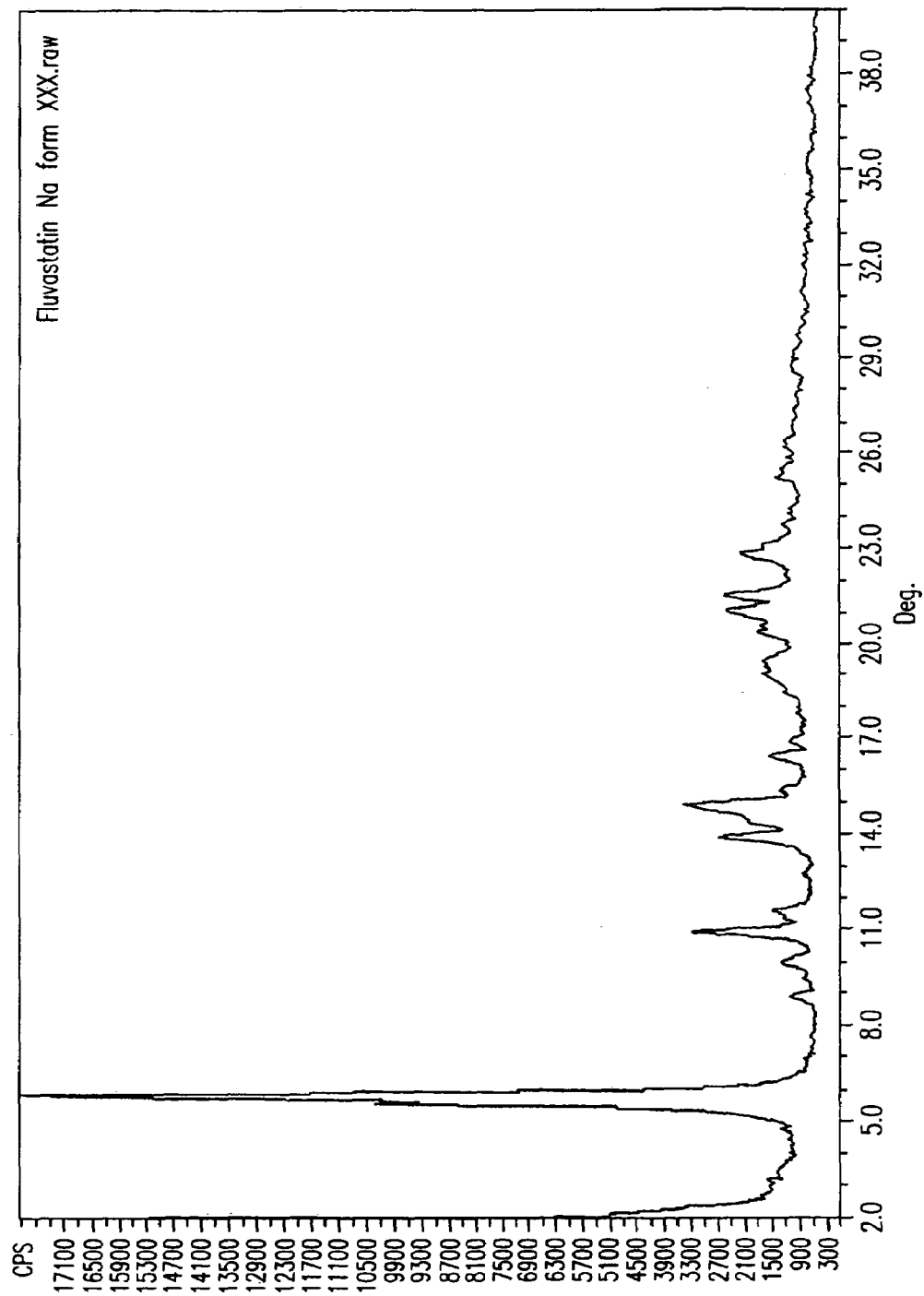
FIG. 52 depicts a powder X-ray diffractogram of fluvastatin sodium Form XXX.
Figure 53:
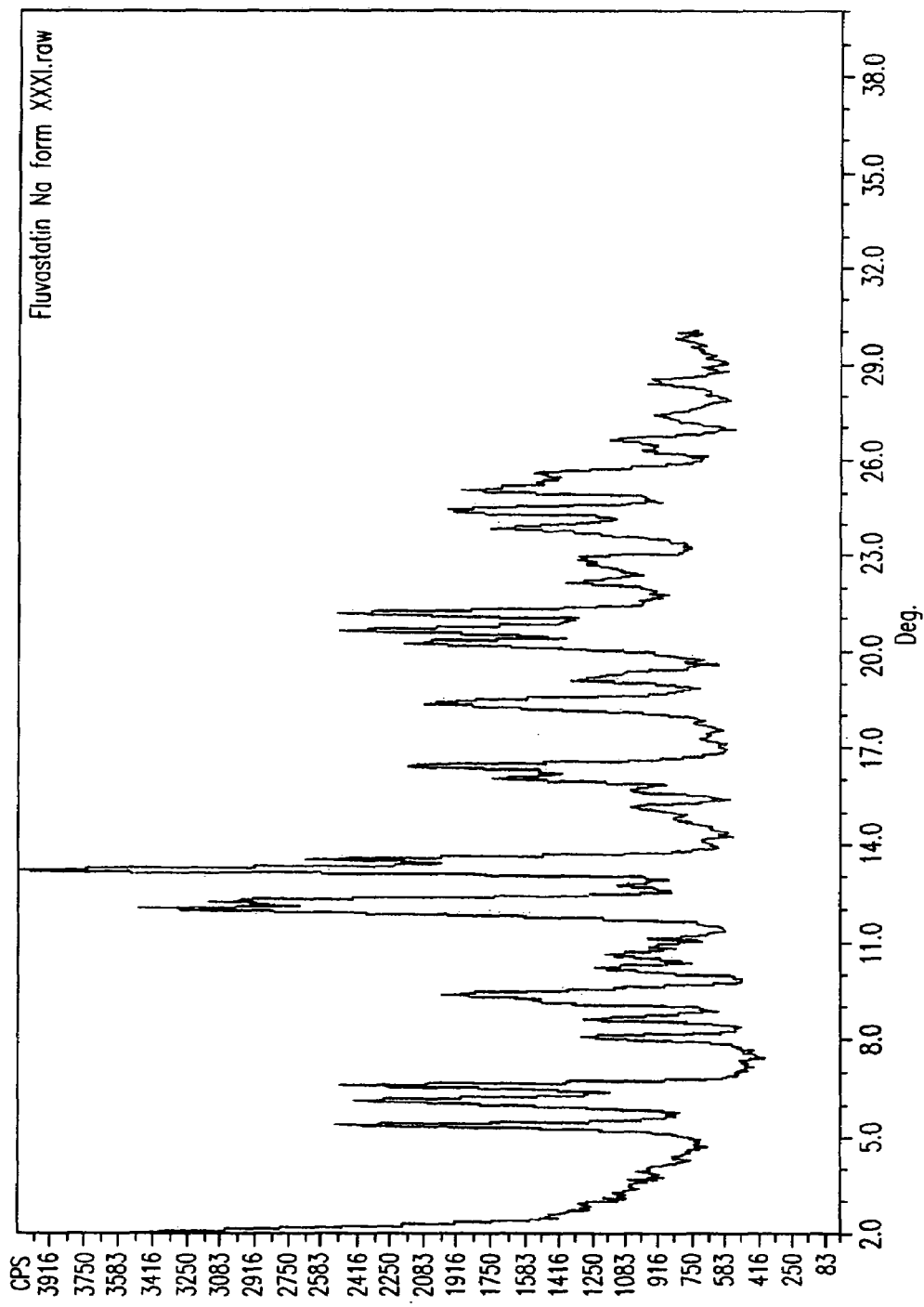
FIG. 53 depicts a powder X-ray diffractogram of fluvastatin sodium Form XXXI.
Figure 54:
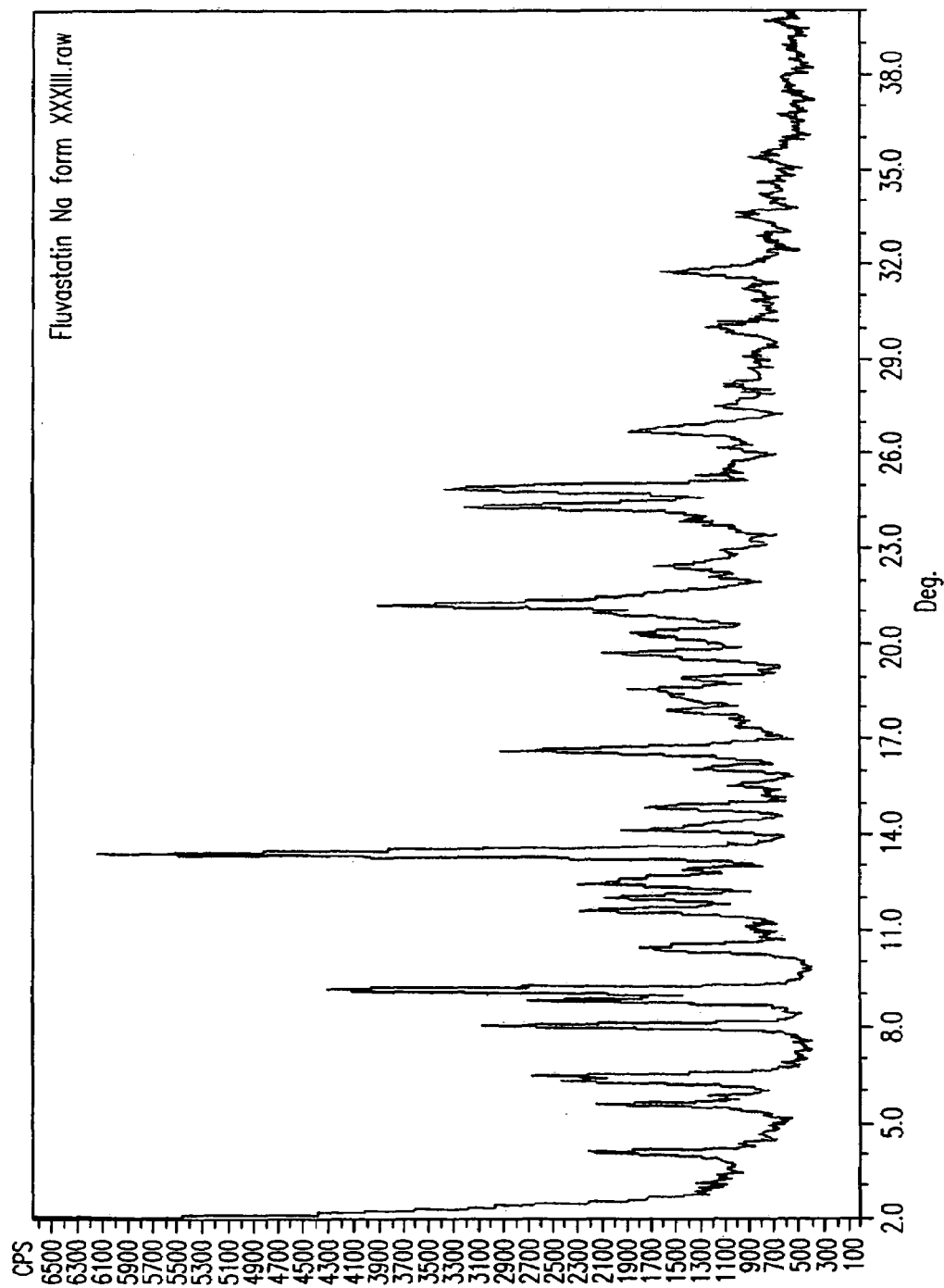
FIG. 54 depicts a powder X-ray diffractogram of fluvastatin sodium Form XXXIII.

131. A crystalline form of fluvastatin sodium characterized by a PXRD pattern with peaks at 3.4, 10.2, 13.6, 17.9 and 18.7±0.2 degrees two-theta.
132. The crystalline form of embodiment 131 further characterized by peaks at 6.9, 10.7, 12.0, 22.5 and 25.4±0.2 degrees two-theta.
133. The crystalline form of embodiment 132 wherein the crystalline form is characterized by a PXRD pattern substantially as depicted in FIG. 48.
134. The crystalline form of embodiment 131 wherein the crystalline form is fluvastatin sodium Form XXIV.
135. A process for preparing crystalline fluvastatin sodium Form XXIV comprising:
    a) dissolving a fluvastatin sodium in water,
    b) precipitating Form XXIV from the water, and
    c) separating the water from the Form XXIV.
136. A crystalline form of fluvastatin sodium characterized by a PXRD pattern with peaks at 3.8, 15.0, 18.5, 21.6 and 25.8±0.2 degrees two-theta.
137. The crystalline form of embodiment 136 further characterized by peaks at 11.7, 15.9, 16.2, 24.3 and 35.2±0.2 degrees two-theta.
138. The crystalline form of embodiment 137 wherein the crystalline form is characterized by a PXRD pattern substantially as depicted in FIG. 49.
139. The crystalline form of embodiment 136 wherein the crystalline form is fluvastatin sodium Form XXIV.
140. A process for preparing crystalline fluvastatin sodium Form XXVI comprising:
    a) dissolving fluvastatin sodium in a mixture of 1,4-dioxane:water at elevated temperature,
    b) cooling the mixture to indue precipitation of Form XXVI, and
    c) separating the mixture from Form XXVI.
141. A crystalline form of fluvastatin sodium characterized by a PXRD pattern with peaks at 3.3, 3.9, 15.9, 18.4 and 21.6±0.2 degrees two-theta.
142. The crystalline form of embodiment 141 further characterized by peaks at 8.4, 15.0, 17.9, 24.3 and 25.7±0.2 degrees two-theta.
143. The crystalline form of embodiment 142 wherein the crystalline form is characterized by a PXRD pattern substantially as depicted in FIG. 50.
144. The crystalline form of embodiment 141 wherein the crystalline form is fluvastatin sodium Form XXVII.
145. A process for preparing crystalline fluvastatin sodium Form XXVII comprising:
    a) dissolving fluvastatin sodium in a mixture of 1,4-dioxane:water at elevated temperature,
    b) adding hexanes to the mixture at elevated temperature,
    c) cooling the mixture,
    d) precipitating Form XXVII, and
    e) separating the 1,4-dioxane, water and hexanes from the Form XXVII.
146. A crystalline form of fluvastatin sodium characterized by a PXRD pattern with peaks at 4.4, 5.9, 6.8, 7.9, 10.8±0.2 degrees two-theta.
147. The crystalline form of embodiment 146 further characterized by peaks at 14.3, 15.6, 17.5, 19.7, 21.3, 22.7±0.2 degrees two-theta.
148. The crystalline form of embodiment 147 further characterized by a PXRD pattern substantially as depicted in FIG. 51.
149. The crystalline form of embodiment 146 wherein the crystalline form is fluvastatin sodium Form XXIX.
150. A process for preparing fluvastatin sodium Form XXIX comprising the steps of:
    a) forming a heterogeneous mixture of fluvastatin sodium Form XV and 1,4-dioxane,
    b) maintaining the heterogeneous mixture for a period of time sufficient to substantially convert Form XV to Form XXIX, and
    c) separating the Form XXIX from the 1,4-dioxane.
151. A crystalline form of fluvastatin sodium characterized by a PXRD pattern with peaks at 5.4, 5.8, 10.8, 13.8 and 14.8±0.2 degrees two-theta.
152. The crystalline form of embodiment 151 further characterized by peaks at 16.4, 19.0, 19.5, 20.2, 20.8, 21.5, 22.7±0.2 degrees two-theta.
153. The crystalline form of embodiment 152 further characterized by a PXRD pattern substantially as depicted in FIG. 52.
154. The crystalline form of embodiment 151 wherein the crystalline form is fluvastatin sodium Form XXX.
155. A process for preparing fluvastatin sodium Form XXX comprising:
    a) forming a heterogeneous mixture of fluvastatin sodium Form XV and a diluent selected from the group consisting of methyl ethyl ketone, tetrahydrofuran, acetone, butan-2-ol and butan-1-ol,
    b) maintaining the heterogeneous mixture to convert Form XV to Form XXX, and
    c) separating the diluent from Form XXX.
156. A process for preparing fluvastatin sodium Form XXX comprising:
    a) dissolving a lower alkyl ester of fluvastatin in a solution containing a molar excess of sodium hydroxide relative to the fluvastatin in a mixture of methanol and water,
    b) adding acetone to the solution at elevated temperature to induce precipitation of Form XXX, and
    c) separating the methanol and water from the Form XXX.
157. A crystalline form of fluvastatin sodium characterized by a PXRD pattern with peaks at 5.3, 6.1, 6.5, 11.9, 13.2±0.2 degrees two-theta.
158. The crystalline form of embodiment 157 further characterized by peaks at 8.0, 8.5, 9.3, 16.3, 18.3, 20.2, 20.6, 21.1±0.2 degrees two-theta.
159. The crystalline form of embodiment 158 further characterized by a PXRD pattern substantially as depicted in FIG. 53.
160. The crystalline form of embodiment 157 wherein the crystalline form is fluvastatin sodium Form XXXI.
161. A process for preparing fluvastatin sodium Form XXXI comprising:
    a) forming a heterogeneous mixture of fluvastatin sodium Form XV and ethanol,
    b) maintaining the mixture for a period of time sufficient to effect conversion of Form XV to Form XXXI, and
    c) separating the ethanol from Form XXXI.
162. A crystalline form of fluvastatin sodium characterized by a PXRD pattern with peaks at 4.0, 5.5, 8.0, 9.1, 13.4, 16.6, 21.2±0.2 degrees two-theta.
163. The crystalline form of embodiment 162 further characterized by peaks at 6.6, 8.8, 10.4, 11.6, 12.0, 14.1, 14.8, 16.1, 17.9, 18.5, 19.7, 20.3, 24.3, 24.9, 26.7±0.2 degrees two-theta.
164. The crystalline form of embodiment 163 further characterized by a PXRD pattern as substantially depicted in FIG. 54.
165. The crystalline form of embodiment 162 wherein the crystalline form is fluvastatin sodium Form XXXIII.

166. The crystalline form of embodiment 162 having a water content of about 7 weight percent.

167. A process for preparing crystalline fluvastatin sodium Form XXXIII comprising:
a) forming a heterogeneous mixture of fluvastatin sodium Form XV or Form B and ethanol,
b) maintaining the mixture for a period of time sufficient to substantially convert the Form XV or Form B to Form XXXIII, and
c) recovering the fluvastatin sodium Form XXXIII from the mixture.

168. The process of embodiment 167 wherein the heterogeneous mixture is maintained at elevated temperature and then cooled or allowed to cool before recovering Form XXXIII.

169. A crystalline form of fluvastatin sodium characterized by a PXRD pattern having peaks at 5.4, 6.1, 7.6, 18.5, 21.1±0.2 degrees two-theta.

170. The crystalline form of embodiment 169 further characterized by peaks at 8.8, 9.3, 12.4, 13.1, 14.3, 15.2, 15.9, 17.2, 17.6, 20.5, 22.2, 24.1, 25.4, 26.2±0.2 degrees two-theta.

Figure 55:
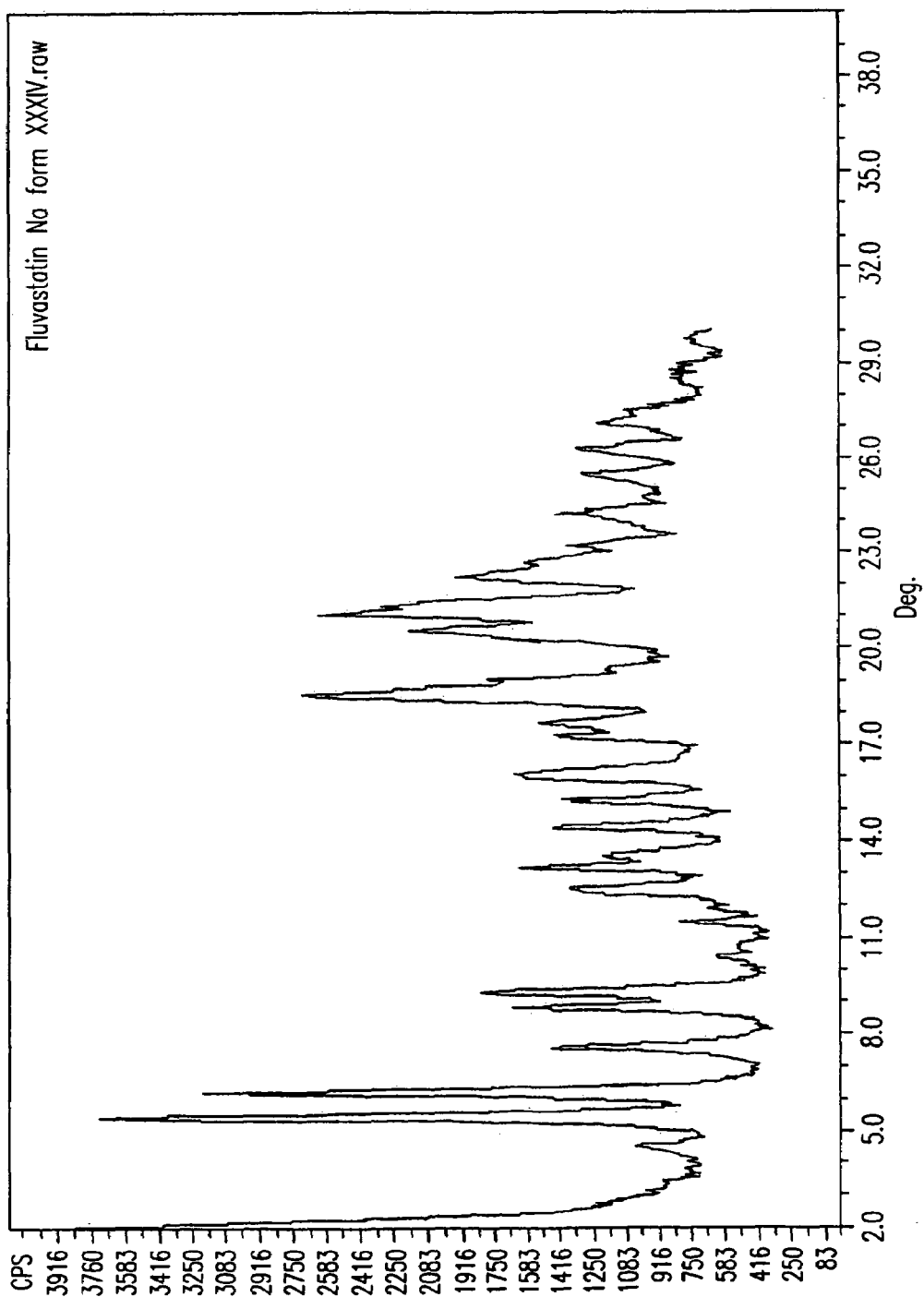
FIG. 55 depicts a powder X-ray diffractogram of fluvastatin sodium Form XXXIV.

171. The crystalline form of embodiment 170 further characterized by a PXRD pattern substantially as depicted in FIG. 55.

172. The crystalline form of embodiment 169 wherein the crystalline form is fluvastatin sodium Form XXXIV.

173. A process for preparing crystalline fluvastatin sodium Form XXXIV comprising:
a) forming a heterogeneous mixture of fluvastatin sodium Form XV for a sufficient time and DMSO,
b) maintaining the mixture for a period of time sufficient to substantially convert Form XV to Form XXXIV, and
c) recovering fluvastatin sodium Form XXXIV from the mixture.

174. A crystalline form of fluvastatin sodium characterized by a PXRD pattern having peaks at 5.4, 6.0, 9.9, 14.8, 21.0±0.2 degrees two-theta.

175. The crystalline form of embodiment 174 further characterized by peaks at 16.7, 18.6, 19.8, 22.6±0.2 degrees two-theta.

Figure 56:
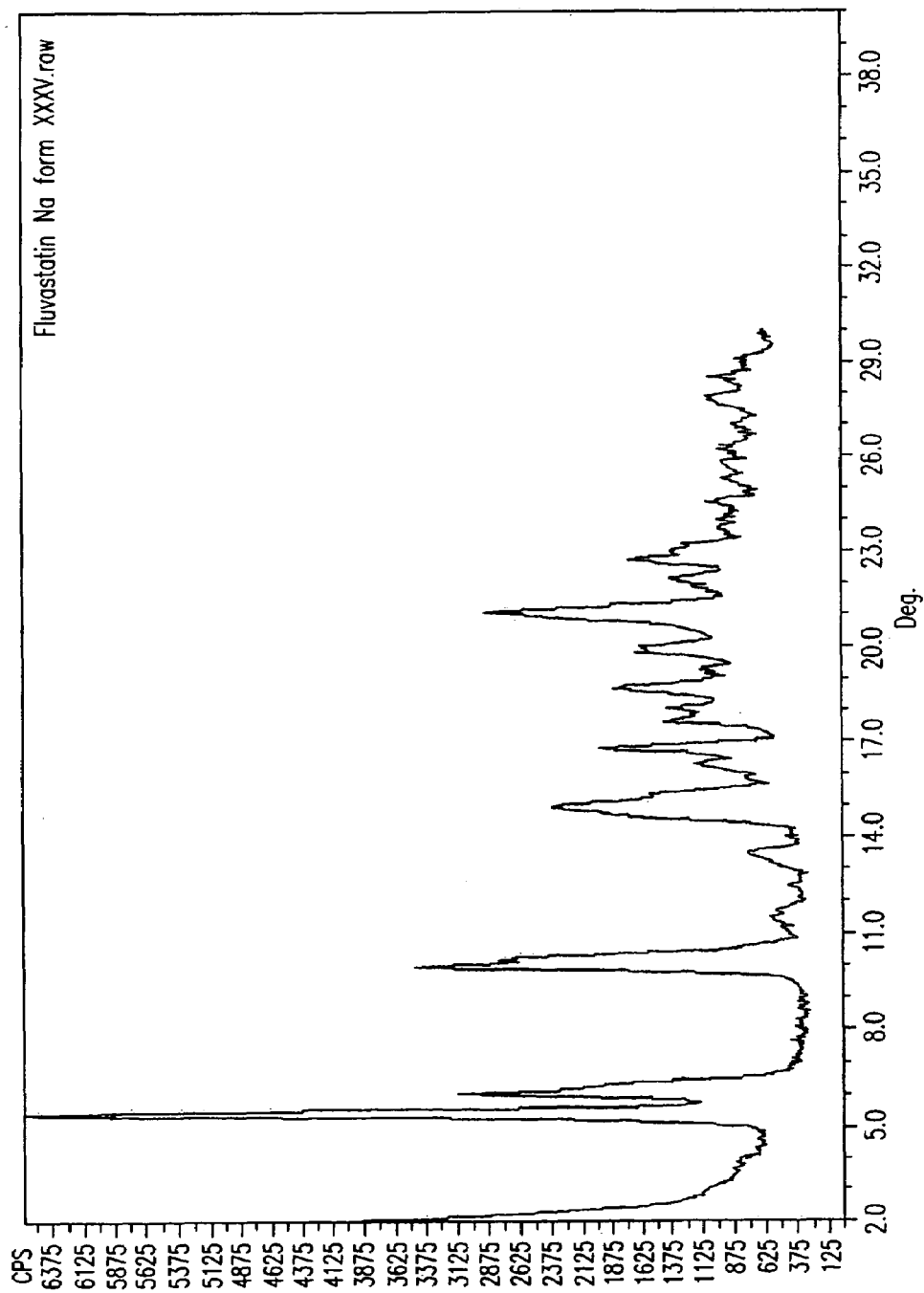
FIG. 56 depicts a powder X-ray diffractogram of fluvastatin sodium Form XXXV.

176. The crystalline form of embodiment 175 further characterized by a PXRD pattern substantially as depicted in FIG. 56.

177. The crystalline form of embodiment 174 wherein the crystalline form is fluvastatin sodium Form XXXV 178. A process for preparing the crystalline fluvastatin sodium Form XXXV comprising:
a) forming a heterogeneous mixture of fluvastatin sodium Form XV and DMF,
b) maintaining the heterogeneous mixture for a period of time sufficient to substantially convert Form XV to Form XXXV, and
c) recovering Form XXXV from the heterogeneous mixture.

179. A crystalline form of fluvastatin sodium characterized by a PXRD pattern with peaks at 3.0, 9.2, 11.5, 14.4 and 20.2±0.2 degrees two-theta.

180. The crystalline form of embodiment 179 further characterized by peaks at 9.6, 12.3 and 12.8±0.2 degrees two-theta.

Figure 57:
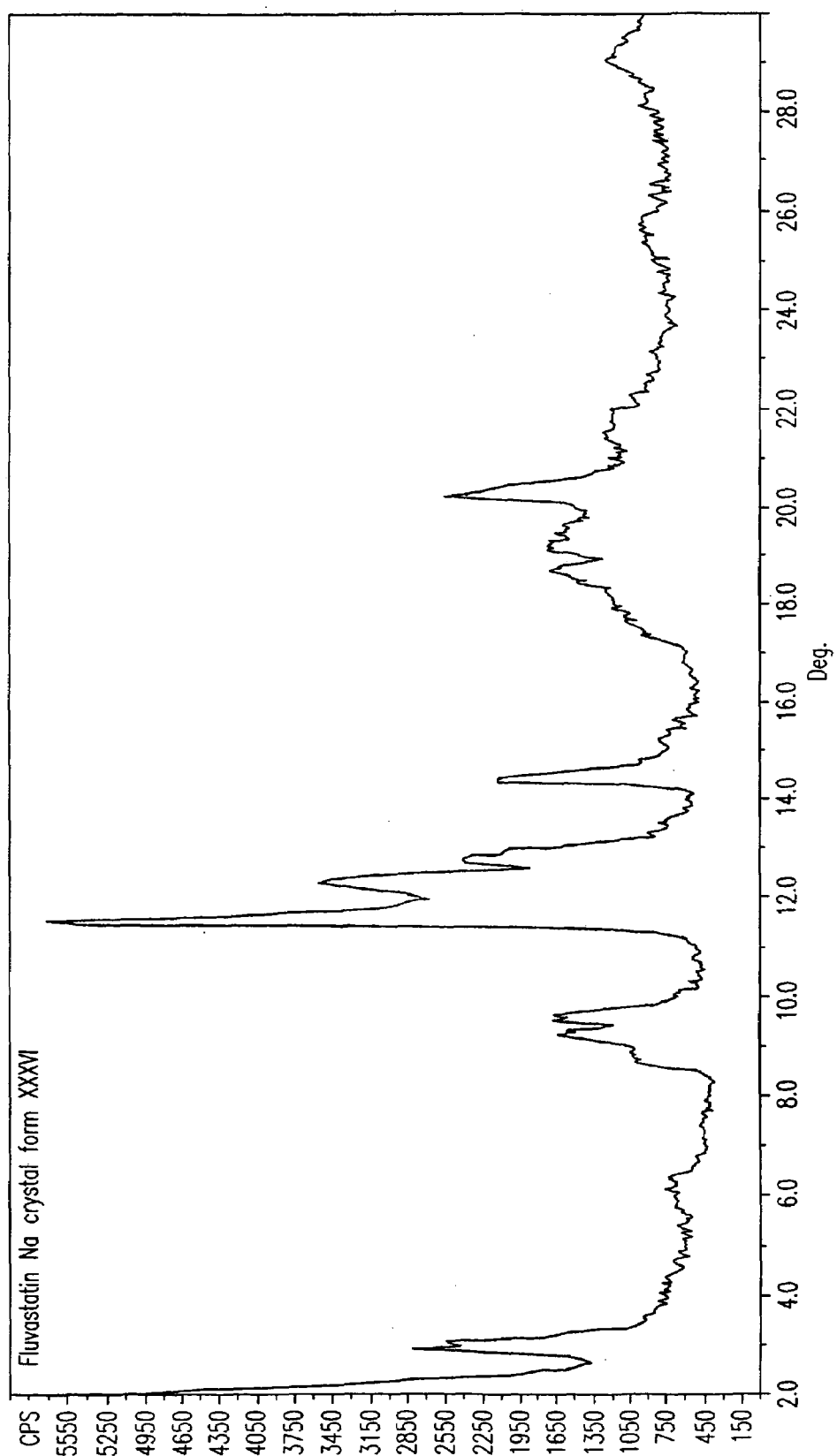
FIG. 57 depicts a powder X-ray diffractogram of fluvastatin sodium Form XXXVI.

181. The crystalline form of embodiment 180 wherein the crystalline form is characterized by a PXRD pattern substantially as depicted in FIG. 57.

182. The crystalline form of embodiment 179 wherein the crystalline form is fluvastatin sodium Form XXXVI.

183. A process for preparing crystalline fluvastatin sodium Form XXXVI comprising:
a) suspending fluvastatin sodium Form XI-wet in water for a period time sufficient to effect the conversion of Form XI-wet to Form XXXVI, and
b) separating the water from Form XXXVI.

184. A crystalline form of fluvastatin sodium characterized by a PXRD pattern with peaks at 3.63, 10.36, 13.74, 17.93, 18.34±0.2 degrees two-theta.

185. The crystalline form of embodiment 184 further characterized by peaks at 11.26, 12.16, 12.91, 19.44, 20.57±0.2 degrees two-theta.

Figure 58:
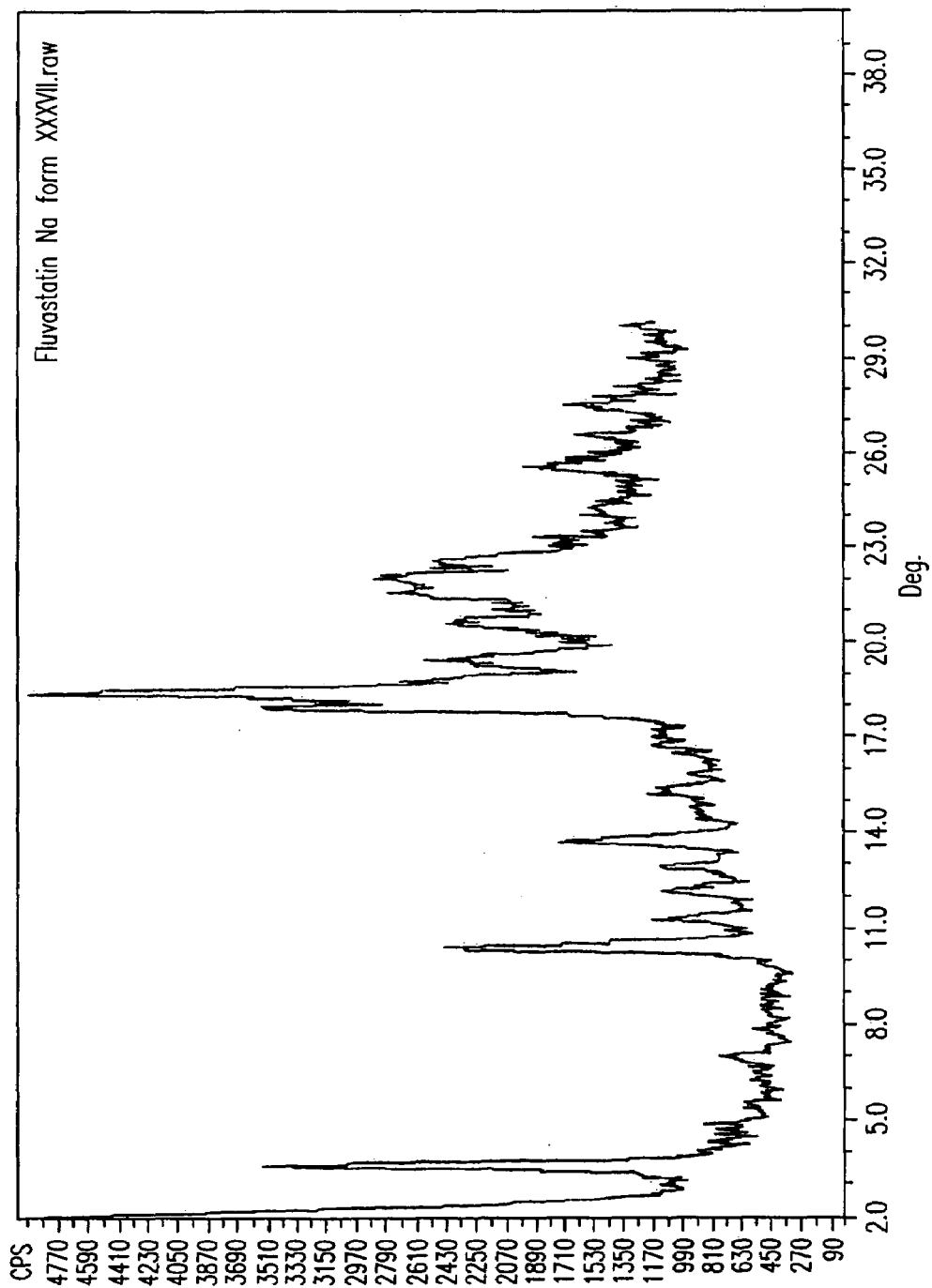
FIG. 58 depicts a powder X-ray diffractogram of fluvastatin sodium Form XXXVII.

186. The crystalline form of embodiment 185 further characterized by a PXRD pattern substantially as depicted in FIG. 58.

187. The crystalline form of embodiment 184 wherein the crystalline form is Fluvastatin sodium Form XXXVII.

188. A process for preparing crystalline fluvastatin sodium Form XXXVII comprising:
a) forming a heterogeneous mixture of fluvastatin sodium Form XI and water at ambient temperature,
b) maintaining the heterogeneous mixture at ambient temperature to convert Form XI to Form XXXVII, and
c) recovering fluvastatin sodium Form XXXVII from the mixture.

189. A crystalline form of fluvastatin sodium characterized by a PXRD pattern having peaks at 3.64, 4.66, 7.30, 8.84, 11.61±0.2 degrees two-theta.

190. The crystalline form of embodiment 189 further characterized by peaks at 19.08, 19.65, 21.15, 22.59, 24.20±0.2 degrees two-theta.

Figure 59:
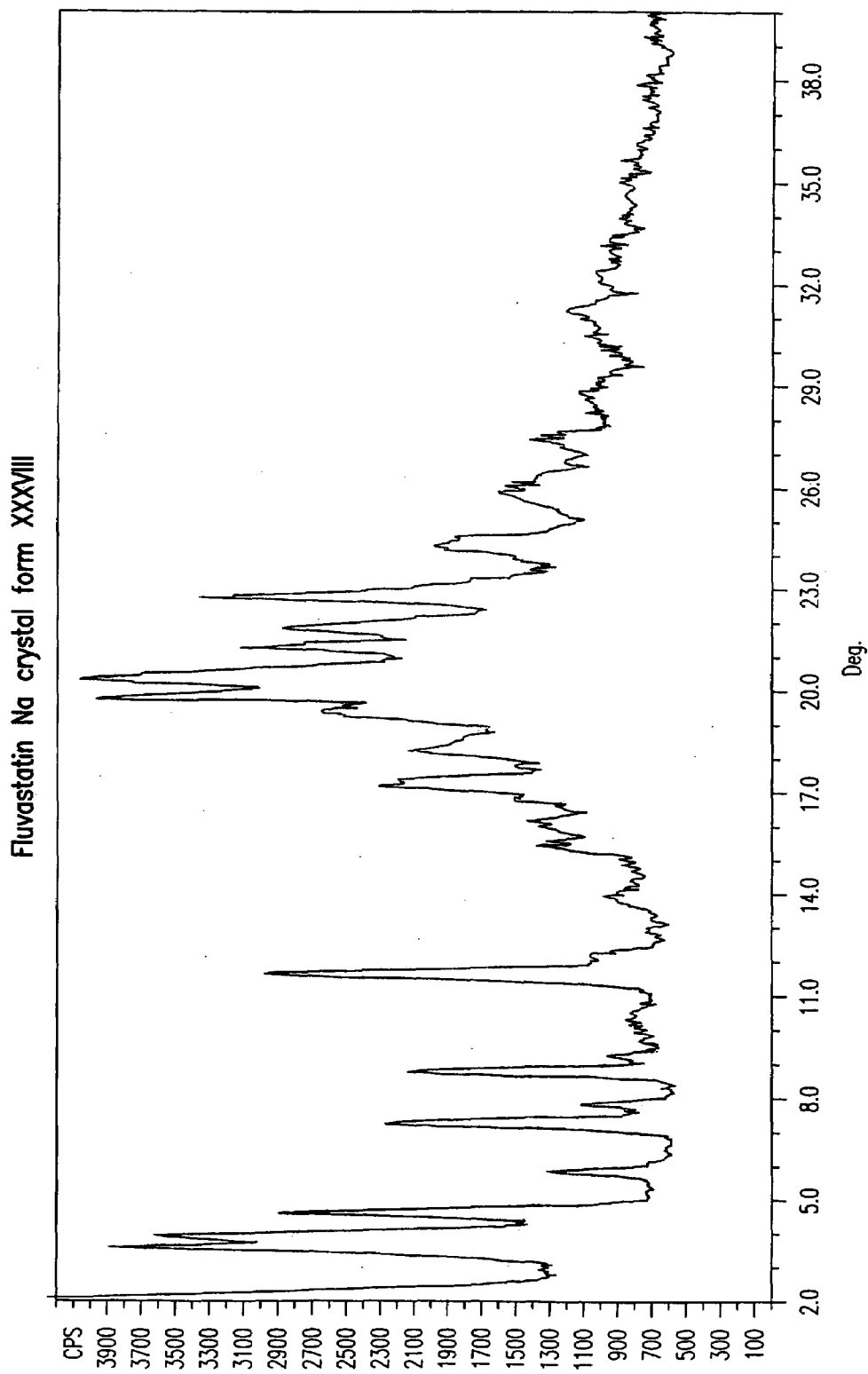
FIG. 59 depicts a powder X-ray diffractogram of fluvastatin sodium Form XXXVIII.

191. The crystalline form of embodiment 190 further characterized by a PXRD pattern substantially as depicted in FIG. 59.

192. The crystalline form of embodiment 189 wherein the crystalline form is fluvastatin sodium Form XXXVIII.

193. A process for preparing crystalline fluvastatin sodium Form XXXVIII comprising:
a) forming a heterogeneous mixture of fluvastatin sodium Form XI and absolute ethanol,
b) maintaining the mixture to convert Form XI to Form XXXVIII, and
c) recovering Form XXXVIII from the mixture.

194. A process for preparing crystalline fluvastatin sodium Form XXXVIII comprising:
a) dissolving a lower alkyl ester of fluvastatin in a solution of about one molar equivalent of sodium hydroxide in ethanol,
b) inducing precipitation of Form XXXVIII by addition of ethyl acetate, and
c) separating Form XXXVIII from the ethanol and ethyl acetate.

195. A crystalline form of fluvastatin sodium characterized by a PXRD pattern with peaks at 3.7, 4.5, 8.5, 17.8, 20.1±0.2 degrees two-theta.

196. The crystalline form of embodiment 195 further characterized by peaks at 6.9, 11.2, 16.8, 19.6 and 21.6±0.2 degrees two-theta.

Figure 60:
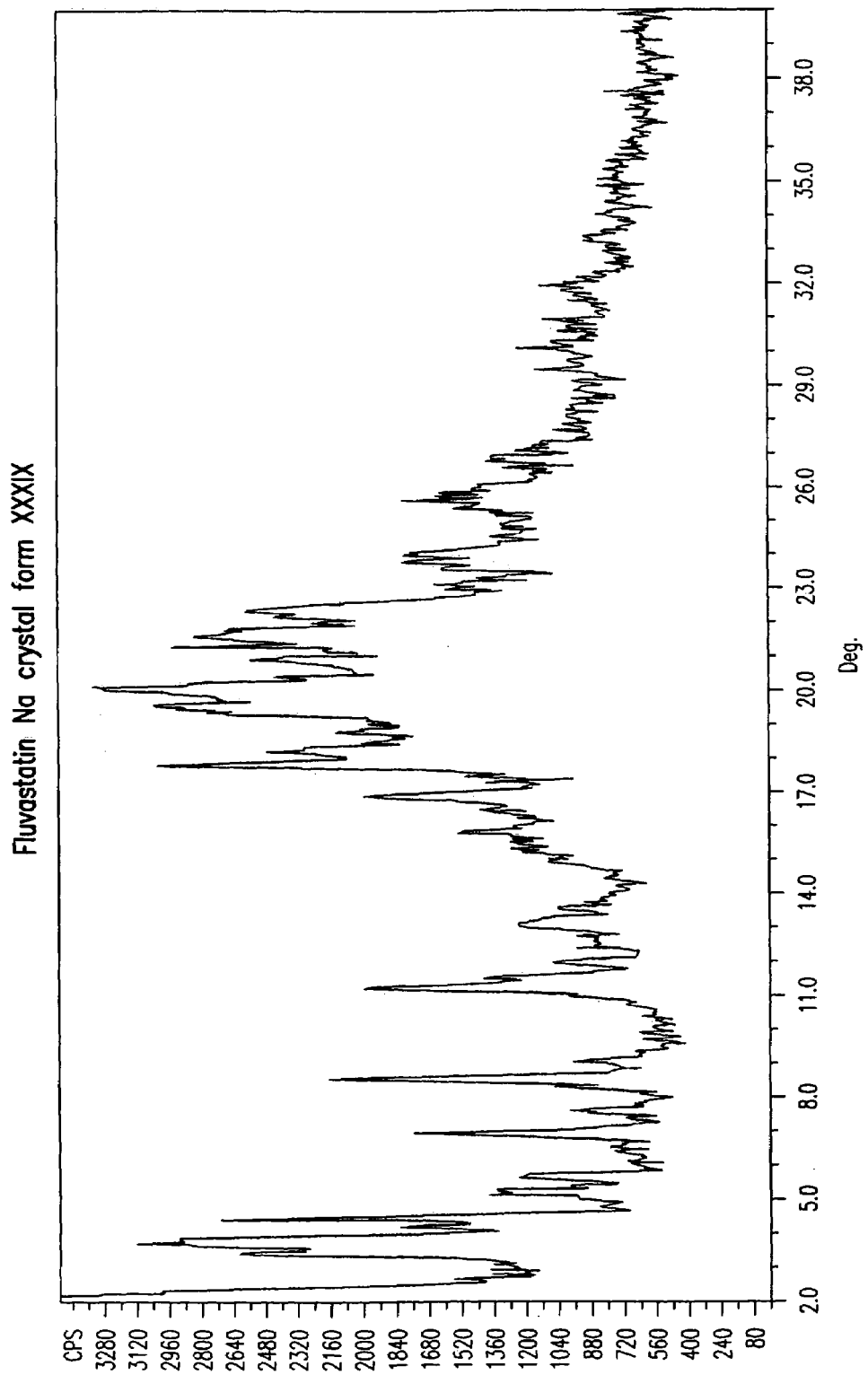
FIG. 60 depicts a powder X-ray diffractogram of fluvastatin sodium Form XXXIX.

197. The crystalline form of embodiment 196 wherein the crystalline form is characterized by a PXRD pattern substantially as depicted in FIG. 60.

198. The crystalline form of embodiment 195 wherein the crystalline form is fluvastatin sodium Form XXXIX.

199. A process for preparing crystalline fluvastatin sodium Form XXXIX comprising:
a) hydrolyzing a lower alkyl ester of fluvastatin with about one molar equivalent of sodium hydroxide in ethanol, b) adding an excess of propan-2-ol with respect to the ethanol to the ethanol, c) precipitating Form XXXIX, and d) separating the ethanol and propan-2-ol from the Form XXXIX.

200. A crystalline form of fluvastatin sodium characterized by a PXRD pattern having peaks at 3.75, 4.31, 9.10, 11.00±0.2 degrees two-theta.

201. The crystalline form of embodiment 200 further characterized by peaks at 5.60, 7.30, 7.55, 14.50, 18.04±0.2 degrees two-theta.

Figure 61:
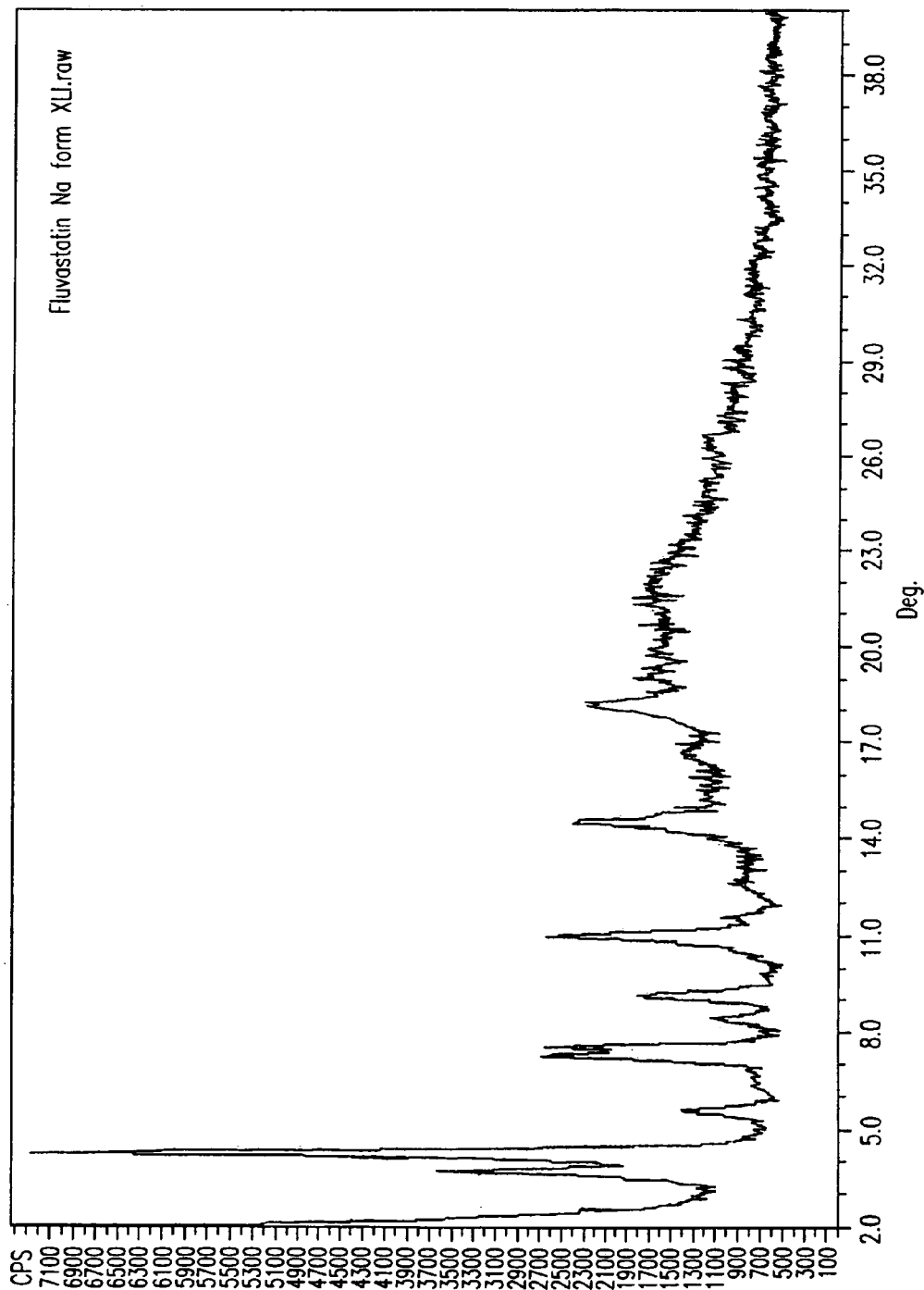
FIG. 61 depicts a powder X-ray diffractogram of fluvastatin sodium Form XLI.

202. The crystalline form of embodiment 201 further characterized by a PXRD pattern substantially as depicted in FIG. 61.

203. The crystalline form of embodiment 200 wherein the crystalline form is fluvastatin sodium form XLI.

204. A process for preparing crystalline fluvastatin sodium Form XLI comprising:

a) dissolving fluvastatin sodium in water, b) adding acetonitrile to the water to induce precipitation of Form XLI, and c) separating the acetonitrile and water from Form XLI.

205. A crystalline form of fluvastatin sodium characterized by a PXRD pattern having peaks at 3.4, 9.7, 11.0, 18.9±0.2 degrees two-theta.

206. The crystalline form of embodiment 205 further characterized by peaks at 5.7, 14.8, 16.1, 17.0, 22.6±0.2 degrees two-theta.

Figure 62:
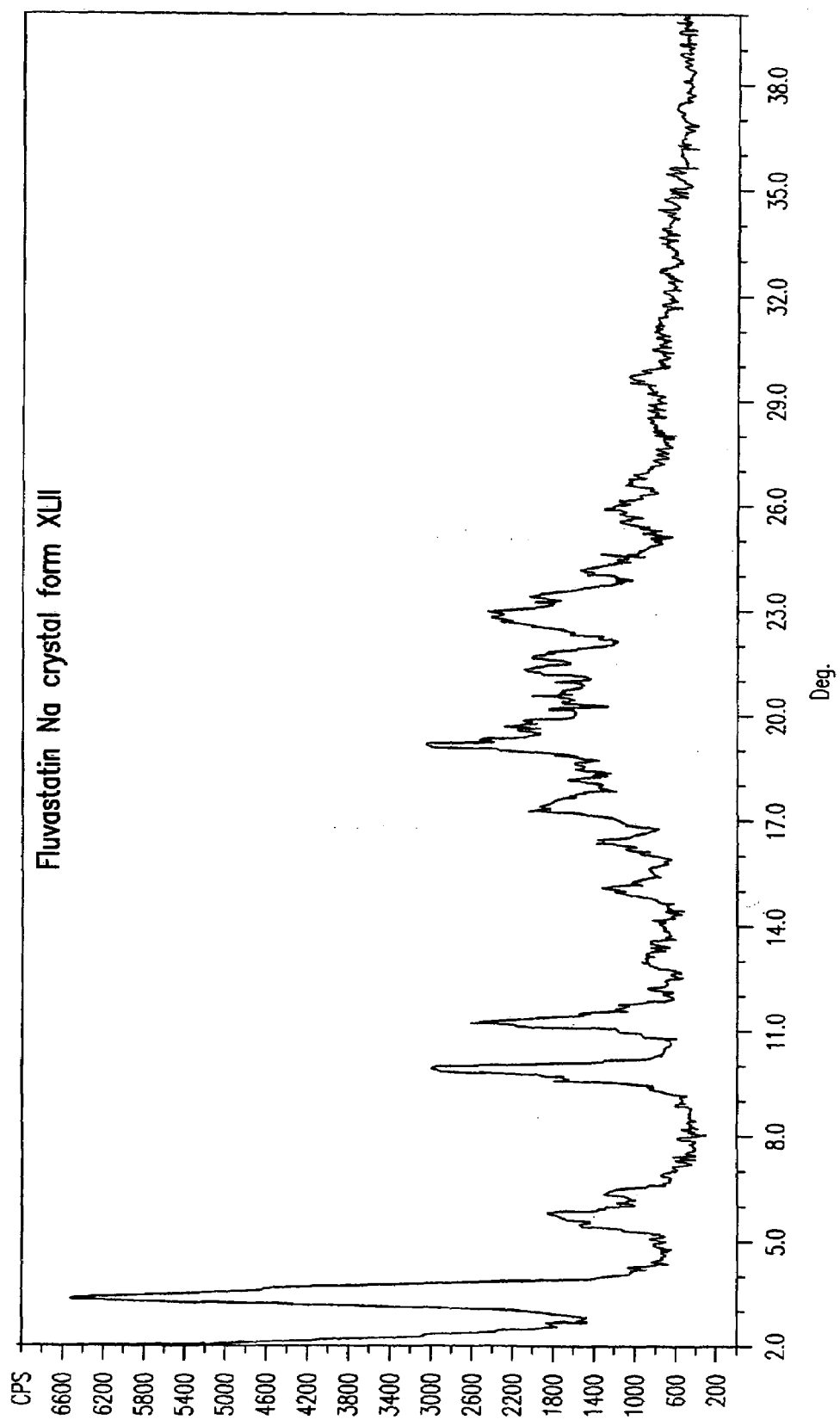
FIG. 62 depicts a powder X-ray diffractogram of fluvastatin sodium Form XLII

207. The crystalline form of embodiment 206 wherein the crystalline form is characterized by a PXRD pattern substantially as depicted in FIG. 62.

208. The crystalline form of embodiment 205 wherein the crystalline form is fluvastatin sodium Form XLII.

209. A process for preparing fluvastatin sodium Form XLII comprising:

a) dissolving fluvastatin in methyl ethyl ketone, b) adding a solution of sodium hydroxide in methanol to the solution to induce precipitation of Form XLII; and c) separating the solution from Form XLII.

210. A process for preparing fluvastatin sodium Form XLII, comprising:

a) dissolving fluvastatin in methanol, b) adding solid sodium hydroxide to the solution at elevated temperature, c) cooling the solution, d) adding ethyl acetate to form a slurry of Form XLII in the methanol, and e) separating Form XLII from the methanol.

211. A process for preparing fluvastatin sodium Form XLII comprising:

a) dissolving fluvastatin diol in a solution of dichloromethane, b) adding NaOH (s) dissolved in methanol to the solution to induce precipitation of Form XLII; and c) separating the solution from Form XLII.

212. A process for preparing fluvastatin sodium Form XLII comprising:

a) dissolving fluvastatin in dichloromethane, b) adding ethanolic or methanolic sodium hydroxide to the solution, c) precipitating Form XLII from the solution, and d) separating Form XLII from the solution.

213. A crystalline form of fluvastatin sodium characterized by a PXRD pattern having peaks at 4.25, 5.29, 6.59, 8.60±0.2 degrees two-theta.

214. The crystalline form of embodiment 213 further characterized by peaks at 12.75, 14.26±0.2 degrees two-theta.

Figure 63:
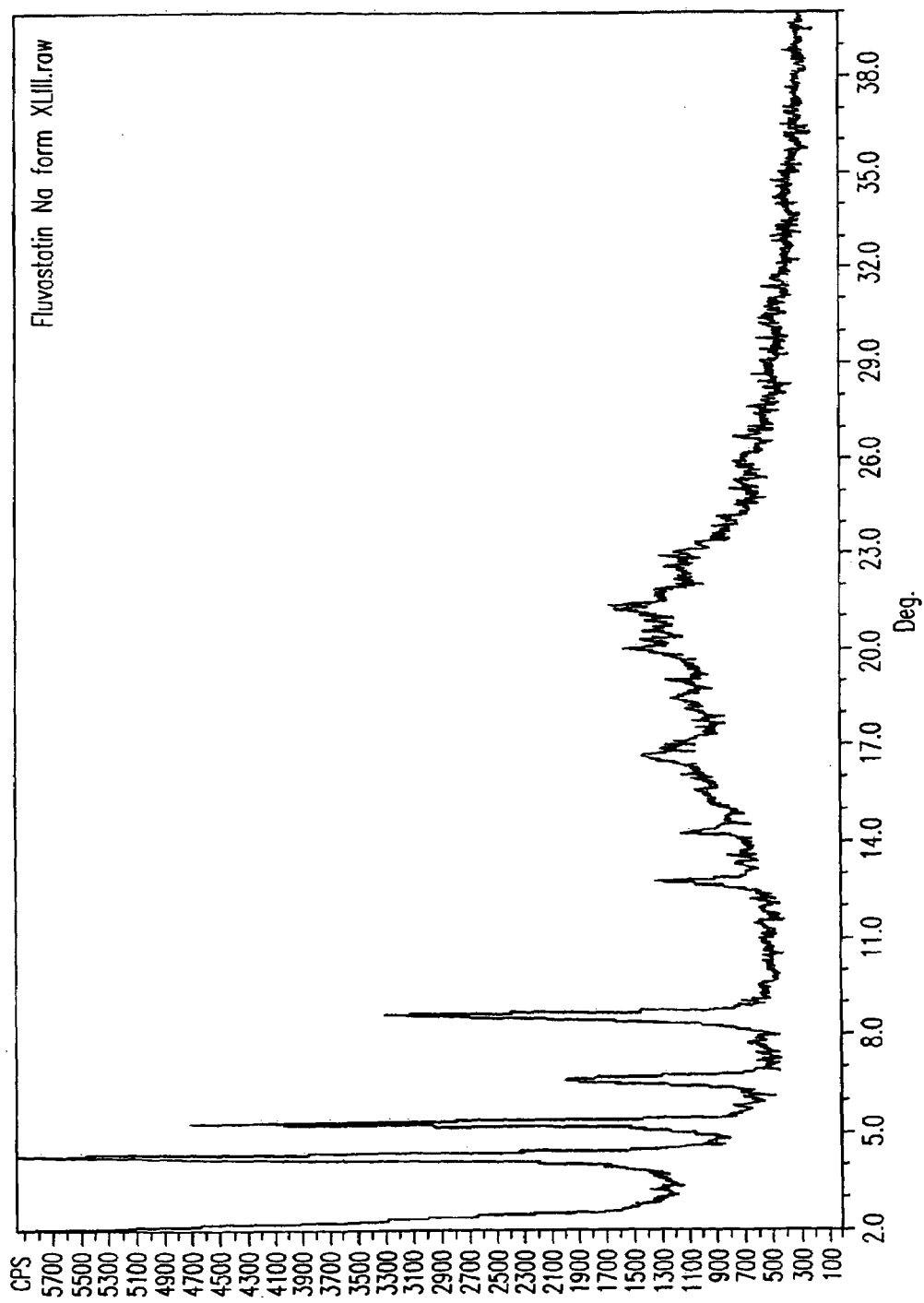
FIG. 63 depicts a powder X-ray diffractogram of fluvastatin sodium Form XLIII.

215. The crystalline form of embodiment 214 further characterized by a PXRD pattern substantially as depicted in FIG. 63.

216. The crystalline form of embodiment 213 wherein the crystalline form is fluvastatin sodium Form XLIII.

217. A process for preparing crystalline fluvastatin sodium Form XLIII comprising:

a) dissolving fluvastatin sodium in water, b) adding propan-2-ol to induce precipitation of Form XLIII, and c) separating the water and propan-2-ol from the Form XLIII.

218. A process for preparing crystalline fluvastatin sodium Form XLIII comprising:

a) dissolving a lower alkyl ester of fluvastatin in a solution of NaOH in water, b) adding propan-2-ol to the solution to induce precipitation of Form XLIII, and c) separating the solution from Form XLIII.

219. A crystalline form of fluvastatin sodium characterized by a PXRD pattern having peaks at 3.46, 4.05, 9.19, 10.14, 20.56±0.2 degrees two-theta.

220. The crystalline form of embodiment 219 further characterized by peaks at 6.26, 10.91, 11.12, 11.38, 15.98, 20.02, 22.21, 23.52, 25.45±0.2 degrees two-theta.

Figure 64:
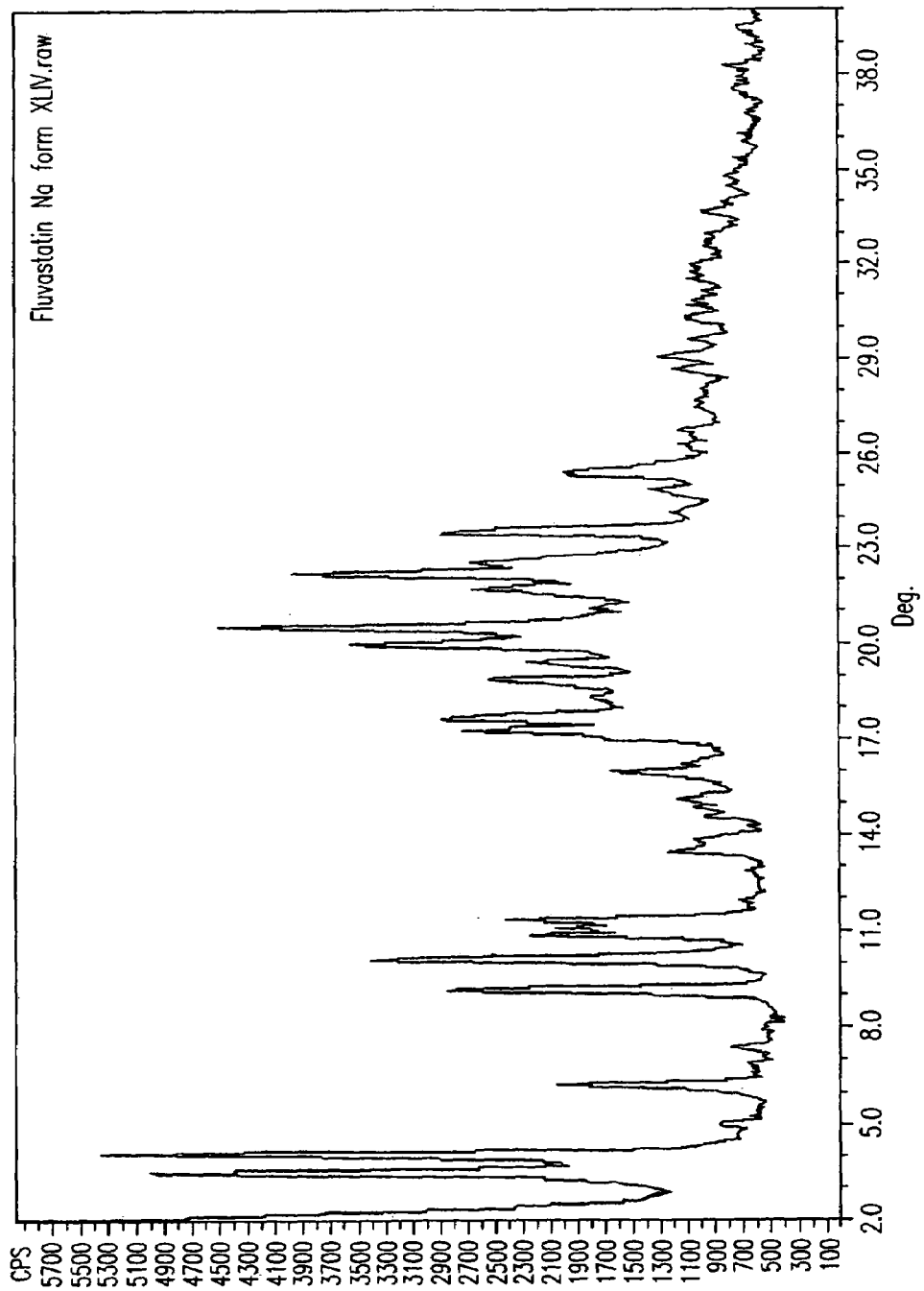
FIG. 64 depicts a powder X-ray diffractogram of fluvastatin sodium Form XLIV.

221. The crystalline form of embodiment 220 further characterized by a PXRD pattern substantially as depicted in FIG. 64.

222. The crystalline form of embodiment 219 wherein the crystalline form is Fluvastatin sodium form XLIV.

223. A process for preparing crystalline fluvastatin sodium Form XLIV comprising:

a) forming a heterogeneous mixture of amorphous fluvastatin sodium and propan-2-ol, b) maintaining the heterogeneous mixture at reflux temperature for a period of time to substantially convert amorphous fluvastatin sodium to Form XLIV, and c) recovering Form XLIV from the mixture.

224. A process for preparing crystalline fluvastatin sodium Form XLIV comprising:

a) dissolving fluvastatin free acid, lactone or mixture thereof in acetone to form a solution, b) mixing an ethanolic solution of sodium with the solution, c) maintaining the mixture for a period of time sufficient to precipitate fluvastatin sodium Form XLIV, and d) separating Form XLIV from the acetone and ethanol.

225. A crystalline form of fluvastatin sodium characterized by a PXRD pattern with peaks at 3.7, 5.1, 10.7, 17.8 and 20.3±0.2 degrees two-theta.

226. The crystalline form of embodiment 225 further characterized by peaks at 6.2, 14.5, 21.6, 22.6 and 25.2±0.2 degrees two-theta.

Figure 65:
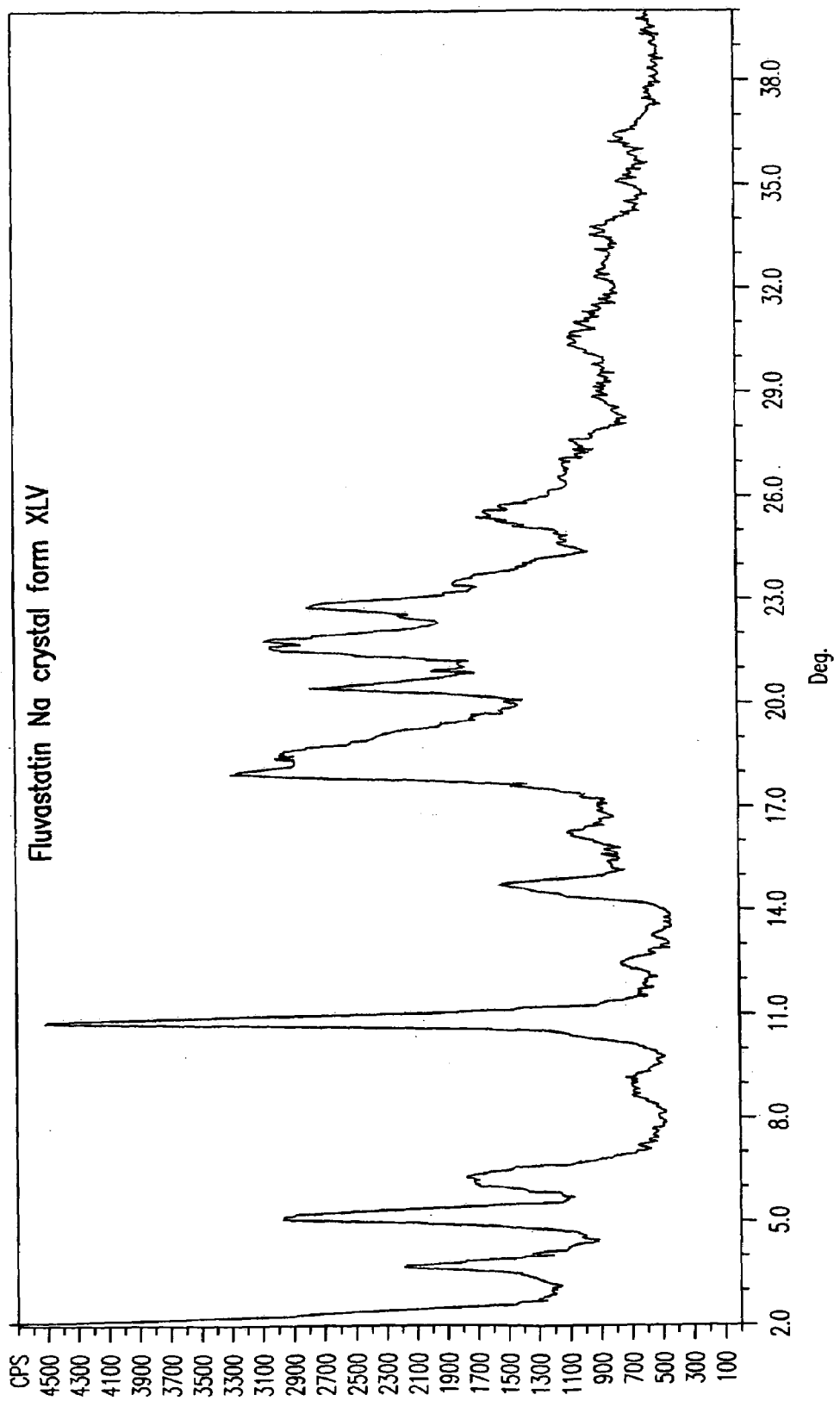
FIG. 65 depicts a powder X-ray diffractogram of fluvastatin sodium Form XLV.

227. The crystalline form of embodiment 226 wherein the crystalline form is characterized by a PXRD pattern substantially as depicted in FIG. 65.

228. The crystalline form of embodiment 225 wherein the crystalline form is fluvastatin sodium Form XLV.

229. A process for preparing crystalline fluvastatin sodium Form XLV comprising:

a) suspending amorphous fluvastatin sodium in propan-2-ol at room temperature to obtain Form XLV, and b) separating the propan-2-ol from the Form XLV.

230. A crystalline form of fluvastatin sodium characterized by a PXRD pattern with peaks at 3.3, 3.5, 10.2, 11.2 and 21.1±0.2 degrees two-theta.

231. The crystalline form of embodiment 230 further characterized by peaks at 9.7, 12.1, 17.2 and 19.0±0.2 degrees two-theta.

Figure 66:
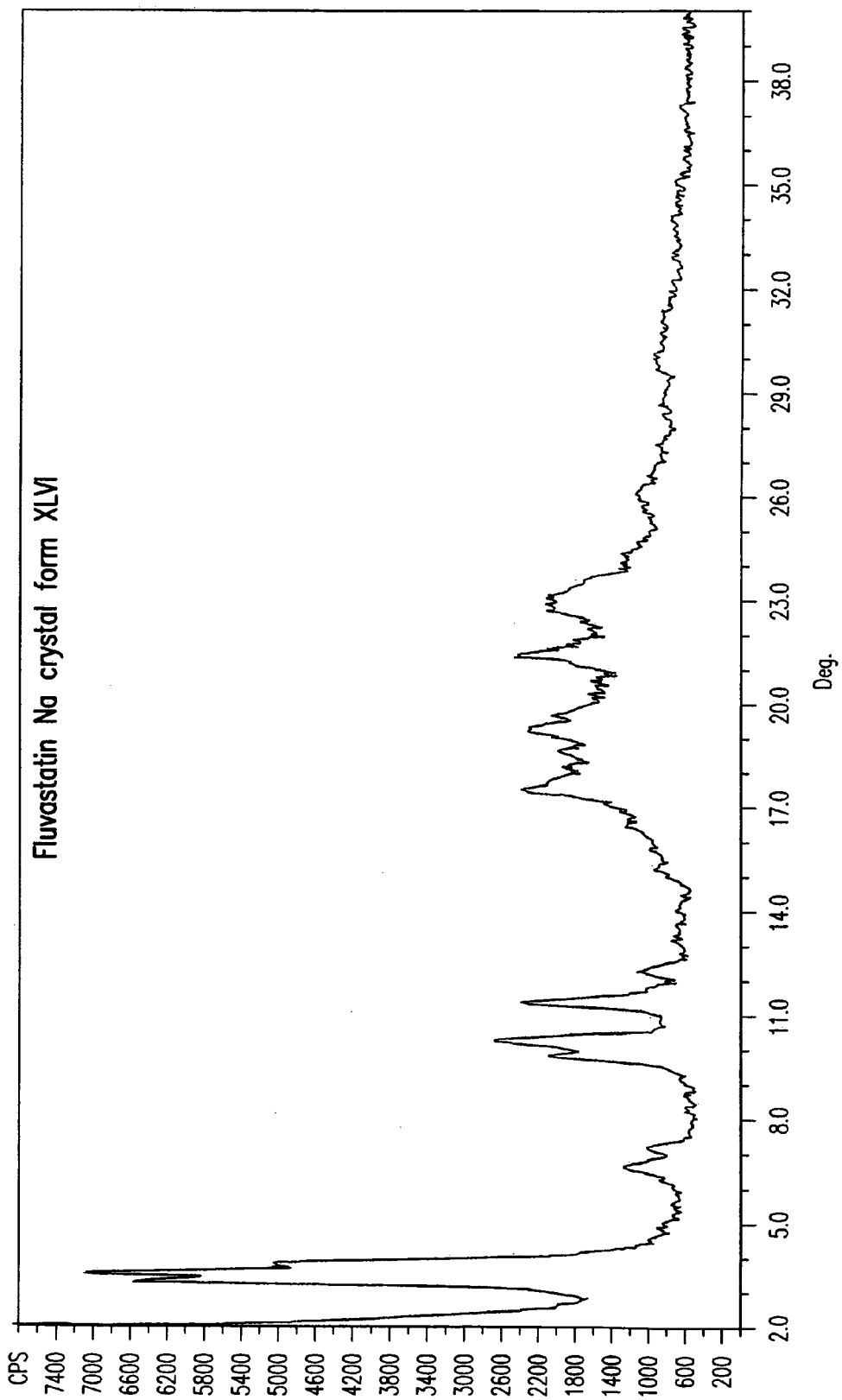
FIG. 66 depicts a powder X-ray diffractogram of fluvastatin sodium Form XLVI.

232. The crystalline form of embodiment 231 wherein the crystalline form is characterized by a PXRD pattern substantially as depicted in FIG. 66.

233. The crystalline form of embodiment 230 wherein the crystalline form is fluvastatin sodium Form XLVI.

234. A process for preparing crystalline fluvastatin sodium Form XLVI comprising:
   a) contacting a lower alkyl ester of fluvastatin with about one molar equivalent of sodium in ethanol,
   b) adding an excess of acetonitrile relative to the ethanol,
   c) precipitating Form XLVI from the mixture of ethanol and acetonitrile, and
   d) separating the ethanol and acetonitrile from the Form XLVI.

235. A crystalline form of fluvastatin sodium characterized by a PXRD pattern with peaks at 3.3, 10.2 and 18.0±0.2 degrees two-theta.

236. The crystalline form of embodiment 235 further characterized by peaks at 8.3, 10.8, 13.6, 20.7 and 21.3±0.2 degrees two-theta.

Figure 67:
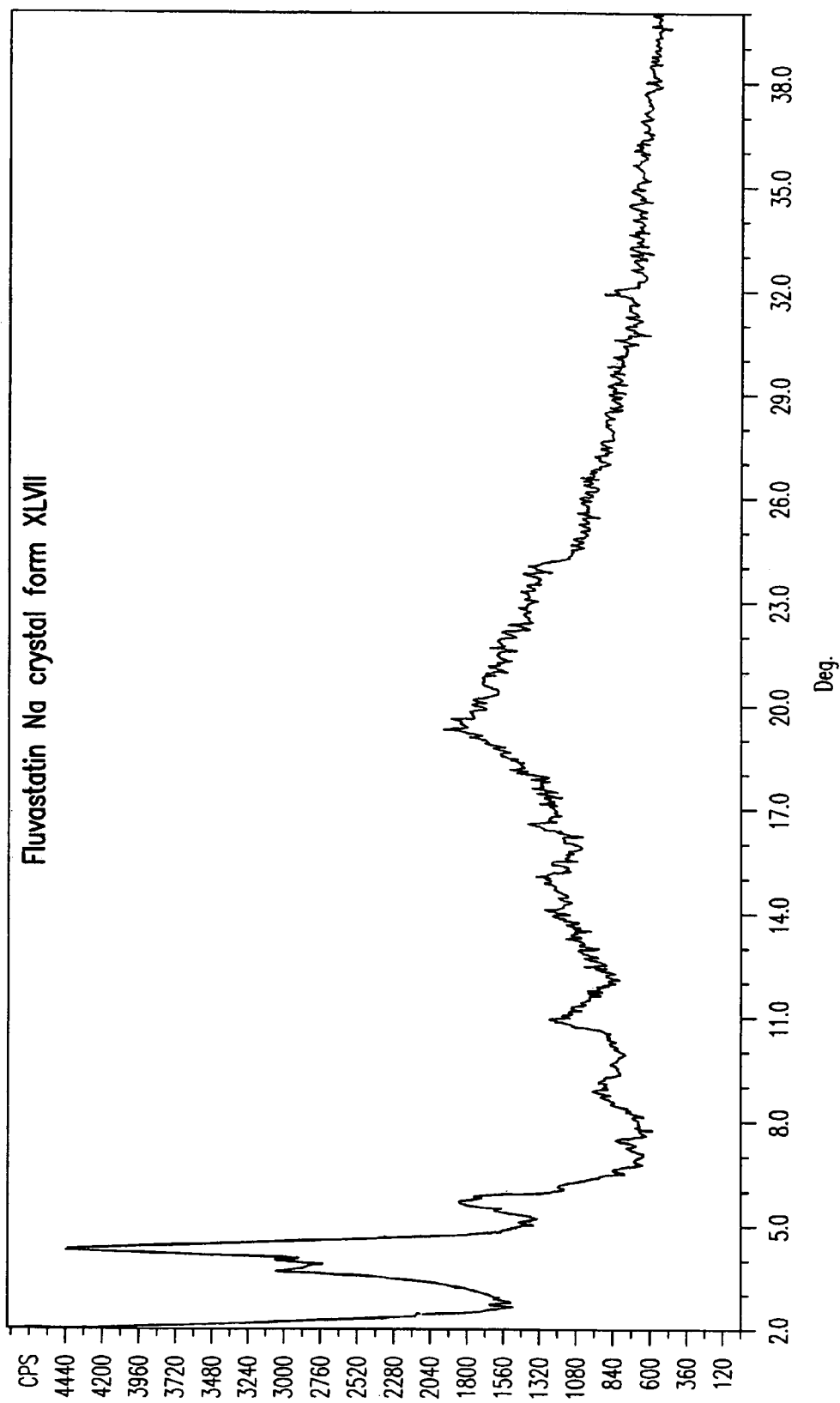
FIG. 67 depicts a powder X-ray diffractogram of fluvastatin sodium Form XLVII.

237. The crystalline form of embodiment 236 wherein the crystalline form is characterized by a PXRD pattern substantially as depicted in FIG. 67.

238. The crystalline form of embodiment 235 wherein the crystalline form is fluvastatin sodium Form XLVII.

239. A process for preparing crystalline fluvastatin sodium Form XLVII comprising:
   a) contacting fluvastatin sodium Form XVIII with water vapor in a vessel containing an atmosphere of controlled elevated humidity relative to the atmosphere outside of the vessel to convert the Form XV into Form XII, and
   b) ceasing control of the humidity within the vessel or removing the Form XV from the vessel.

240. A crystalline form of fluvastatin sodium characterized by a PXRD pattern having peaks at 4.5, 6.7, 7.0, 10.9, 19.1, 21.7±0.2 degrees two-theta.

241. The crystalline form of embodiment 240 further characterized by peaks at 8.9, 12.9, 13.1, 13.5, 15.2, 16.8, 17.6, 18.3, 19.7, 20.6±0.2 degrees two-theta.

Figure 68:
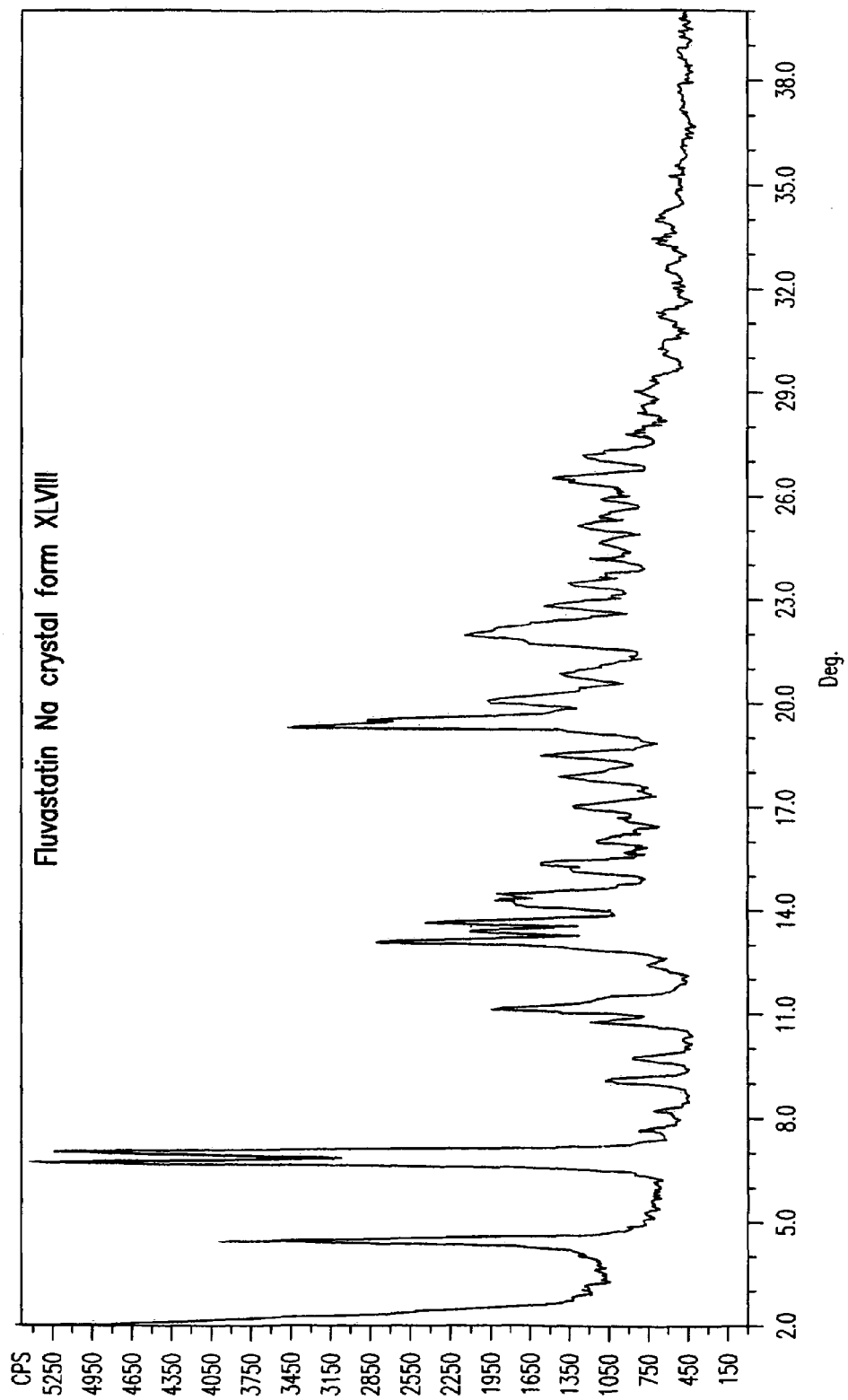
FIG. 68 depicts a powder X-ray diffractogram of fluvastatin sodium Form XLVIII.

242. The crystalline form of embodiment 241 further characterized by a PXRD pattern substantially as depicted in FIG. 68.

243. The crystalline form of embodiment 240 wherein the crystalline form is fluvastatin sodium Form XLVIII.

244. A process for preparing crystalline fluvastatin sodium Form XLVIII comprising:
   a) dissolving a lower alkyl ester of fluvastatin in a solution of NaOH in methanol to hydrolyze the ester,
   b) adding acetonitrile to the solution to induce precipitation of fluvastatin sodium, and
   c) separating fluvastatin sodium from the methanol and acetonitrile.

245. A process for preparing crystalline fluvastatin sodium Form XLVIII comprising:
   a) slurrying fluvastatin sodium Form B in methanol at reflux temperature,
   b) cooling the slurry,
   c) stirring the slurry solution at room temperature,
   d) separating fluvastatin sodium from the methanol as Form XLVIII.

246. A process for preparing crystalline fluvastatin sodium Form XLVIII comprising:
   a) dissolving fluvastatin sodium in methanol at ambient temperature,
   b) heating the solution to reflux temperature to induce precipitation of Form XLVIII,
   c) cooling the resulting slurry to room temperature,
   d) stirring the slurry solution at room temperature, and
   e) separating Form XLVIII from the methanol.

247. A process for preparing crystalline fluvastatin sodium Form XLVIII comprising:
   a) dissolving fluvastatin in refluxing methanol,
   b) adding solid sodium hydroxide to the solution at reflux temperature to induce precipitation of Form XLVIII,
   c) cooling the resulting slurry to ambient temperature,
   d) stirring the slurry at room temperature; and
   e) separating Form XLVIII from the methanol.

248. A process for preparing crystalline fluvastatin sodium Form XLVIII comprising:
   a) dissolving fluvastatin in methanol at reflux temperature,
   b) adding solid sodium hydroxide to the resulting solution at reflux temperature to induce precipitation of Form XLVIII,
   c) cooling the resulting slurry to ambient temperature,
   d) adding acetone to the slurry, and
   e) separating Form XLVIII from the methanol and acetone.

249. A crystalline form of fluvastatin sodium characterized by a PXRD pattern with peaks at 3.5, 5.0, 12.1, 13.5 and 20.2±0.2 degrees two-theta.

250. The crystalline form of embodiment 249 further characterized by peaks at 6.3, 10.1 and 17.1±0.2 degrees two-theta.

Figure 69:
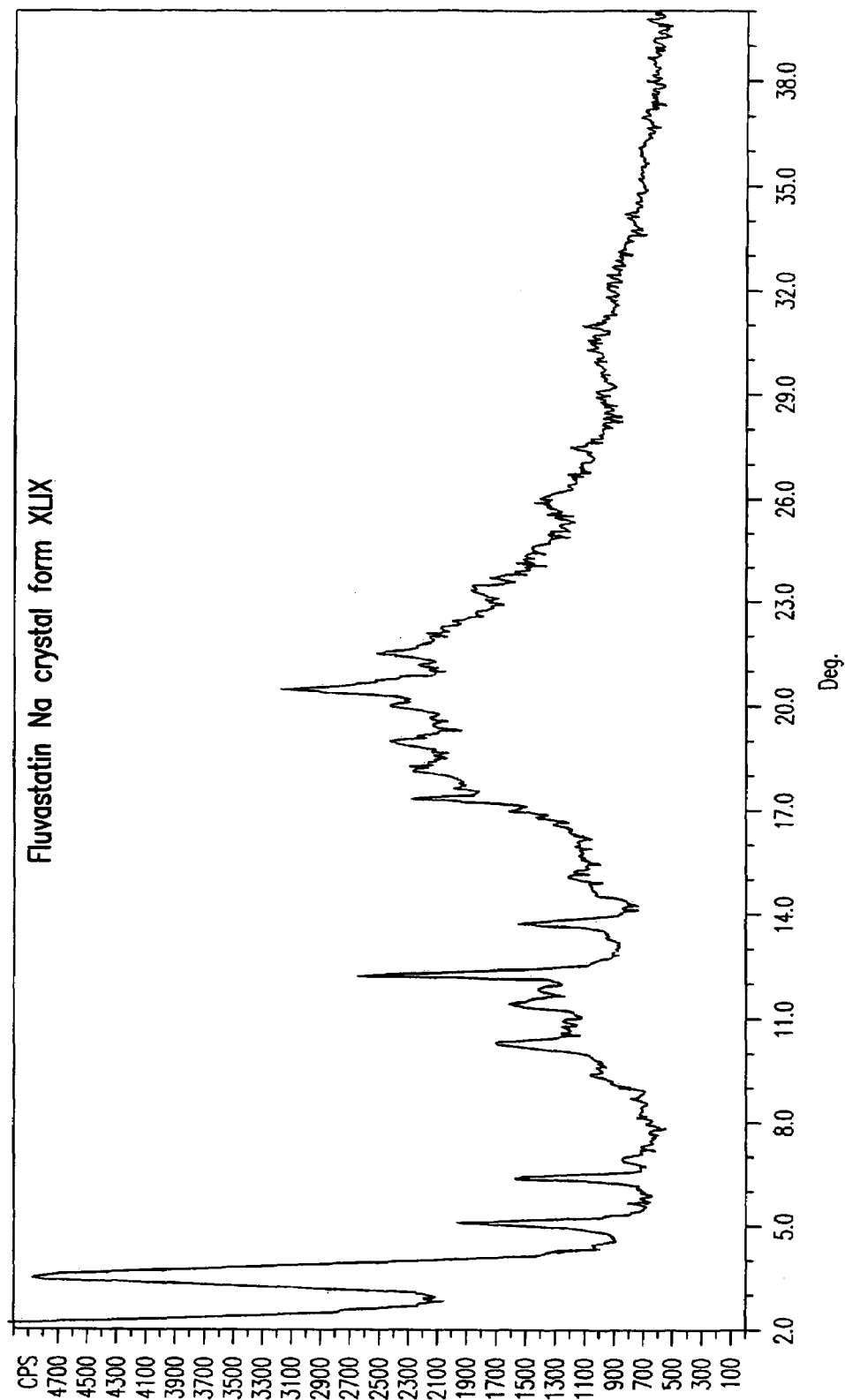
FIG. 69 depicts a powder X-ray diffractogram of fluvastatin sodium Form XLIX.

251. The crystalline form of embodiment 250 wherein the crystalline form is characterized by a PXRD pattern substantially as depicted in FIG. 69.

252. The crystalline form of embodiment 249 wherein the crystalline form is fluvastatin sodium Form XLIX.

253. A process for preparing crystalline fluvastatin sodium Form XLIX comprising:
   a) heating a solution of fluvastatin sodium in methanol to an elevated temperature,
   b) adding methyl tert-butyl ether to the methanol at elevated temperature to induce precipitation of Form XLIX, and
   c) separating the methanol and methyl tert-butyl ether from the Form XLIX.

254. A crystalline form of fluvastatin sodium characterized by a PXRD pattern having peaks at 6.48, 6.92, 9.72, 12.64, 21.49±0.2 degrees two-theta.

255. The crystalline form of embodiment 254 further characterized by peaks at 4.53, 12.06, 13.50, 14.79, 15.79, 16.32, 19.15, 23.19±0.2 degrees two-theta.

Figure 70:
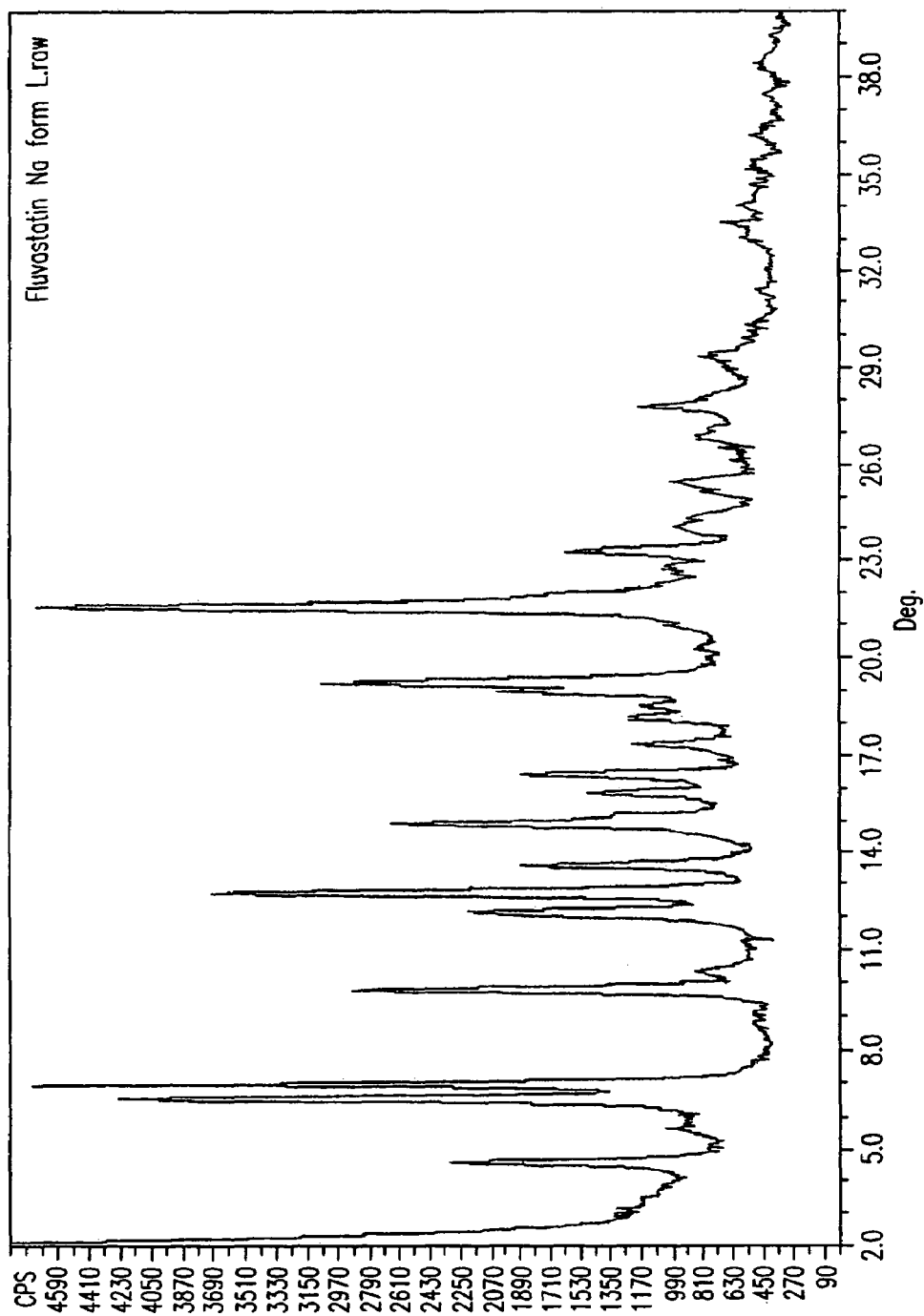
FIG. 70 depicts a powder X-ray diffractogram of fluvastatin sodium Form L.

256. The crystalline form of embodiment 255 further characterized by a PXRD pattern substantially as depicted in FIG. 70.

257. The crystalline form of embodiment 254 wherein the crystalline form is fluvastatin sodium Form L.

258. A process for preparing crystalline fluvastatin sodium Form L comprising:
   a) dissolving fluvastatin sodium in methanol,
   b) adding ethyl acetate to the solution at ambient temperature to induce precipitation of Form L, and
   c) separating the methanol and ethyl acetate from Form L.

259. A crystalline form of fluvastatin sodium characterized by a PXRD pattern with peaks at 6.2, 10.8, 14.5 and 20.7±0.2 degrees two-theta.

260. The crystalline form of embodiment 259 further characterized by peaks at 8.9, 11.5 and 23.1±0.2 degrees two-theta.

Figure 71:
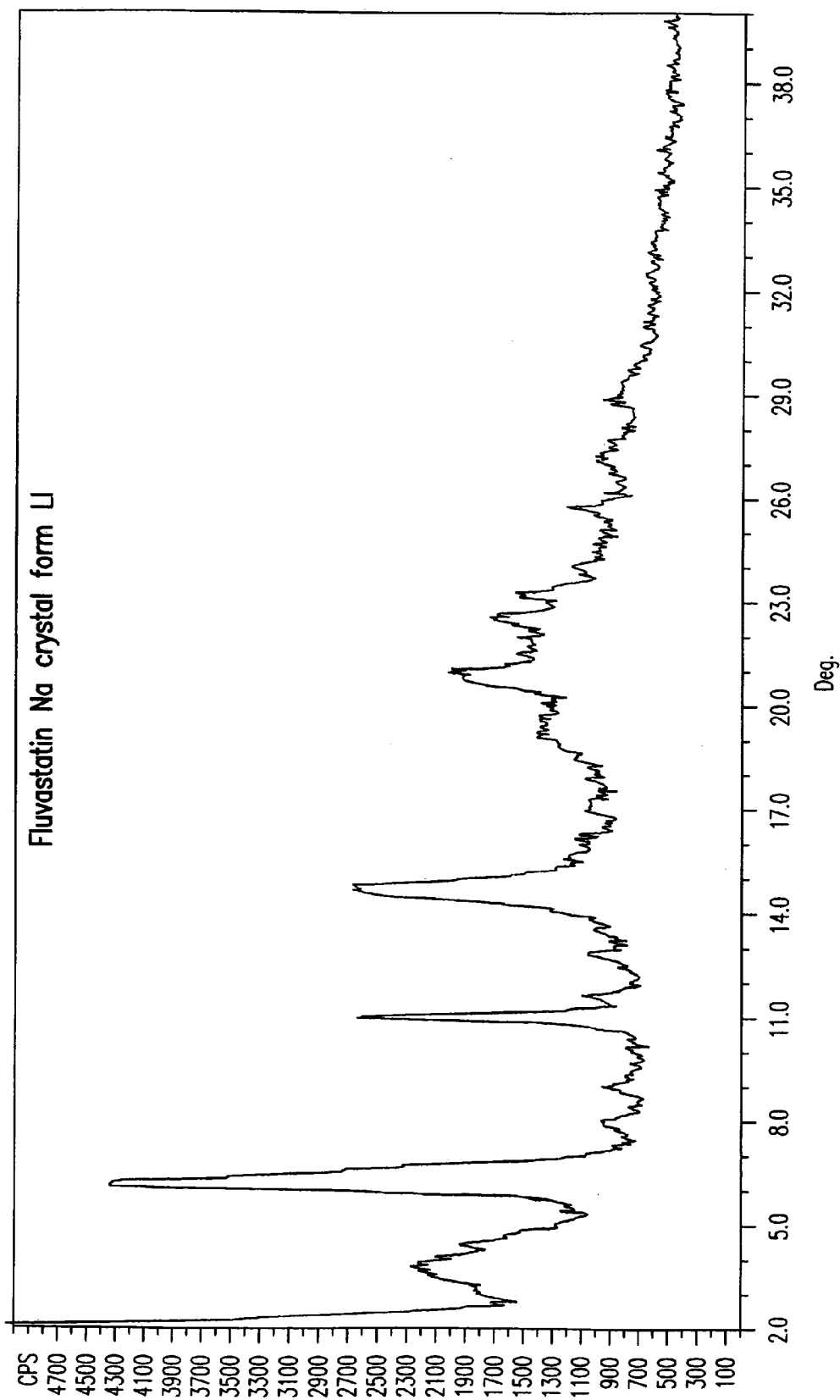
FIG. 71 depicts a powder X-ray diffractogram of fluvastatin sodium Form LI.
Figure 72:
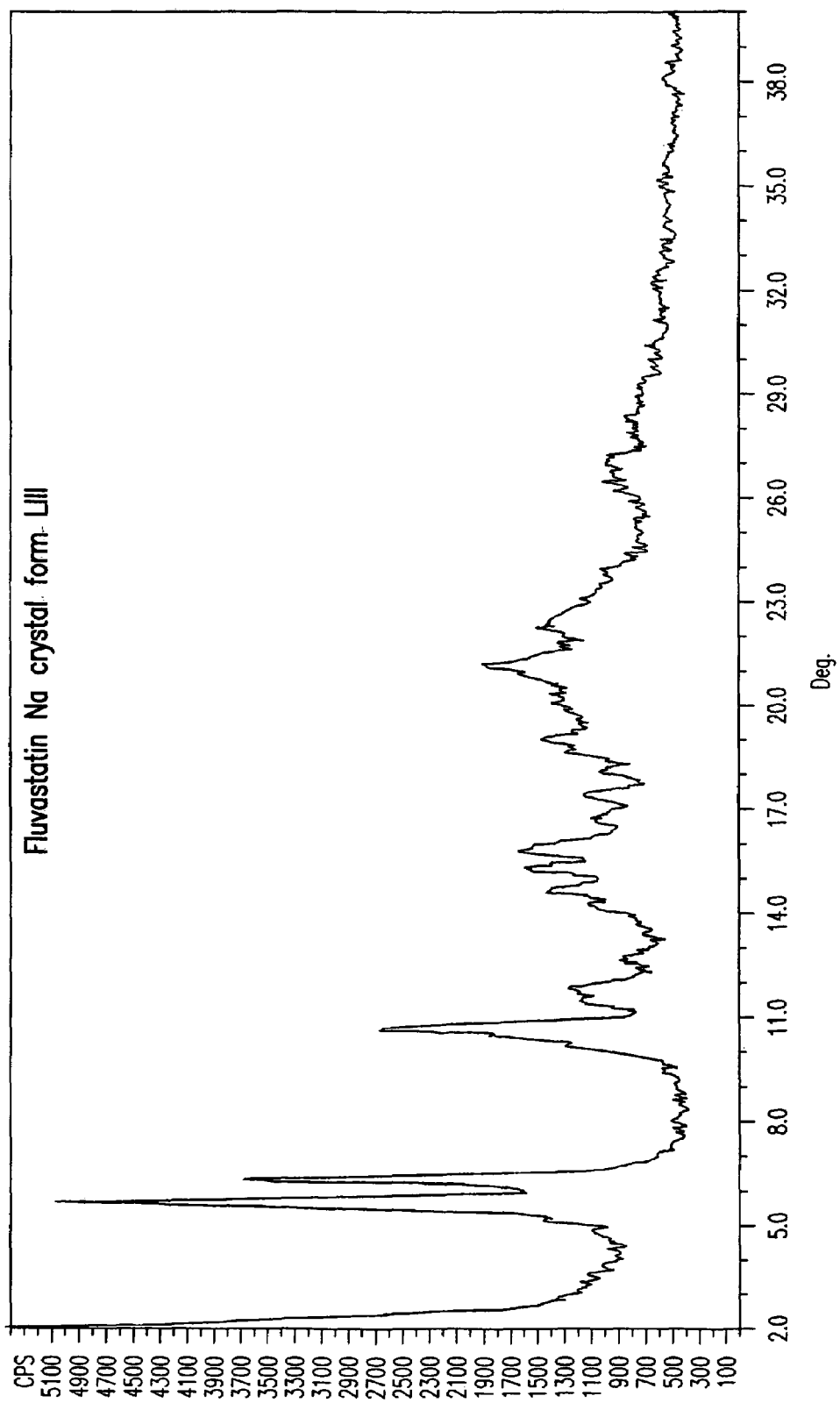
FIG. 72 depicts a powder X-ray diffractogram of fluvastatin sodium Form LIII.
Figure 73:
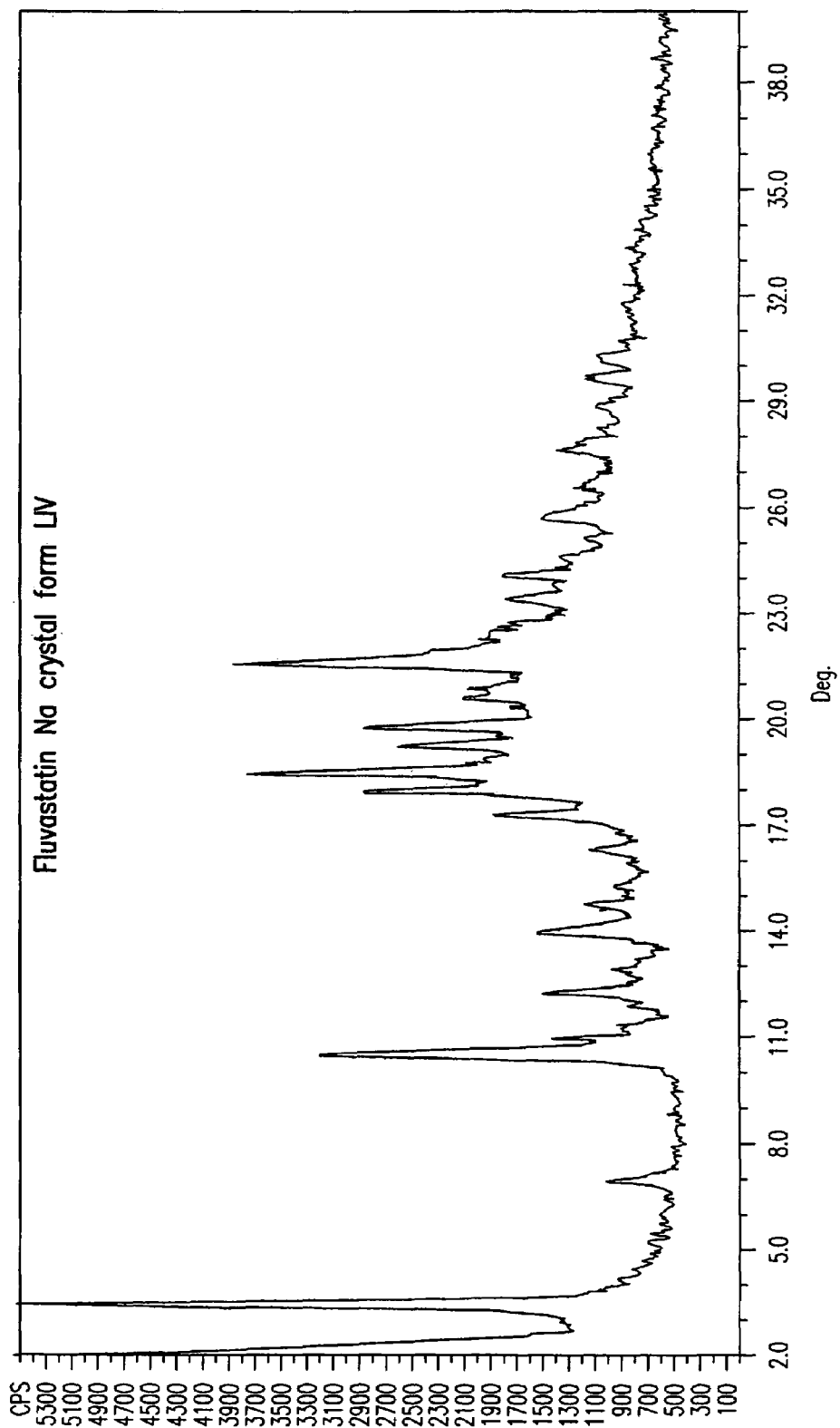
FIG. 73 depicts a powder X-ray diffractogram of fluvastatin sodium Form LIV.
Figure 74:
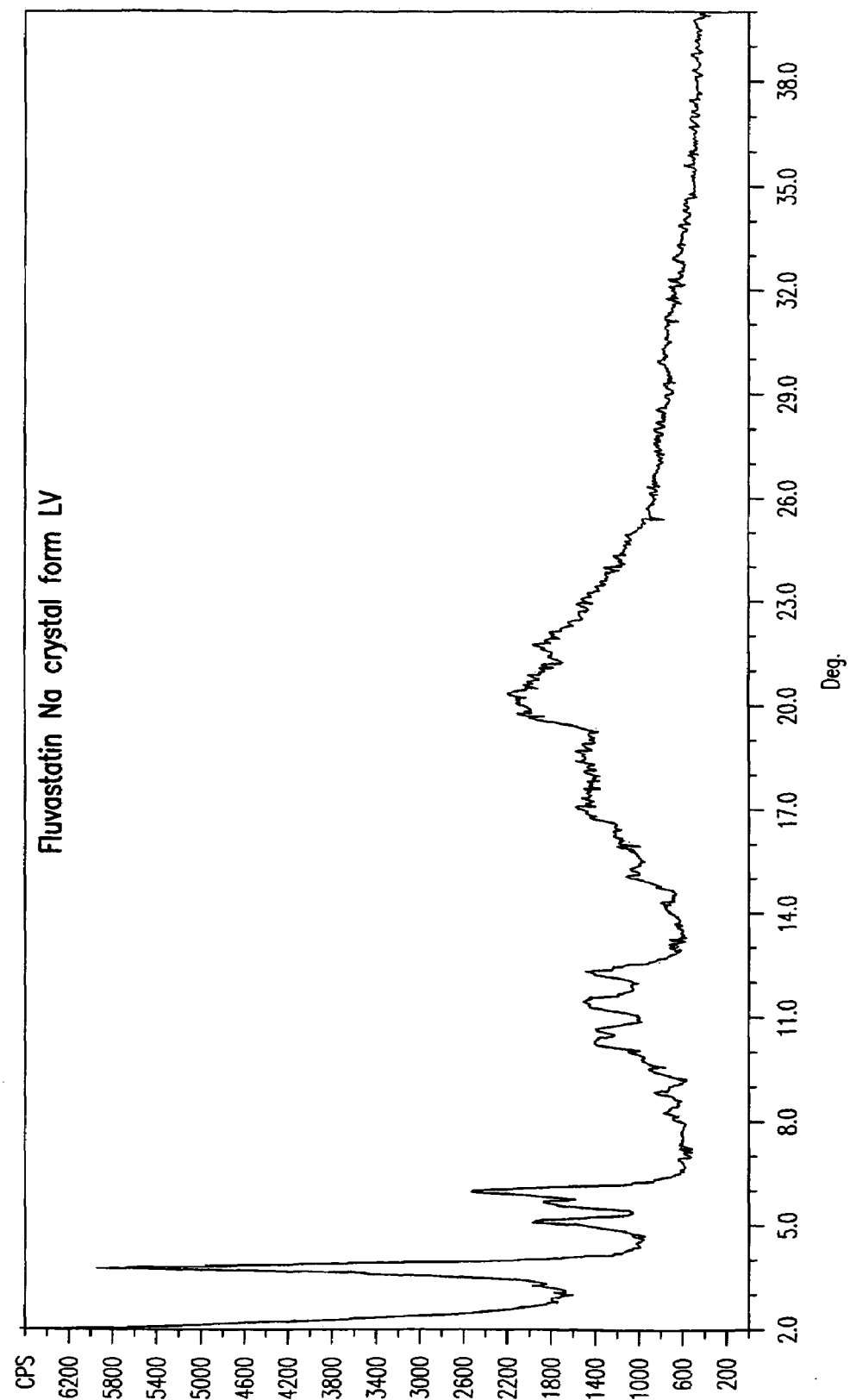
FIG. 74 depicts a powder X-ray diffractogram of fluvastatin sodium Form LV.
Figure 75:
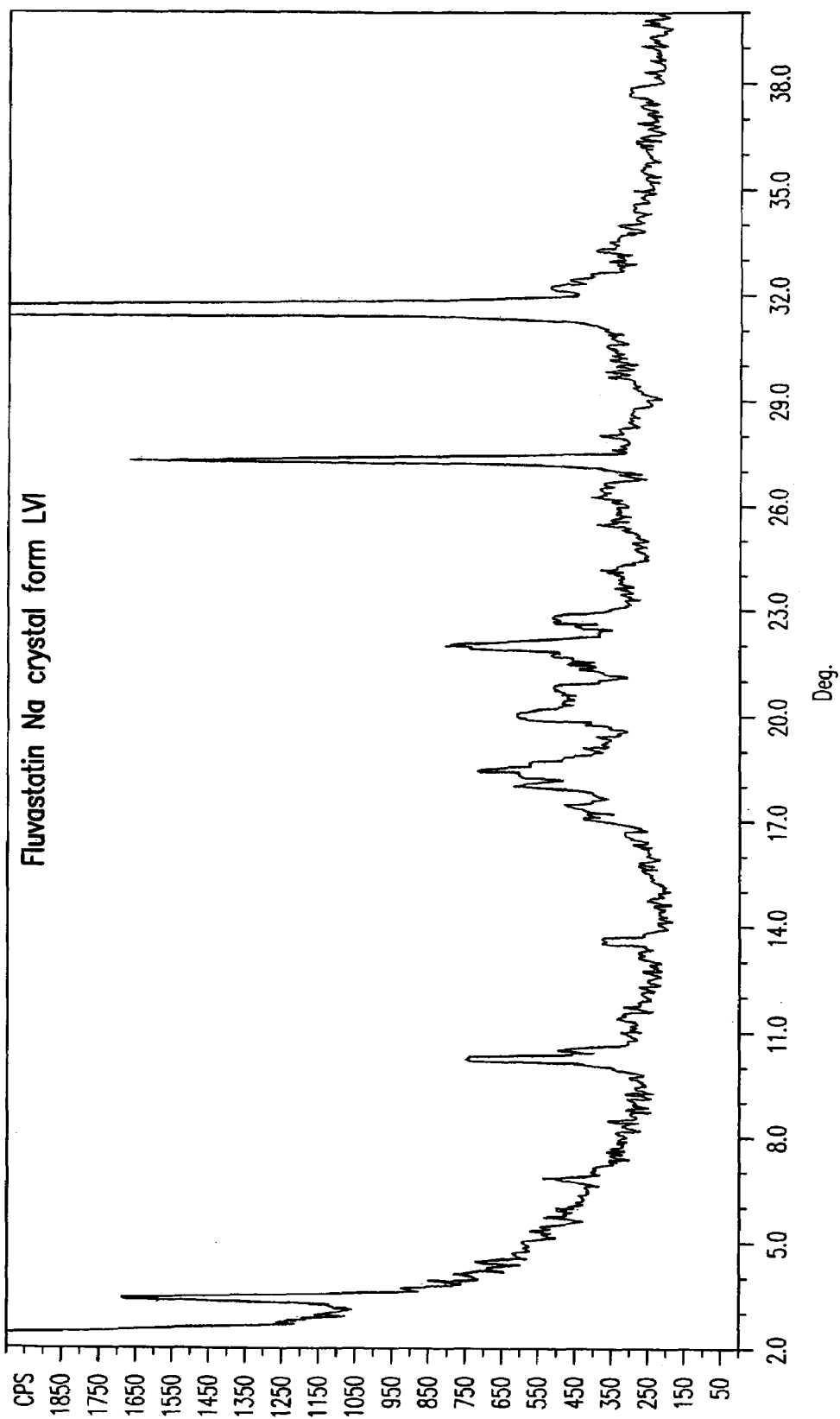
FIG. 75 depicts a powder X-ray diffractogram of fluvastatin sodium Form LVI.
Figure 76:
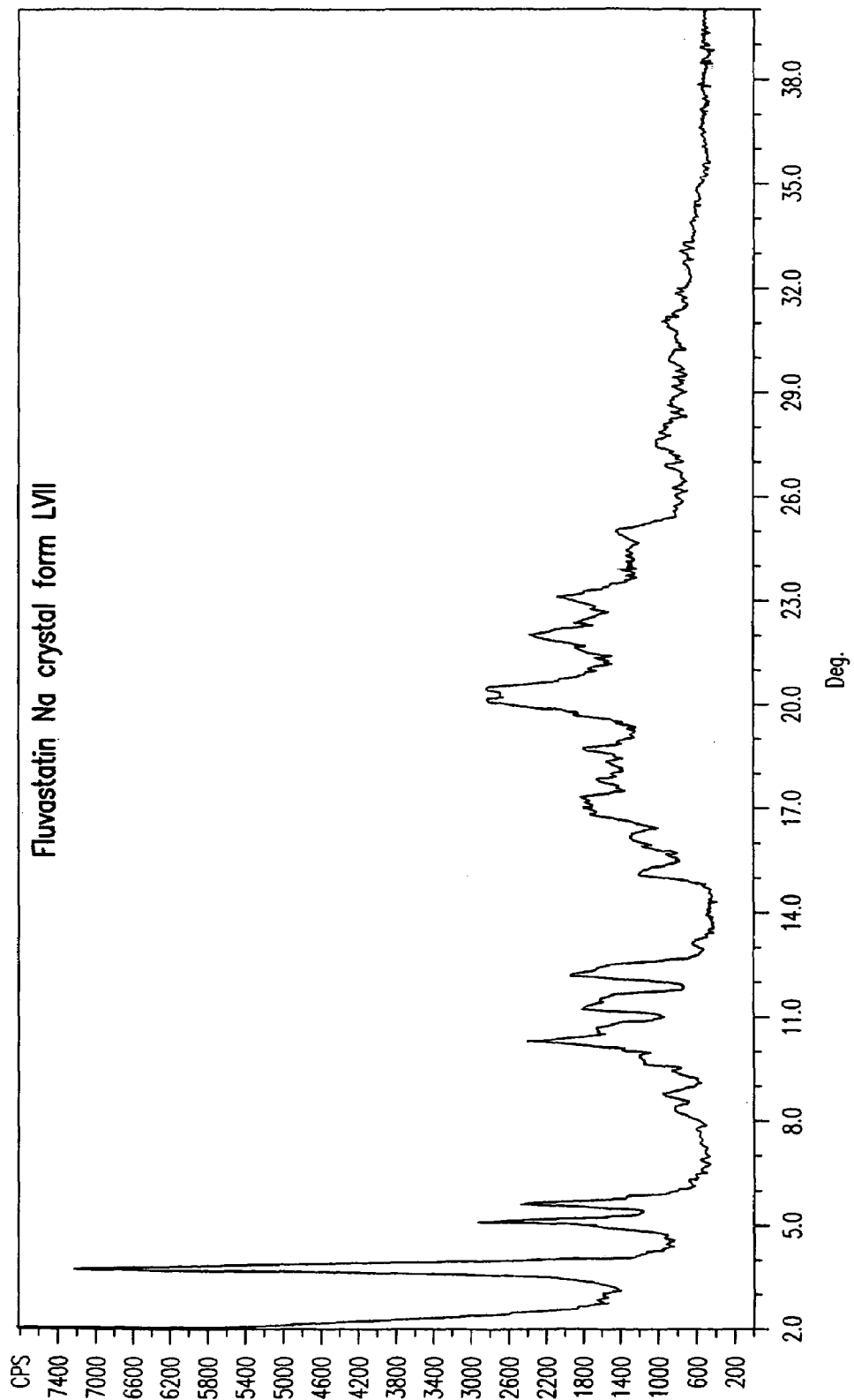
FIG. 76 depicts a powder X-ray diffractogram of fluvastatin sodium Form LVII
Figure 77:
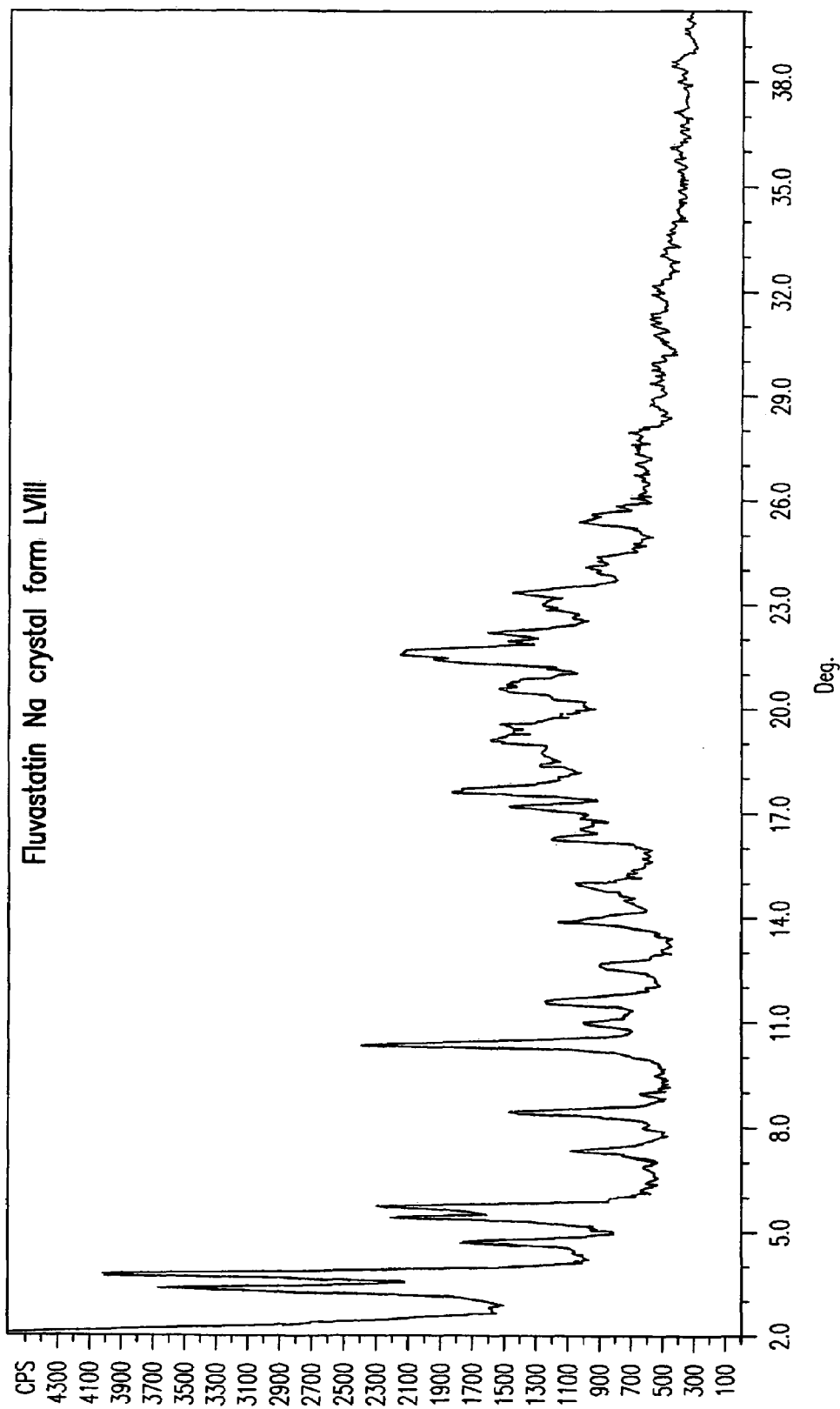
FIG. 77 depicts a powder X-ray diffractogram of fluvastatin sodium Form LVIII.

261. The crystalline form of embodiment 260 wherein the crystalline form is characterized by a PXRD pattern substantially as depicted in FIG. 71.
262. The crystalline form of embodiment 259 wherein the crystalline form is fluvastatin sodium Form LI.
263. A process for preparing crystalline fluvastatin sodium Form LI comprising:
   a) heating a solution of fluvastatin sodium in methanol to an elevated temperature,
   b) adding acetonitrile to the methanol at elevated temperature to induce precipitation of Form LI, and
   c) separating the methanol and acetonitrile from the Form LI.
264. A crystalline form of fluvastatin sodium characterized by a PXRD pattern with peaks at 5.6, 6.3, 10.5, 20.9±0.2 degrees two-theta.
265. The crystalline form of embodiment 264 further characterized by peaks at 14.3, 15.1, 15.6 and 17.1±0.2 degrees two-theta.
266. The crystalline form of embodiment 265 wherein the crystalline form is characterized by a PXRD pattern substantially as depicted in FIG. 72.
267. The crystalline form of embodiment 264 wherein the crystalline form is fluvastatin sodium Form LIII.
268. A process for preparing crystalline fluvastatin sodium Form LIII comprising:
   a) heating a solution of fluvastatin sodium in methanol to an elevated temperature,
   b) adding ethyl acetate to the methanol at elevated temperature to induce precipitation of Form LIII, and
   c) separating the methanol and ethyl acetate from the Form LIII.
269. A crystalline form of fluvastatin sodium, wherein the crystalline form is characterized by a PXRD pattern with peaks at 3.4, 10.4, 18.2, 19.6, 21.3±0.2 degrees two-theta.
270. The crystalline form of embodiment 269 wherein the crystalline form is further characterized by a PXRD pattern with peaks at 6.9, 12.1, 13.8, 17.7, 19.0±0.2 degrees two-theta.
271. The crystalline form of embodiment 270 wherein the crystalline form is characterized by a PXRD pattern substantially as depicted in FIG. 73.
272. The crystalline form of embodiment 269 wherein the crystalline form is fluvastatin form LIV.
273. A process for preparing crystalline fluvastatin sodium Form LIV comprising:
   a) contacting fluvastatin with an aqueous sodium hydroxide for a period of time sufficient to form a suspension, and
   b) separating Form LIV from the water.
274. A crystalline form of fluvastatin sodium characterized by a PXRD pattern having peaks at 3.7, 5.0, 5.9, 12.2±0.2 degrees two-theta.
275. The crystalline form of 274 embodiment wherein the crystalline form is further characterized by peaks at 5.6, 8.7, 10.1, 11.2±0.2 degrees two-theta.
276. The crystalline form of embodiment 275 wherein the crystalline form is characterized by a PXRD pattern substantially as depicted in FIG. 74.
277. The crystalline form of embodiment 274 wherein the crystalline form is Fluvastatin sodium form LV.
278. A process for preparing crystalline fluvastatin sodium Form LV comprising:
   a) dissolving a lower alkyl ester of fluvastatin in acetonitrile,
   b) adding a solution of about one equivalent of sodium hydroxide in methanol,
   c) precipitating fluvastatin sodium Form LV from the solution, and
   d) separating fluvastatin sodium Form LV from the solution.
279. A crystalline form of fluvastatin sodium characterized by a PXRD pattern with peaks at 3.4, 22.1 and 27.4±0.2 degrees two-theta.
280. The crystalline form of embodiment 279 further characterized by peaks at 6.8, 10.2, 13.6, 18.5 and 20.0±0.2 degrees two-theta.
281. The crystalline form of embodiment 280 wherein the crystalline form is characterized by a PXRD pattern substantially as depicted in FIG. 75.
282. The crystalline form of embodiment 279 wherein the crystalline form is fluvastatin sodium Form LVI.
283. A process for preparing crystalline fluvastatin sodium Form LVI comprising:
   a) cleaving the ketal group a lower alkyl ester derivative of fluvastatin having a ketal protecting group on the ∃and * hydroxyl groups in a tetrahydrofuran solution under acidic conditions,
   b) adding sodium hydroxide to neutralize the solution,
   c) evaporating the tetrahydrofuran to leave a residue,
   d) dissolving the residue in acetone,
   e) adding about a molar equivalent of sodium hydroxide to the acetone,
   f) precipitation Form LVI from the acetone, and
   g) separating the acetone from the Form LVI.
284. A crystalline form of fluvastatin sodium characterized by a PXRD pattern having peaks at 3.7, 5.0, 5.5, 10.1, 12.1±0.2 degrees 2 theta.
285. The crystalline form of embodiment 284 wherein the crystalline form is further characterized by peaks at 8.6, 11.1, 14.9, 21.7, 22.8±0.2 degrees two-theta.
286. The crystalline form of embodiment 285 wherein the crystalline form is characterized by a PXRD pattern as substantially depicted in FIG. 76.
287. The crystalline form of embodiment 284 wherein the crystalline form is fluvastatin sodium Form LVII.
288. A process for preparing crystalline fluvastatin sodium Form LVII comprising:
   a) forming a heterogeneous mixture of fluvastatin sodium Form VII in ethanol,
   b) maintaining the heterogeneous mixture to convert Form VII into fluvastatin sodium Form LVII, and
   c) separating the Form LVII from the ethanol.
289. A crystalline form of Fluvastatin sodium characterized by a PXRD pattern having peaks at 3.4, 3.8, 5.4, 5.7, 10.3±0.2 degrees two-theta.
290. The crystalline form of embodiment 289 wherein the crystalline form is further characterized by peaks at 4.7, 7.2, 8.4, 11.5, 17.5, 20.4, 21.4, 23.1±0.2 degrees two-theta.
291. The crystalline form of embodiment 290 further characterized by a PXRD pattern substantially as depicted in FIG. 77.
292. The crystalline form of embodiment 289 wherein the crystalline form is fluvastatin sodium form LVIII.
293. A process for preparing crystalline Fluvastatin Na Form LVIII comprising:
   a) forming a heterogeneous mixture of fluvastatin sodium Form B in propan-2-ol,
   b) maintaining the mixture to convert Form B into fluvastatin sodium Form LVIII, and
   c) separating Form LVIII from the propan-2-ol.
294. A crystalline form of fluvastatin sodium characterized by a PXRD pattern with peaks at 3.5, 5.7, 10.8, 18.2 and 21.6±0.2 degrees two-theta.

295. The crystalline form of embodiment 294 further characterized by peaks at 12.4, 14.7, 20.4, 22.4 and 25.4±0.2 degrees two-theta.

Figure 84:
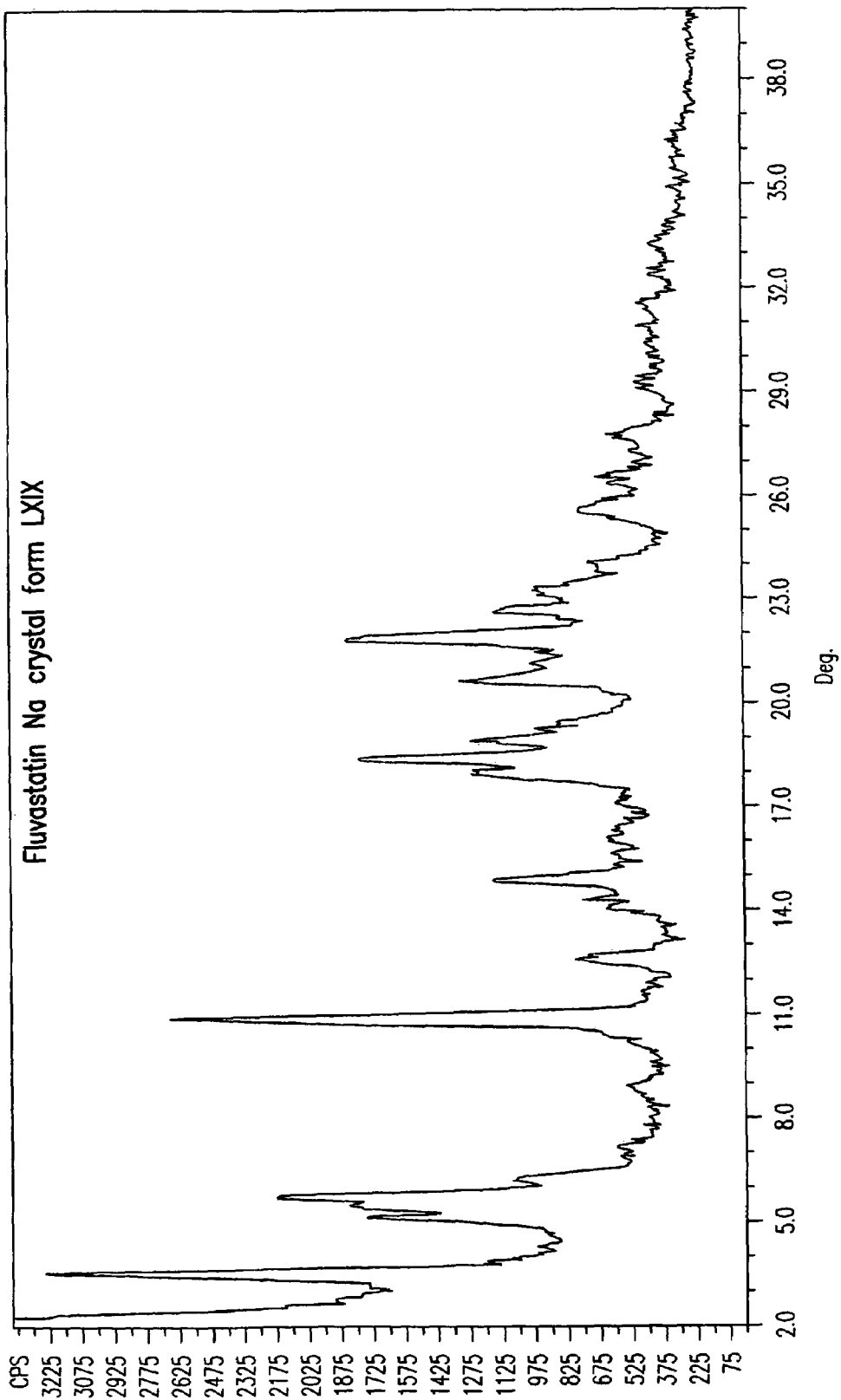
FIG. 84 depicts a powder X-ray diffractogram of fluvastatin sodium Form LXIX.

296. The crystalline form of embodiment 295 wherein the crystalline form is characterized by a PXRD pattern substantially as depicted in FIG. 84.

297. The crystalline form of embodiment 294 wherein the crystalline form is fluvastatin sodium Form LXIX.

298. A process for preparing crystalline fluvastatin sodium Form LXIX comprising:
   a) forming a heterogeneous mixture of fluvastatin sodium Form VI and propan-2-ol,
   b) maintaining the heterogeneous mixture for a period of time sufficient to convert Form VI to Form LXIX, and
   c) separating the propan-2-ol from the Form LXIX.

299. A crystalline form of fluvastatin sodium characterized by a PXRD pattern with peaks at 3.0, 3.4, 5.9, and 13.8±0.2 degrees two-theta.

300. The crystalline form of embodiment 299 further characterized by peaks at 8.2, 8.9, 18.6, 21.1 and 22.4±0.2 degrees two-theta.

Figure 85:
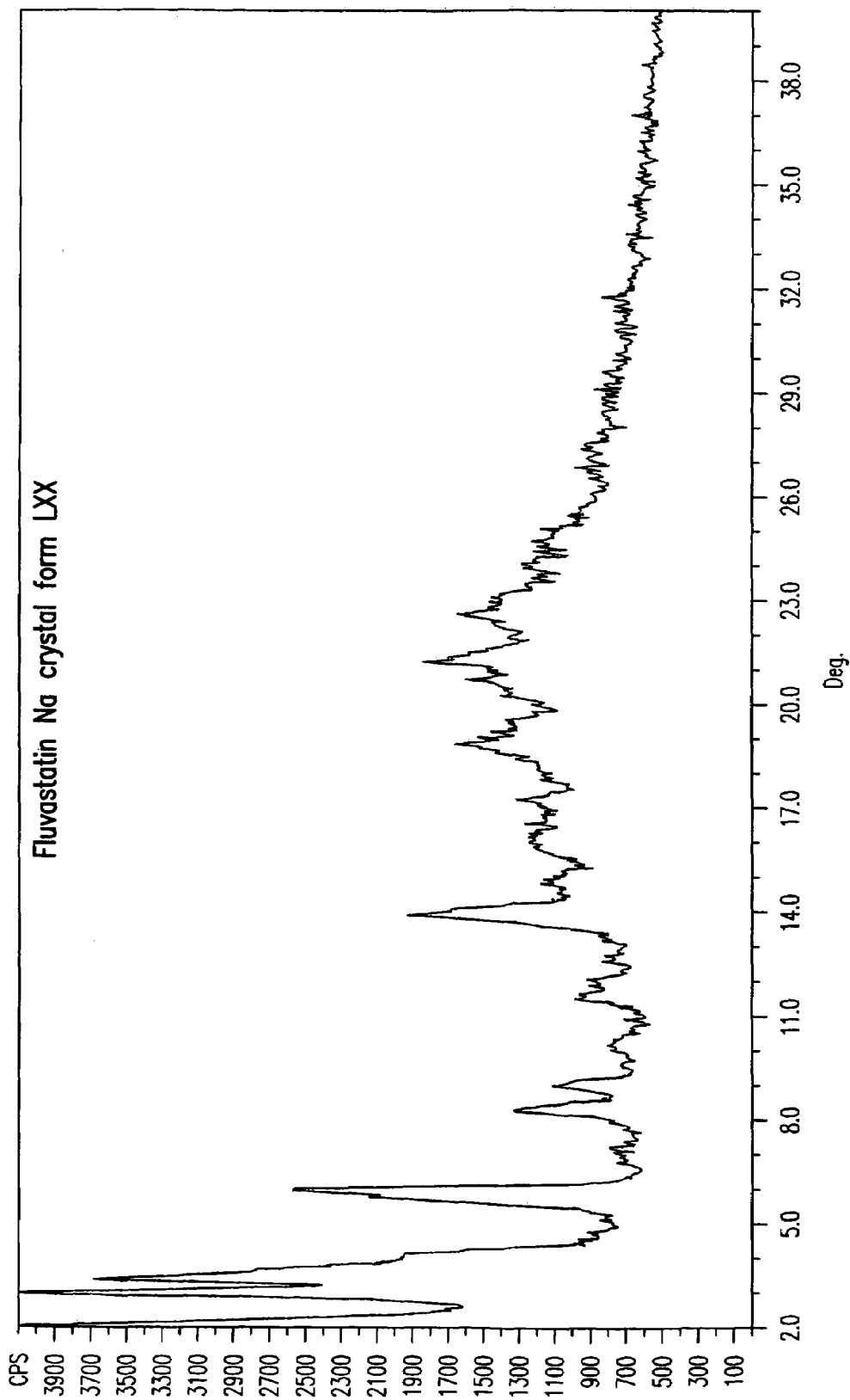
FIG. 85 depicts a powder X-ray diffractogram of fluvastatin sodium Form LXX.

301. The crystalline form of embodiment 300 wherein the crystalline form is characterized by a PXRD pattern substantially as depicted in FIG. 85.

302. The crystalline form of embodiment 299 wherein the crystalline form is fluvastatin sodium Form LXX.

303. A process for preparing crystalline fluvastatin sodium Form LXX comprising:
   a) dissolving in water at elevated temperature,
   b) adding an excess of acetone to the water to induce precipitation of Form LXX, and
   c) separating the water and acetone from the Form LXX.

304. A crystalline form of fluvastatin sodium characterized by a PXRD pattern with peaks at 3.9, 7.8, 11.6 and 15.5±0.2 degrees two-theta.

305. The crystalline form of embodiment 304 further characterized by peaks at 9.2, 13.3, 19.0 and 23.2±0.2 degrees two-theta.

Figure 86:
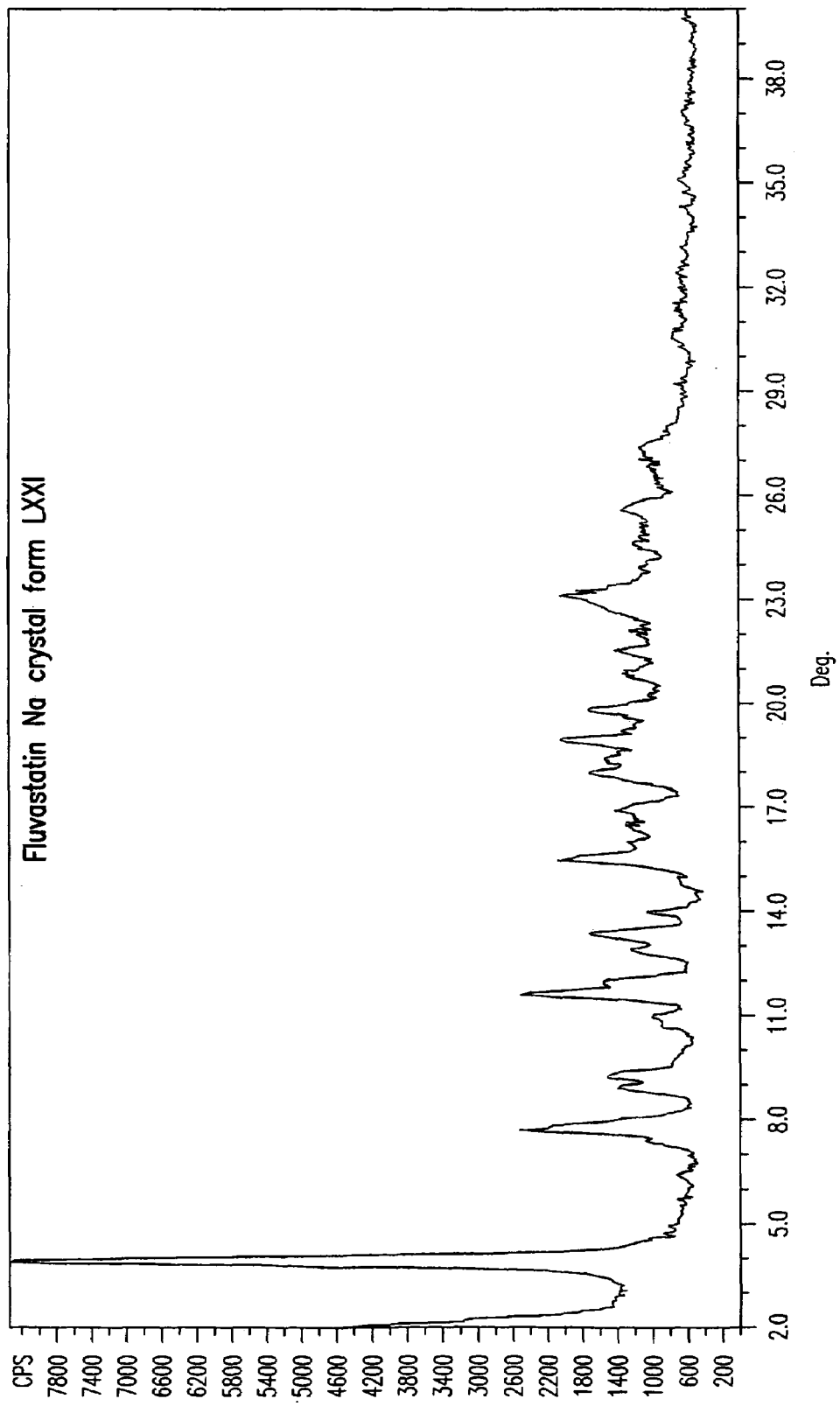
FIG. 86 depicts a powder X-ray diffractogram of fluvastatin sodium Form LXXI.

306. The crystalline form of embodiment 305 wherein the crystalline form is characterized by a PXRD pattern substantially as depicted in FIG. 86.

307. The crystalline form of embodiment 304 wherein the crystalline form is fluvastatin sodium Form LXXI.

308. A process for preparing crystalline fluvastatin sodium Form LXXI comprising:
   a) dissolving fluvastatin sodium in water at elevated temperature,
   b) adding an excess of acetone to the water to induce precipitation of Form LXXI, and
   c) separating the water and acetone from the Form LXXI.

309. A crystalline form of fluvastatin sodium characterized by a PXRD pattern with peaks at 3.7, 5.7 and 12.1±0.2 degrees two-theta.

310. The crystalline form of embodiment 309 further characterized by peaks at 5.0, 10.8, 16.8 and 20.1±0.2 degrees two-theta.

Figure 87:
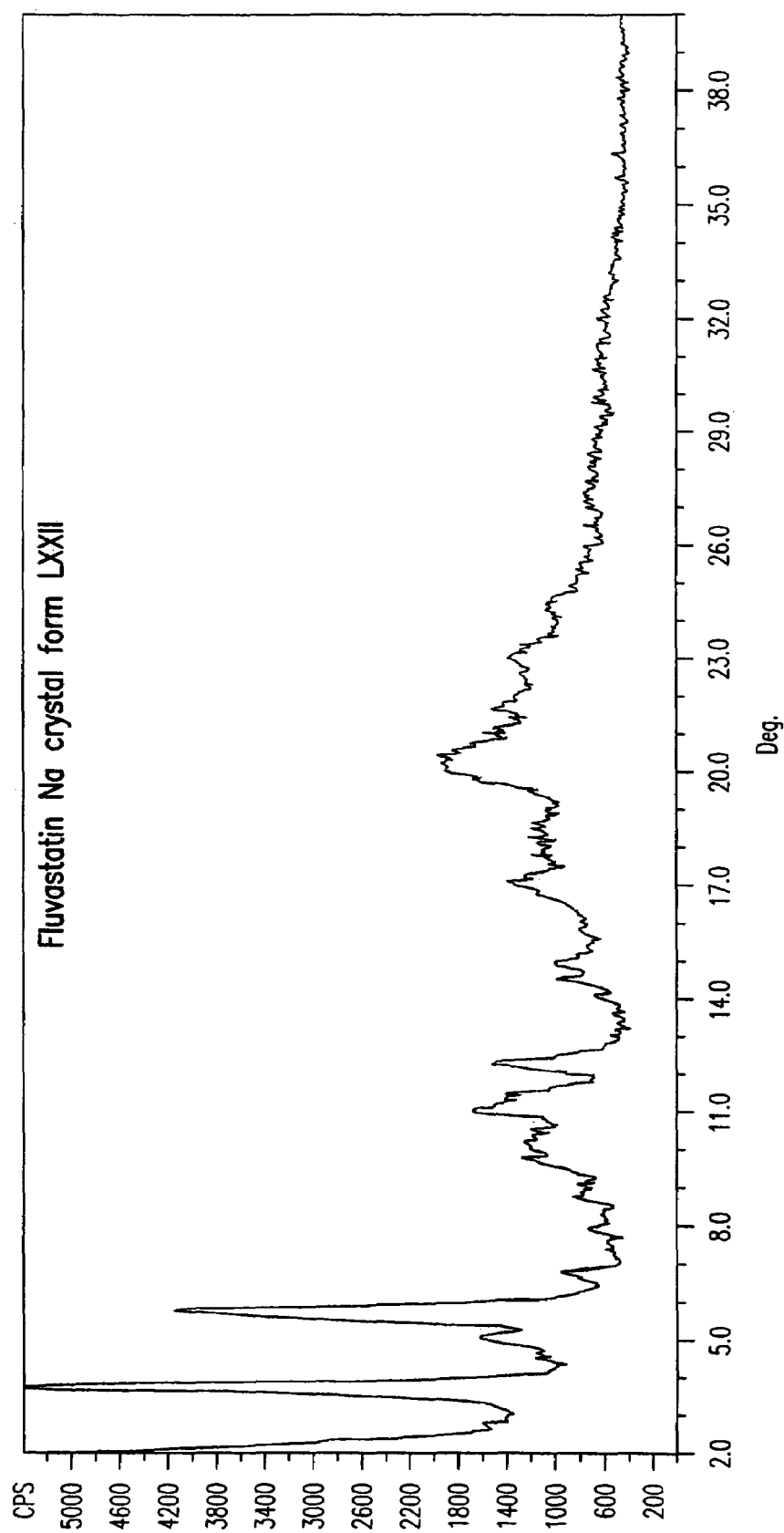
FIG. 87 depicts a powder X-ray diffractogram of fluvastatin sodium Form LXXII.
Figure 88:
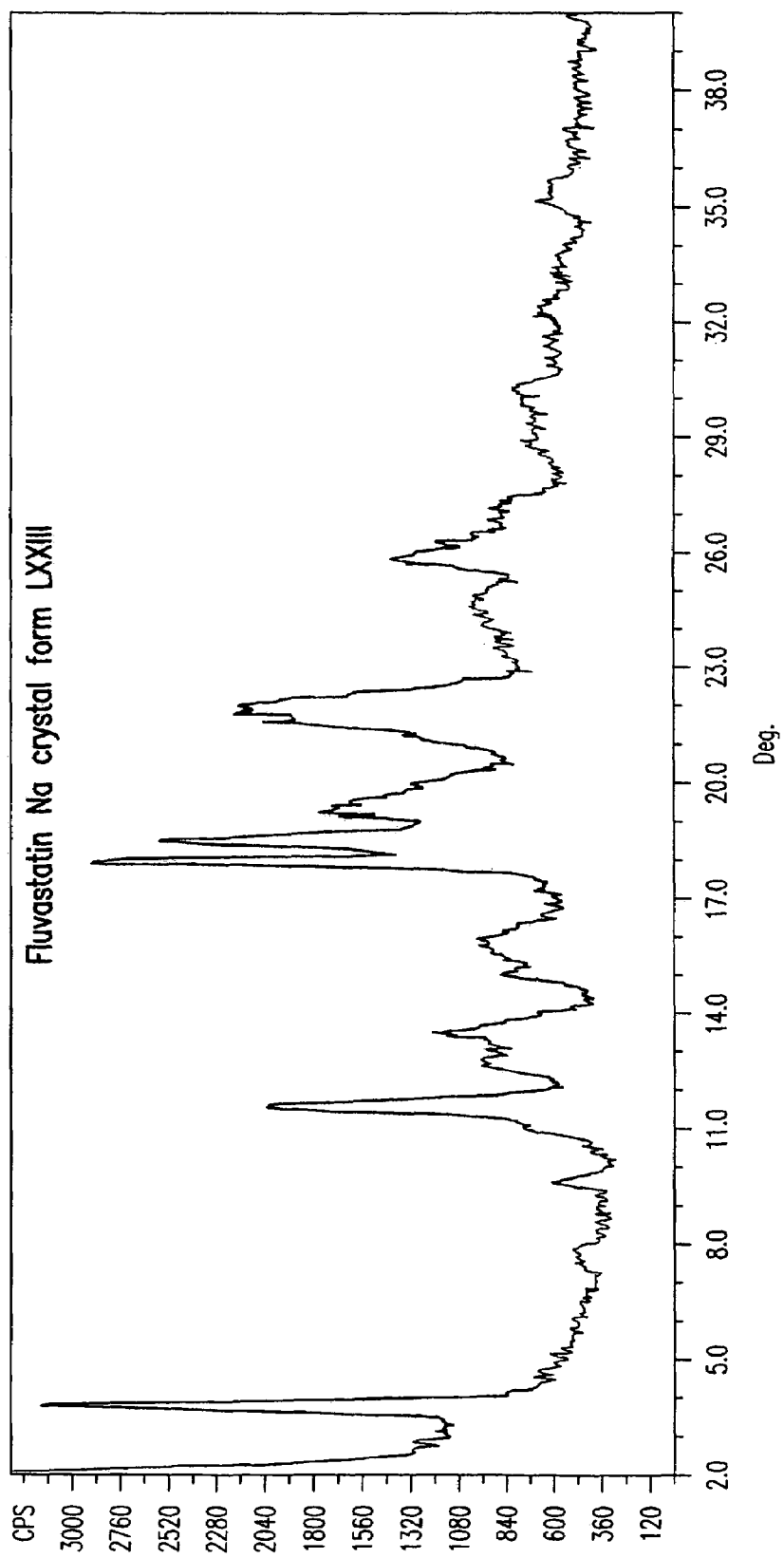
FIG. 88 depicts a powder X-ray diffractogram of fluvastatin sodium Form LXXIII.

311. The crystalline form of embodiment 310 wherein the crystalline form is characterized by a PXRD pattern substantially as depicted in FIG. 87.

312. The crystalline form of embodiment 309 wherein the crystalline form is fluvastatin sodium Form LXXII.

313. A process for preparing crystalline fluvastatin sodium Form LXXII comprising:
   a) forming a heterogeneous mixture of fluvastatin sodium Form VI and a diluent selected from the group consisting of acetonitrile and mixtures of acetone and water,
   b) maintaining the heterogeneous mixture at elevated temperature for a period of time sufficient to convert Form VI to Form LXXII, and
   c) separating the diluent from Form LXXII.

314. A crystalline form of fluvastatin sodium characterized by a PXRD pattern with peaks at 4.0, 12.8, 19.0, 19.9 and 25.8±0.2 degrees two-theta.

315. The crystalline form of embodiment 314 further characterized by peaks at 5.4, 11.8, 13.4, 18.0 and 24.6±0.2 degrees two-theta.

Figure 89:
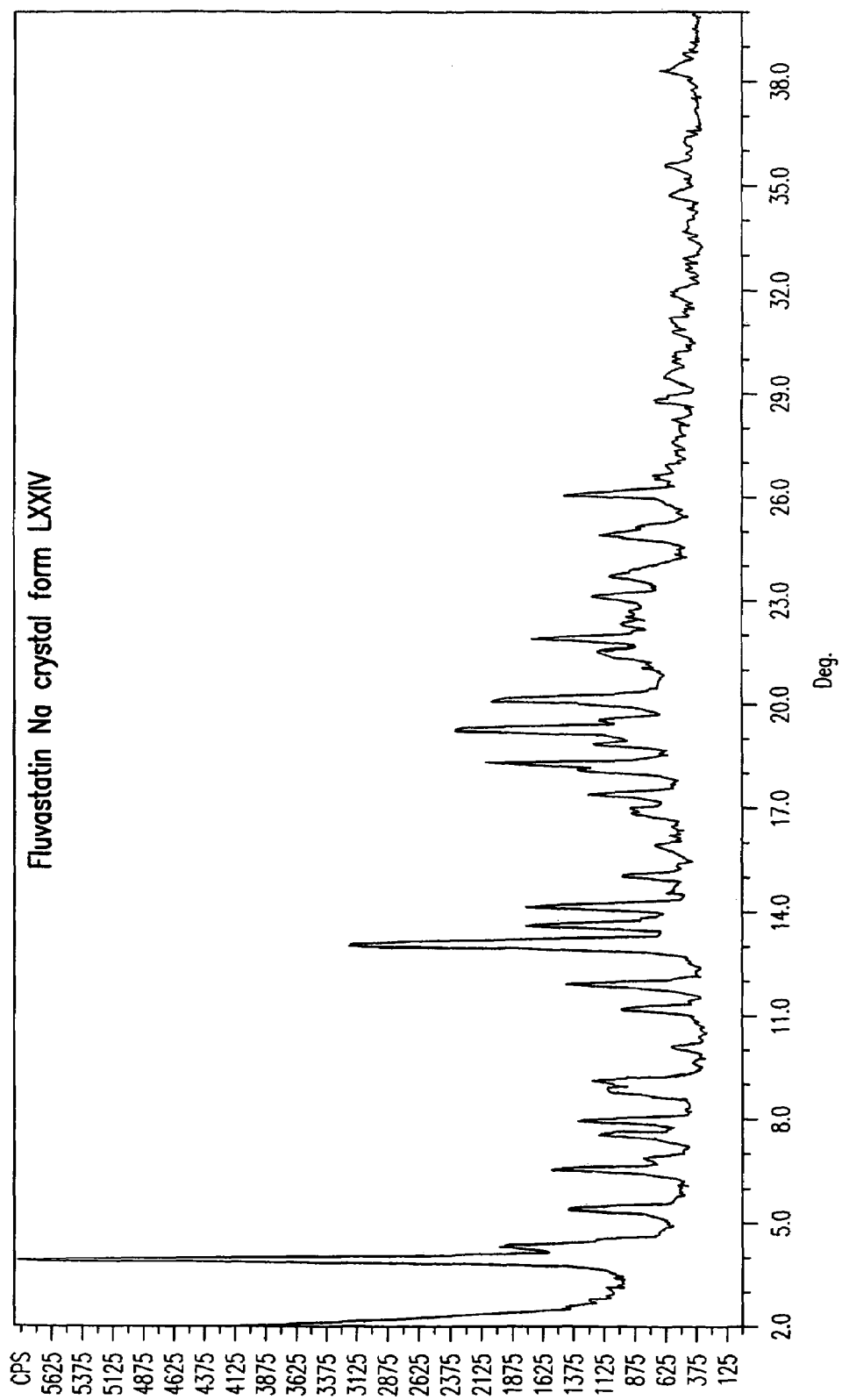
FIG. 89 depicts a powder X-ray diffractogram of fluvastatin sodium Form LXXIV.

316. The crystalline form of embodiment 315 wherein the crystalline form is characterized by a PXRD pattern substantially as depicted in FIG. 89.

317. The crystalline form of embodiment 314 wherein the crystalline form is fluvastatin sodium Form LXXIV.

318. A process for preparing crystalline fluvastatin sodium Form LXXIV comprising:
   a) forming a heterogeneous mixture of fluvastatin sodium Form B and a mixture of propan-2-ol and water,
   b) maintaining the mixture for a period of time sufficient to effect the conversion to Form LXXIV, and
   c) separating the propan-2-ol and water from the Form LXXIV.

319. A crystalline form of fluvastatin sodium characterized by a PXRD pattern with peaks at 4.4, 6.6, 10.8, 14.3 and 22.2±0.2 degrees two-theta.

320. The crystalline form of embodiment 319 further characterized by peaks at 7.8, 15.0, 19.8, 20.4 and 21.4±0.2 degrees two-theta.

Figure 90:
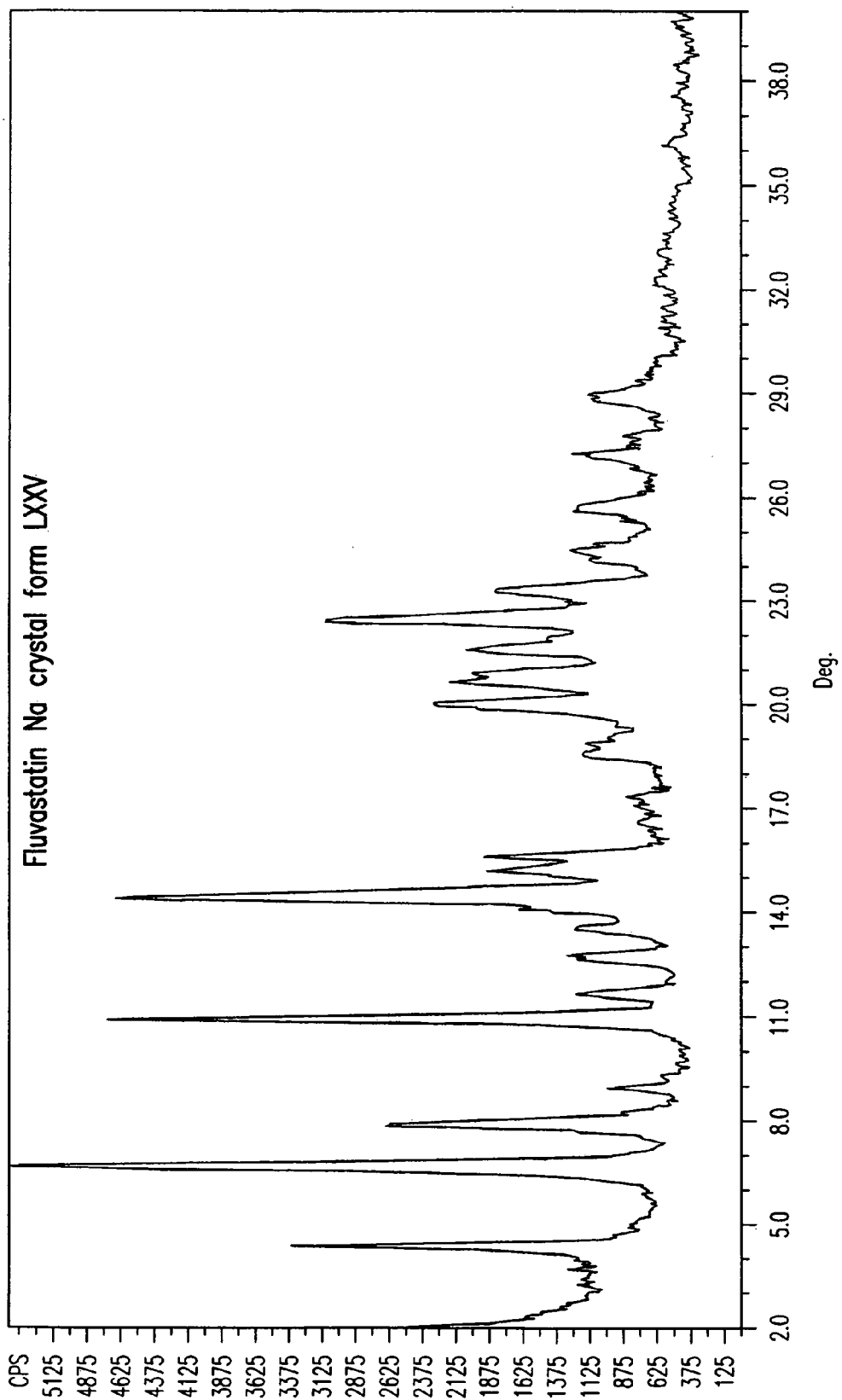
FIG. 90 depicts a powder X-ray diffractogram of fluvastatin sodium Form LXXV.

321. The crystalline form of embodiment 320 wherein the crystalline form is characterized by a PXRD pattern substantially as depicted in FIG. 90.

322. The crystalline form of embodiment 320 wherein the crystalline form is fluvastatin sodium Form LXXV.

323. A process for preparing crystalline fluvastatin sodium Form LXXV comprising:
   a) forming a heterogeneous mixture of fluvastatin sodium Form XXX and methanol,
   b) maintaining the mixture for a period of time sufficient to convert Form XXX to Form LXV, and
   c) separating the methanol from the Form LXV.

324. A crystalline form of fluvastatin sodium characterized by a PXRD pattern with peaks at 3.5, 7.0, 10.5 and 13.0±0.2 degrees two-theta.

Figure 91:
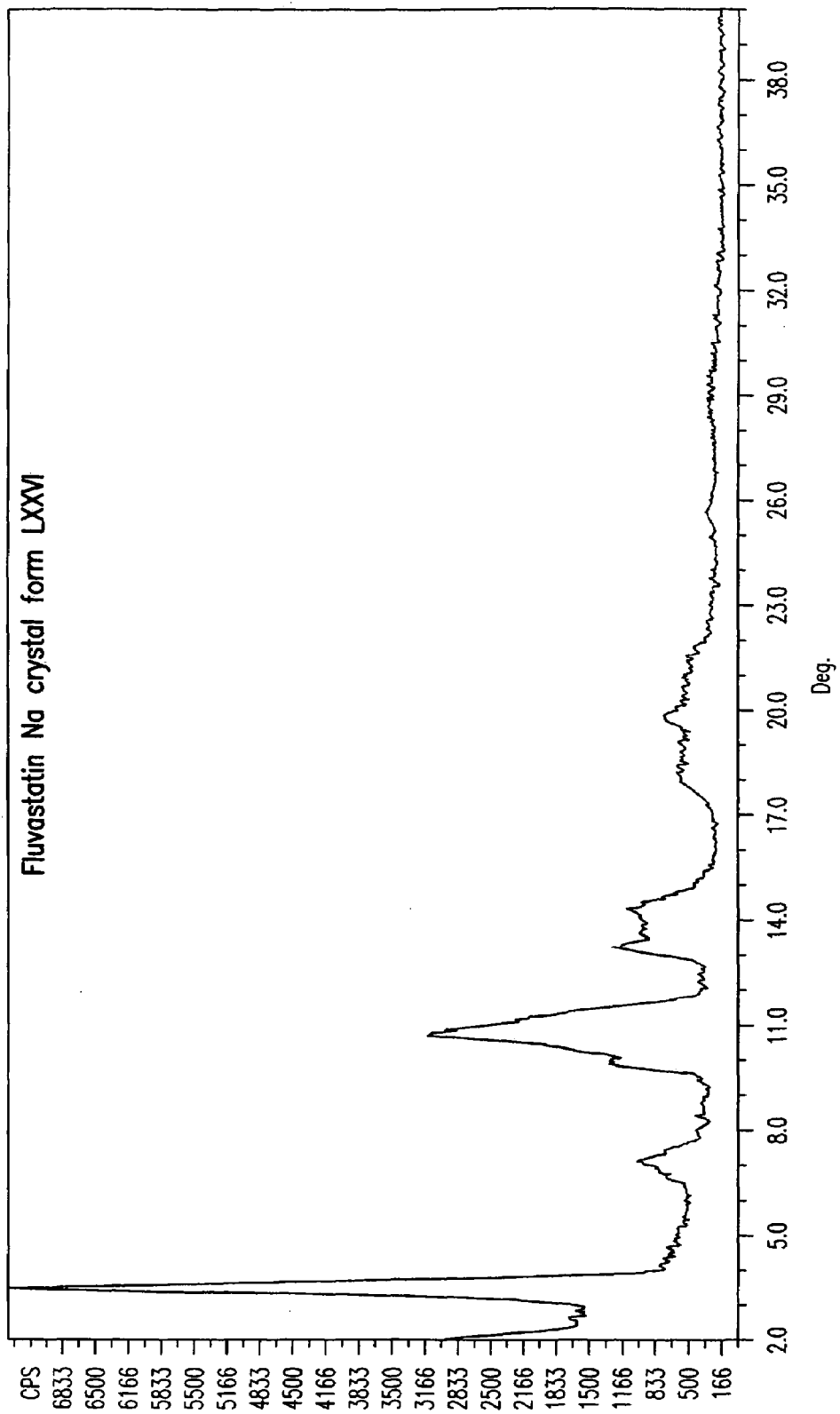
FIG. 91 depicts a powder X-ray diffractogram of fluvastatin sodium Form LXXVI.

325. The crystalline form of embodiment 324 wherein the crystalline form is characterized by a PXRD pattern substantially as depicted in FIG. 91.

326. The crystalline form of embodiment 324 wherein the crystalline form is fluvastatin sodium Form LXXVI.

327. A process for preparing crystalline fluvastatin sodium Form LXXVI comprising:
   a) hydrolyzing a lower alkyl ester of fluvastatin with about a molar equivalent of a sodium base catalyst in a mixture of ethanol and water,
   b) evaporating a portion of the ethanol and water mixture,
   c) adding water to the remaining mixture,
   d) extracting the mixture with a water immiscible extraction solvent,
   e) evaporating the ethanol and water to leave a residue that is Form LXXVI.

328. A crystalline form of fluvastatin sodium characterized by a PXRD pattern with peaks at 3.6, 8.8, 11.0, 12.8 and 17.8±0.2 degrees two-theta.

329. The crystalline form of embodiment 328 further characterized by peaks at 7.3, 20.2 and 31.0±0.2 degrees two-theta.

Figure 92:
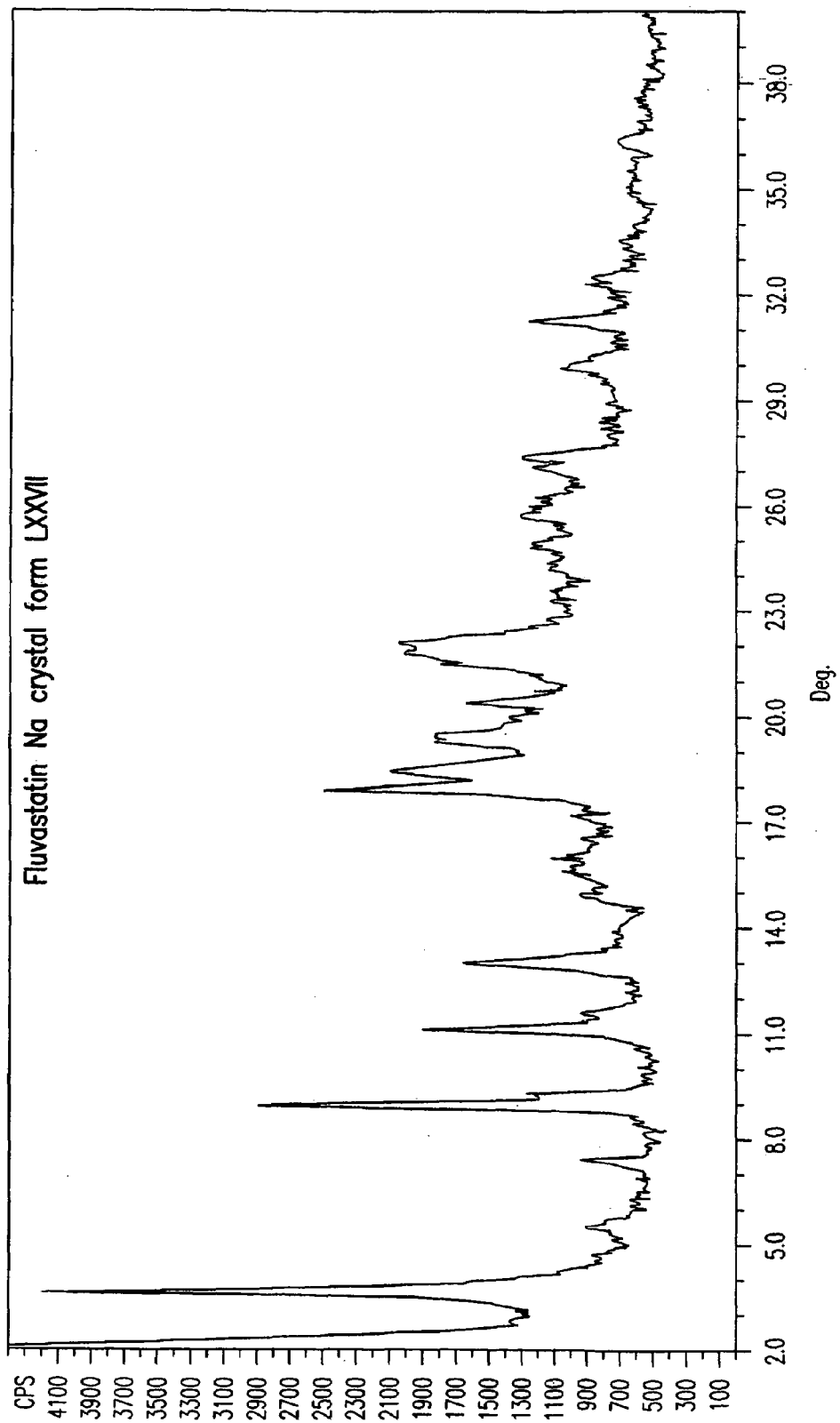
FIG. 92 depicts a powder X-ray diffractogram of fluvastatin sodium Form LXXVII.

330. The crystalline form of embodiment 329 wherein the crystalline form is characterized by a PXRD pattern substantially as depicted in FIG. 92.

331. The crystalline form of embodiment 328 wherein the crystalline form is fluvastatin sodium Form LXXVII.

332. A process for preparing crystalline fluvastatin sodium Form LXXVII comprising:
   a) hydrolyzing a lower alkyl ester of fluvastatin with a molar excess of sodium base catalyst in a mixture of water and ethyl acetate,
   b) precipitating Form LXXVII from the mixture, and
   c) separating Form LXXVII from the water, ethyl acetate and residual sodium base catalyst.

333. A crystalline form of fluvastatin sodium characterized by a PXRD pattern with peaks at 8.8, 19.1, 27.2, 29.6 and 30.9±0.2 degrees two-theta.

334. The crystalline form of embodiment 333 further characterized by peaks at 3.4, 11.3, 17.7, 22.5 and 32.2±0.2 degrees two-theta.

Figure 93:
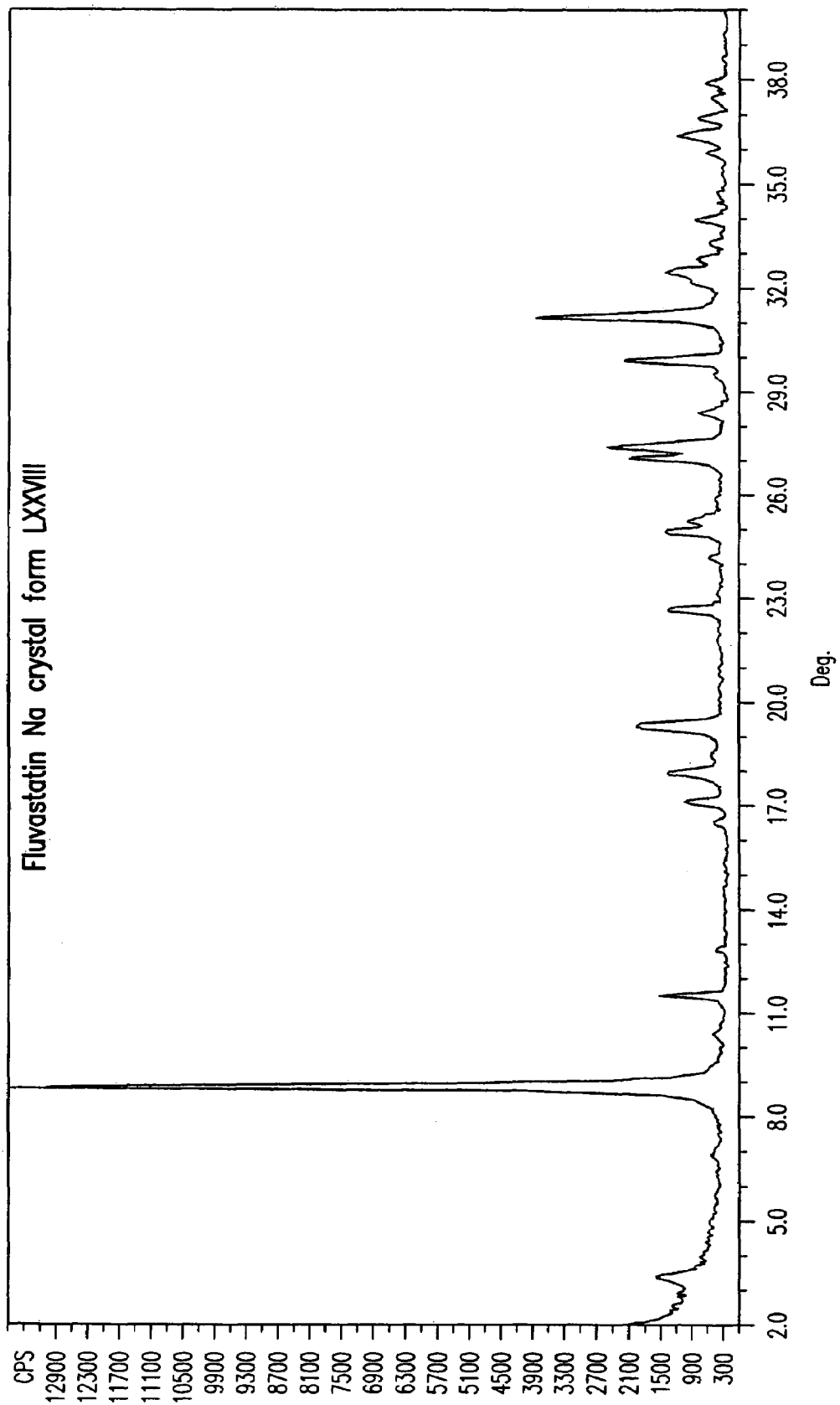
FIG. 93 depicts a powder X-ray diffractogram of fluvastatin sodium Form LXXVIII.
Figure 94:
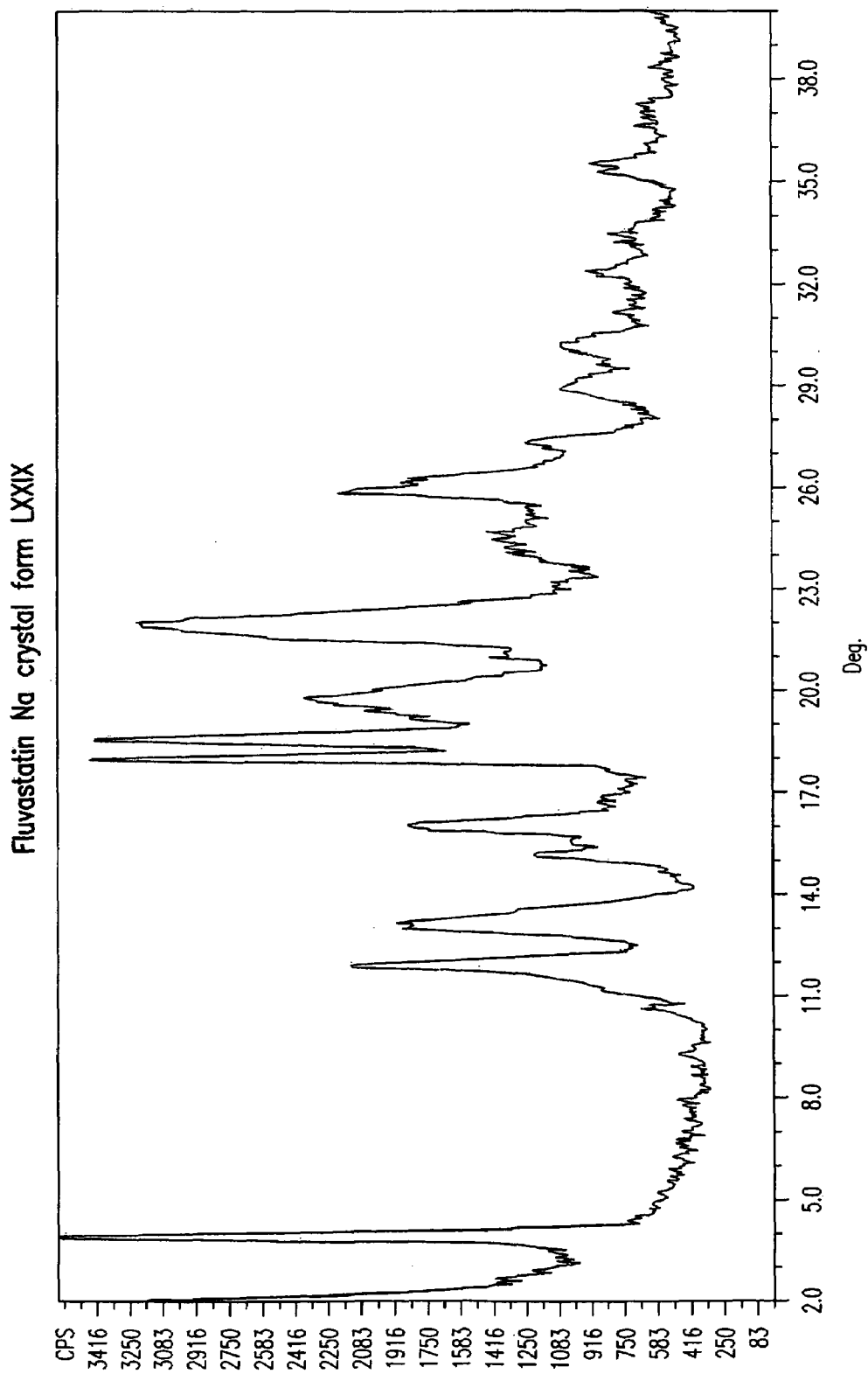
FIG. 94 depicts a powder X-ray diffractogram of fluvastatin sodium Form LXXIX.
Figure 95:
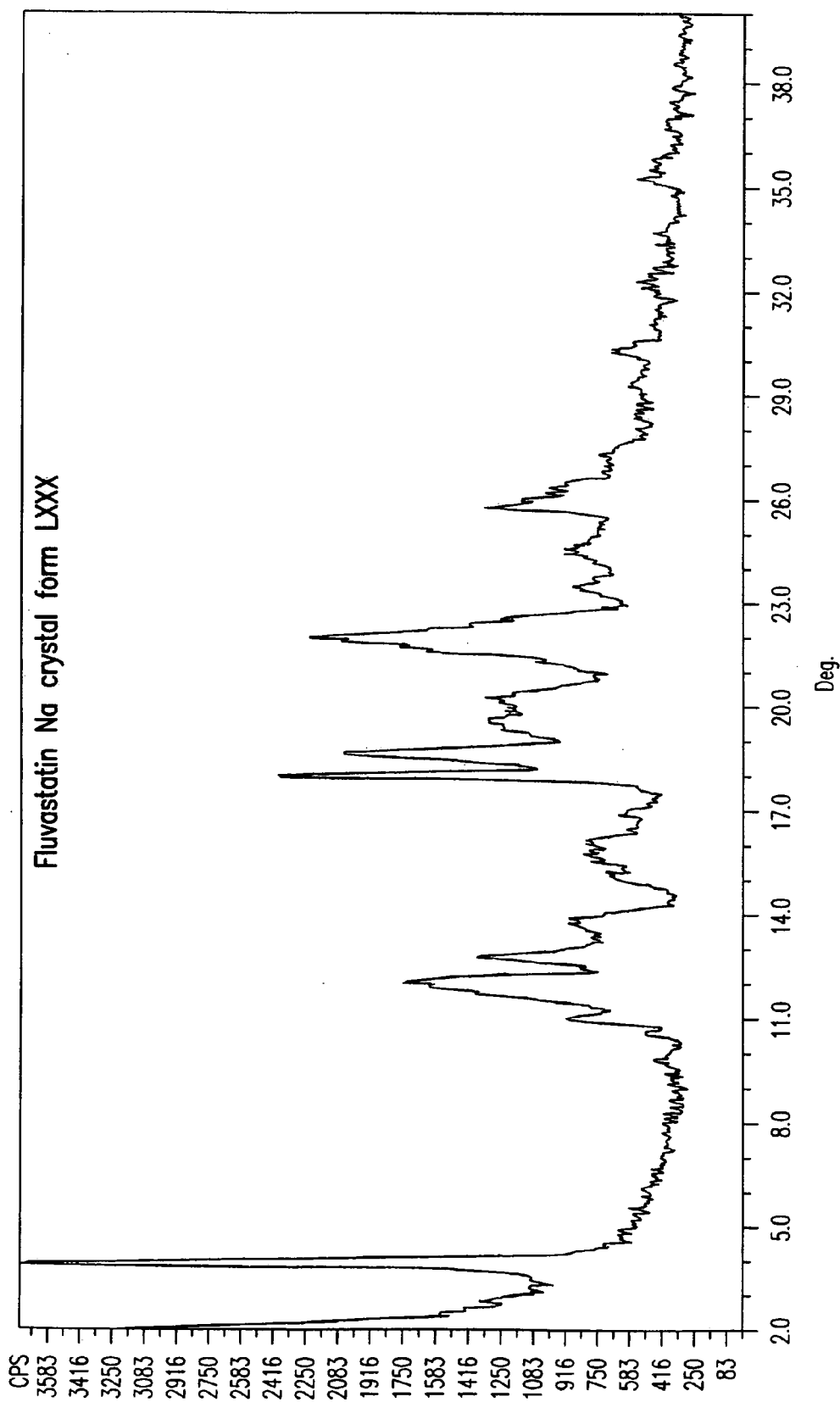
FIG. 95 depicts a powder X-ray diffractogram of fluvastatin sodium Form LXXX.
Figure 96:
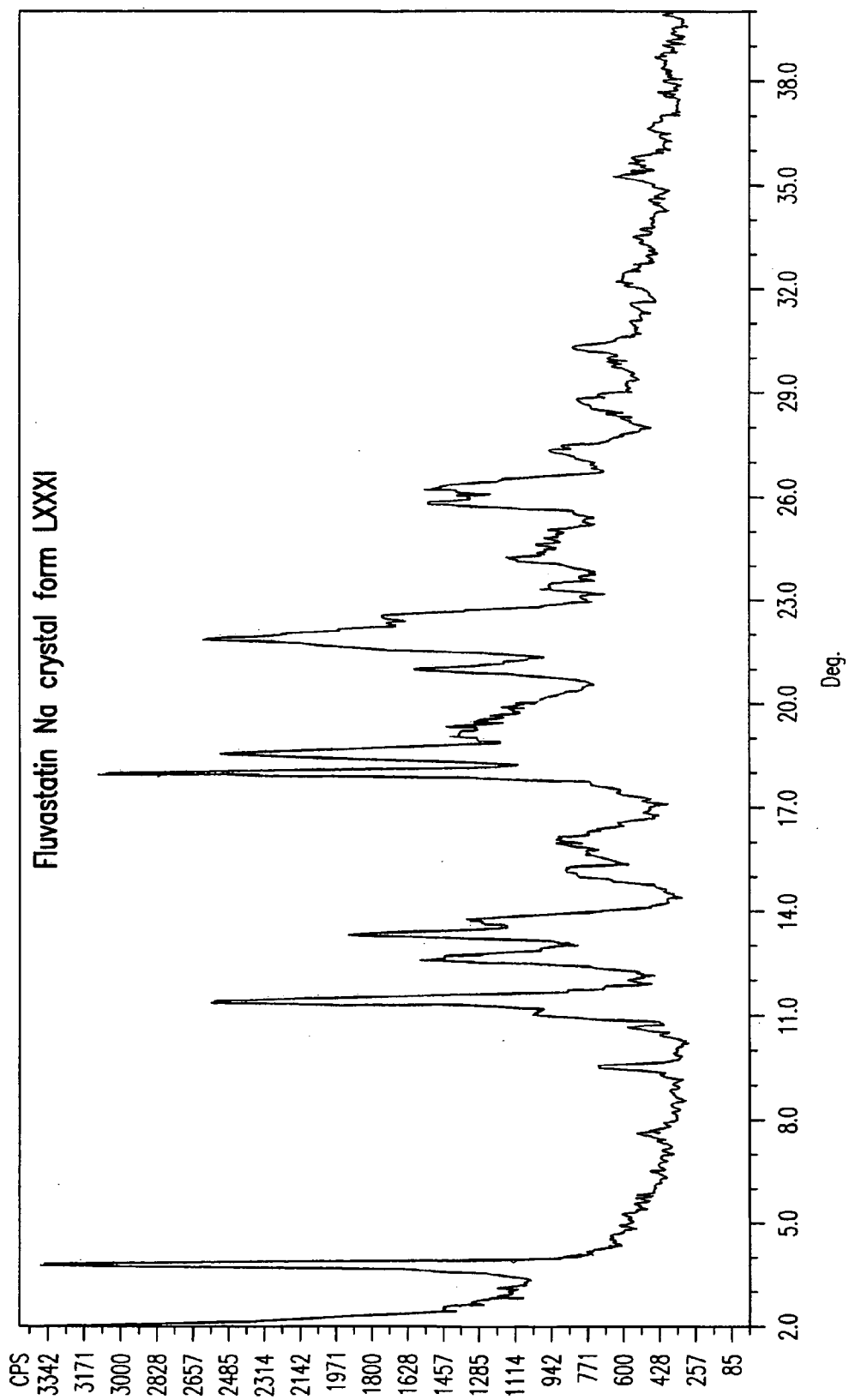
FIG. 96 depicts a powder X-ray diffractogram of fluvastatin sodium Form LXXXI.

335. The crystalline form of embodiment 334 wherein the crystalline form is characterized by a PXRD pattern substantially as depicted in FIG. 93.

336. The crystalline form of embodiment 333 wherein the crystalline form is fluvastatin sodium Form LXXVIII.

337. A process for preparing crystalline fluvastatin sodium Form LXXVIII comprising:
   a) hydrolyzing a lower alkyl ester of fluvastatin with a sodium base catalyst in water,
   b) contacting the water with a water-immiscible extraction solvent,
   c) evaporating the water to leave a residue,
   d) contacting the residue with a liquid selected from the group consisting of propan-2-ol and acetonitrile to convert the residue into Form LXXVIII, and
   e) separating the liquid from the Form LXXVIII.

338. A semi-crystalline form of fluvastatin sodium characterized by a PXRD pattern with peaks at 3.2 and 9.6±0.2 degrees two-theta.

339. The semi-crystalline form of fluvastatin sodium of embodiment 338 further characterized by peaks at 11.8 and 19.8±0.2 degrees two-theta.

Figure 97:
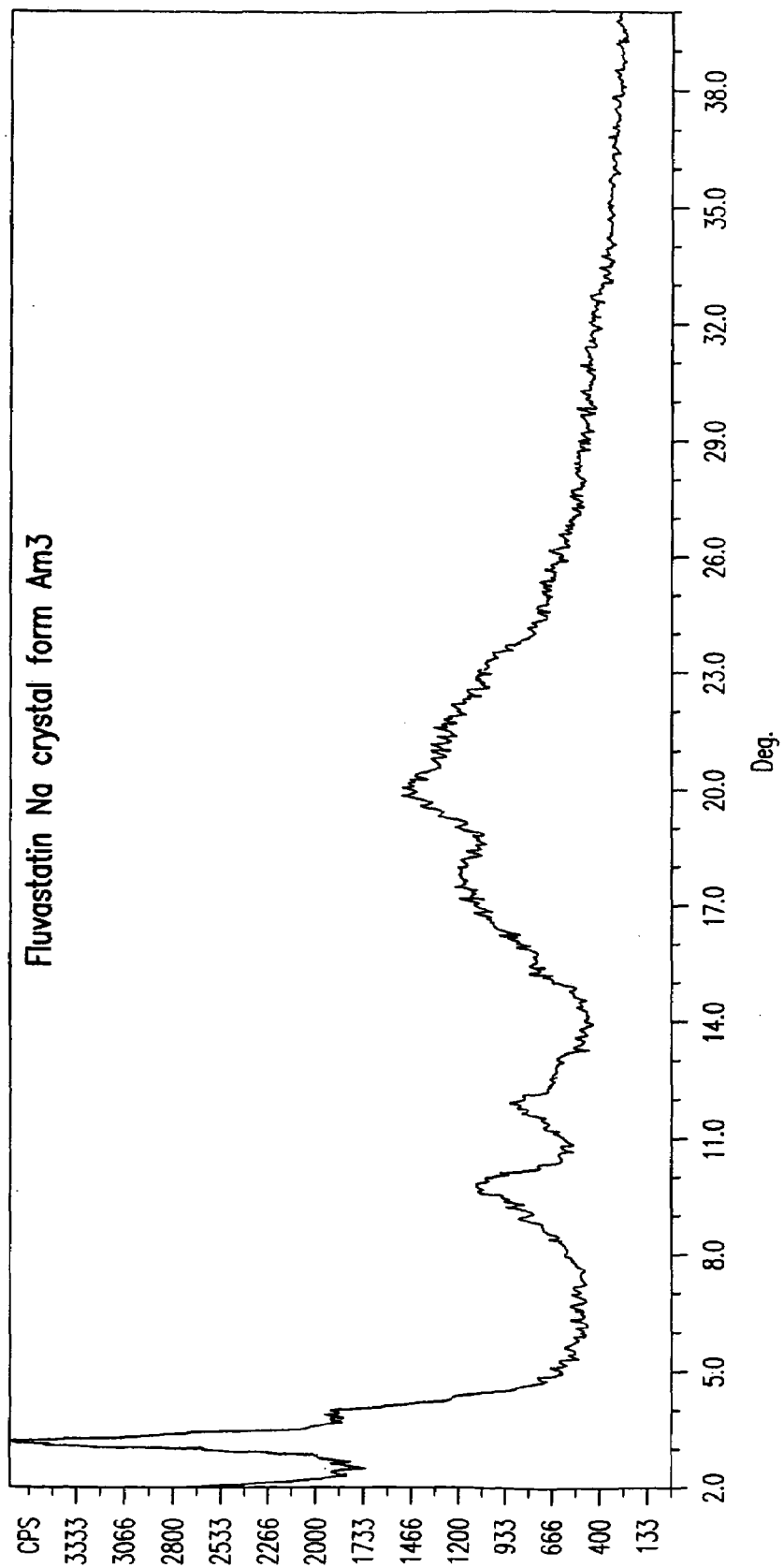
FIG. 97 depicts a powder X-ray diffractogram of fluvastatin sodium Form XC.

340. The semi-crystalline form of embodiment 339 wherein the semi-crystalline form is characterized by a PXRD pattern substantially as depicted in FIG. 97.

341. The semi-crystalline form of embodiment 338 wherein the semi-crystalline form is fluvastatin sodium Form XC.

342. A process for preparing semi-crystalline fluvastatin sodium Form XC comprising:
   a) dissolving fluvastatin sodium in ethanol,
   b) adding cyclohexane to the ethanol to induce precipitation of Form XC, and
   c) separating the ethanol and cyclohexane from the Form XC.

343. A semi-crystalline form of fluvastatin sodium characterized by a PXRD pattern with peaks at 4.7, 5.6 and 13.8±0.2 degrees two-theta.

344. The semi-crystalline form of fluvastatin sodium of embodiment 343 further characterized by peaks at 7.3, 9.6, 10.8, 16.4, 17.6, 19.8, 20.8 and 23.1±0.2 degrees two-theta.

Figure 98:
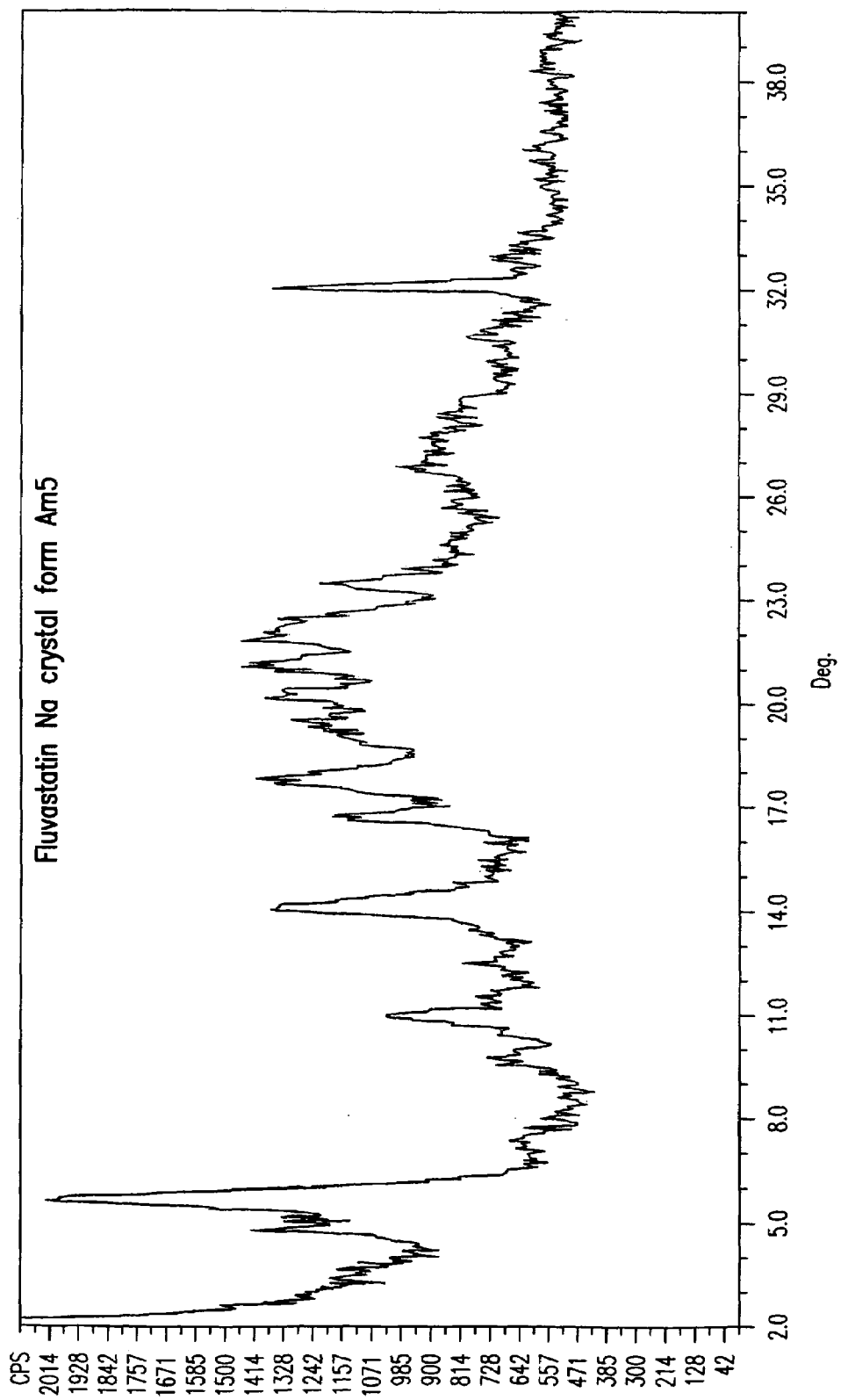
FIG. 98 depicts a powder X-ray diffractogram of fluvastatin sodium Form XCI.

345. The semi-crystalline form of embodiment 344 wherein the semi-crystalline form is characterized by a PXRD pattern substantially as depicted in FIG. 98.

346. The semi-crystalline form of embodiment 343 wherein the semi-crystalline form is fluvastatin sodium Form XCI.

347. A process for preparing semi-crystalline fluvastatin sodium Form XCI comprising:
   a) forming a heterogeneous mixture of Form XV and ethyl acetate,
   b) maintaining the mixture for a period of time sufficient to effect the conversion to Form XCI, and
   c) separating the ethyl acetate from the Form XCI.

348. A semi-crystalline form of fluvastatin sodium characterized by a PXRD pattern with peaks at 3.4, 10.1 and 11.8±0.2 degrees two-theta.

349. The semi-crystalline form of fluvastatin sodium of embodiment 348 further characterized by peaks at 4.1, 17.8, 20.1, 21.7, 23.4 and 25.3±0.2 degrees two-theta.

Figure 99:
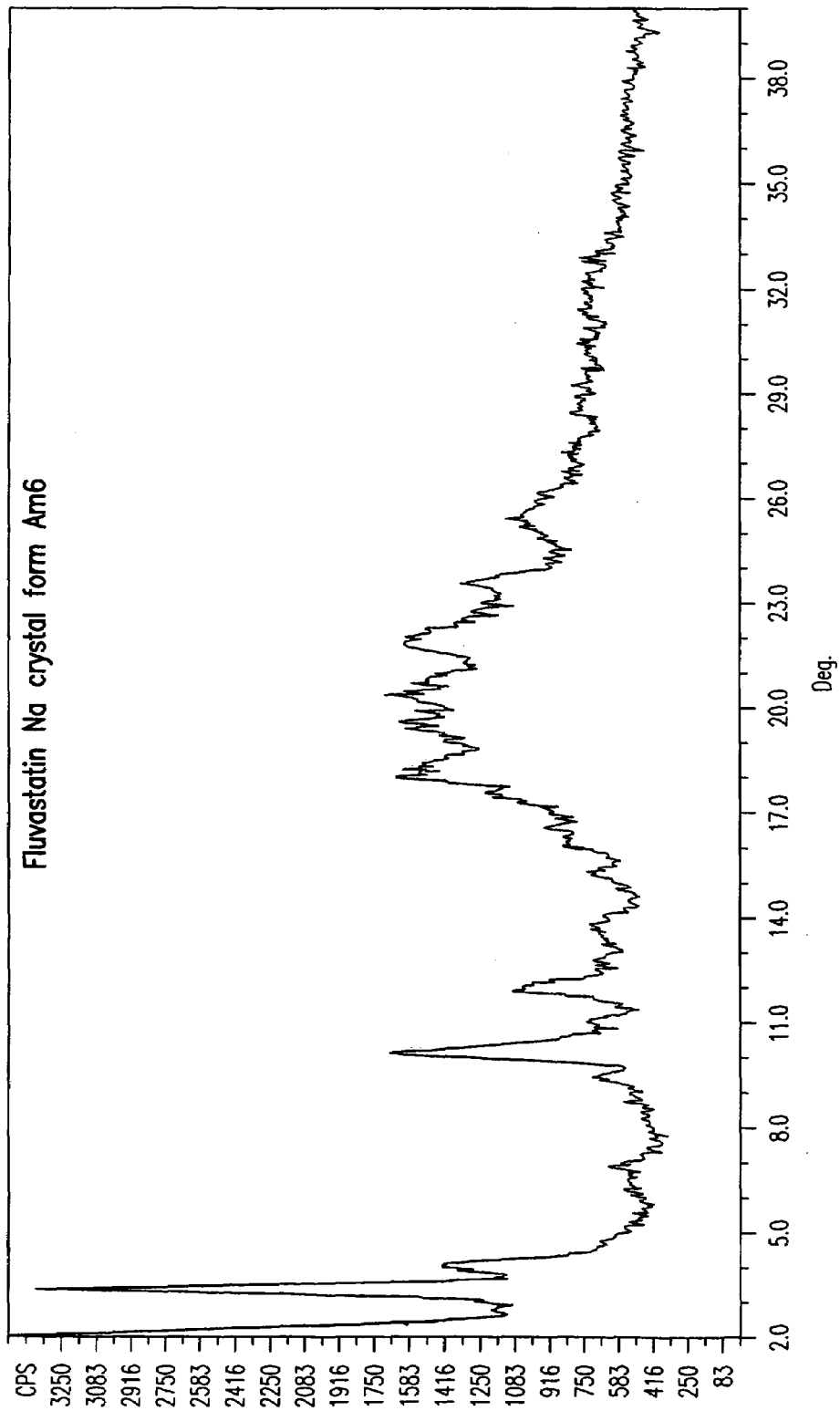
FIG. 99 depicts a powder X-ray diffractogram of fluvastatin sodium Form XCII.

350. The semi-crystalline form of embodiment 349 wherein the semi-crystalline form is characterized by a PXRD pattern substantially as depicted in FIG. 99.

351. The semi-crystalline form of embodiment 348 wherein the semi-crystalline form is fluvastatin sodium Form XCII.

352. A process for preparing semi-crystalline fluvastatin sodium Form XCII comprising:
   a) dissolving fluvastatin sodium Form B in an ethanol: methanol mixture at elevated temperature,
   b) adding hexanes to the mixture to induce precipitation of fluvastatin sodium in Form XCII, and
   c) separating the ethanol, methanol and hexanes from the Form XCII.

353. A semi-crystalline form of fluvastatin sodium characterized by a PXRD pattern with peaks at 4.6, 9.2 and 20.3±0.2±0.2 degrees two-theta.

354. The semi-crystalline form of fluvastatin sodium of embodiment 353 further characterized by peaks at 4.1, 6.7, 13.0, 15.8, 17.7, 21.7 and 23.0±0.2 degrees two-theta.

Figure 101:
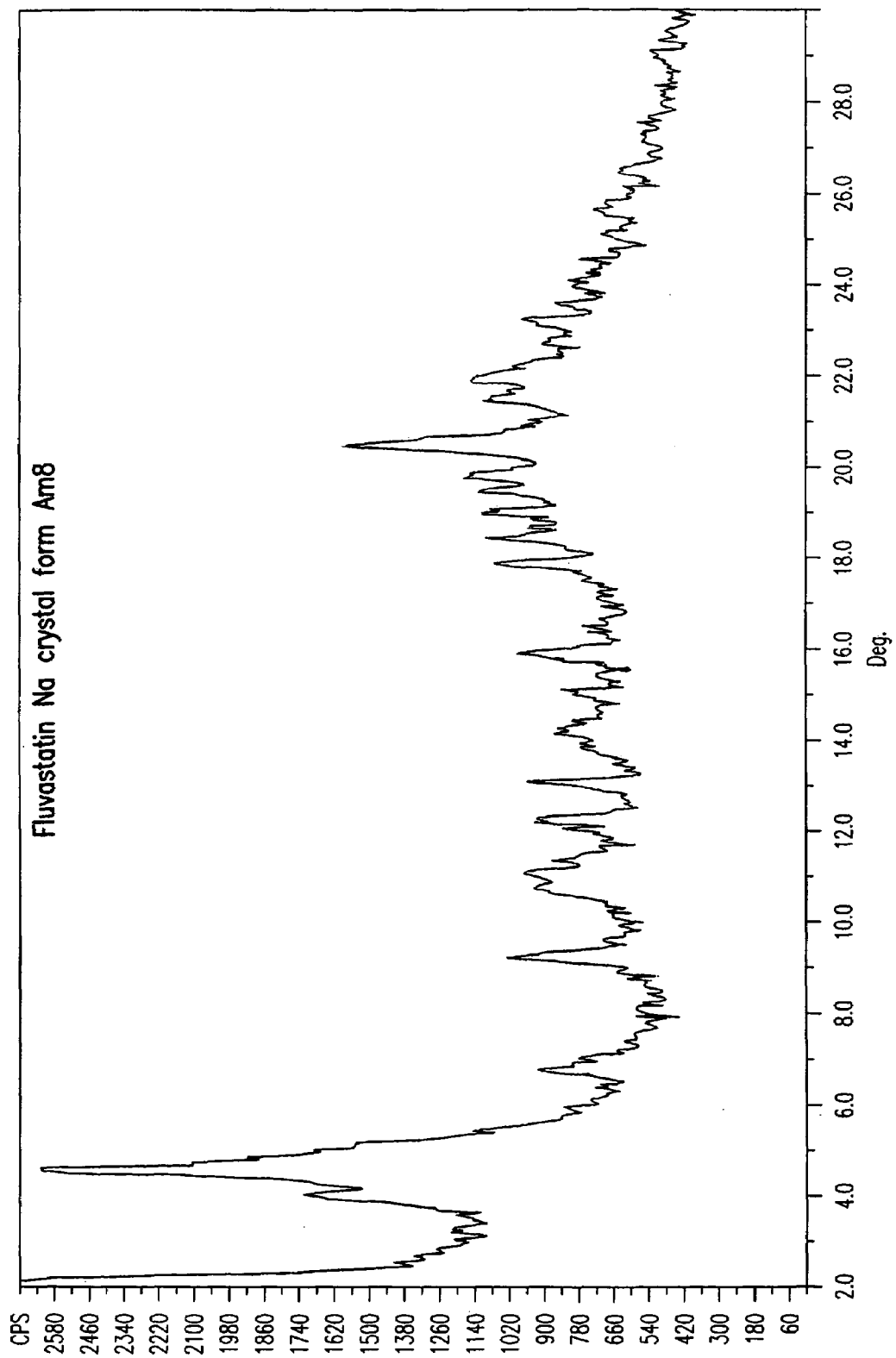
FIG. 101 depicts a powder X-ray diffractogram of fluvastatin sodium Form XCIV.

355. The semi-crystalline form of embodiment 354 wherein the semi-crystalline form is characterized by a PXRD pattern substantially as depicted in FIG. 101.

356. The semi-crystalline form of embodiment 353 wherein the semi-crystalline form is fluvastatin sodium Form XCIV.

357. A process for preparing semi-crystalline fluvastatin sodium Form XCIV comprising:
   a) forming a heterogeneous mixture of fluvastatin sodium Form XV in butan-1-ol at ambient temperature,
   b) maintaining the heterogeneous mixture at ambient temperature for a sufficient period to convert Form XV into Form XCIV, and
   c) separating the butan-1-ol from the Form XCIV.

358. A semi-crystalline form of fluvastatin sodium characterized by a PXRD pattern with peaks at 5.7, 13.0, 19.8 and 20.5±0.2 degrees two-theta.

359. The semi-crystalline form of fluvastatin sodium of embodiment 358 further characterized by peaks at 4.2, 4.7, 12.3 and 15.9±0.2 degrees two-theta.

Figure 102:
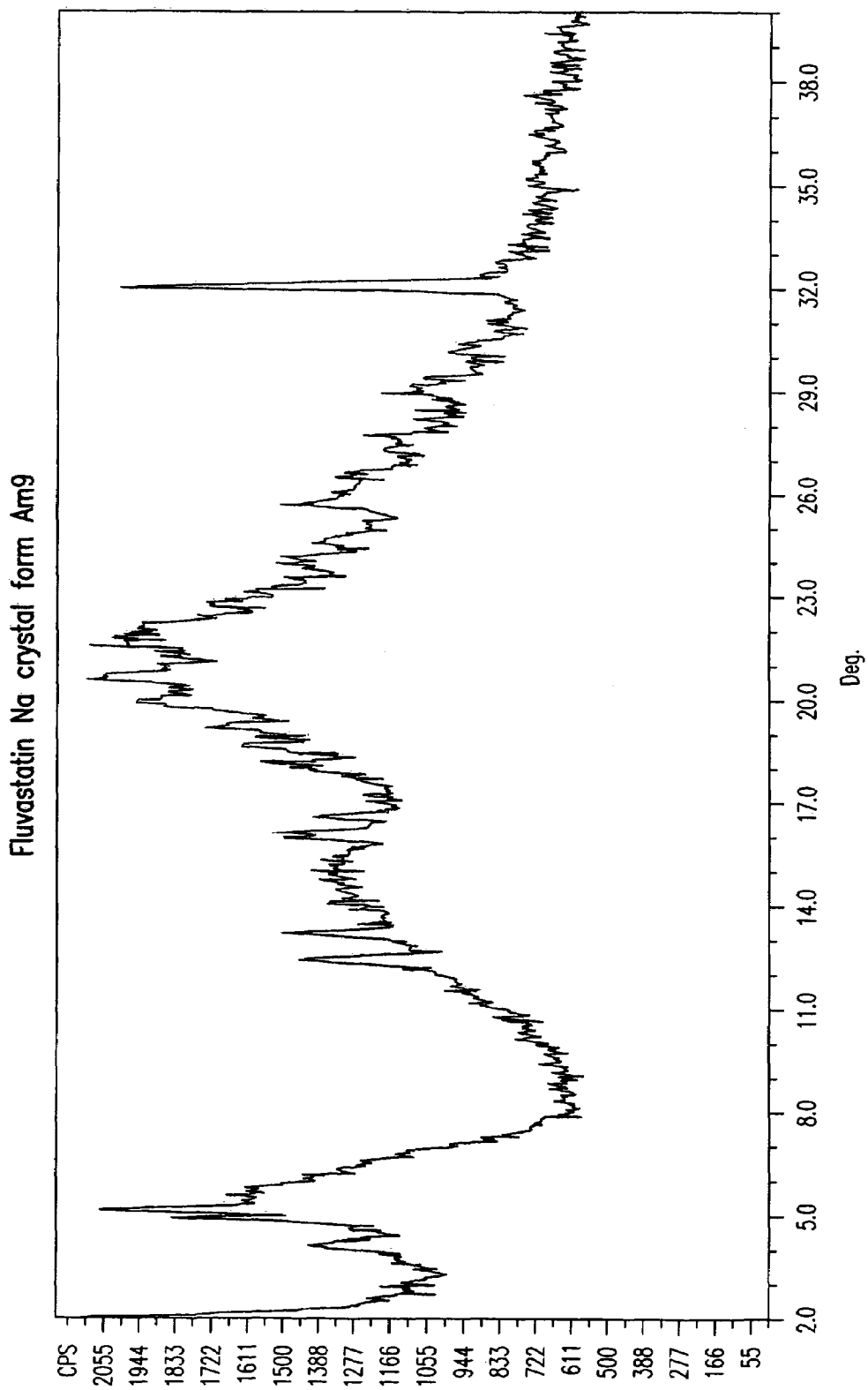
FIG. 102 depicts a powder X-ray diffractogram of fluvastatin sodium Form XCV.

360. The semi-crystalline form of embodiment 359 wherein the semi-crystalline form is characterized by a PXRD pattern substantially as depicted in FIG. 102.

361. The semi-crystalline form of embodiment 358 wherein the semi-crystalline form is fluvastatin sodium Form XCV.

362. A process for preparing semi-crystalline fluvastatin sodium Form XCV comprising:
   a) forming a heterogeneous mixture of fluvastatin sodium Form XV in a diluent selected from the group consisting of ethyl acetate, acetone, 1,4-dioxane and MEK at ambient temperature,
   b) maintaining the mixture at ambient temperature for a sufficient period to convert Form XV into Form XCV, and
   c) separating the diluent from the Form XCV.

363. A semi-crystalline form of fluvastatin sodium characterized by a PXRD pattern with peaks at 3.7, 11.0, 12.9 and 18.2±0.2 degrees two-theta.

364. The semi-crystalline form of fluvastatin sodium of embodiment 363 further characterized by peaks at 5.2, 8.3, 17.7, 21.5 and 25.5±0.2 degrees two-theta.

Figure 103:
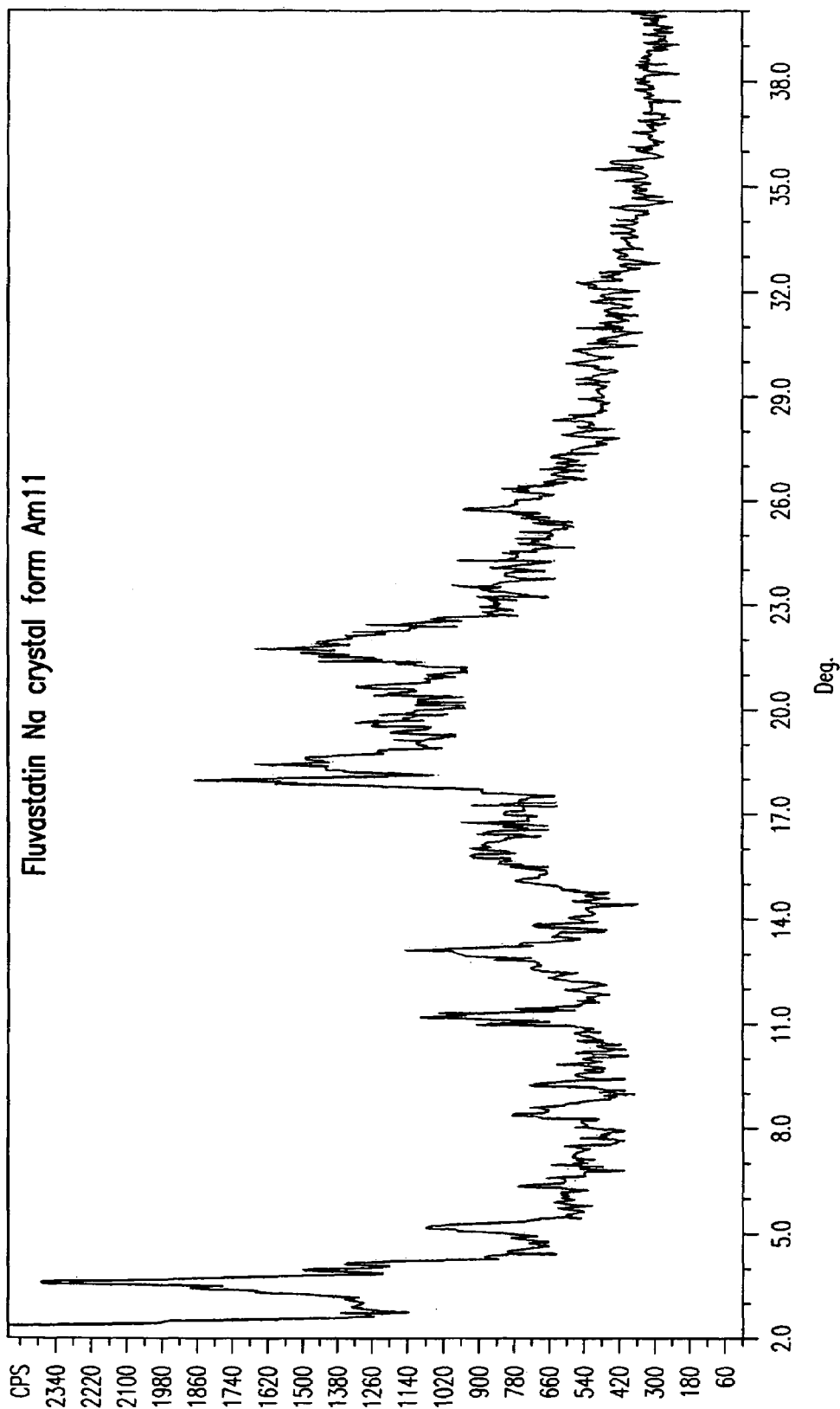
FIG. 103 depicts a powder X-ray diffractogram of fluvastatin sodium Form XCVI.

365. The semi-crystalline form of embodiment 364 wherein the semi-crystalline form is characterized by a PXRD pattern substantially as depicted in FIG. 103.

366. The semi-crystalline form of embodiment 363 wherein the semi-crystalline form is fluvastatin sodium Form XCVI.

367. A process for preparing semi-crystalline fluvastatin sodium Form XCVI comprising:
a) forming a heterogeneous mixture of fluvastatin sodium Form XV and THF at ambient temperature,
b) maintaining the suspension at ambient temperature for a sufficient period to convert Form XV into Form XCVI, and
c) separating the THF from the Form XCV.

368. A semi-crystalline form of fluvastatin sodium characterized by a PXRD pattern with a peak at 3.5±0.2 degrees two-theta.

369. The semi-crystalline form of fluvastatin sodium of embodiment 368 further characterized by peaks at 9.4, 18.4, 20.0, 21.2 and 22.0±0.2 degrees two-theta.

Figure 104:
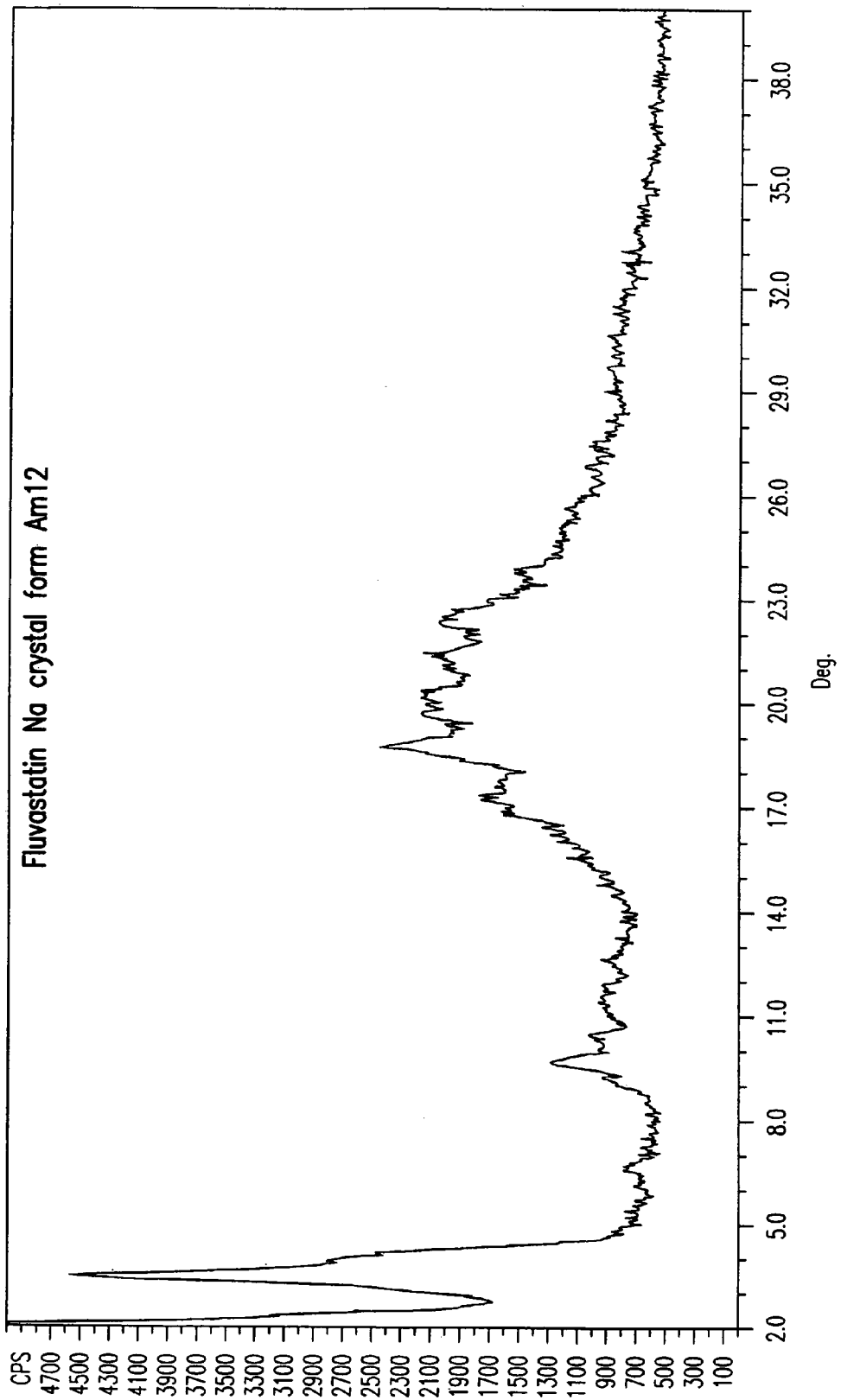
FIG. 104 depicts a powder X-ray diffractogram of fluvastatin sodium Form XCVII.

370. The semi-crystalline form of embodiment 369 wherein the semi-crystalline form is characterized by a PXRD pattern substantially as depicted in FIG. 104.

371. The semi-crystalline form of embodiment 368 wherein the semi-crystalline form is fluvastatin sodium Form XCVII.

372. A process for preparing semi-crystalline fluvastatin sodium Form XCVII comprising:
a) hydrolyzing a lower alkyl ester of fluvastatin with sodium hydroxide in cyclohexane,
b) precipitating Form XCVII from the cyclohexane, and
c) separating the cyclohexane from the Form XCVII.

373. A semi-crystalline form of fluvastatin sodium characterized by a PXRD pattern with peaks at 3.8 and 10.8±0.2 degrees two-theta.

374. The semi-crystalline form of fluvastatin sodium of embodiment 373 further characterized by peaks at 6.4 and 14.4±0.2 degrees two-theta.

Figure 105:
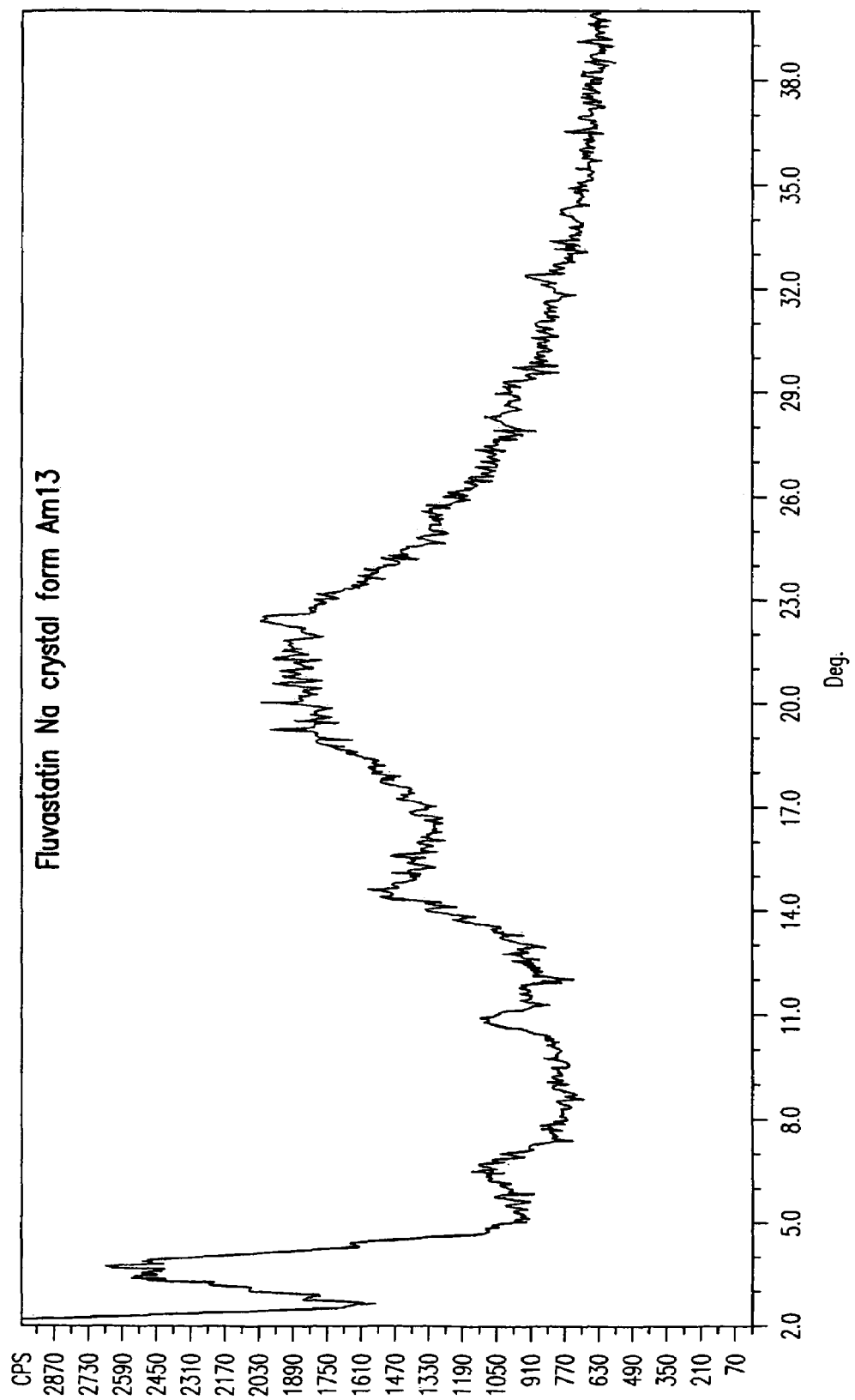
FIG. 105 depicts a powder X-ray diffractogram of fluvastatin sodium Form XCVIII.

375. The semi-crystalline form of embodiment 374 wherein the semi-crystalline form is characterized by a PXRD pattern substantially as depicted in FIG. 105.

376. The semi-crystalline form of embodiment 373 wherein the semi-crystalline form is fluvastatin sodium Form XCVIII.

377. A process for preparing semi-crystalline fluvastatin sodium Form XCVIII comprising:
a) hydrolyzing a lower alkyl ester of fluvastatin with sodium hydroxide in a concentrated methanol solution at elevated temperature,
b) adding a large excess of acetonitrile to the methanol at elevated temperature,
c) precipitating Form XCVIII from the methanol and acetonitrile, and
d) separating the methanol and acetonitrile from the Form XCVIII.

378. A semi-crystalline form of fluvastatin sodium characterized by a PXRD pattern with peaks at 3.6, 5.3, 8.7 and 10.4±0.2 degrees two-theta.

379. The semi-crystalline form of fluvastatin sodium of embodiment 378 further characterized by peaks at 17.9 and 21.5±0.2 degrees two-theta.

Figure 106:
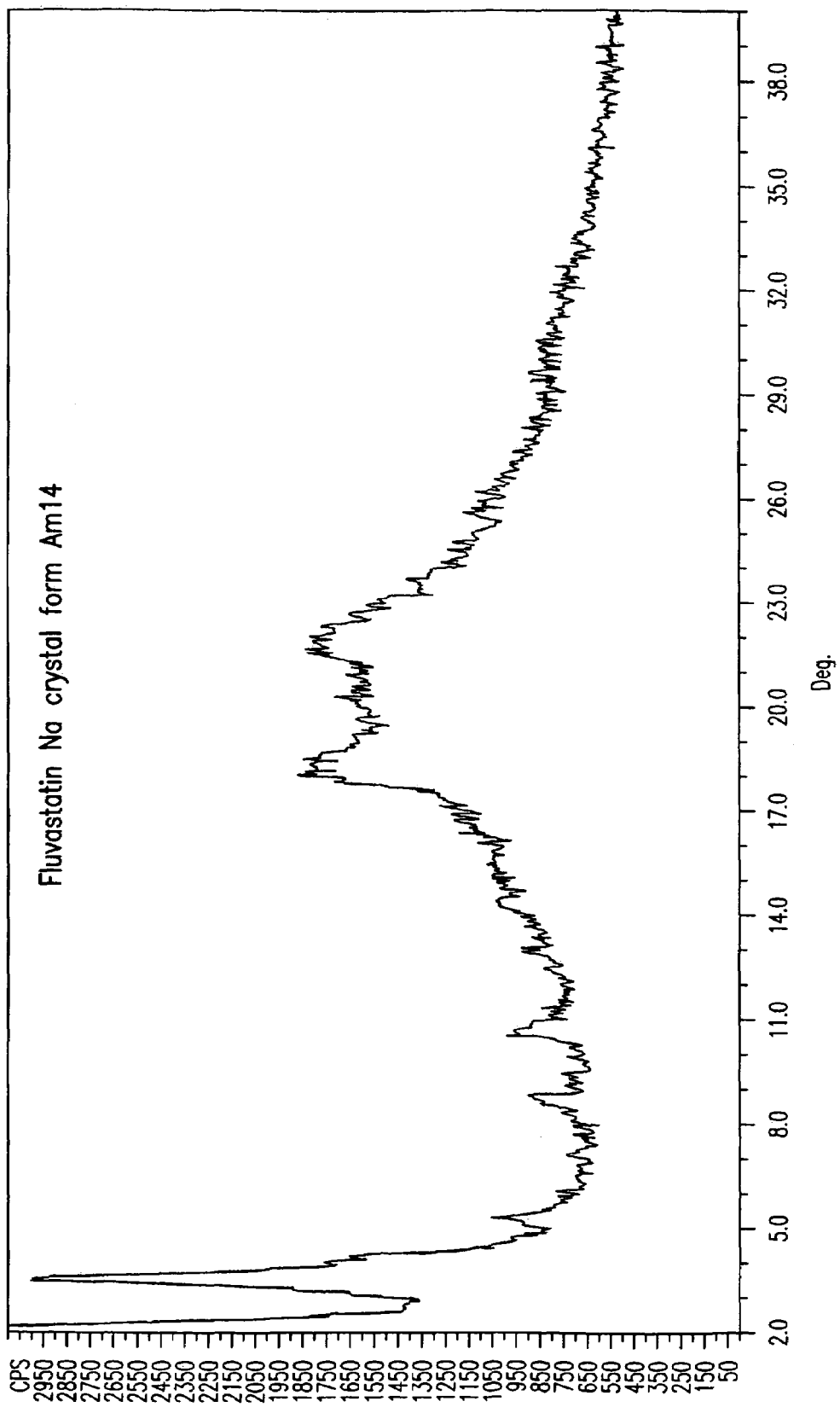
FIG. 106 depicts a powder X-ray diffractogram of fluvastatin sodium Form XCIX.

380. The semi-crystalline form of embodiment 379 wherein the semi-crystalline form is characterized by a PXRD pattern substantially as depicted in FIG. 106.

381. The semi-crystalline form of embodiment 378 wherein the semi-crystalline form is fluvastatin sodium Form XCIX.

382. A process for preparing semi-crystalline fluvastatin sodium Form XCIX comprising:
a) forming a heterogeneous mixture of fluvastatin sodium Form VI and ethanol at ambient temperature,
b) maintaining the heterogeneous mixture at ambient temperature for a sufficient period to convert Form VI into Form XCIX, and
c) separating the ethanol from the Form VI.

383. A semi-crystalline form of fluvastatin sodium characterized by a PXRD pattern with peaks at 3.3, 9.8, 11.0, 19.0 and 22.7±0.2 degrees two-theta.

384. The semi-crystalline form of fluvastatin sodium of embodiment 383 further characterized by peaks at 6.2, 17.2 and 21.3±0.2 degrees two-theta.

Figure 107:
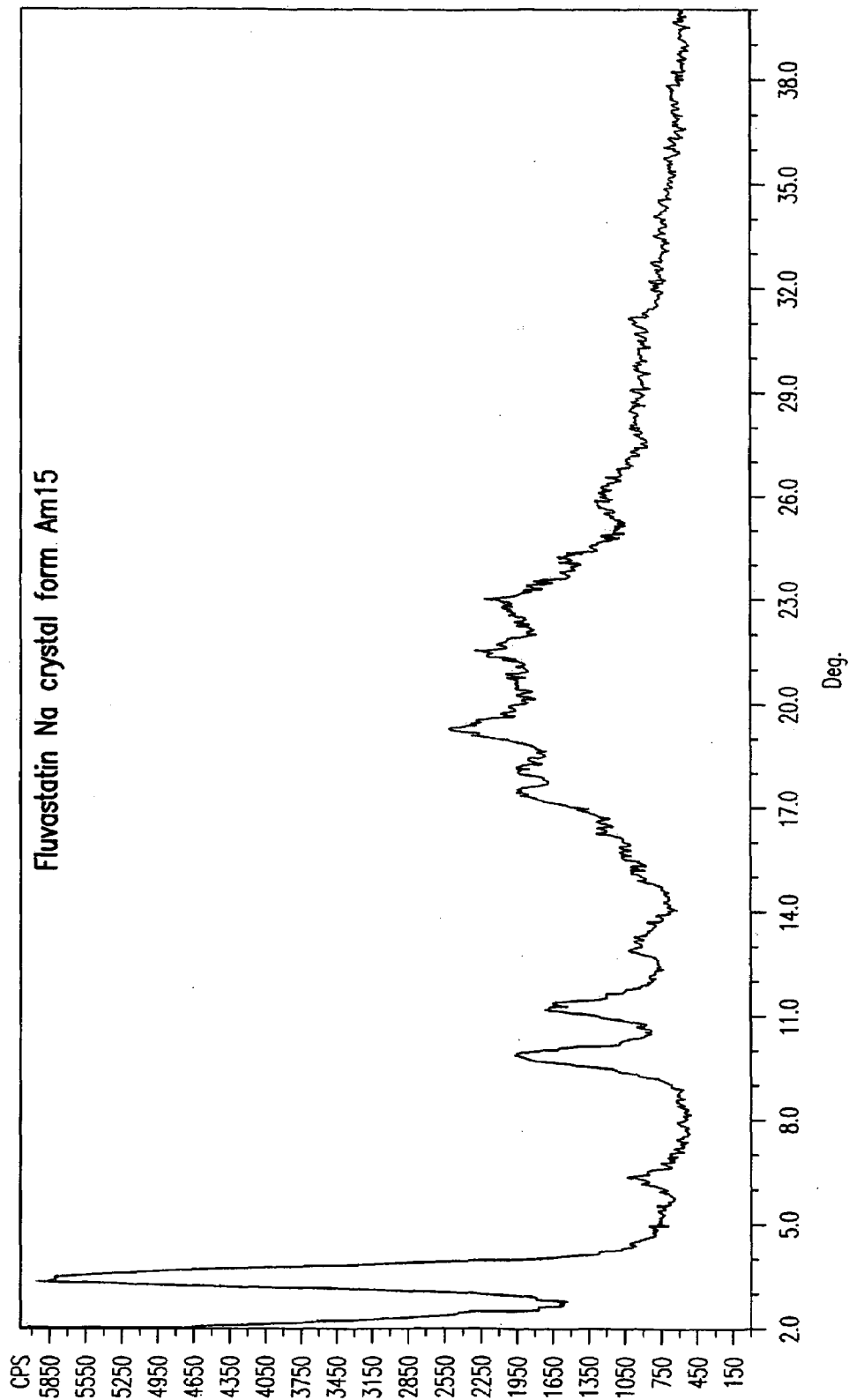
FIG. 107 depicts a powder X-ray diffractogram of fluvastatin sodium Form C.

385. The semi-crystalline form of embodiment 384 wherein the semi-crystalline form is characterized by a PXRD pattern substantially as depicted in FIG. 107.

386. The semi-crystalline form of embodiment 383 wherein the semi-crystalline form is fluvastatin sodium Form C.

387. A process for preparing semi-crystalline fluvastatin sodium Form C comprising:
a) hydrolyzing a lower alkyl ester of fluvastatin with sodium hydroxide in dichloromethane at room temperature,
b) precipitating fluvastatin sodium Form C from the dichloromethane, and
c) separating the dichloromethane from the Form C.

388. A semi-crystalline form of fluvastatin sodium characterized by a PXRD pattern with peaks at 4.5 and 11.2±0.2 degrees two-theta.

389. The semi-crystalline form of fluvastatin sodium of embodiment 388 further characterized by peaks at 5.7 and 19.3±0.2 degrees two-theta.

Figure 108:
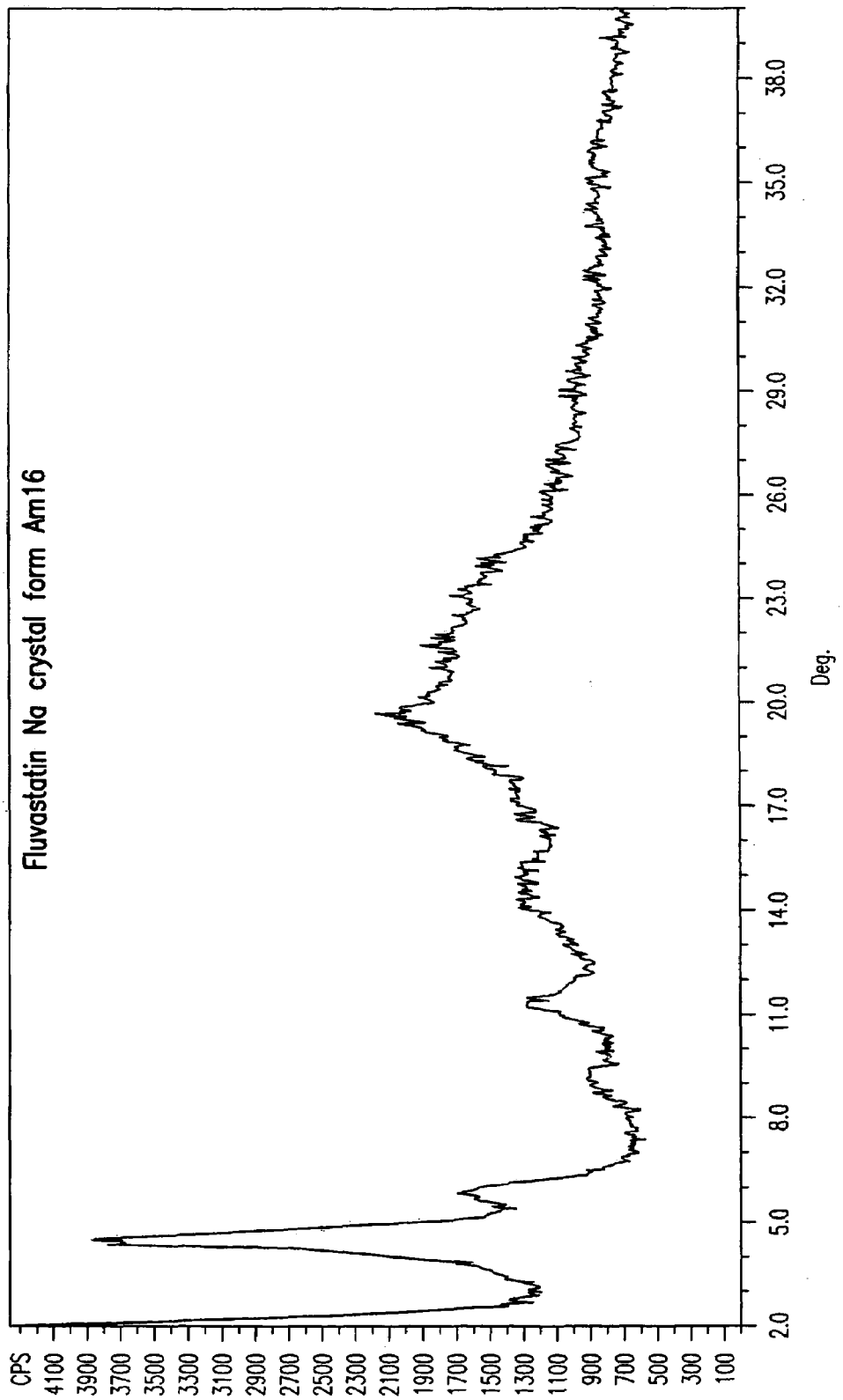
FIG. 108 depicts a powder X-ray diffractogram of fluvastatin sodium Form CI.

390. The semi-crystalline form of embodiment 389 wherein the semi-crystalline form is characterized by a PXRD pattern substantially as depicted in FIG. 108.

391. The semi-crystalline form of embodiment 388 wherein the semi-crystalline form is fluvastatin sodium Form CI.

392. A process for preparing semi-crystalline fluvastatin sodium Form CI comprising:
a) hydrolyzing a lower alkyl ester of fluvastatin with sodium hydroxide in a mixture of acetone and methanol.
b) precipitating Form CI from the mixture, and
c) separating the mixture from the Form CI.

393. A semi-crystalline form of fluvastatin sodium characterized by a PXRD pattern with a peak at 4.3±0.2 degrees two-theta.

394. The semi-crystalline form of fluvastatin sodium of embodiment 393 further characterized by peaks at 8.7, 11.0 and 19.2±0.2 degrees two-theta.

Figure 109:
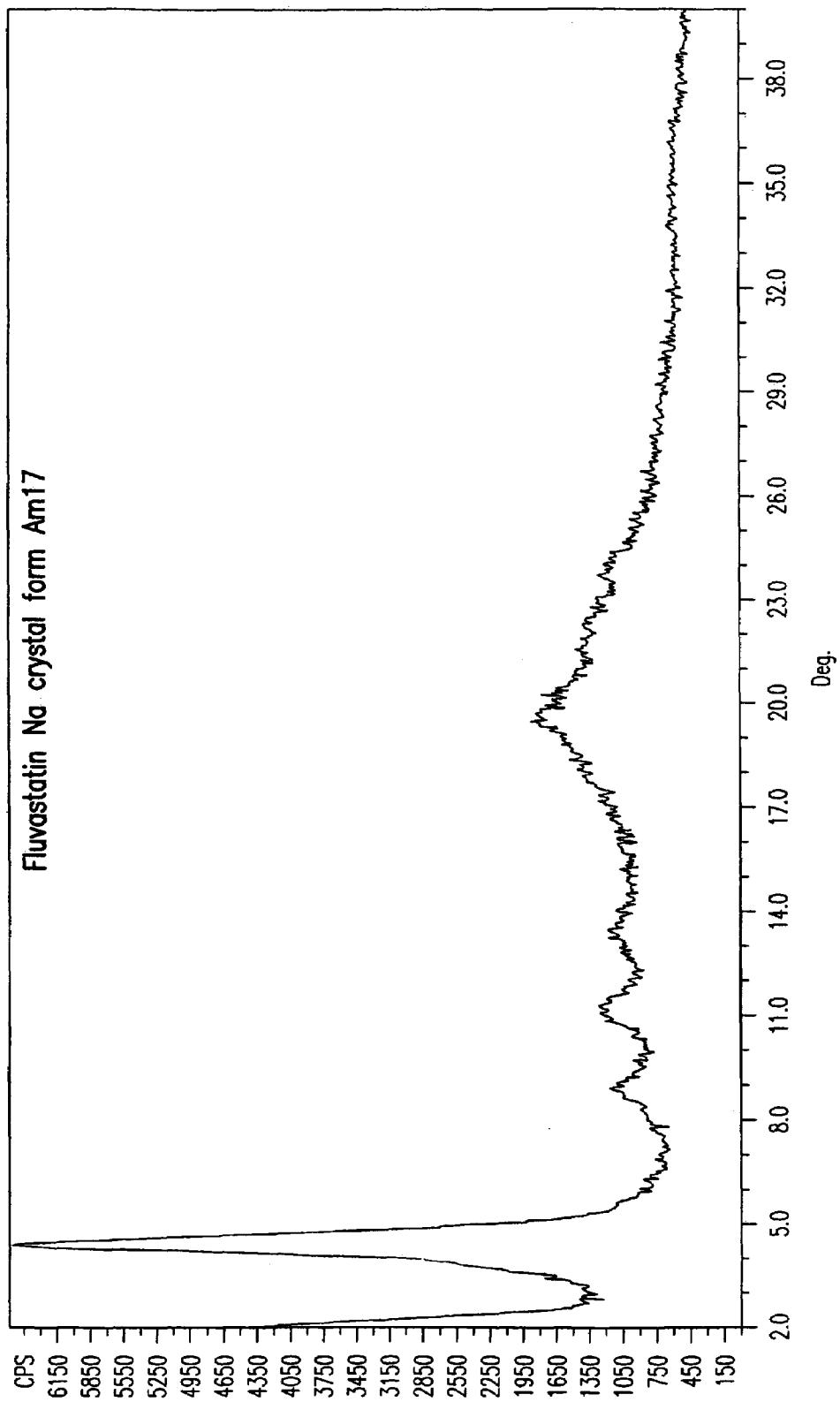
FIG. 109 depicts a powder X-ray diffractogram of fluvastatin sodium Form CII.

395. The semi-crystalline form of embodiment 394 wherein the semi-crystalline form is characterized by a PXRD pattern substantially as depicted in FIG. 109.

396. The semi-crystalline form of embodiment 393 wherein the semi-crystalline form is fluvastatin sodium Form CII.

397. A process for preparing semi-crystalline fluvastatin sodium Form CII comprising:
a) hydrolyzing a lower alkyl ester of fluvastatin with sodium hydroxide in a mixture of acetone and methanol,
b) precipitating Form CII from the mixture, and
c) separating the mixture from the Form CII.

398. A semi-crystalline form of fluvastatin sodium characterized by a PXRD pattern with peaks at 4.5, 20.4, 25.9 and 30.6±0.2 degrees two-theta.

399. The semi-crystalline form of fluvastatin sodium of embodiment 398 further characterized by peaks at 5.6, 10.1, 12.5, 19.0 and 29.7±0.2 degrees two-theta.

Figure 110:
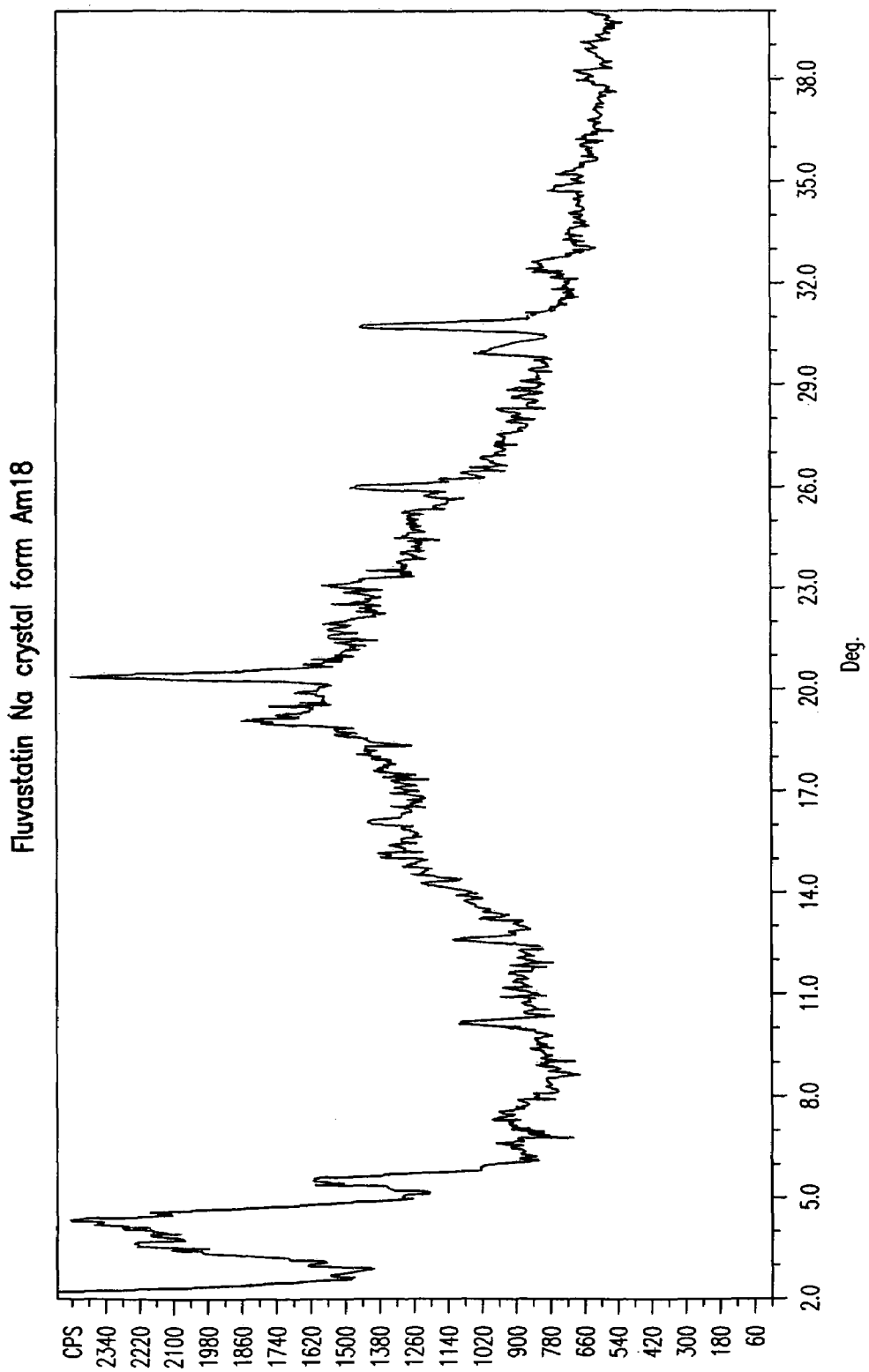
FIG. 110 depicts a powder X-ray diffractogram of fluvastatin sodium Form CIII.

400. The semi-crystalline form of embodiment 399 wherein the semi-crystalline form is characterized by a PXRD pattern substantially as depicted in FIG. 110.

401. The semi-crystalline form of embodiment 398 wherein the semi-crystalline form is fluvastatin sodium Form CIII.

402. A process for preparing semi-crystalline fluvastatin sodium Form CIII comprising:
  a) hydrolyzing a lower alkyl ester of fluvastatin with sodium hydroxide in a mixture of acetone and water,
  b) precipitating Form CIII from the mixture, and
  c) separating the mixture from the Form CIII.

403. A semi-crystalline form of fluvastatin sodium characterized by a PXRD pattern with peaks at 3.7, 9.7, 18.3, 19.9, 21.8±0.2 degrees two-theta.

404. The semi-crystalline form of fluvastatin sodium of embodiment 403 further characterized by peaks at 5.6, 11.3, 14.8, 22.6±0.2 degrees two-theta.

Figure 111:
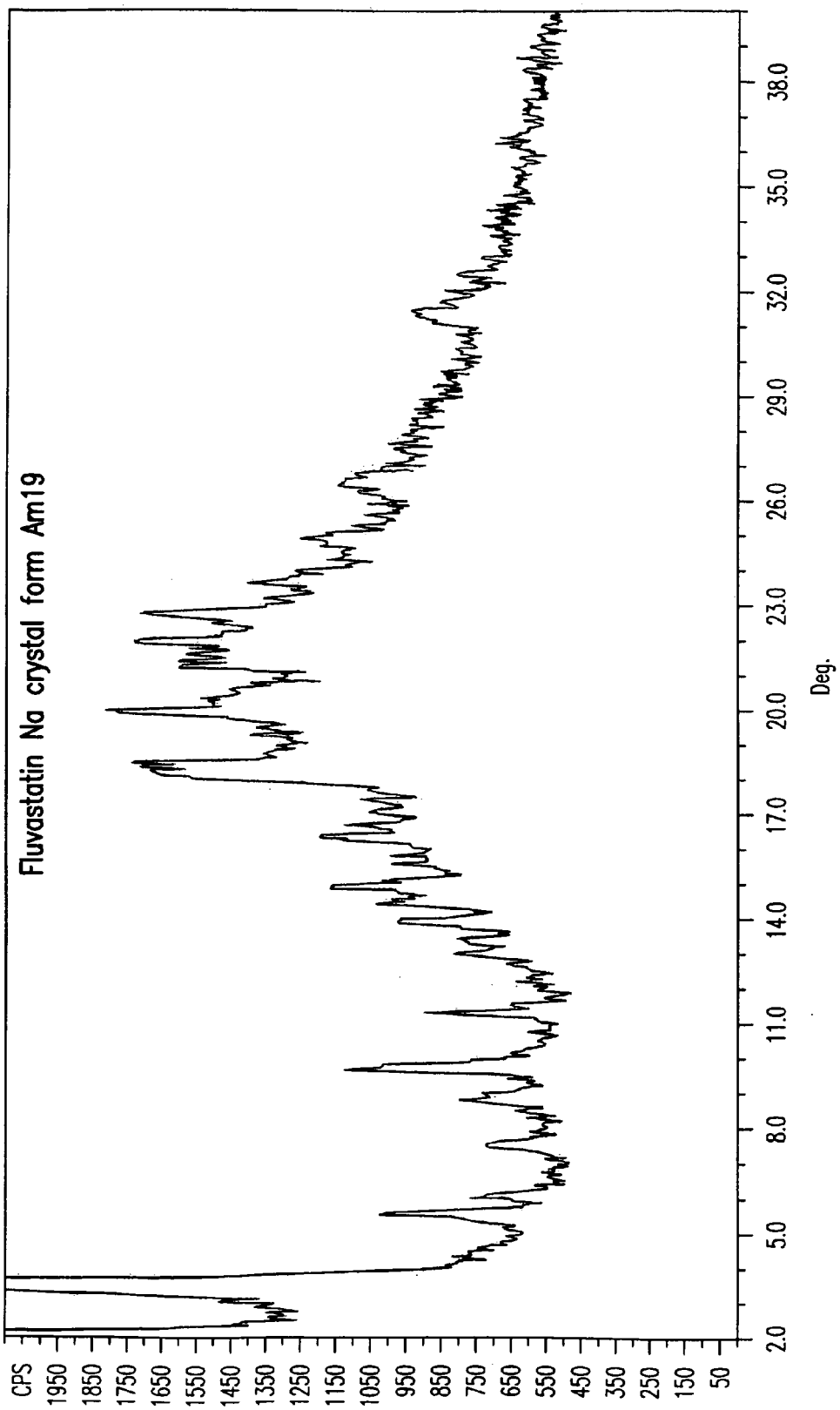
FIG. 111 depicts a powder X-ray diffractogram of fluvastatin sodium Form CIV.

405. The semi-crystalline form of embodiment 404 wherein the semi-crystalline form is characterized by a PXRD pattern substantially as depicted in FIG. 111.

406. The semi-crystalline form of embodiment 403 wherein the semi-crystalline form is fluvastatin sodium Form CIV.

407. A process for preparing semi-crystalline fluvastatin sodium Form CIV comprising:
  a) hydrolyzing a lower alkyl ester of fluvastatin with sodium hydroxide in THF,
  b) adding hexanes to the THF to induce precipitation of Form CIV, and
  c) separating the THF and hexanes from the Form CIV.

408. A semi-crystalline form of fluvastatin sodium characterized by a PXRD pattern with peaks at 3.7, 8.9, 19.1, 22.5, 29.7±0.2 degrees two-theta.

409. The semi-crystalline form of fluvastatin sodium of embodiment 408 further characterized by peaks at 11.5, 17.0, 25.1, 26.9, 28.2±0.2 degrees two-theta.

Figure 112:
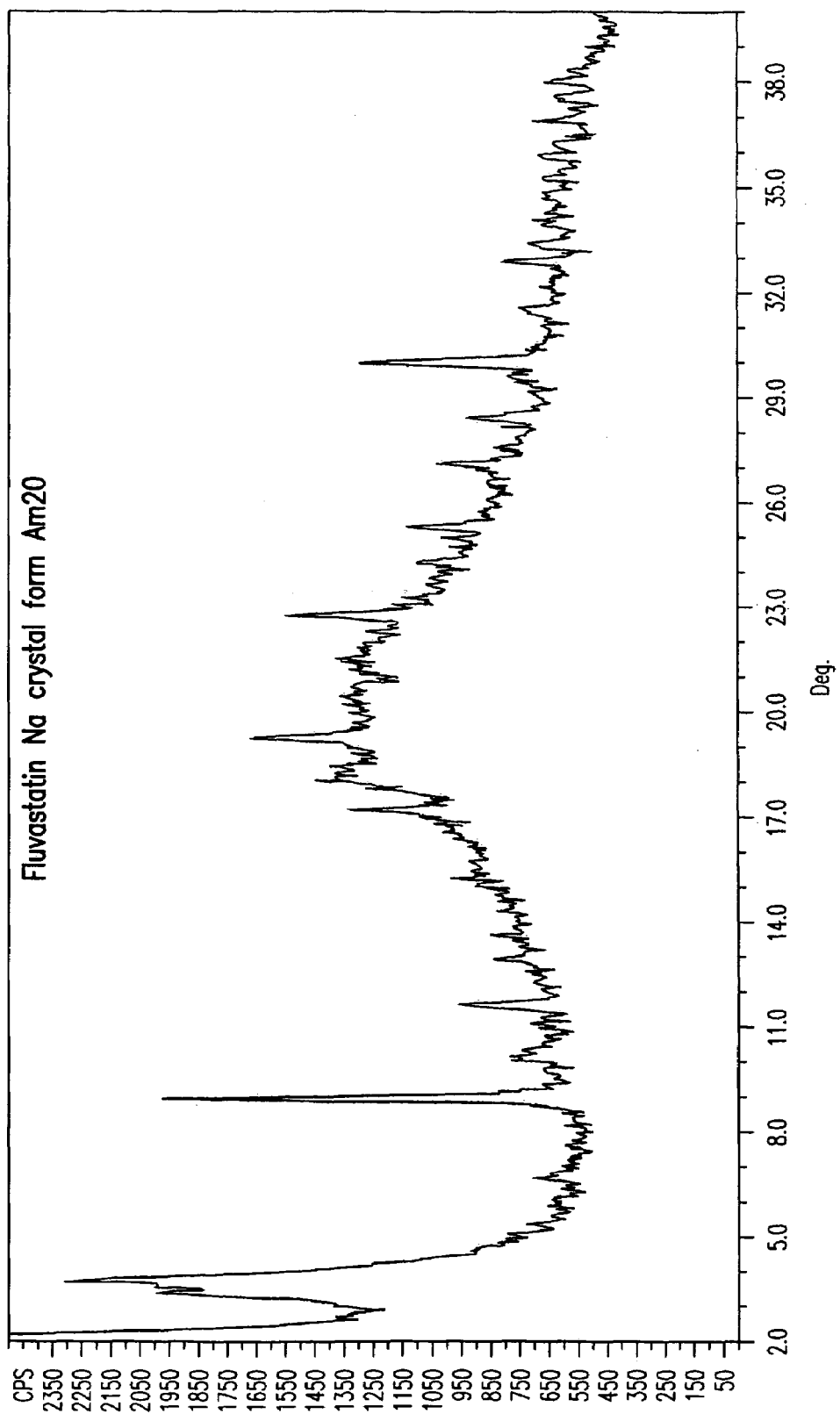
FIG. 112 depicts a powder X-ray diffractogram of fluvastatin sodium Form CV.

410. The semi-crystalline form of embodiment 409 wherein the semi-crystalline form is characterized by a PXRD pattern substantially as depicted in FIG. 112.

411. The semi-crystalline form of embodiment 408 wherein the semi-crystalline form is fluvastatin sodium Form CV.

412. A process for preparing semi-crystalline fluvastatin sodium Form CV comprising:
  a) hydrolyzing a lower alkyl ester of fluvastatin with sodium hydroxide in acetonitrile at elevated temperature,
  b) cooling the acetonitrile,
  c) precipitating Form CV from the acetonitrile, and
  d) separating the acetonitrile from the Form CV.

413. A pharmaceutical composition comprising an effective amount of a fluvastatin sodium form selected from the group consisting of Form I, II, III, IV, IV-1, V, VI, VII, VIII, IX, IX-1, XI, XI-2, XII, XIII, XVI, XVII, XVIII, XIX, XIX-1, XX, XXII, XXIII, XXIV, XXVI, XXVII, XXIX, XXX, XXXI, XXXIII, XXXIV, XXXV, XXXVI, XXXVII, XXXVIII, XXXIX, XLI, XLII, XLIII, XLIV, XLV, XLVI, XLVII, XLVIII, XLIX, L, LI, LIII, LIV, LV, LVI, LVII, LVIII, LX, LXIV, LXV, LXVI, LXVII, LXVIII, LXIX, LXX, LXXI, LXXII, LXXIV, LXXV, LXXVI, LXXVII, LXXVIII, XC, XCI, XCII, XCIII, XCIV, XCV, XCVI, XCVII, XCVIII, XCIX, C, CI, CII, CIII, CIV, CV and mixtures thereof and a pharmaceutically acceptable excipient.

414. A pharmaceutical dosage form comprising an effective amount of a fluvastatin sodium form selected from the group consisting of Form I, II, III, IV, IV-1, V, VI, VII, VIII, IX, IX-1, XI, XI-2, XII, XIII, XVI, XVII, XVIII, XIX, XIX-1, XX, XXII, XXIII, XXIV, XXVI, XXVII, XXIX, XXX, XXXI, XXXIII, XXXIV, XXXV, XXXVI, XXXVII, XXXVIII, XXXIX, XLI, XLII, XLIII, XLIV, XLV, XLVI, XLVII, XLVIII, XLIX, L, LI, LIII, LIV, LV, LVI, LVII, LVIII, LX, LXIV, LXV, LXVI, LXVII, LXVIII, LXIX, LXX, LXXI, LXXII, LXXIV, LXXV, LXXVI, LXXVII, LXXVIII, XC, XCI, XCII, XCIII, XCIV, XCV, XCVI, XCVII, XCVIII, XCIX, C, CI, CII, CIII, CIV, CV and mixtures thereof and a pharmaceutically acceptable excipient.

415. A method of treating a patient suffering from hypercholesterolemia or hyperlipidemia comprising the step of administering to the patient an effective amount of a fluvastatin sodium form selected from the group consisting of Form I, II, III, IV, IV-1, V, VI, VII, VIII, IX, IX-1, XI, XI-2, XII, XIII, XVI, XVII, XVIII, XIX, XIX-1, XX, XXII, XXIII, XXIV, XXVI, XXVII, XXIX, XXX, XXXI, XXXIII, XXXIV, XXXV, XXXVI, XXXVII, XXXVIII, XXXIX, XLI, XLII, XLIII, XLIV, XLV, XLVI, XLVII, XLVIII, XLIX, L, LI, LIII, LIV, LV, LVI, LVII, LVIII, LX, LXIV, LXV, LXVI, LXVII, LXVIII, LXIX, LXX, LXXI, LXXII, LXXIV, LXXV, LXXVI, LXXVII, LXXVIII, XC, XCI, XCII, XCIII, XCIV, XCV, XCVI, XCVII, XCVIII, XCIX, C, CI, CII, CIII, CIV, CV and mixtures thereof.

416. A process for preparing fluvastatin sodium Form B comprising:
  a) dissolving fluvastatin free acid, lactone or mixture thereof in a mixture of methanol and water,
  b) adding methyl tert-butyl ether to the solution to induce precipitation of Form B, and
  c) separating the methanol, water and methyl tert-butyl ether from the Form B.

417. A process for preparing amorphous fluvastatin sodium comprising:
  a) dissolving fluvastatin sodium in 1,4-dioxane at elevated temperature,
  b) cooling the solution to induce precipitation of amorphous fluvastatin sodium, and
  c) separating the amorphous fluvastatin sodium from the 1,4-dioxane.

418. A crystalline form of fluvastatin sodium characterized by a PXRD pattern with peaks at 3.7 and 4.4±±0.2 degrees two-theta.

419. The crystalline form of embodiment 418 further characterized by peaks at 5.6 and 10.8±0.2 degrees two-theta.

420. A process for preparing crystalline fluvastatin sodium Form LXVII comprising combining a solution of a lower alkyl ester of fluvastatin in acetone with a sodium hydroxide and methanol to precipitate the crystalline form.

421. A crystalline form of fluvastatin characterized by an PXRD pattern with peaks at 5.6, 6.3 and 10.5±0.2 degrees two-theta.

422. The crystalline form of embodiment 421, further characterized by peaks at 4.1, 5.0, 11.0, 15.7, 17.2 and 19.6±0.2 degrees two-theta.

423. A process for preparing fluvastatin sodium Form LX comprising heating a solution of fluvastatin sodium in methanol and combining the solution with ethyl acetate to precipitate the crystalline form.

424. A crystalline form of fluvastatin sodium characterized by an PXRD pattern with peaks at 5.8, 13.9 and 14.7±0.2 degrees two-theta.

425. The crystalline form of embodiment 424, further characterized by peaks at 5.1, 9.3, 11.7 and 19.4±0.2 degrees two-theta.

426. A process for preparing crystalline fluvastatin Form LXIV comprising precipitating the crystalline form from a mixture of acetone and methanol.

427. A crystalline form of fluvastatin sodium characterized by an PXRD pattern with peaks at 5.8, 13.9 and 14.7±0.2 degrees two-theta.

428. The crystalline form of embodiment 427, further characterized by peaks at 5.1, 9.3, 11.7 and 19.4±0.2 degrees two-theta.

429. A process for preparing fluvastatin sodium Form LXV comprising adding propan-2-ol to a solution of fluvastatin sodium in methanol to precipitate the crystalline form.

430. A crystalline form of fluvastatin sodium characterized by an PXRD pattern with peaks at 3.6, 10.8, 17.8, 18.3 and 21.6±0.2 degrees two-theta.

431. The crystalline form of embodiment 430 further characterized by peaks at 7.2, 12.2, 14.4 and 25.5±0.2 degrees two-theta.

432. A process for preparing crystalline fluvastatin Form LXVI comprising heating a solution of fluvastatin sodium in water and cooling the solution to precipitate the crystalline form.

433. A crystalline form of fluvastatin sodium characterized by an PXRD with peaks at 3.6, 5.9, 10.8 and 11.6±0.2 degrees two-theta.

434. The crystalline form of embodiment 433, further characterized by peaks at 9.3, 15.4, 17.0, 18.4 and 23.0±0.2 degrees two-theta.

435. A process for preparing crystalline fluvastatin sodium Form LXVIII comprising combining a solution of a lower alkyl ester of fluvastatin in acetone with a sodium hydroxide and methanol to precipitate the crystalline form.

436. A process for preparing crystalline fluvastatin sodium Form II comprising:
a) heating solid fluvastatin sodium in a solvent selected from butan-1-ol and propan-2-ol,
b) crystallizing Form II from the solvent, and
c) separating the solvent from Form II.

437. A process for preparing crystalline fluvastatin sodium Form III comprising:
a) heating fluvastatin sodium in a solvent selected from the group consisting of butan-1-ol, ethyl acetate and THF,
b) slowly adding an anti-solvent selected from the group consisting of MTBE, hexanes and cyclohexane to the solvent to induce precipitation of Form III, and
c) separating the solvent and anti-solvent from Form III.

438. A process for preparing crystalline fluvastatin sodium Form III comprising:
a) heating amorphous fluvastatin sodium in refluxing ethanol,
b) precipitating Form III from the ethanol, and
c) separating the ethanol from the Form III.

439. A process for preparing crystalline fluvastatin sodium Form V comprising:
a) heating fluvastatin sodium in refluxing butan-1-ol,
b) slowly adding heptane to the refluxing solution,
c) precipitating Form V from the solution, and
d) separating the butan-1-ol and heptane from the Form V.

440. A process for preparing crystalline fluvastatin sodium Form V comprising:
a) heating fluvastatin sodium in a ternary solvent system of ethanol:ethyl acetate:propan-1-ol at reflux temperature,
b) adding n-hexane to the solution,
c) precipitating Form V from the solution, separating the ethanol, ethyl acetate, propan-1-ol and n-hexane from the Form V.

441. A process for preparing crystalline fluvastatin sodium Form IX-1 comprising:
a) heating fluvastatin sodium in a solvent selected from the group consisting of butan-1-ol, ethyl acetate, isobutyl acetate, ethanol, toluene, tetrahydrofuran and methyl ethyl ketone,
b) inducing precipitation of Form IX-1 by adding of an anti-solvent selected from the group consisting of n-pentane, diethyl ether, methyl tert-butyl ether, dichloromethane, hexanes and cyclohexane to the solvent, and
c) separating the solvent and anti-solvent from the Form IX-1.

442. A process for preparing crystalline fluvastatin sodium Form XII comprising:
a) heating fluvastatin sodium in butan-1-ol,
b) inducing precipitation of Form XII by adding 1,4-dioxane to the butan-1-ol, and
c) separating the 1,4-dioxane and butan-1-ol from the Form XII.

443. A crystalline form of fluvastatin sodium characterized by an PXRD pattern with peaks at 4.9, 5.9, 7.2 and 12.3±0.2 degrees two-theta.

444. The crystalline form of embodiment 443, further characterized by peaks at 9.7, 10.9 and 13.9±0.2 degrees two-theta.

445. A process for preparing fluvastatin sodium Form XCIII comprising suspending fluvastatin sodium Form XV in propan-1-ol to obtain Form XCIII.

DETAILED DESCRIPTION OF THE PREFERRED EMBODIMENTS

As used herein, a lower alkyl group refers to a $C_1$ to $C_4$ alkyl group.

The present invention provides novel crystal forms of [R*,S*-(E)]-(±)-7-[3-(4-fluorophenyl)-1-(1-methylethyl)-1H-indol-2-yl]-3,5-dihydroxy-6-heptenoic acid monosodium (fluvastatin sodium). The novel crystalline forms of fluvastatin sodium have been designated Forms I, II, III, IV, IV-1, V, VI, VII, IX, IX-1, XI, XI-2, XII, XIII, XVI, XVII, XVIII, XIX, XIX-1, XX, XXII, XXIII, XXIV, XXVI, XXVII, XXIX, XXX, XXXI, XXXIII, XXXIV, XXXV, XXXVI, XXXVII, XXXVIII, XXXIX, XLI, XLII, XLIII, XLIV, XLV, XLVI, XLVII, XLVIII, XLIX, L, LI, LIII, LIV, LV, LVI, LVII, LVIII, LX, LXIV, LXV, LXVI, LXVII, LXVIII, LXIX, LXX, LXXI, LXXII, LXXIV, LXXV, LXXVI, LXXVII, LXXVIII, XC, XCI, XCII, XCIII, XCIV, XCV, XCVI, XCVII, XCVIII, XCIX, C, CI, CII, CIII, CIV, and CV. In so doing we have opted to use Roman numerals as labels for the crystals instead of the Roman alphabetical labels used by others working in the field to label other crystalline forms of fluvastatin sodium.

Fluvastatin sodium crystal forms XIV, LXXIII, LXXIX, LXXX and LXXXVII appear in the priority applications of the present invention, and are present in another application filed on the same day.

Whether the two enantiomers of [R*,S*-(E)]-(±) fluvastatin sodium co-crystallize in a single unit cell or whether they crystallize in separate unit cells that are mirror images of each other has yet to be determined for all of the new crystals forms. Accordingly, the crystal forms of this invention are considered to include crystals that exhibit substantially the same PXRD patterns as those depicted in the figures whether they are prepared starting from pure or enriched [R*,S*-(E)]-(+) and [R*,S*-(E)]-(−) fluvastatin sodium or racemic fluvastatin sodium.

Many of the novel forms can be obtained by crystallization methods and are stable under normal humidity conditions. Those skilled in the art, after reading this disclosure will appreciate that some of the crystallization processes by which the new forms can be made share certain traits. Generally speaking, in those processes fluvastatin sodium is dissolved in a solvent, the selection of which is taught with reference to each particular crystalline form in the sections of this disclosure that follow. While the solution of fluvastatin sodium in the solvent is refluxing, a selected anti-solvent (the selection of which also is taught below) is added to the solution to induce precipitation of fluvastatin sodium in the crystalline form desired. The anti-solvent addition and precipitation can be performed, and preferably are performed, at elevated temperature. Additional precipitation, of course, will occur in many cases during subsequent cooling of the mixture. It will also be seen that in other processes heating of the solvent is not preferred.

By the crystallization processes of this invention, each of the novel crystal forms of fluvastatin sodium is obtained substantially free from other crystal forms, which means less than 5% of any other crystal form as measured by X-ray powder diffraction. Although these processes have been found to yield the novel crystal forms, and yield them in high purity, other processes that produce the crystal forms of this invention in either greater or lesser purity may yet be found.

The yields of the various processes for preparing the new fluvastatin sodium crystal forms vary greatly depending upon the form desired. As those skilled in the art will appreciate, a low yield of the desired crystal form does not necessarily mean that precious unconverted starting material is lost. It, or another crystalline or amorphous form of fluvastatin sodium or fluvastatin free acid or lactone can be recovered from the separated solvent or diluent, such as by evaporating the separated diluent or solvent used in the process to leave a residue containing fluvastatin.

Some of the new forms of fluvastatin sodium are hydrated. The level of water in fluvastatin sodium is measured by Karl Fisher using methods known in the art. Some of the new crystal forms of fluvastatin sodium contain residual solvent in addition to water, which is seen by the fact that the TGA weight loss value is significantly larger than the Karl Fisher value. Some of the solvated crystal forms contain only small quantities of residual solvent. In this latter group fluvastatin sodium can be found in the following hydrated states: hemihydrate (water content about 2%); monohydrate (water content about 3-4%); sesquihydrate (water content about 5-6%); dihydrate (water content about 7-8%); hemipentahydrate (water content about 9-10%); trihydrate (water content about 11-13%); tetrahydrate (water content about 14-16%); pentahydrate (water content 17-18%); hexahydrate (water content about 19-20%); 8-hydrate (water content about 25%); 9-hydrate (water content about 27-28%).

Fluvastatin is a known compound that can be purchased from commercial sources or synthesized by known processes such as the process disclosed in U.S. Pat. No. 4,739,073, which is incorporated herein by reference in its entirety. In particular, U.S. Pat. No. 4,739,073 is incorporated herein for its disclosure of how to prepare fluvastatin and fluvastatin sodium. In the processes of this invention that use fluvastatin sodium as a starting material, fluvastatin sodium Form B is the preferred starting material unless otherwise indicated.

As used in this disclosure, the term "elevated temperature" means a temperature above ambient temperature or above about 25EC. Preferred elevated temperatures are 50EC and above and especially preferred elevated temperatures, when used in reference to contacting with particular liquids, are the boiling points of such liquids.

The term "anti-solvent" means a liquid that, when added to a solution of fluvastatin sodium in a solvent, induces precipitation of fluvastatin sodium. Precipitation of fluvastatin sodium is induced by the anti-solvent when addition of the anti-solvent causes fluvastatin sodium to precipitate from the solution more rapidly or to a greater extent than fluvastatin sodium precipitates from a solution containing an equal concentration of fluvastatin in the same solvent when the solution is maintained under the same conditions for the same period of time but without adding the anti-solvent. Precipitation can be perceived visually as a clouding of the solution or formation of distinct particles of fluvastatin sodium suspended in or on the surface of the solution or collected on the walls or at the bottom of the vessel containing the solution.

Fluvastatin Sodium Crystal Form I

Fluvastatin sodium Form I produces a PXRD diffractogram with characteristic peaks at 3.7, 11.3, 13.1, 17.9, 18.4 and 21.8 degrees two-theta (FIG. 1).

Fluvastatin sodium Form I can be prepared directly from a lower alkyl ester of fluvastatin such as fluvastatin methyl ester. The ester is dissolved in a solution of about one molar equivalent of sodium in a solvent selected from acetone and acetonitrile. The sodium can be conveniently provided by dissolving the appropriate quantity of sodium hydroxide pellets in water, acetone or acetonitrile, while exercising caution since the dissolution in water is highly exothermic. Fluvastatin sodium Form I forms as a precipitate in the solvent and can be conventionally separated therefrom by a known method of isolation such as filtering, decanting, centrifuging and the like, preferably filtering under a nitrogen stream.

Form I can also be prepared by crystallization from acetone or a mixture of butan-2-ol and water, with a 10:1 butan-2-ol: water mixture being especially preferred. Preferably Form B is dissolved in the solvent at the solvent's reflux temperature a reflux temperature by adding the Form B to the refluxing solvent.

According to a preferred procedure about 0.05:1 (w/v) of Form B is added to refluxing acetone. If Form B does not completely dissolve after a reasonable period of time, the hot solution may be filtered to remove any undissolved particles. Next, about 1:3 (v/v) of MTBE is added to the solution. The mixture is then allowed to cool. If Form I does not precipitate after cooling to ambient temperature, then an additional quantity of MTBE can be added to the solution and it can be partially concentrated on a rotary evaporator to induce precipitation. The product is then isolated using conventional methods.

According to another preferred procedure, about 1:20 (w/v) of Form B is added to a refluxing 10:1 butan-2-ol:water mixture. After dissolution is complete, the mixture is cooled or allowed to cool to induce precipitation after which Form I is isolated conventionally.

Fluvastatin Sodium Crystal Form II

Fluvastatin sodium Form II produces a PXRD diffractogram (FIG. 2) with a characteristic peak at 3.6±0.2 degrees two-theta and other peaks at 5.4, 5.7, 10.7 and 20.3±0.2 degrees two-theta.

Form II can be prepared from either fluvastatin sodium such as Form B or amorphous fluvastatin. Starting from Form B, the starting material is taken up in refluxing butan-1-ol. The solution is then cooled or allowed to cool to ambient temperature and is allowed to stand without seeding until a precipitate is observed. Starting with amorphous fluvastatin sodium, about 1:21 (w/v) of the starting material is suspended in refluxing propan-2-ol. The suspension is then allowed to cool and stand until precipitation occurs.

Following either procedure, the precipitate is separated from the diluent by conventional techniques such as filtering, decanting, centrifuging and the like. Drying may be carried out at 50EC in a vacuum oven.

Fluvastatin Sodium Crystal Form III

Fluvastatin sodium Form III produces a PXRD diffractogram with characteristic peaks at 3.5, 9.5, 10.1, 10.9 and 20.1 degrees two-theta (FIG. 2).

Like Form II, Form III can be prepared from a form of fluvastatin sodium such as either Form B or amorphous fluvastatin sodium. In addition, it can be prepared from fluvastatin sodium Form XIV.

Starting from Form B, the starting material is dissolved in a solvent selected from the group consisting of butan-1-ol, ethyl acetate and THF. Form B is preferably dissolved at the reflux temperature of the solvent. If the Form B does not completely dissolve, the hot solution can be filtered to obtain a clear filtrate. While at reflux temperature, an anti-solvent selected from the group consisting of MTBE, hexanes and cyclohexane, is slowly added to the solution (dropwise addition on the bench scale). Addition of the anti-solvent may induce precipitation at elevated temperature. If it does not, Form III should precipitate upon cooling the solution to ambient temperature.

Starting from amorphous fluvastatin sodium, about 1:6 (w/v) of the starting material is dissolved in refluxing ethanol. While the solution is refluxing, Form III should be seen to come out of solution. If it does not precipitate within about an hour, the solution can be cooled to ambient temperature, which should induce precipitation of Form III.

Starting from fluvastatin sodium Form XIV, about 1:7 (w/v) of the starting material is suspended in refluxing ethanol for a period of time sufficient to effect the conversion to Form III, which may take several hours or days. Thereafter the suspension is cooled to ambient temperature and the precipitate is isolated.

In each of these procedures for making fluvastatin sodium Form III, the product may be separated from the diluent by conventional techniques such as filtering, decanting, centrifuging and the like. Drying may be carried out at 50EC in a vacuum oven.

Fluvastatin Sodium Crystal Form IV

Figure 5:
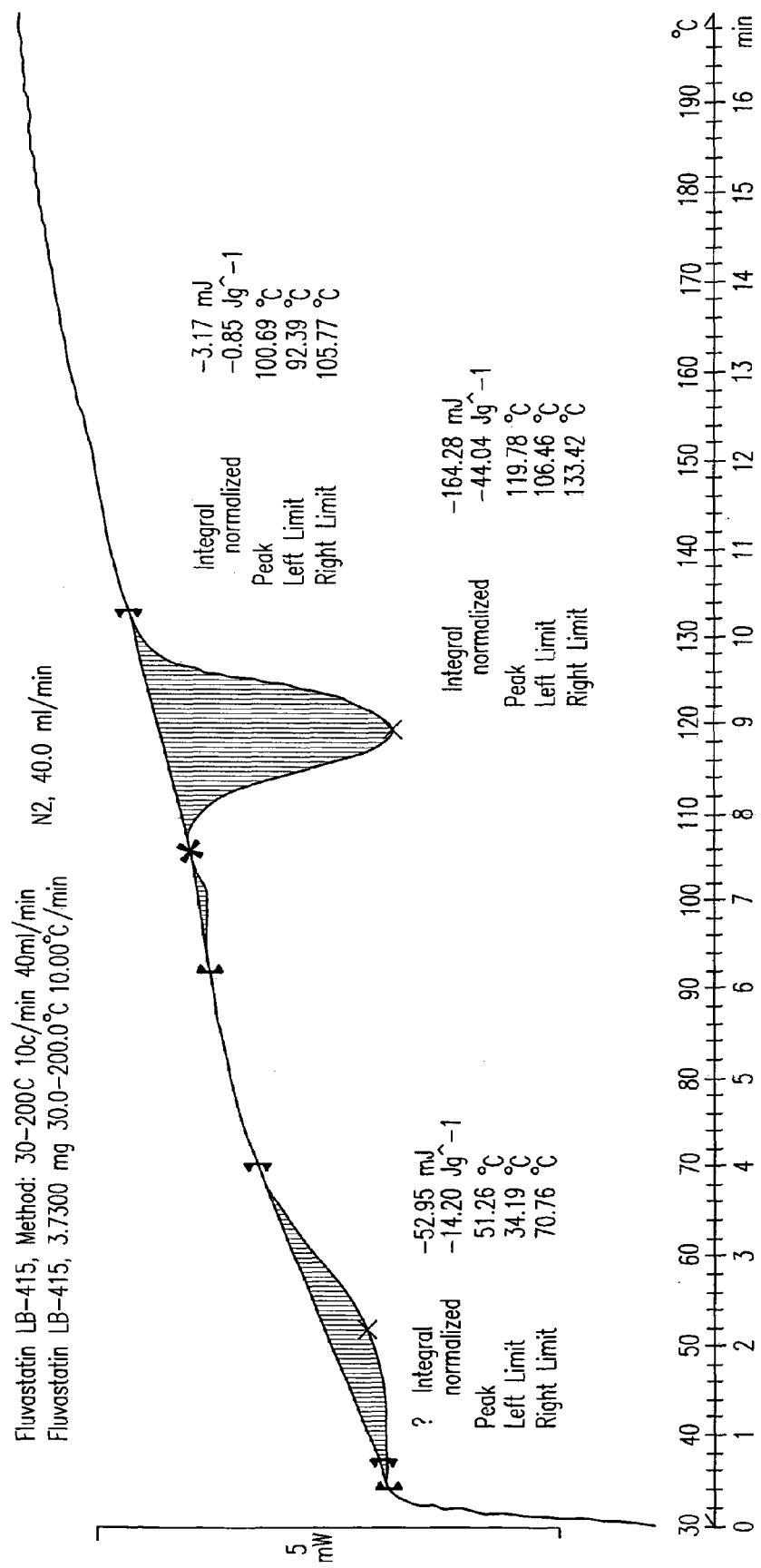
FIG. 5 depicts a DSC thermogram of fluvastatin sodium Form IV.
Figure 6:
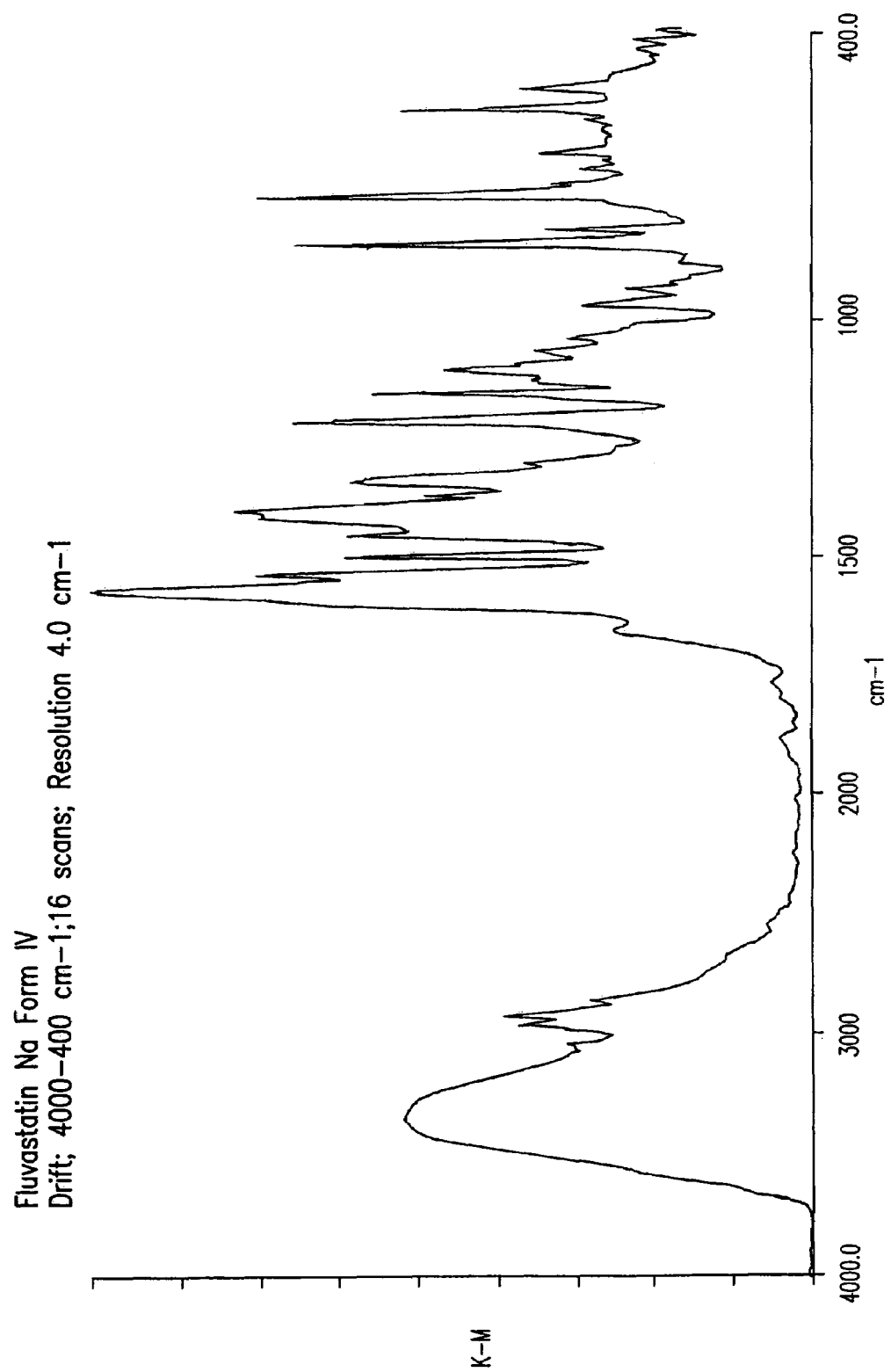
FIG. 6 depicts an IR spectrum of fluvastatin sodium Form IV scanned from 4000 to 400 cm$^{-1}$, while FIG. 6a expands the 4000-1500 cm$^{-1}$ region of the spectrum and FIG. 6b expands the 1500-400 cm$^{-1}$ region of the spectrum.
Figure 6B:
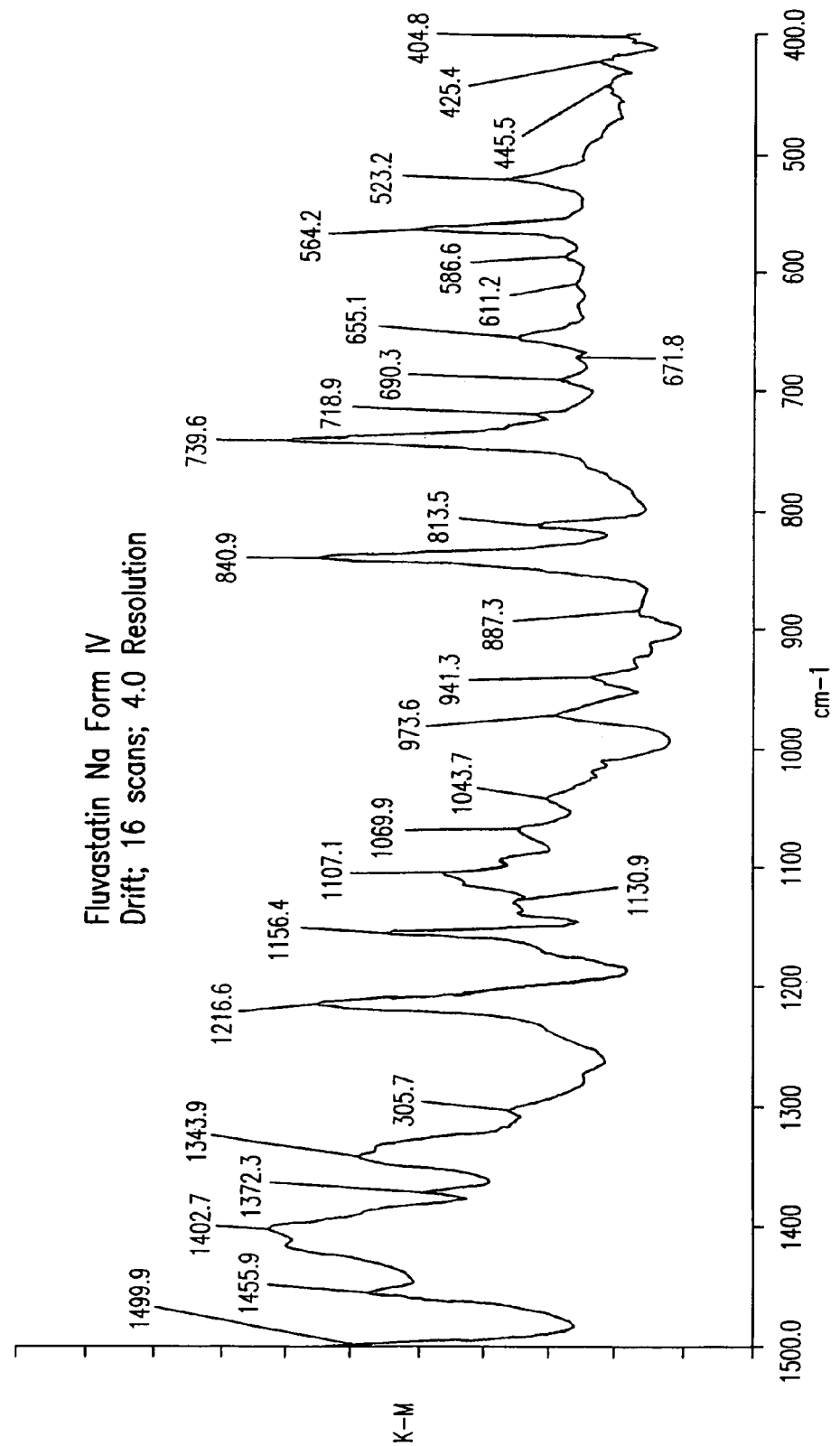

Fluvastatin sodium Form IV produces a PXRD diffractogram with characteristic peaks at 3.6, 4.0, 9.8, 10.8 and 22.0±0.2 degrees two-theta and additional peaks at 6.5, 12.8, 16.3, 16.9, 17.2, 18.3, 19.5, 20.6 and 22.9±0.2 degrees two-theta (FIG. 4). Fluvastatin sodium Form IV produced the DSC thermogram shown in FIG. 5, in which a main endothermic peak can be seen below 70° C. and at about 120° C. The water content of the sample, measured by Karl Fisher, is about 4 wt. %. The weight loss by TGA is 8.3%. The IR spectrum of fluvastatin sodium Form IV is shown in FIGS. 6, 6a and 6b.

Fluvastatin sodium Form IV can be prepared by dissolving fluvastatin sodium in refluxing tetrahydrofuran ("THF") and adding dropwise organic anti-solvents like chloroform, dichloromethane, 1,2-dichloroethane, diethyl ether and n-pentane to the refluxing solution. Form IV should precipitate from the refluxing mixture. The mixture may be maintained at reflux temperature for any amount of time necessary to achieve the desired yield of Form IV. Afterwards the mixture is allowed to cool to room temperature and Form IV can be isolated by a known method of isolation such as filtering, decanting, centrifuging and the like, preferably filtering under nitrogen stream. Fluvastatin sodium Form IV also can be prepared by the same procedure, but substituting butan-1-ol, 1,4-dioxane or propan-2-ol for the THF and using cyclohexane or methyl t-butyl ether ("MTBE") as the anti-solvent.

Fluvastatin Sodium Crystal Form IV-1

Figure 8:
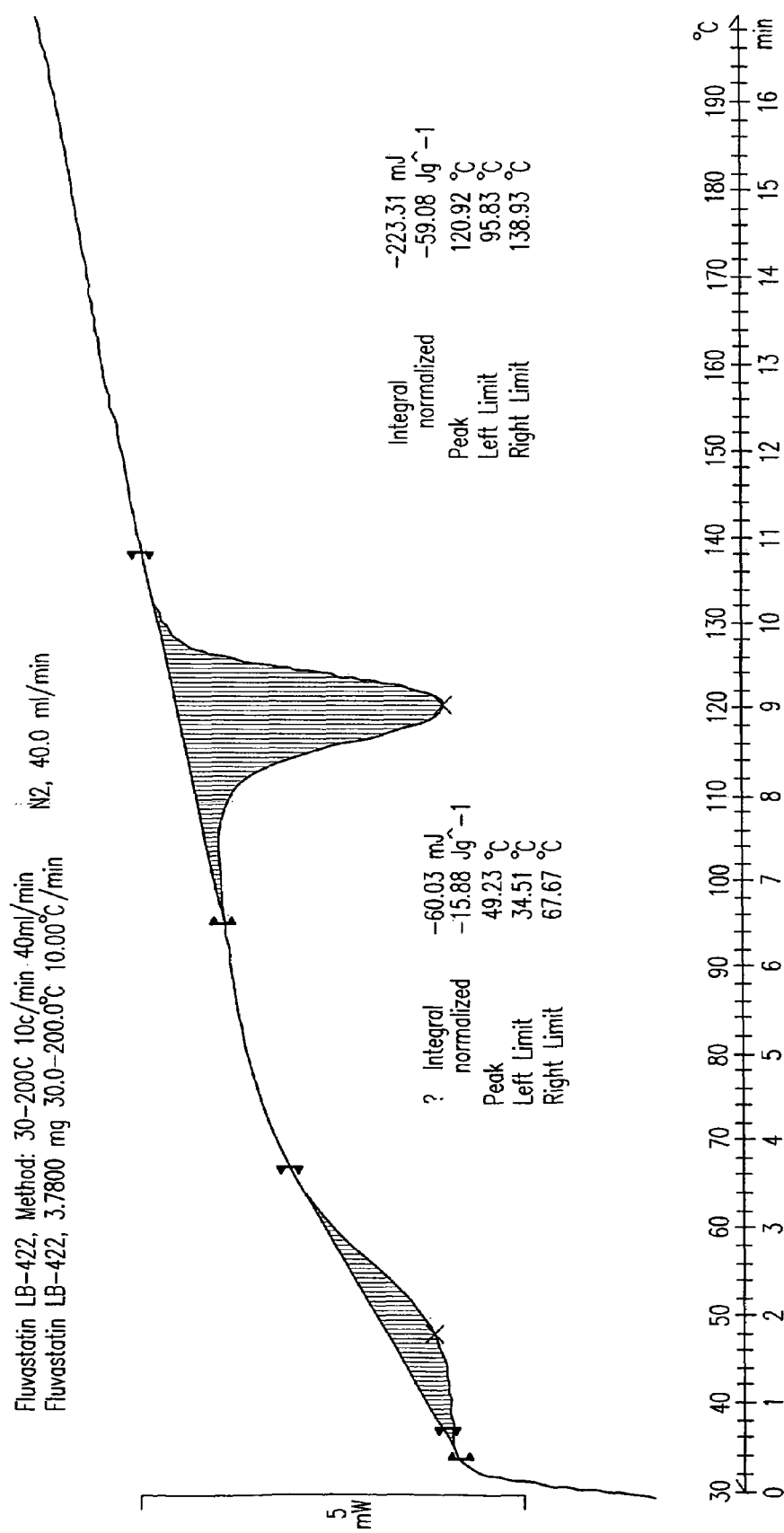
FIG. 8 depicts a DSC thermogram of fluvastatin sodium Form IV-1.
Figure 9A:
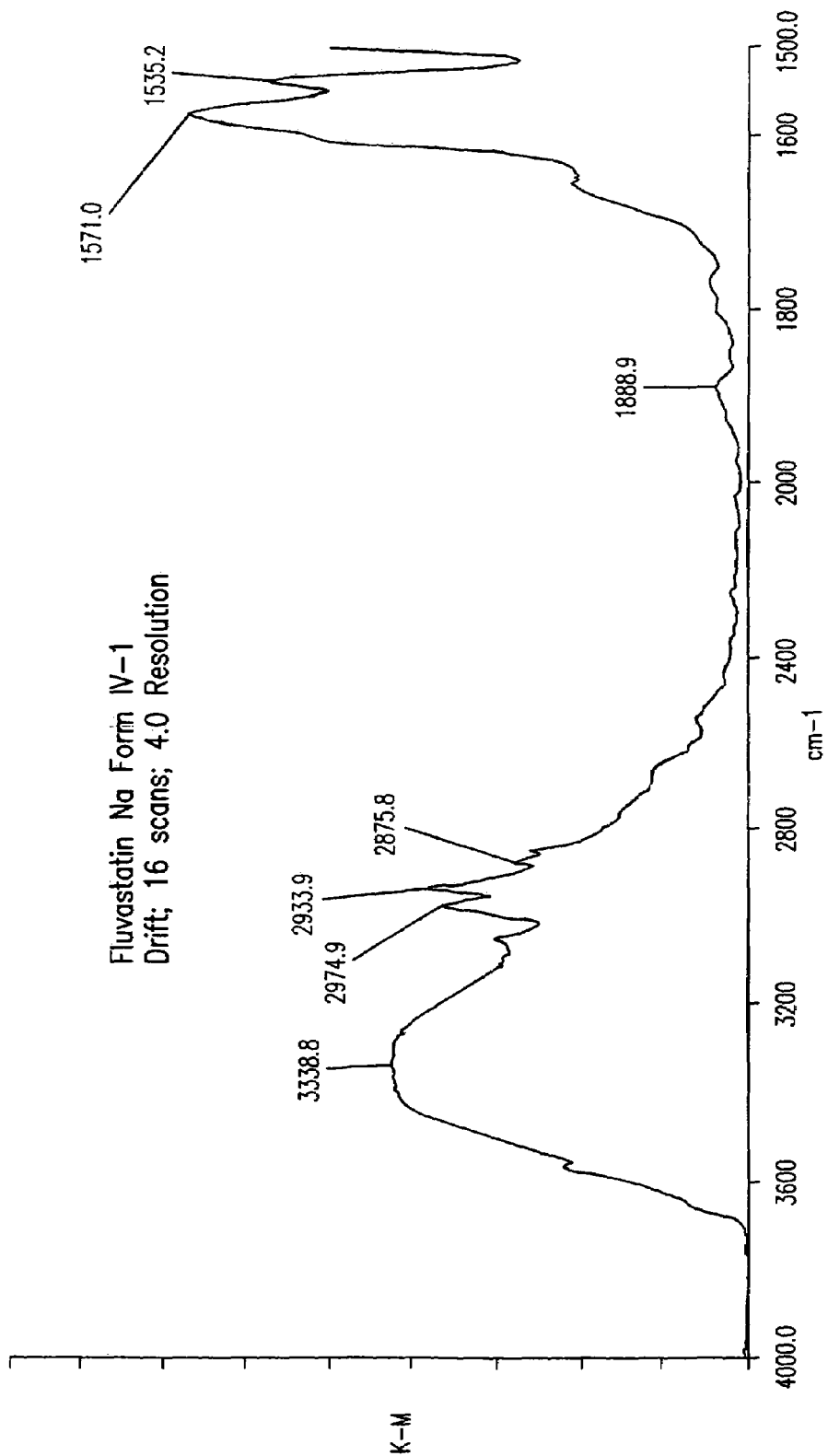
FIG. 9 depicts an IR spectrum of fluvastatin sodium Form IV-1 scanned from 4000 to 400 cm$^{-1}$, while FIG. 9a expands the 4000-1500 cm$^{-1}$ region of the spectrum and FIG. 9b expands the 1500-400 cm$^{-1}$ region of the spectrum.
Figure 9B:
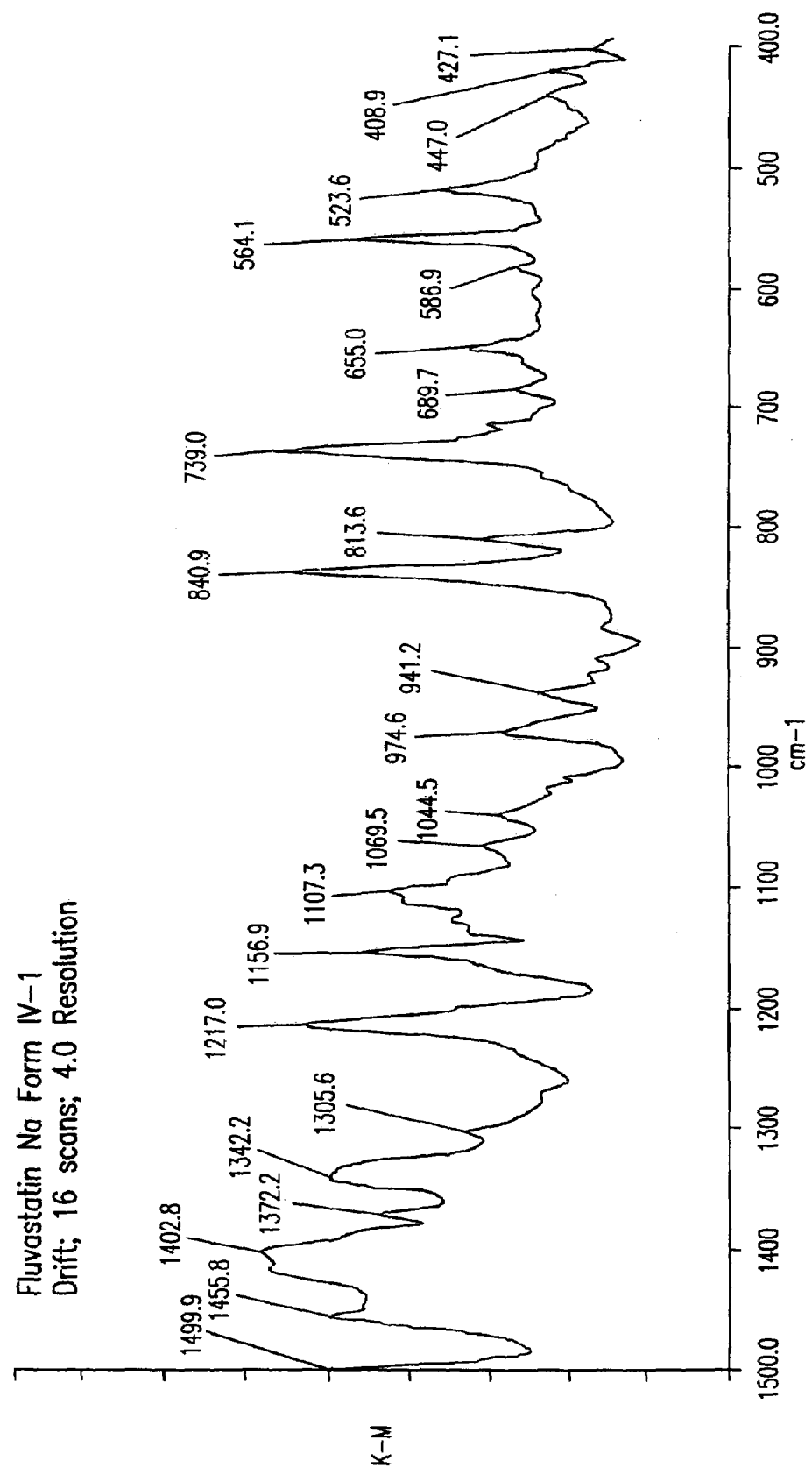

Fluvastatin sodium Form IV-1 produces a PXRD diffractogram with characteristic peaks at 3.6, 4.0, 9.6, 18.5 and 22.2±0.2 degrees two-theta and other peaks at 6.6, 10.4, 11.0, 17.3, 19.5, 20.1, 20.7 and 21.3±0.2 degrees two-theta (FIG. 7). Fluvastatin sodium Form IV-1 produced the DSC thermogram shown in FIG. 8, in which the main endothermic peaks can be seen below 70° C. and at about 120° C. The water content measured by Karl Fisher, is about 2.1-2.6 wt. %. The weight loss by TGA is about 10.5 wt. %. The IR spectrum of fluvastatin sodium Form IV-1 is shown in FIGS. 9, 9a and 9b.

Fluvastatin sodium Form IV-1 can be prepared by dissolving fluvastatin sodium in THF or 1,4-dioxane at reflux, and adding dropwise n-heptane or MTBE. Fluvastatin sodium Form IV-1 can also be prepared by dissolving fluvastatin sodium in butan-2-ol and recrystallizing it during reflux.

Fluvastatin Sodium Crystal Form V

Fluvastatin sodium Form V produces a PXRD diffractogram (FIG. 10) with characteristic peaks at 3.8, 6.3, 9.5 and 21.2±0.2 degrees two-theta.

Two process for making Form V have been discovered to date, both of which employ fluvastatin Form B as the starting material. According to one procedure, Form B is dissolved in refluxing butan-1-ol. After a clear solution is obtained, either by complete dissolution or filtering the solution, heptane is slowly added to the refluxing solution. Thereafter, the solution is cooled and the precipitate is recovered. According to another procedure, Form B is dissolved in a solvent system that is a 5:2:1 ternary mixture of ethanol:ethyl acetate:propan-1-ol at reflux temperature. After a clear solution is obtained, either by complete dissolution or filtering the solution, n-hexane is slowly added to the refluxing solution. The solution is then cooled to ambient temperature and maintained until a precipitate is formed. In either procedure, the product may be separated from the diluent by conventional techniques such as filtering, decanting, centrifuging and the like. Drying may be carried out at 50EC in a vacuum oven.

Fluvastatin Sodium Crystal Form VI

Figure 12:
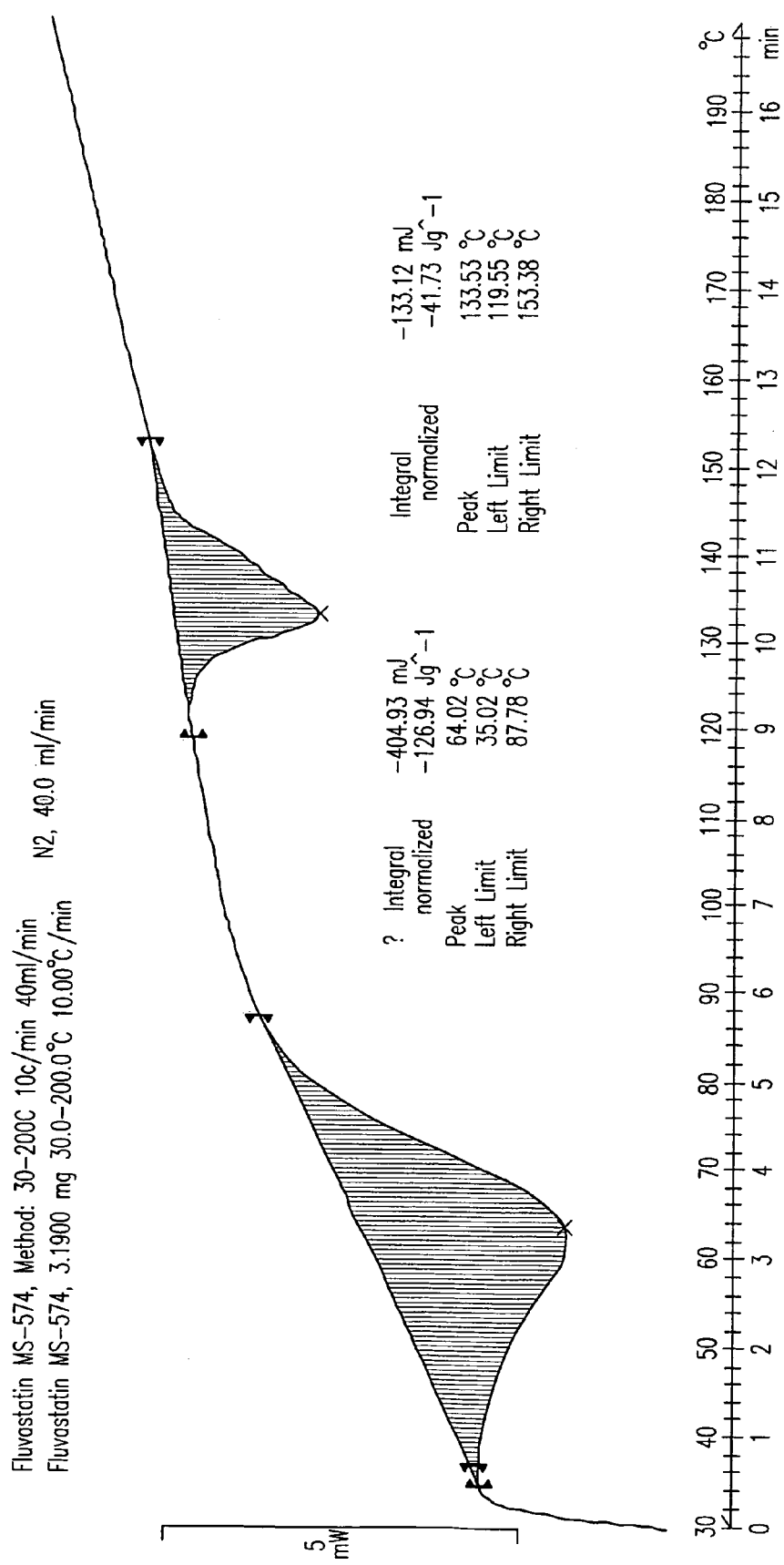
FIG. 12 depicts a DSC thermogram of fluvastatin sodium Form VI.
Figure 13:
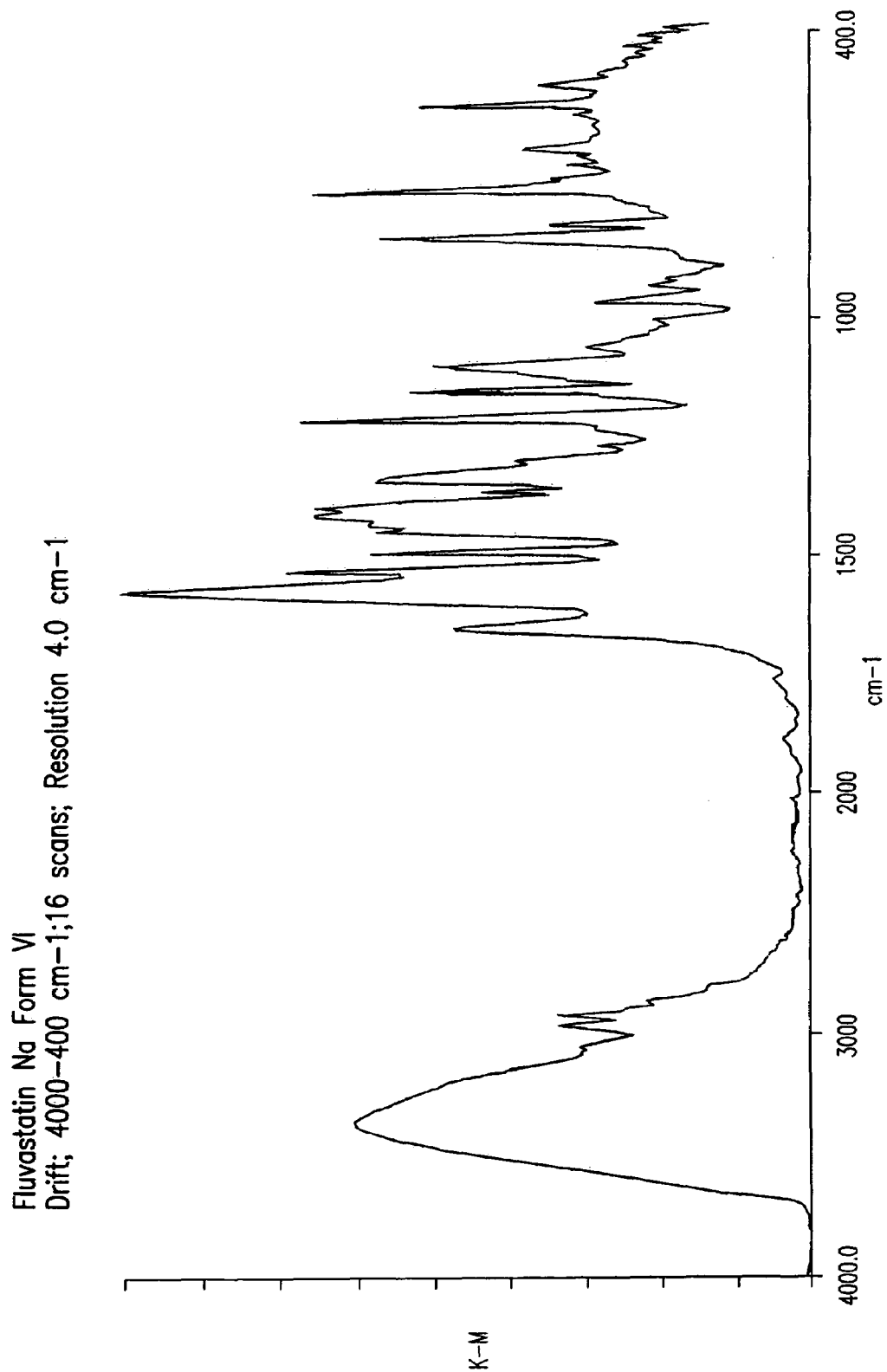
FIG. 13 depicts an IR spectrum of fluvastatin sodium Form VI scanned from 4000 to 400 cm$^{-1}$, while FIG. 13a expands the 4000-1500 cm$^{-1}$ region of the spectrum and FIG. 13b expands the 1500-400 cm$^{-1}$ region of the spectrum.
Figure 13A:
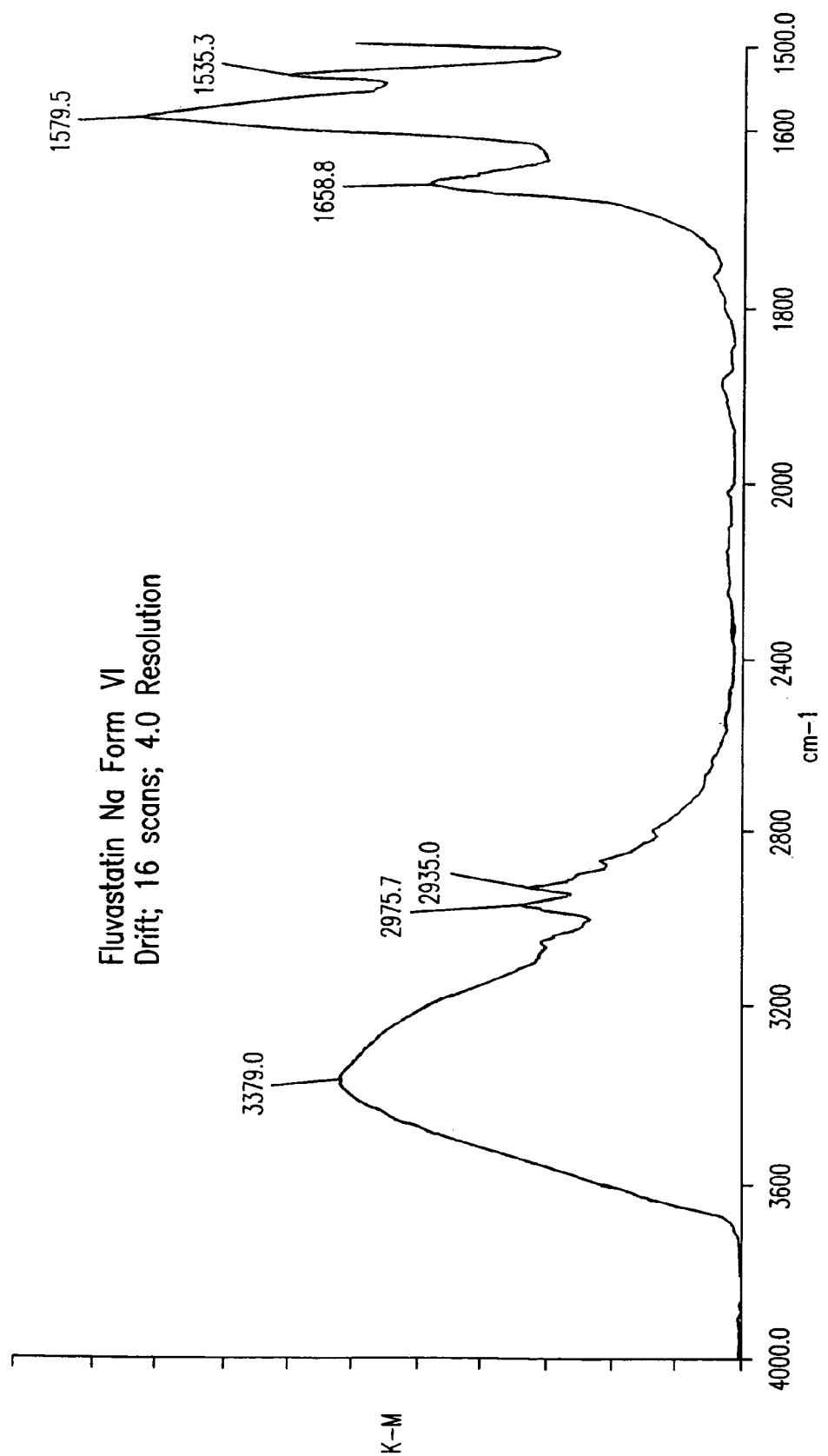
Figure 13B:
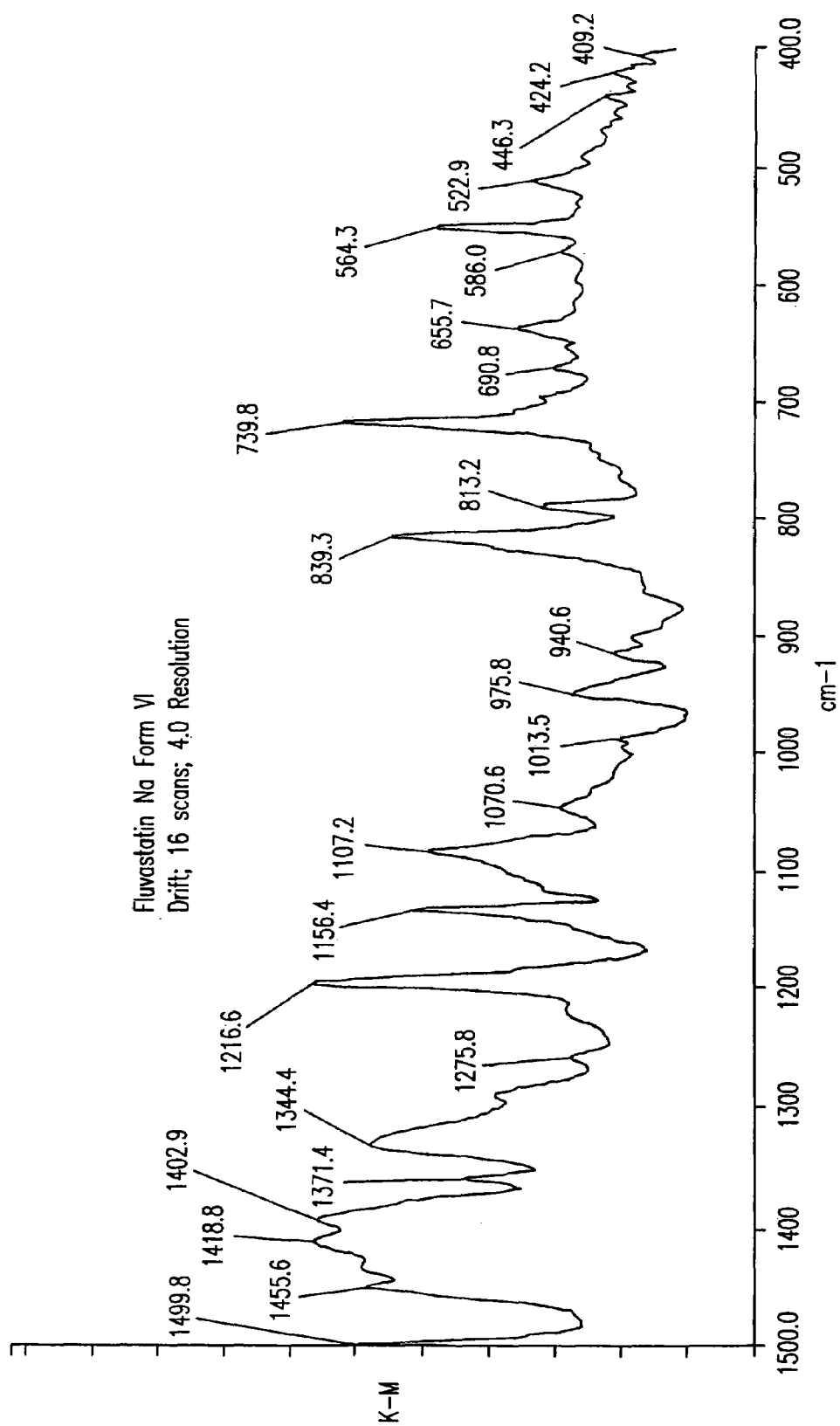

Fluvastatin sodium Form VI produces a PXRD diffractogram with characteristic peaks at 3.7, 4.7, 5.7, 10.9, 12.2 and 19.9±0.2 degrees two-theta and other peaks at 9.1, 9.6, 14.3 16.3, 16.9, 20.4 and 21.3±0.2 degrees two-theta (FIG. 11). Fluvastatin sodium Form VI produced the DSC thermogram shown in FIG. 12, in which the main endothermic peaks can be seen below 90° C. and at about 130° C. The water content measured by Karl Fisher is 5.0-5.6 wt. %. The weight loss by TGA is about 12%. Fluvastatin sodium Form VI was stable after exposure to relative humidities between 0-40% RH for 12 days and equilibrated at water contents between 3-5%. At higher relative humidities, it transformed to fluvastatin sodium form VII and Form D. The IR spectrum of fluvastatin sodium Form VI is shown in FIGS. 13, 13a and 13b.

Fluvastatin sodium Form VI can be prepared by dissolving fluvastatin sodium in DMF at room temperature and adding dropwise organic anti-solvents like diethyl ether or hexanes to precipitate the material. The mixture may be cooled using an ice-bath. Form VI can be separated from the DMF and anti-solvent by methods known in the art such as filtering, decanting centrifuging and the like, preferably filtering under nitrogen stream.

Fluvastatin sodium Form VI also can be prepared directly from a lower alkyl ester of fluvastatin. The starting material is dissolved in a solution of about one molar equivalent of sodium hydroxide in a solvent system selected from the group consisting of methanol, ethanol, mixtures of methanol and water and mixtures of butan-1-ol and water. The preferred methanol:water mixture is 91% methanol, 9% water and the preferred butan-1-ol:water mixture is 94% butan-1-ol, 6% water. The solvent system is preferably heated, e.g. to reflux temperature, to accelerate conversion of any lactone that may be present to the sodium salt, which process can be monitored by HPLC. Once the starting material has completely dissolved. an anti-solvent selected from the group consisting of acetonitrile and acetone is added dropwise to the solution at elevated temperature to induce precipitation. After cooling the mixture to ambient temperature, Form VI can be isolated by conventional techniques such as filtering, decanting, centrifuging and the like. Drying may be carried out at 50EC in a vacuum oven.

Fluvastatin Sodium Crystal Form VII

Figure 15:
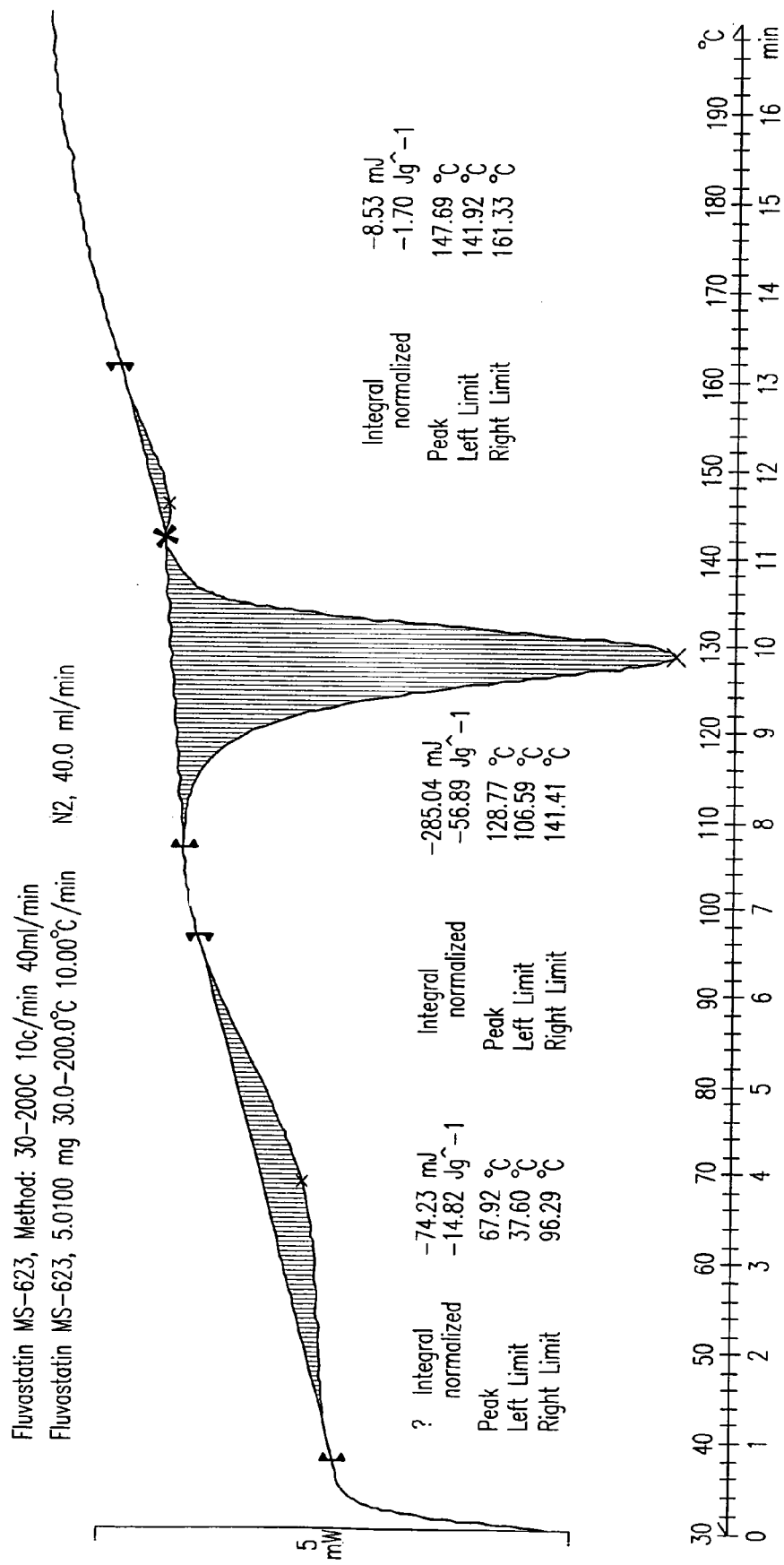
FIG. 15 depicts a DSC thermogram of fluvastatin sodium Form VII.
Figure 16:
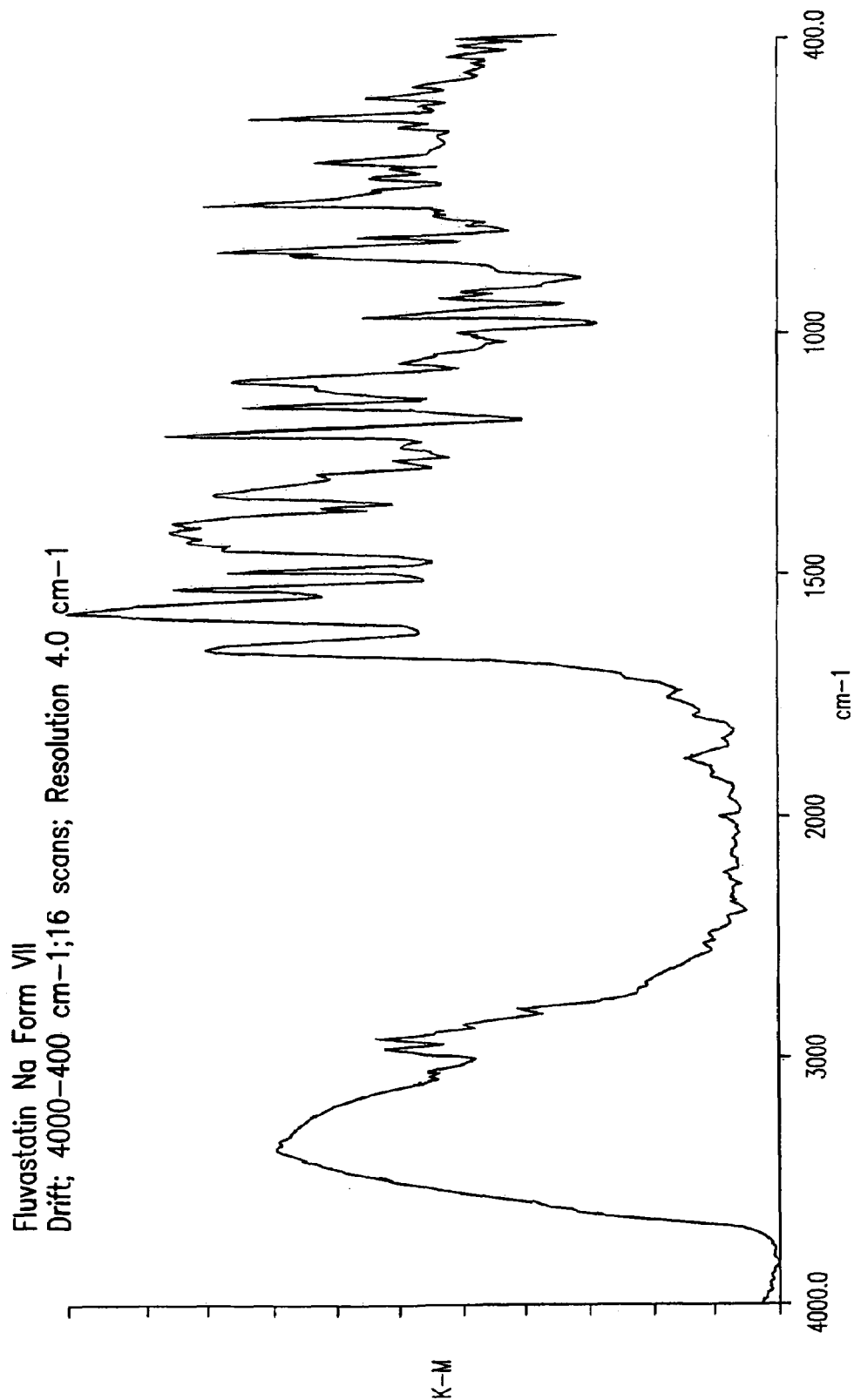
FIG. 16 depicts an IR spectrum of fluvastatin sodium Form VII scanned from 4000 to 400 cm$^{-1}$, while FIG. 16a expands the 4000-1500 cm$^{-1}$ region of the spectrum and FIG. 16b expands the 1500-400 cm$^{-1}$ region of the spectrum.
Figure 16A:
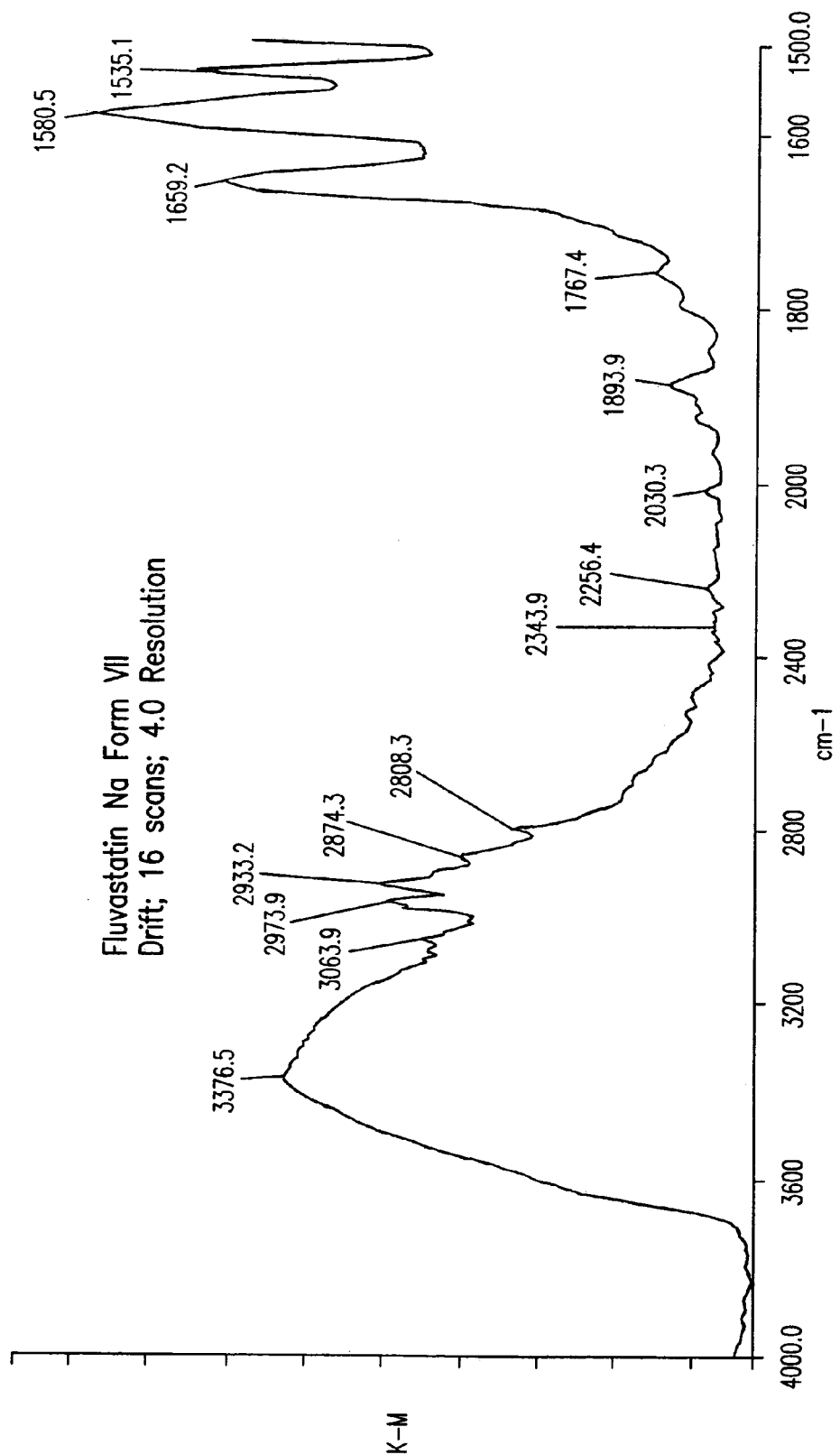
Figure 16B:
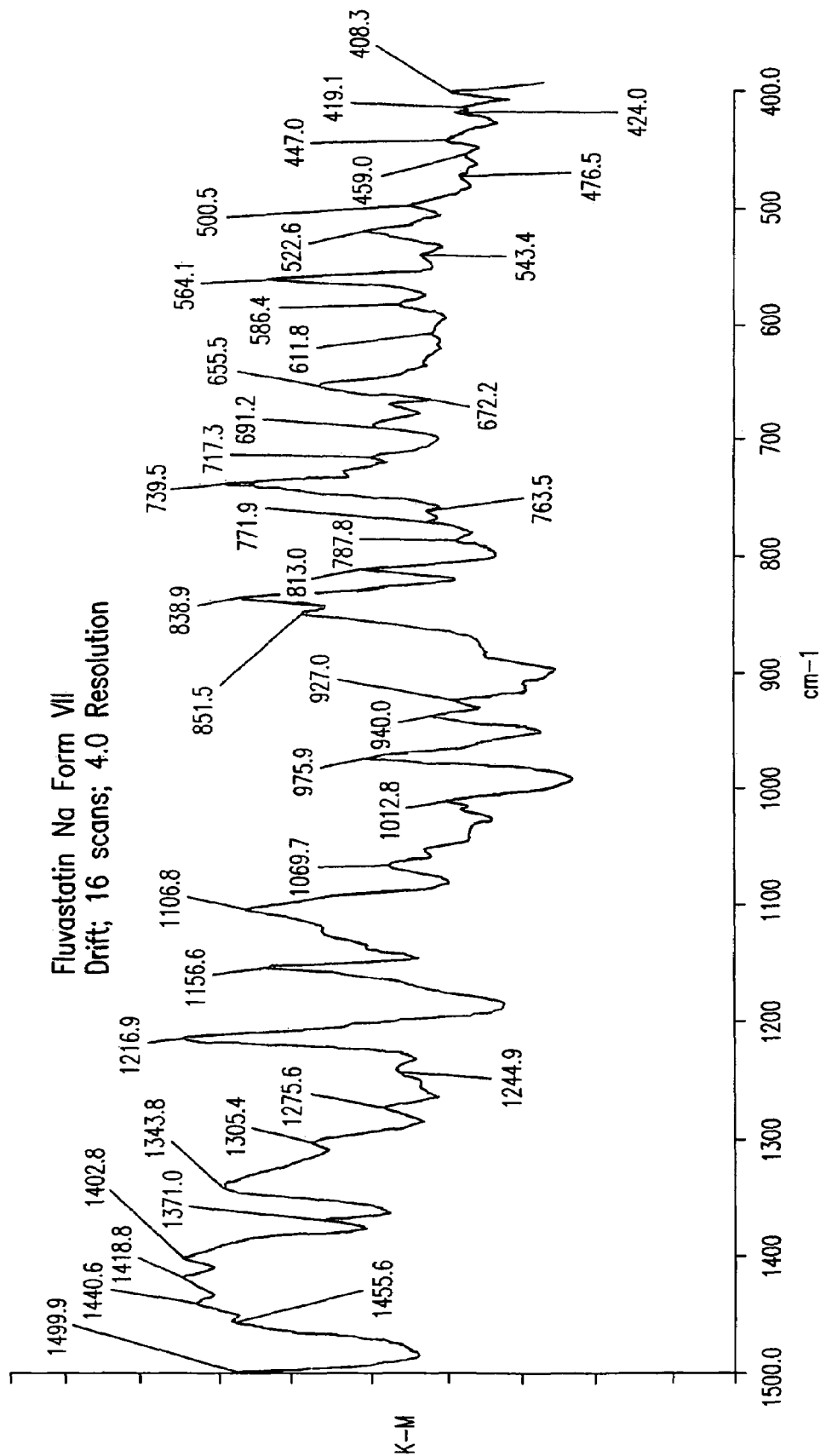

Fluvastatin sodium Form VII produces a PXRD diffractogram with characteristic peaks at 3.7, 4.3, 5.8, 8.6 and 20.7±0.2 degrees two-theta and other peaks at 10.8, 12.3, 13.7, 15.8, 17.3, 19.4, 22.0, 23.9, 25.2, 26.2 and 27.6 degrees two-theta (FIG. 14). Fluvastatin sodium Form VII produced the DSC thermogram shown in FIG. 15, in which the main endothermic peaks can be seen below 90° C. and at about 130° C. The water content, measured by Karl Fisher is about 4.1-4.5 wt. %. The weight loss by TGA 13-14 wt. %. The IR spectrum of fluvastatin sodium Form VII is shown in FIGS. 16, 16*a* and 16*b*.

Fluvastatin sodium Form VII was stable after exposure to relative humidities between 20-60% RH for 11 days and equilibrated at water contents between 1.4-8.6%. After exposure to 80% RH for 11 days, Form VII transformed to novel Form XX (water content: about 19%), and after exposure to 100% RH for 11 days Form VII transformed to novel Form XIV (water content: about 17%). The results are summarized in the next table.

Water uptake (%) and crystal form of Fluvastatin sodium Form VII equilibrated at different relative humidities for 11 days

| RH (%) | Water Content by KF (%) | Weight Loss by TGA (%) | Crystal Form |
|---|---|---|---|
| 20 | 1.4-4.8 | 8.4 | VII |
| 40 | 3.5-4.8 | 10.1 | VII |
| 60 | 6.6-8.6 | 9.6 | VII |
| 80 | 18.7-19.5 | 19.0 | XX |
| 100 | 16.6 | 17.6 | XIV |

Fluvastatin sodium Form VII can be prepared by dissolving fluvastatin sodium in N,N-dimethylformamide ("DMF") at room temperature, and adding dropwise an organic anti-solvent like chloroform, MTBE, dichloromethane, cyclohexane or 1,2-dichloroethane to induce precipitation. The mixture may be cooled using an ice-bath to enhance recovery of Form VII. Form VII can be isolated by methods known in the art such as filtering, decanting, centrifuging and the like, preferably by filtering under a nitrogen stream.

Fluvastatin sodium Form VII also can be prepared by suspending fluvastatin sodium, preferably Form B, in DMF at room temperature and isolating it by methods known in the art such as filtering, decanting, centrifuging and the like, preferably by filtering under a nitrogen stream.

Another way of making fluvastatin sodium Form VII starts from a lower alkyl ester of fluvastatin. The starting material is dissolved in a solution containing about one molar equivalent of sodium hydroxide in a solvent selected from the group consisting of butan-1-ol and mixtures of water and propan-2-ol. The preferred mixture of water and propan-2-ol contains about 8% water and 92% propan-2-ol. The starting material is preferably dissolved at elevated temperature, e.g. the reflux temperature of the solvent. Once a solution has been obtained, an anti-solvent, either acetone, acetonitrile or MTBE, is added to the mixture at elevated temperature to induce precipitation.

Alternatively, the lower alkyl ester of fluvastatin can be taken up in methanol at ambient or elevated temperature, preferably ambient temperature, to form a saturated solution. A saturated solution can be prepared by forming an unsaturated solution and then evaporating solvent until solids or turbidity appears. Then, the solution can be heated, preferably to reflux temperature, until all of the solids are redissolved. Next in this process, acetonitrile is added dropwise to the solution to induce precipitation of fluvastatin sodium Form VII.

In yet another alternative process starting from the lower alkyl ester of fluvastatin, the starting material is dissolved in acetonitrile. To effect dissolution, the acetonitrile can be heated to 40EC. Then, a solution of sodium hydroxide in ethanol is added to the solution. The resulting mixture becomes turbid and over time an oily phase may separate. If this occurs, the mixture should be heated until the oil goes into solution. Then, Form VII can be precipitated by cooling or allowing the solution to cool.

After allowing the mixture to cool to ambient temperature Form VII can be isolated by conventional techniques such as filtering, decanting, centrifuging and the like. Preferably, the liquids are separated by vacuum filtration under an inert gas like nitrogen. A suitable condition for drying the separated product is 50EC under vacuum.

Fluvastatin Sodium Crystal Form IX

Fluvastatin sodium Form IX produces a PXRD diffractogram (FIG. 17) with characteristic peaks at 3.4, 10.0 and 19.7±0.2 degrees two-theta.

Form IX can be prepared by crystallization from a variety of solvent systems following procedures described in greater detail in the Examples. Briefly, Form IX can be precipitated from a solution in 1,4-dioxane by addition of dichloromethane; from a solution in ethanol by addition of ethyl acetate, diethyl ether or n-pentane; or from a mixture of ethanol and methanol by addition of hexanes. In addition, Form IX can be prepared by refluxing a suspension of Form B in ethyl acetate.

Alternatively, Form IX can be prepared directly from a lower alkyl ester of fluvastatin such as fluvastatin methyl ester. The ester is dissolved in a solution of about one molar equivalent of sodium in ethanol. The sodium can be conveniently provided by dissolving the appropriate quantity of sodium hydroxide pellets in water, while exercising caution since the dissolution in water is highly exothermic. The solution is heated for a sufficient period of time to hydrolyze the ester, typically several hours. Then, a large excess (e.g. 7×v/v)

of propan-2-ol is added to the solution. The mixture is then cooled to ambient temperature and maintained until a precipitate forms in the flask.

Form IX can be conventionally separated from the solvent or diluent by a known method of isolation such as filtering, decanting, centrifuging and the like, preferably filtering under a nitrogen stream.

Fluvastatin Sodium Crystal Form IX-1

Fluvastatin sodium Form IX-1 produces a PXRD diffractogram (FIG. 18) with characteristic peaks at 3.4, 6.6, 10.0, 13.2, 19.8±0.2 degrees two-theta.

We have discovered a multitude of ways to make Form IX-1, which are exemplified by starting from fluvastatin Form B. For the sake of brevity, please refer to the Examples for the particulars of how it can be made.

Fluvastatin Sodium Crystal Form XI

Figure 20:
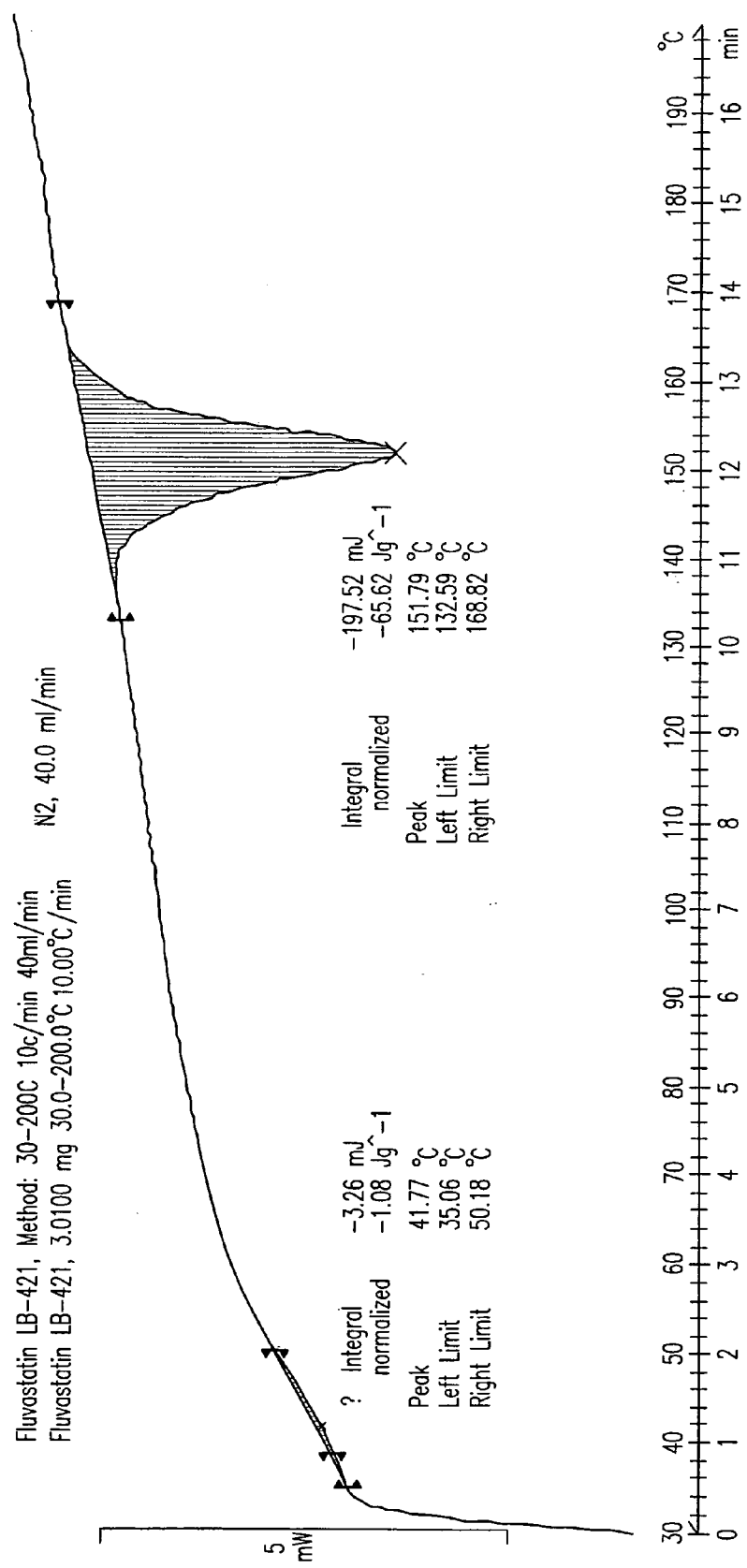
FIG. 20 depicts a DSC thermogram of fluvastatin sodium Form XI.
Figure 21A:
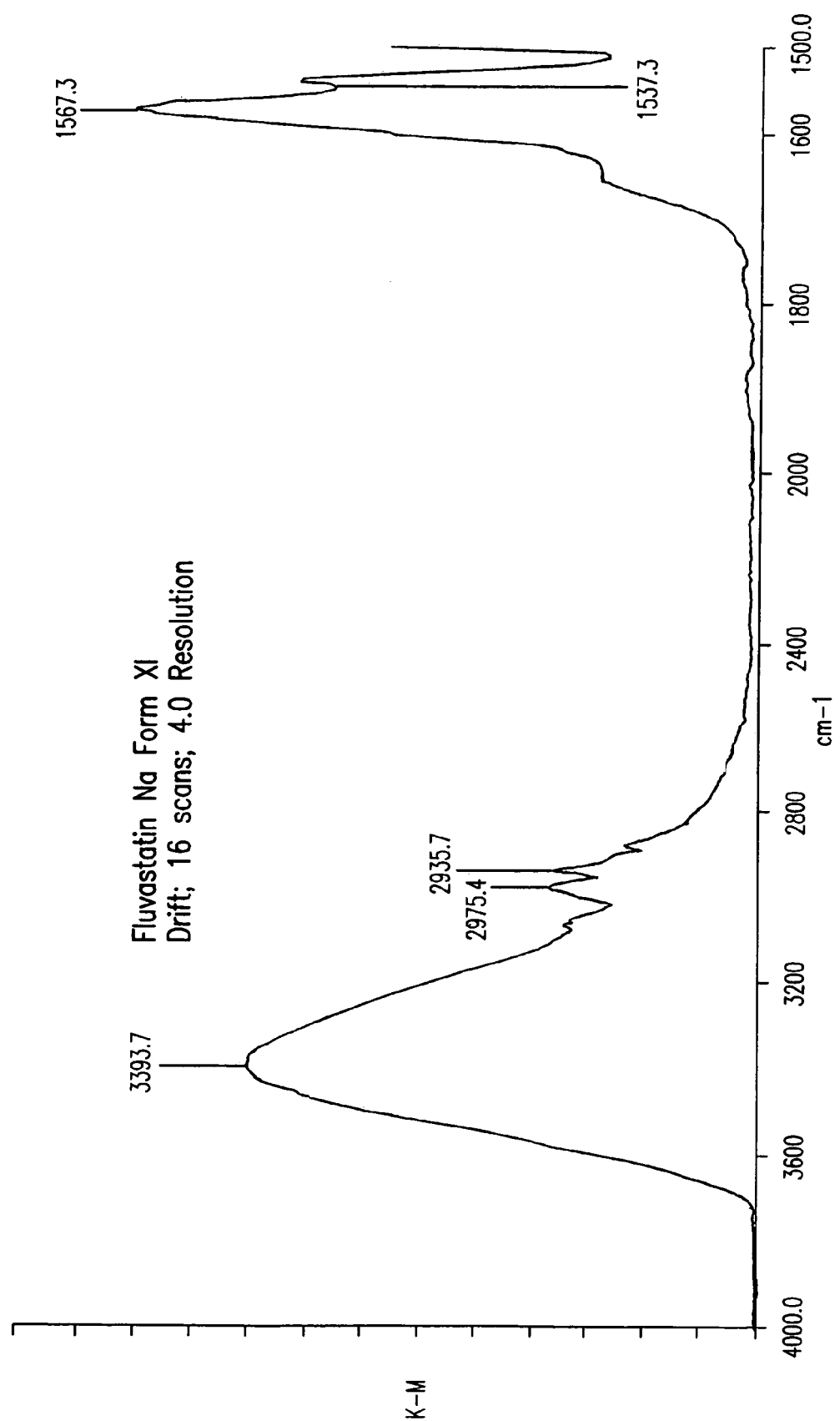
FIG. 21 depicts an IR spectrum of fluvastatin sodium Form XI scanned from 4000 to 400 cm$^{-1}$, while FIG. 21a expands the 4000-1500 cm$^{-1}$ region of the spectrum and FIG. 21b expands the 1500-400 cm$^{-1}$ region of the spectrum.
Figure 21B:
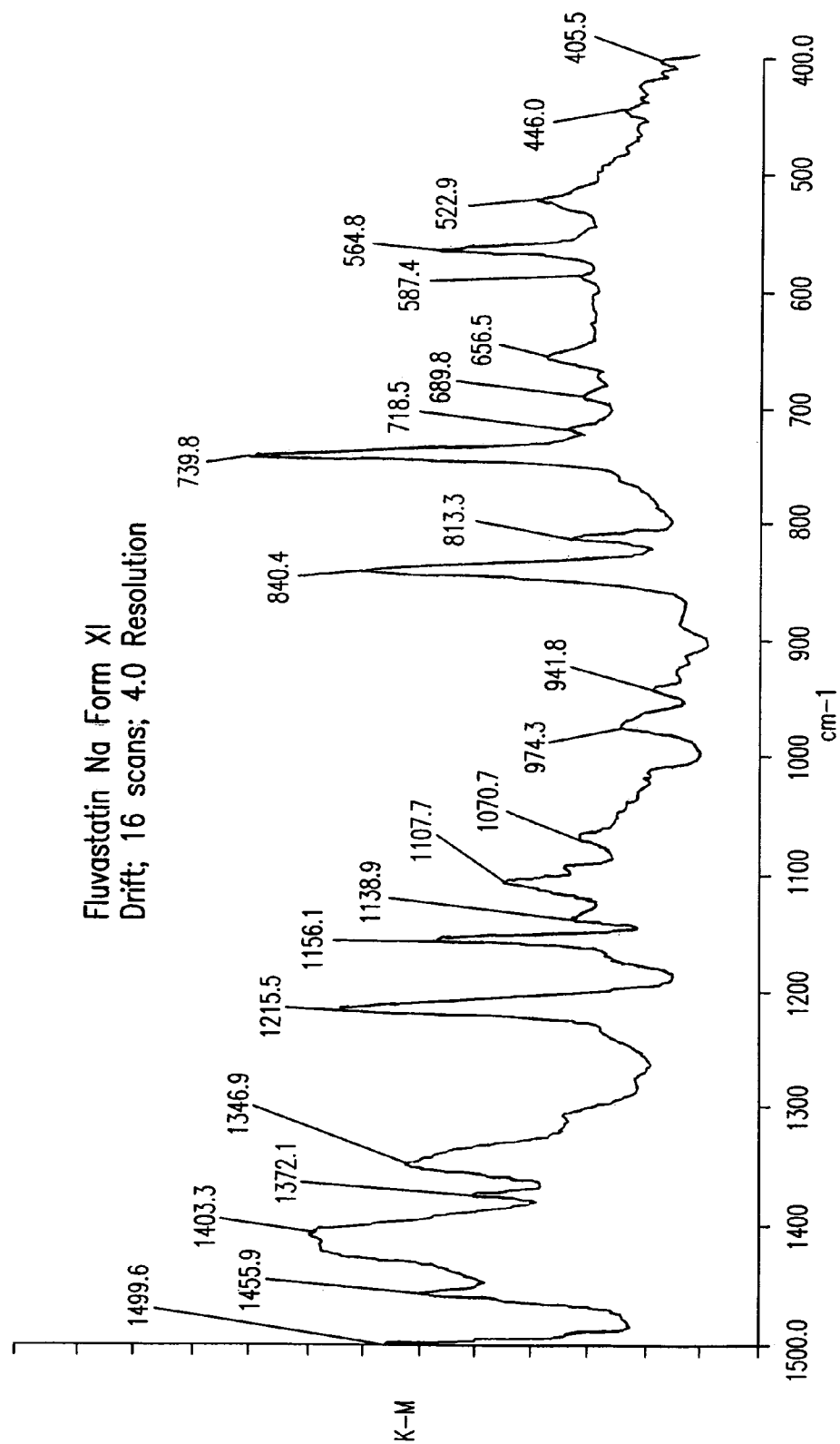

Fluvastatin sodium Form XI produces a PXRD diffractogram with characteristic peaks at 3.3, 3.8, 4.6, 8.3, 10.2 and 25.1±0.2 degrees two-theta and other peaks at 7.2, 11.4, 12.4, 13.6, 16.0, 16.9, 17.4, 20.4, 21.3, 21.9 and 23.1±0.2 degrees two-theta (FIG. 19). Fluvastatin sodium Form XI produced the DSC thermogram shown in FIG. 20 in which one main endothermic peak can be seen at about 150° C. The water content of the sample is about 4-6 wt. %. The weight loss by TGA is 6-8%. The IR spectrum of fluvastatin sodium Form XI is shown in FIGS. 21, 21a and 21b.

Fluvastatin sodium Form XI was stable after exposure to relative humidities between 20-60% RH for 11 days and equilibrated at water contents between 1.1-5.6%. After exposure to 80% and 100% RH for 11 days, Form XI transformed to novel Form XIX (water content: about 19-28%). The results are summarized in the next table.

| Water uptake (%) and Crystal Form of Fluvastatin Sodium Crystal Form XI Equilibrated at Different Relative Humidities for 11 Days | | | |
| --- | --- | --- | --- |
| RH (%) | Water Content by KF (%) | Weight Loss by TGA (%) | Crystal Form |
| 0 | 2.0-2.4 | 6.5 | XI |
| 20 | 1.1-5.6 | 5.0 | XI |
| 40 | 3.0-3.6 | 4.5 | XI |
| 60 | 3.5-3.6 | 4.7 | XI |
| 80 | 19.5-22.6 | 22.0 | XIX |
| 100 | 28.0-28.4 | 26.2 | XIX |

Fluvastatin sodium Form XI can be prepared by dissolving fluvastatin sodium, preferably Form B, in refluxing butan-2-ol. During reflux, the fluvastatin sodium recrystallizes in Form XI. Addition of organic anti-solvents like hexanes, n-pentane, MTBE, diethyl ether, n-heptane and chloroform at reflux tends to increase the yield of precipitate. The mixture may be maintained at reflux temperature for any amount of time necessary to achieve the desired yield of Form XI. Afterwards, the mixture is allowed to cool to room temperature and Form XI can be isolated by a known method of isolation such as filtering, decanting, centrifuging and the like, preferably filtering under a nitrogen stream.

Fluvastatin Sodium Crystal Form XI-2

Figure 23:
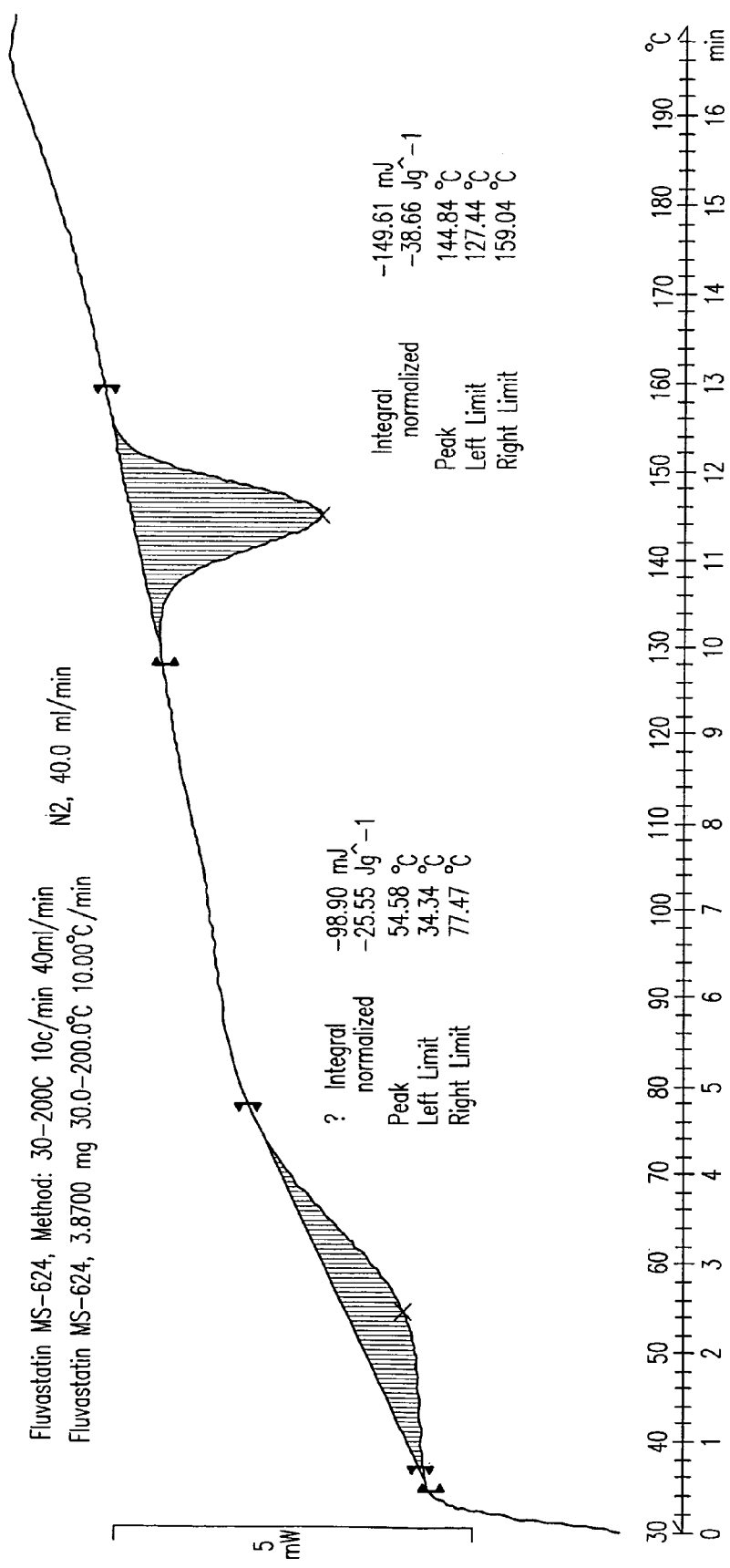
FIG. 23 depicts a DSC thermogram of fluvastatin sodium Form XI-2.
Figure 24:
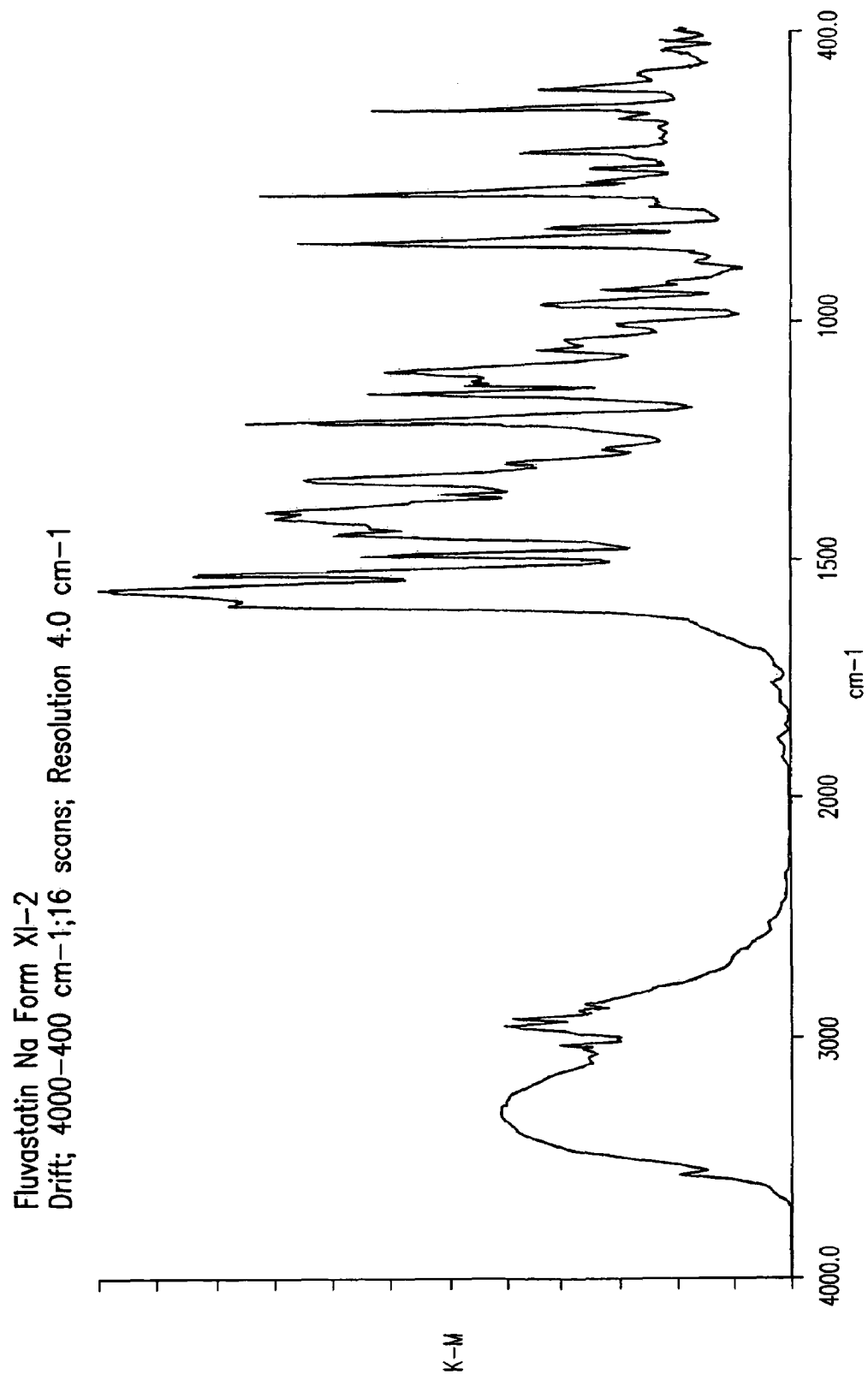
FIG. 24 depicts an IR spectrum of fluvastatin sodium Form XI-2 scanned from 4000 to 400 cm$^{-1}$, while FIG. 24a expands the 4000-1500 cm$^{-1}$ region of the spectrum and FIG. 24b expands the 1500-400 cm$^{-1}$ region of the spectrum.
Figure 24A:
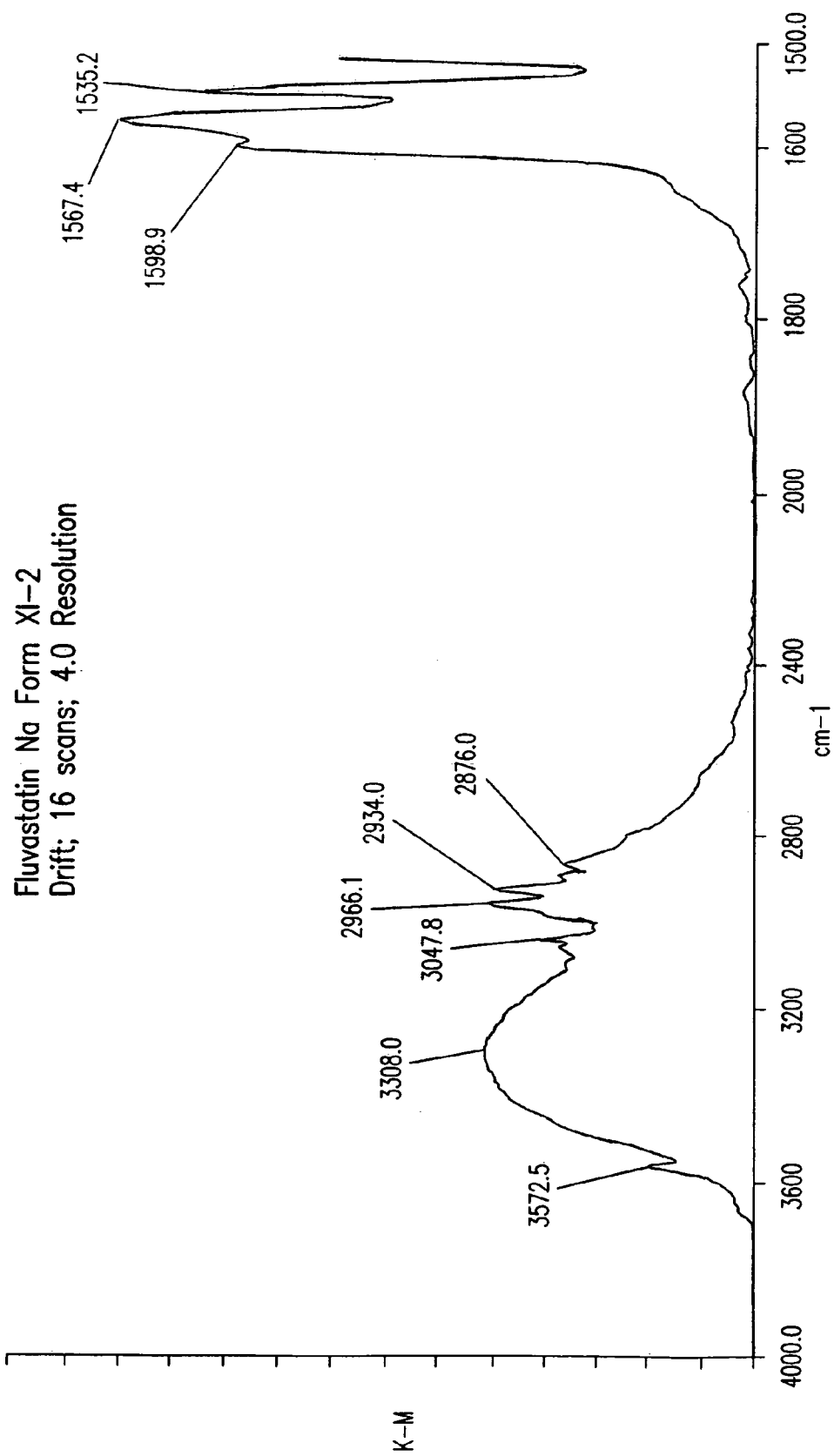
Figure 24B:
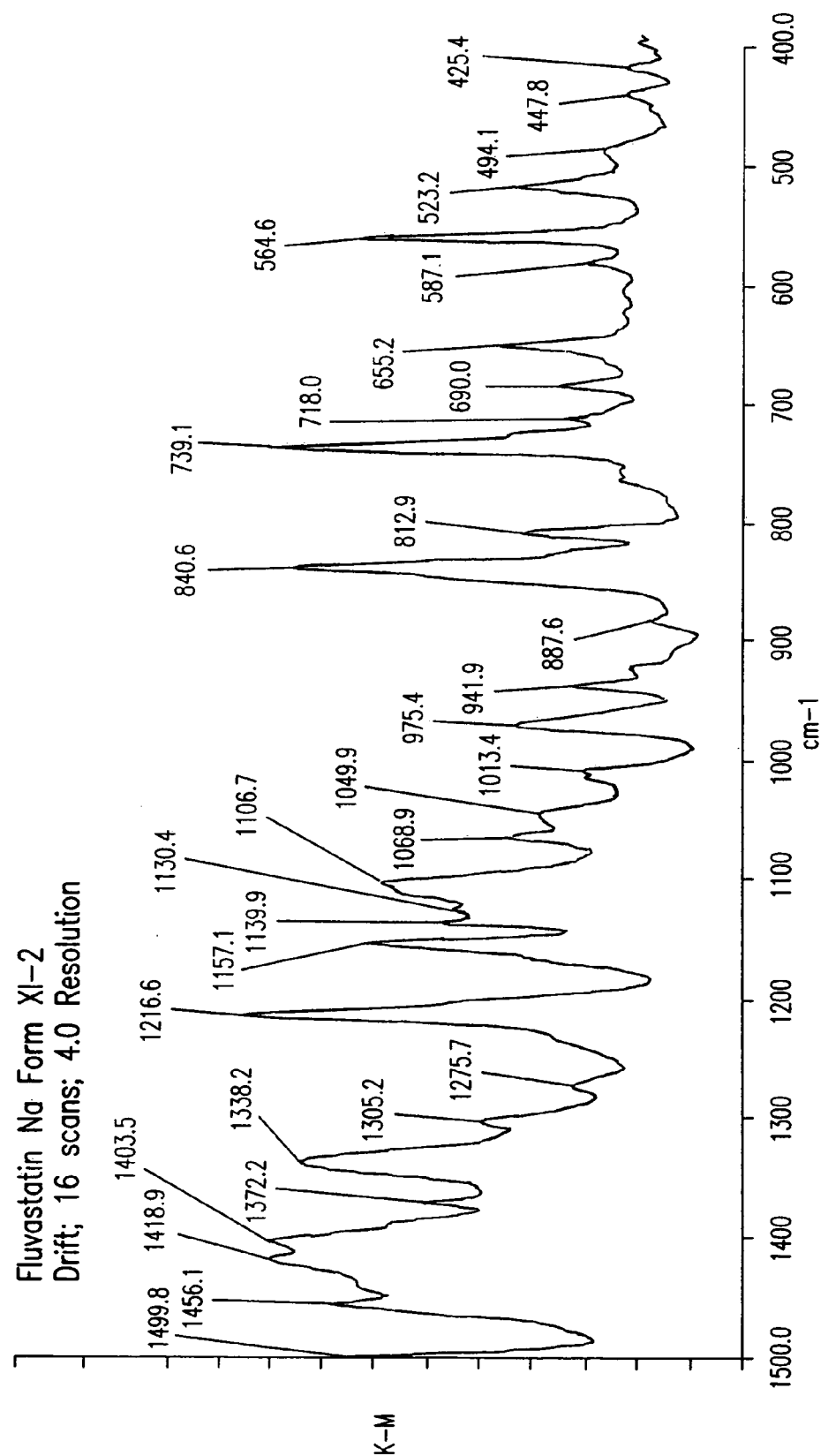

Fluvastatin sodium Form XI-2 produces a PXRD diffractogram with characteristic peaks at 3.5, 3.8, 4.6, 10.4 and 18.5±0.2 degrees two-theta and other peaks at 8.5, 11.2, 12.1, 16.4, 17.0, 17.7, 20.9, 21.2, 21.7, 22.2 and 23.6±0.2 degrees two-theta (FIG. 22). Fluvastatin sodium Form XI-2 produced the DSC thermogram shown in FIG. 23, in which two main endothermic peaks can be seen below 80° C. and at about 145° C. The water content of the sample is about 1.9-3.2 wt. %. The weight loss by TGA is 7.7%. Fluvastatin sodium form XI-2 was stable after exposure to relative humidities between 0-60% RH for 11 days and equilibrated at water contents between 5-7%. At higher relative humidities it transformed into Form D. The IR spectrum of fluvastatin sodium Form XI-2 is shown in FIGS. 24, 24a and 24b.

Fluvastatin sodium Form XI-2 can be prepared by dissolving fluvastatin sodium in refluxing propan-1-ol and adding dropwise organic anti-solvents like hexanes, MTBE and dichloromethane. The mixture may be maintained at reflux temperature for any amount of time necessary to achieve the desired yield of Form XI-2. Afterwards, the mixture is allowed to cool to room temperature and Form XI-2 can be isolated by a known method of isolation like filtering, decanting, centrifuging and the like, preferably filtering under nitrogen stream.

Fluvastatin Sodium Crystal Form XII

Fluvastatin sodium Form XII produces a PXRD diffractogram (FIG. 25) with characteristic peaks at 3.1, 6.5, 9.8, 17.6, 25.9 and 30.9±0.2 degrees two-theta.

Form XII is prepared by crystallization from a mixture of butan-1-ol and 1,4-dioxane. According to a preferred process, Form B is dissolved in refluxing butan-1-ol. 1,4-Dioxane is then added to the refluxing solution until it becomes turbid. Thereafter, the mixture is cooled to ambient temperature at which point additional 1,4-dioxane may be added to enhance recovery of Form XII. Form XII can be separated from the solvent system by conventional techniques such as filtering, decanting, centrifuging and the like, preferably filtering under an inert atmosphere like nitrogen. The separated Form XII may be dried. A suitable drying condition is 50EC under vacuum.

Fluvastatin Sodium Crystal Form XIII

Fluvastatin sodium Form XIII produces a PXRD diffractogram (FIG. 26) with characteristic peaks at 3.8, 5.6, 12.3 and 20.6±0.2 degrees two-theta.

Form XIII can be prepared by suspending fluvastatin sodium Form B in acetonitrile, which is preferably done at elevated temperature and then cooling the suspension to reduced temperature such as 10EC. Form XIII can be separated from the acetonitrile by conventional techniques such as filtering, decanting, centrifuging and the like, preferably filtering under an inert atmosphere like nitrogen. The separated Form XIII may be dried. A suitable drying condition is 50EC under vacuum.

Fluvastatin Sodium Crystal Form XV

Figure 30:
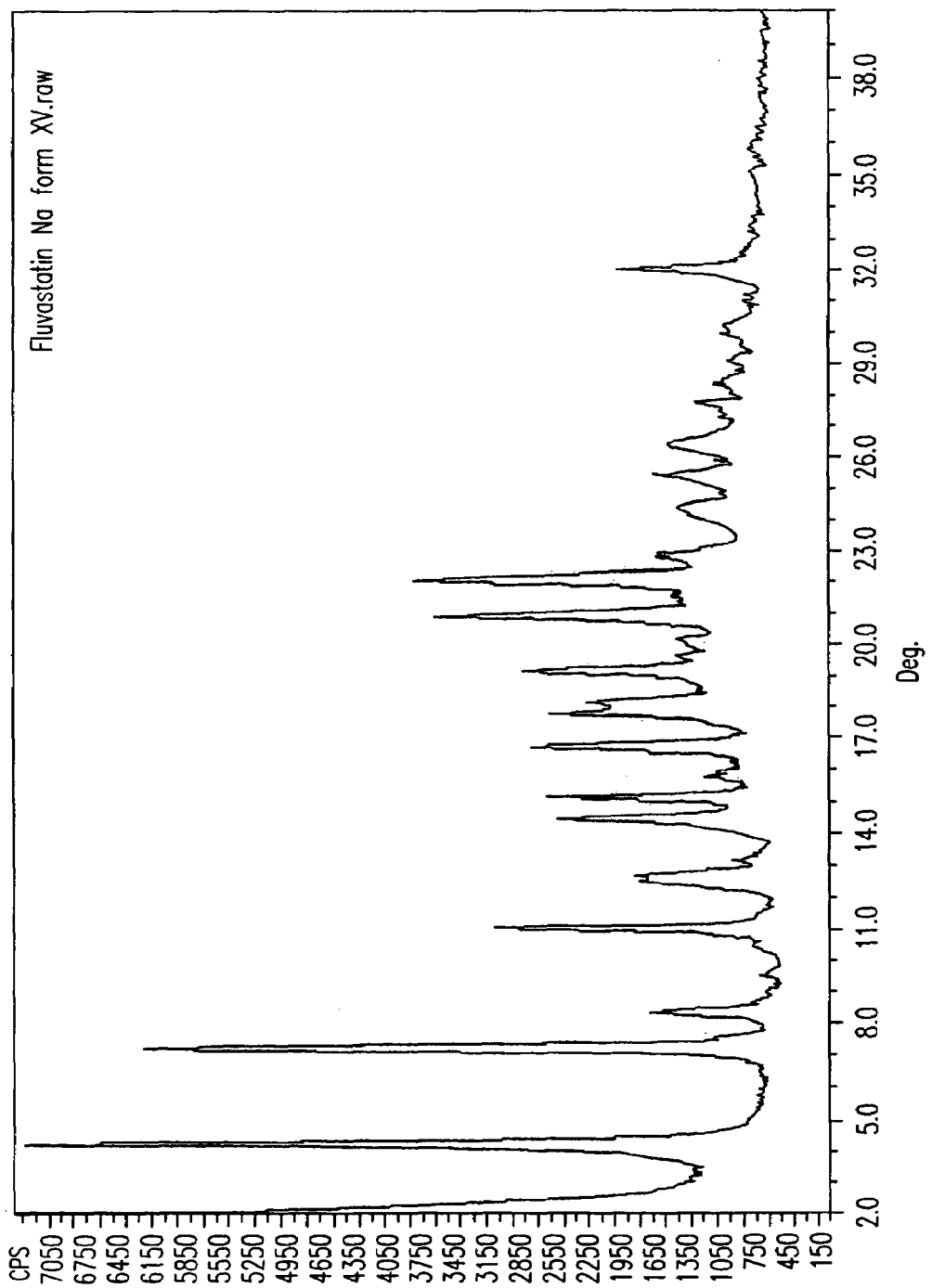
FIG. 30 depicts a powder X-ray diffractogram of fluvastatin sodium Form XV.

The material that was received in Israel in response to a commercial order placed to the Zhejiang Hisun Pharmaceutical Co., Ltd. 46 Waisha Rd., Jiaojiang District, Taizhou City, Zhejiang Province, China, was subjected to PXRD analysis at our facility in Israel and produced the PXRD diffractogram depicted in FIG. 30, which is distinct from the diffractograms produced by each of the other solid state forms of fluvastatin sodium disclosed herein. We have designated this solid state form of fluvastatin sodium Form XV. Form XV has been found useful for producing certain novel solid state forms of fluvastatin sodium, as described below.

Fluvastatin Sodium Crystal Form XVI

Figure 32:
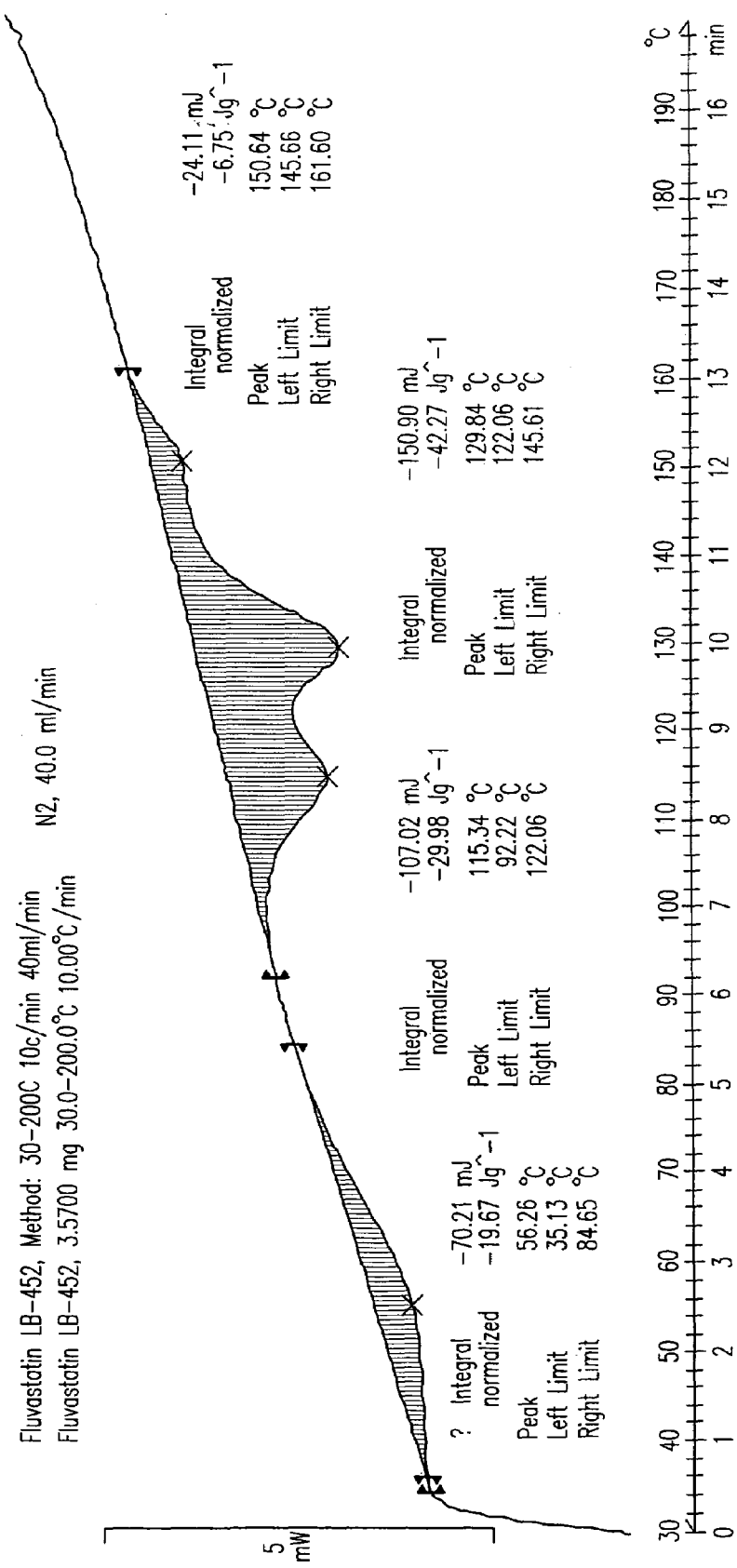
FIG. 32 depicts a DSC thermogram of fluvastatin sodium Form XVI.
Figure 33:
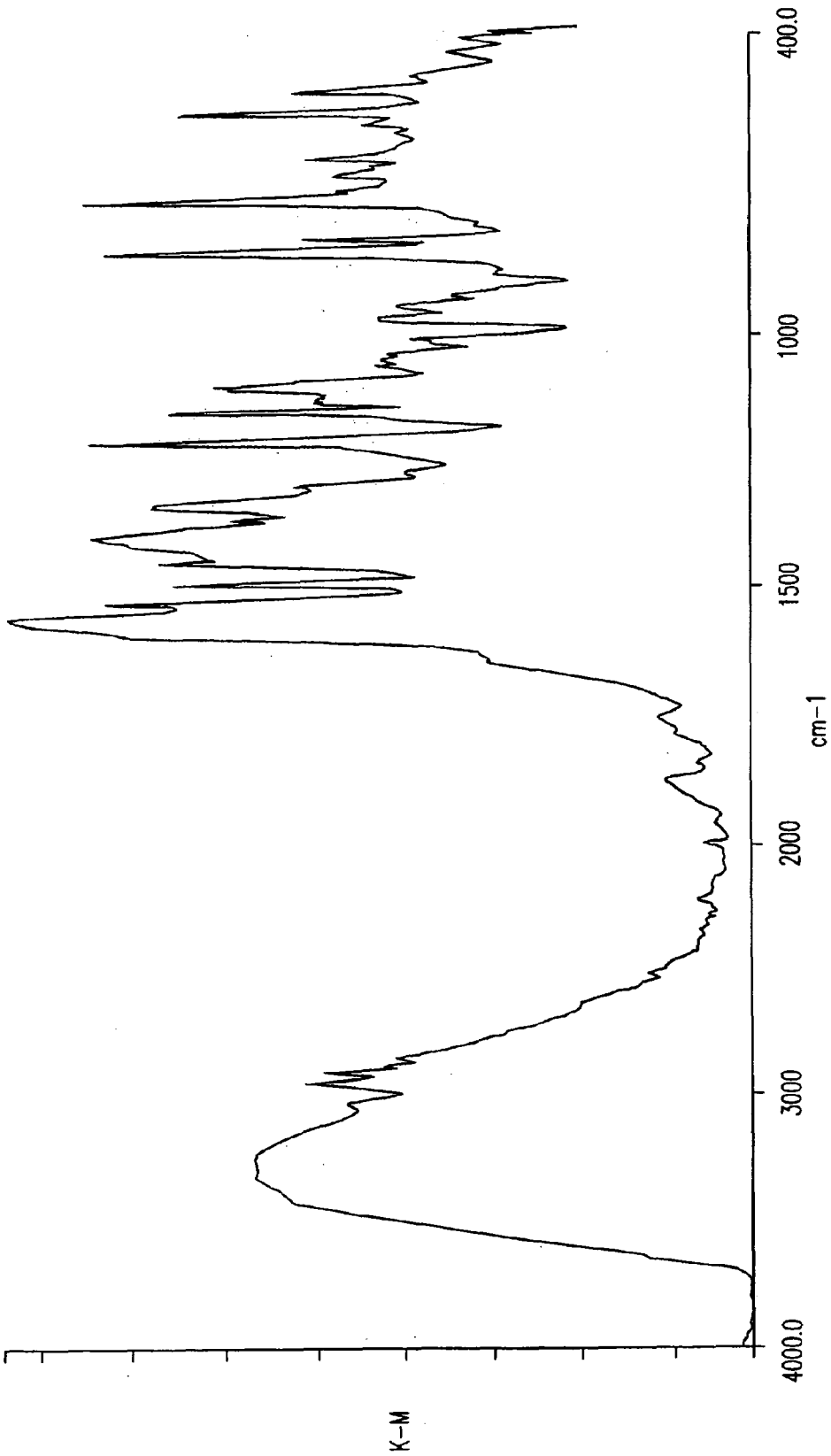
FIG. 33 depicts an IR spectrum of fluvastatin sodium Form XVI scanned from 4000 to 400 cm$^{-1}$, while FIG. 33a expands the 4000-1500 cm$^{-1}$ region of the spectrum and FIG. 33b expands the 1500-400 cm$^{-1}$ region of the spectrum.
Figure 33A:
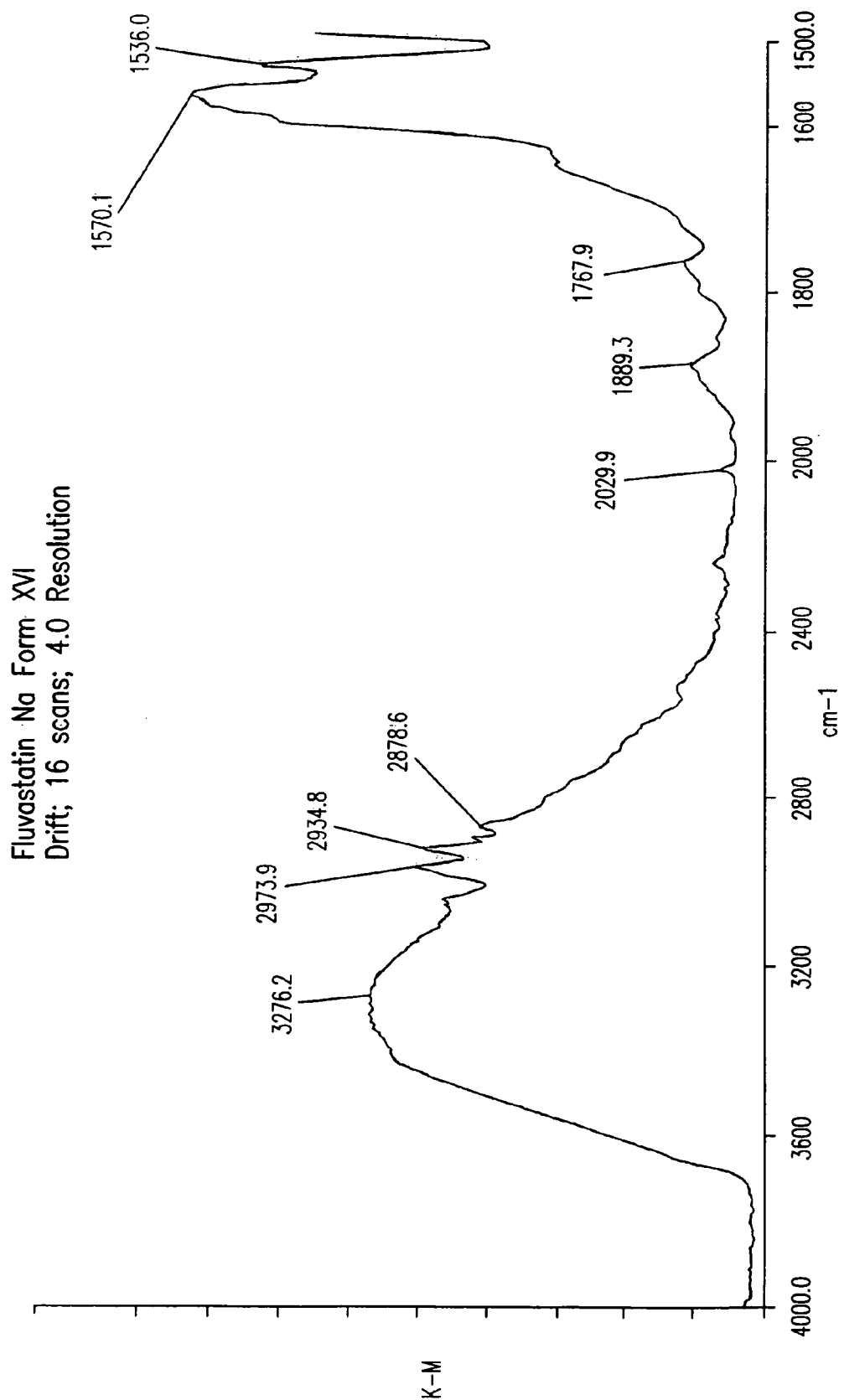
Figure 33B:
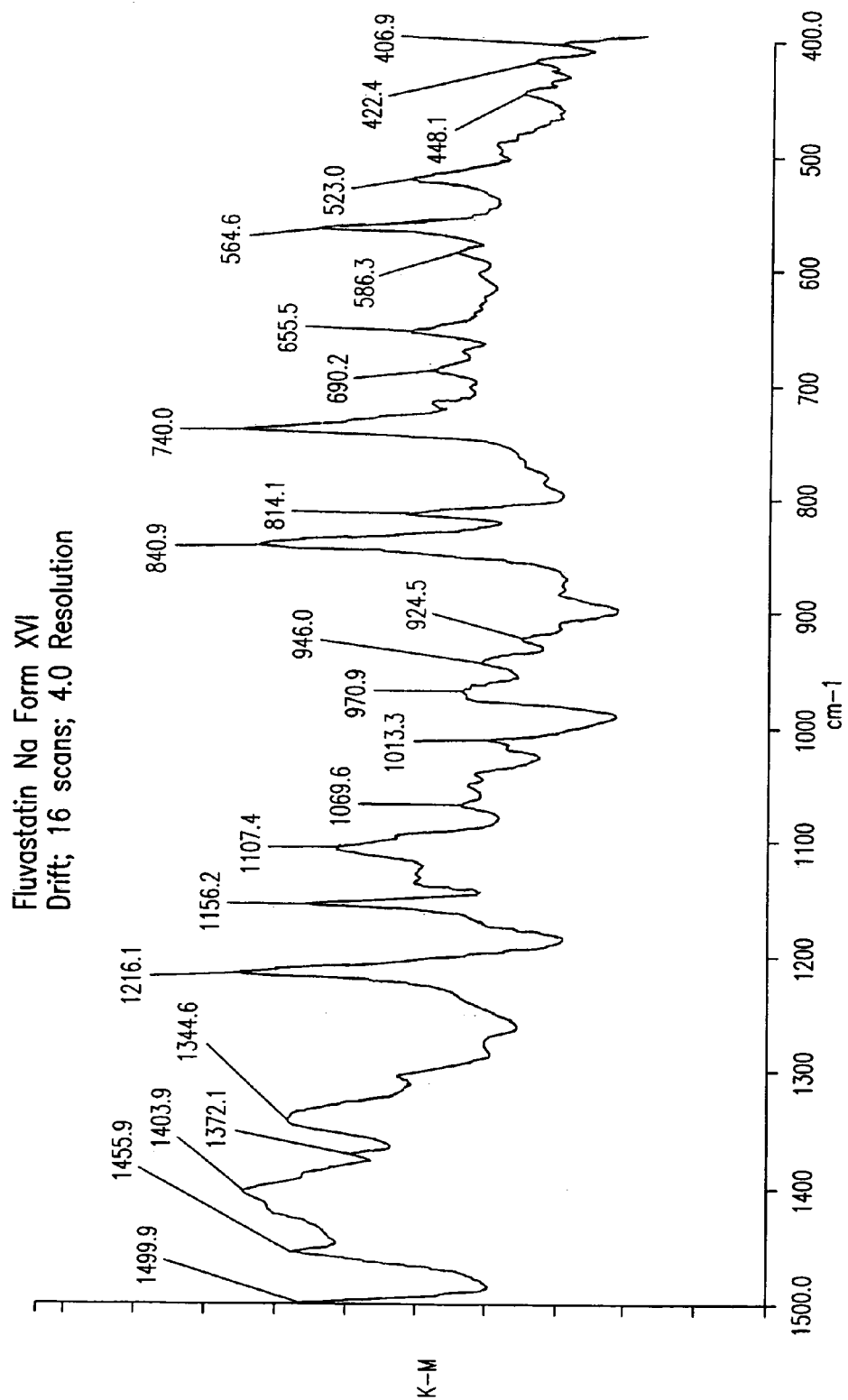

Fluvastatin sodium Form XVI produces a PXRD diffractogram with characteristic peaks at 3.8 and 7.0±0.2 degrees two-theta and other peaks at 4.3, 10.2, 10.7, 11.2, 15.6, 17.8, 18.4 and 19.5±0.2 degrees two-theta. (FIG. 31). Fluvastatin sodium Form XVI produced the DSC thermogram shown in FIG. 32, in which broad endothermic peaks can be seen below 80° C. and between 100-150° C. The water content of the sample is about 3-4 wt. %. The weight loss by TGA is 8.7 wt. %. The IR spectrum of fluvastatin sodium Form XVI is shown in FIGS. 33, 33a and 33b.

Fluvastatin sodium Form XVI can be prepared by dissolving fluvastatin sodium in refluxing propan-2-ol and adding dropwise an organic anti-solvent like dichloromethane. The mixture may be maintained at reflux temperature for any amount of time necessary to achieve the desired yield of Form XVI. Afterwards, the mixture is allowed to cool to room temperature and Form XVI can be isolated by a known method of isolation like filtering, decanting, centrifuging and the like.

Fluvastatin Sodium Crystal Form XVII

Figure 35:
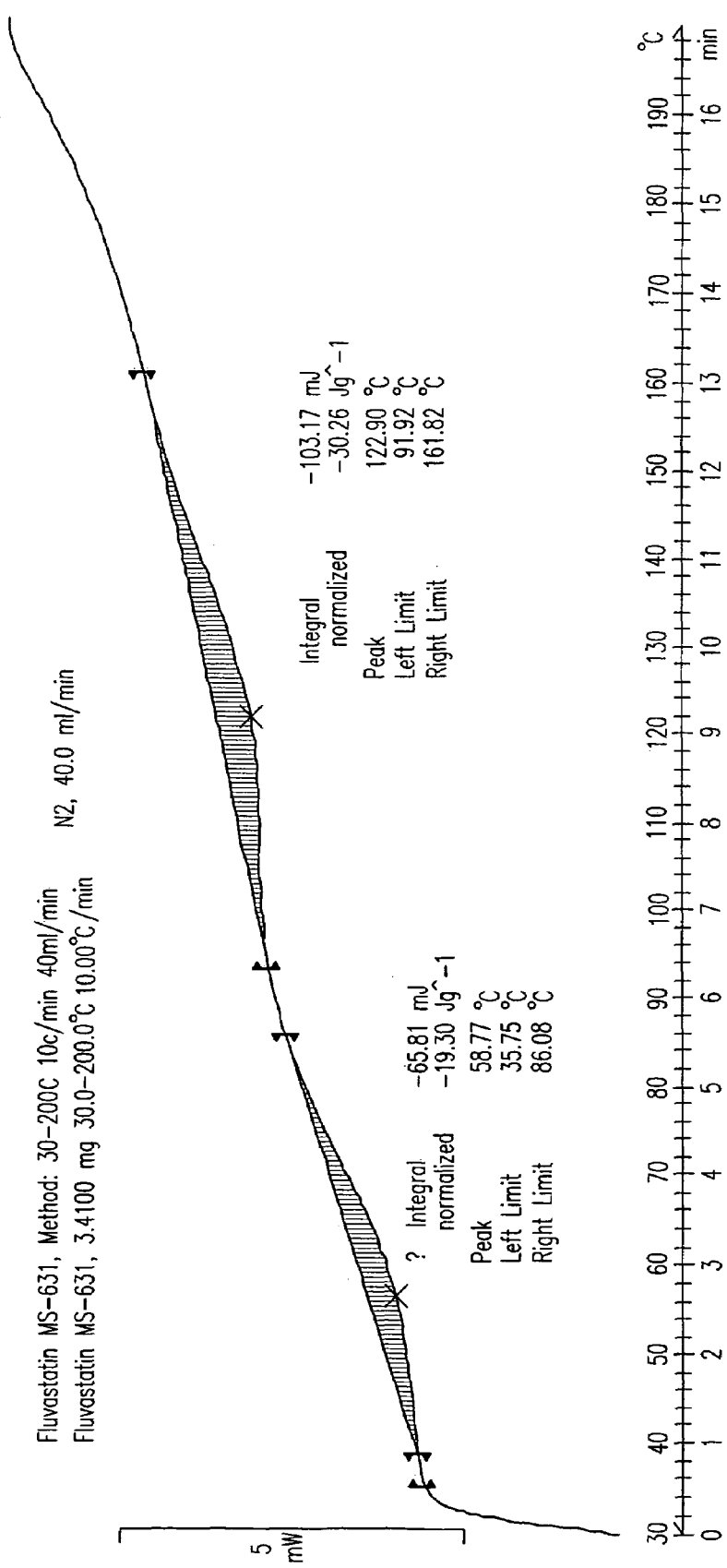
FIG. 35 depicts a DSC thermogram of fluvastatin sodium Form XVII.

Fluvastatin sodium Form XVII produces a PXRD diffractogram with characteristic peaks at 3.5 (broad), 5.4, 5.8 and 13.8±0.2 degrees two-theta and other peaks at 10.8, 14.8, 16.4, 19.4, 21.5 and 22.7±0.2 degrees two-theta. (FIG. 34). Fluvastatin sodium Form XVII produced the DSC thermogram shown in FIG. 35, in which two broad endothermic peaks can be seen at 80 and at about 113° C. respectively. The weight loss by TGA is 8.4 wt. %.

Fluvastatin sodium Form XVII can be prepared by dissolving fluvastatin sodium in propan-1-ol and recrystallizing it from the stirred solution. In a preferred embodiment, the recrystallization is carried out at elevated temperature.

Fluvastatin Sodium Crystal Form XVIII

Figure 37:
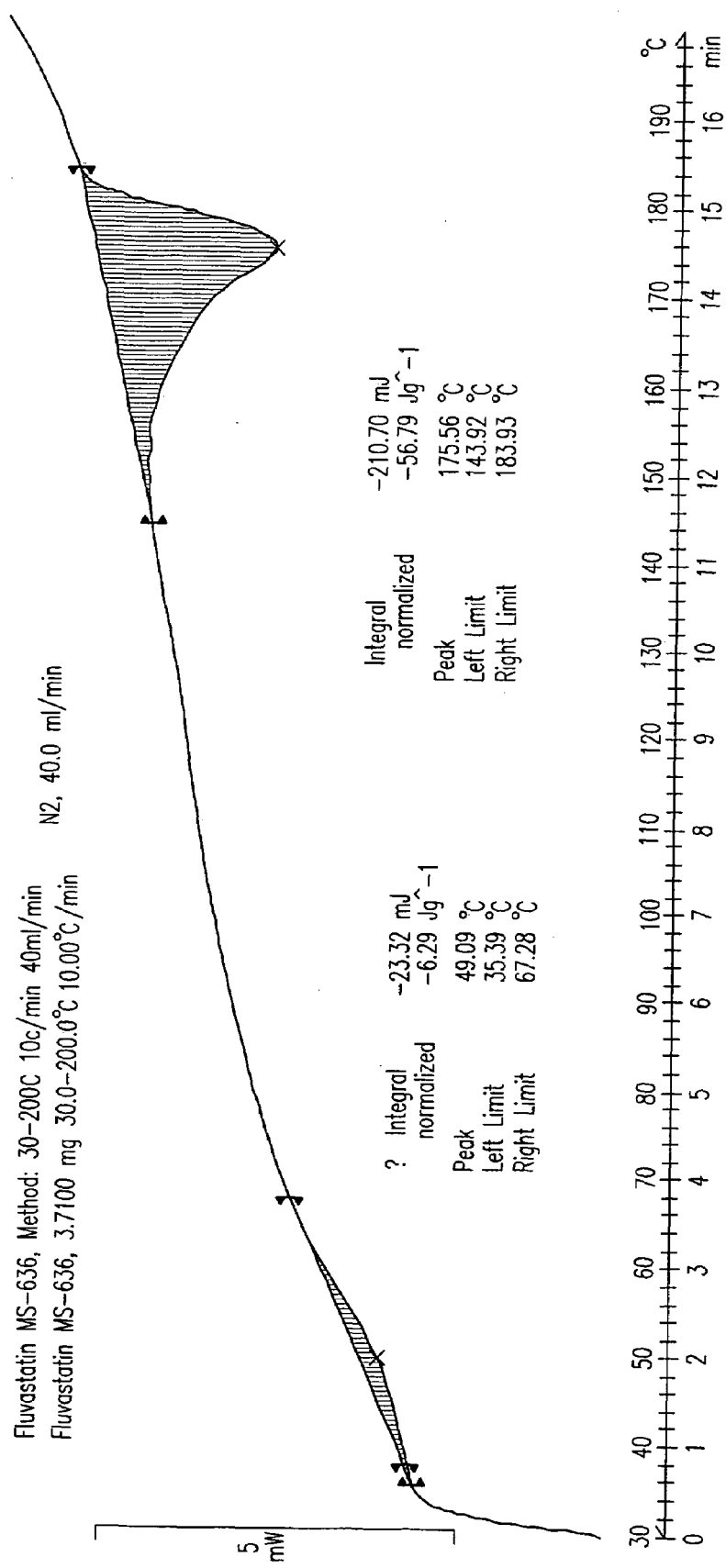
FIG. 37 depicts a DSC thermogram of fluvastatin sodium Form XVIII.
Figure 38:
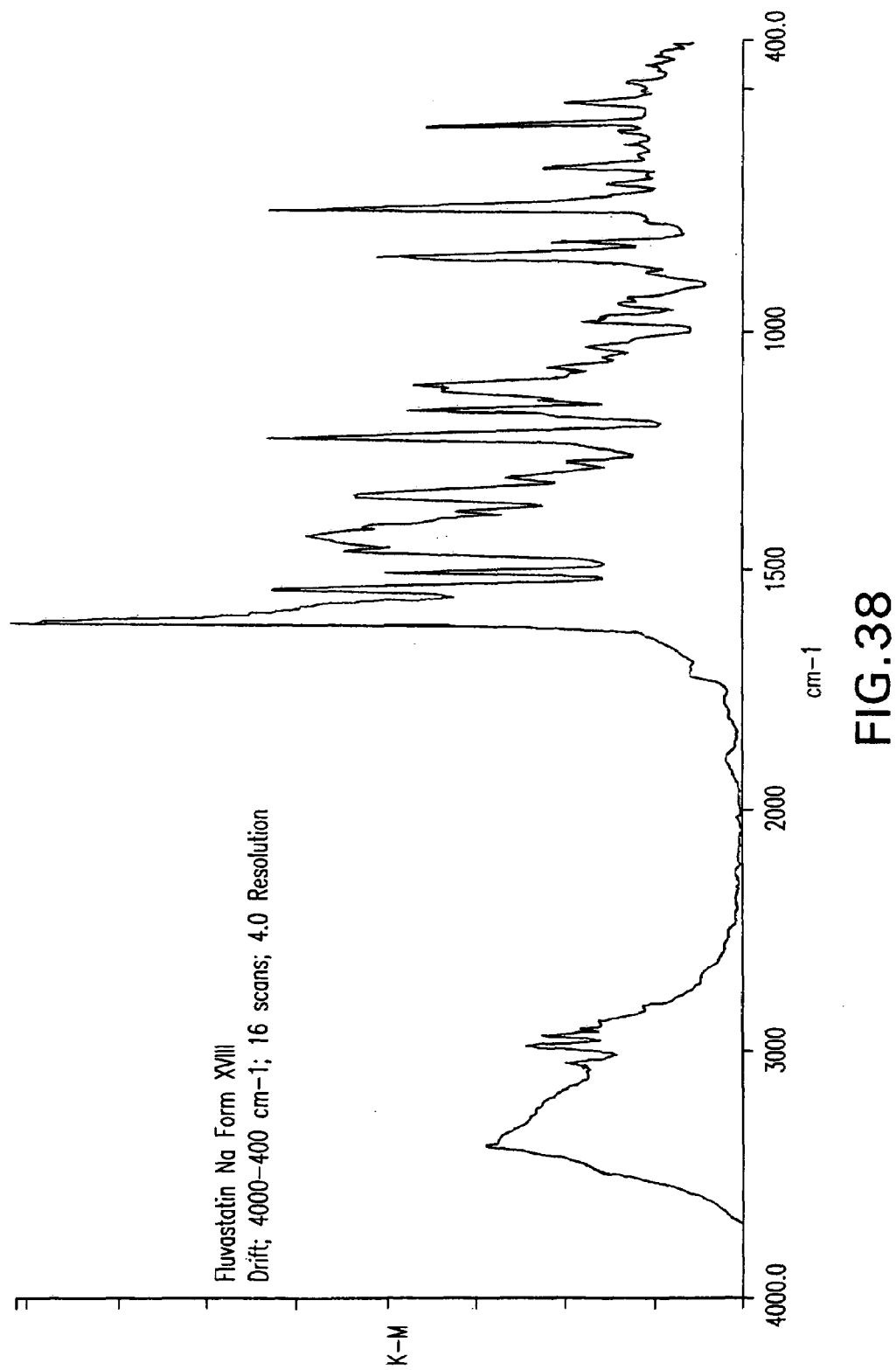
FIG. 38 depicts an IR spectrum of fluvastatin sodium Form XVIII scanned from 4000 to 400 cm$^{-1}$, while FIG. 38a expands the 4000-1500 cm$^{-1}$ region of the spectrum and FIG. 38b expands the 1500-400 cm$^{-1}$ region of the spectrum.
Figure 38A:
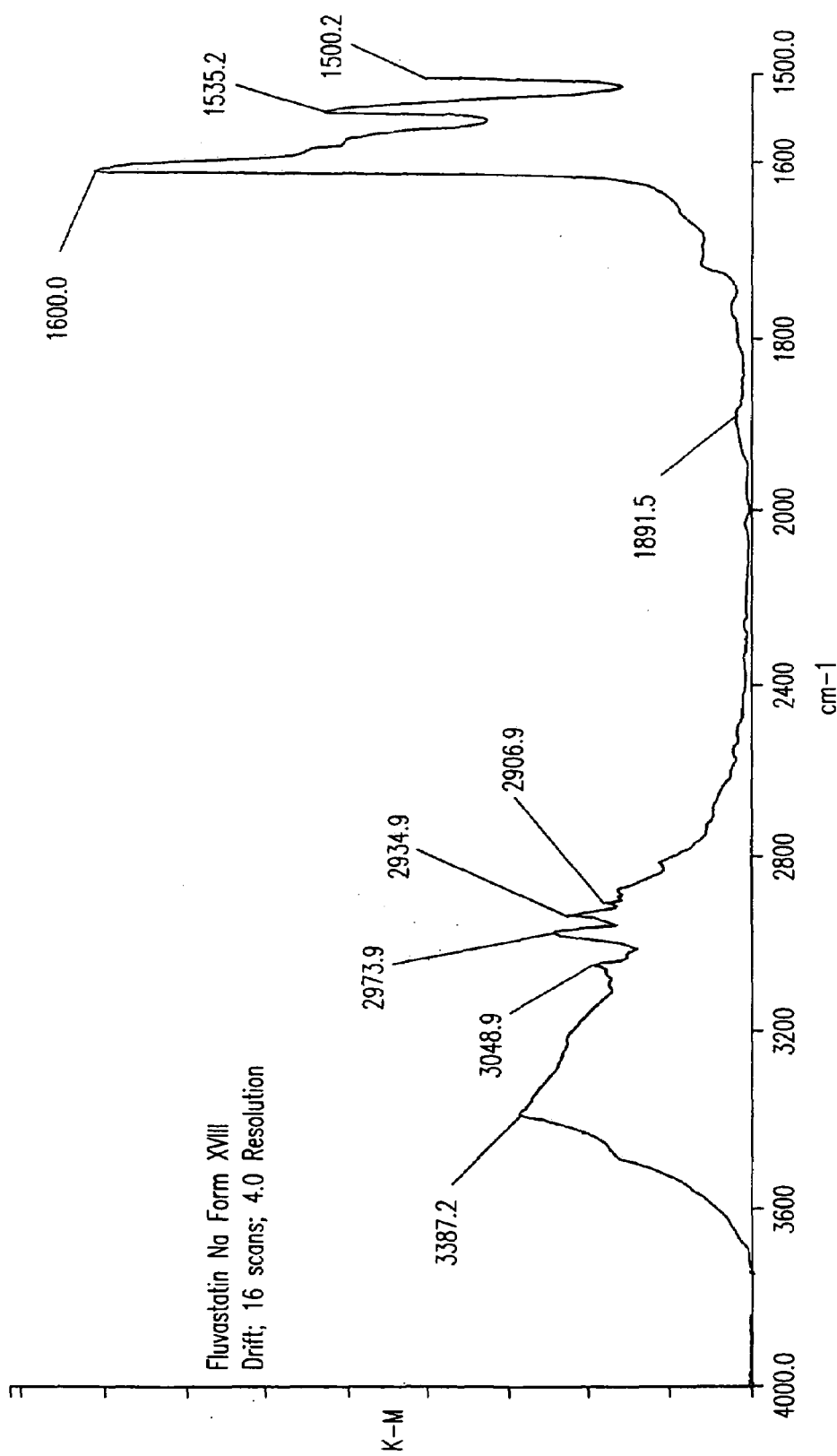
Figure 38B:
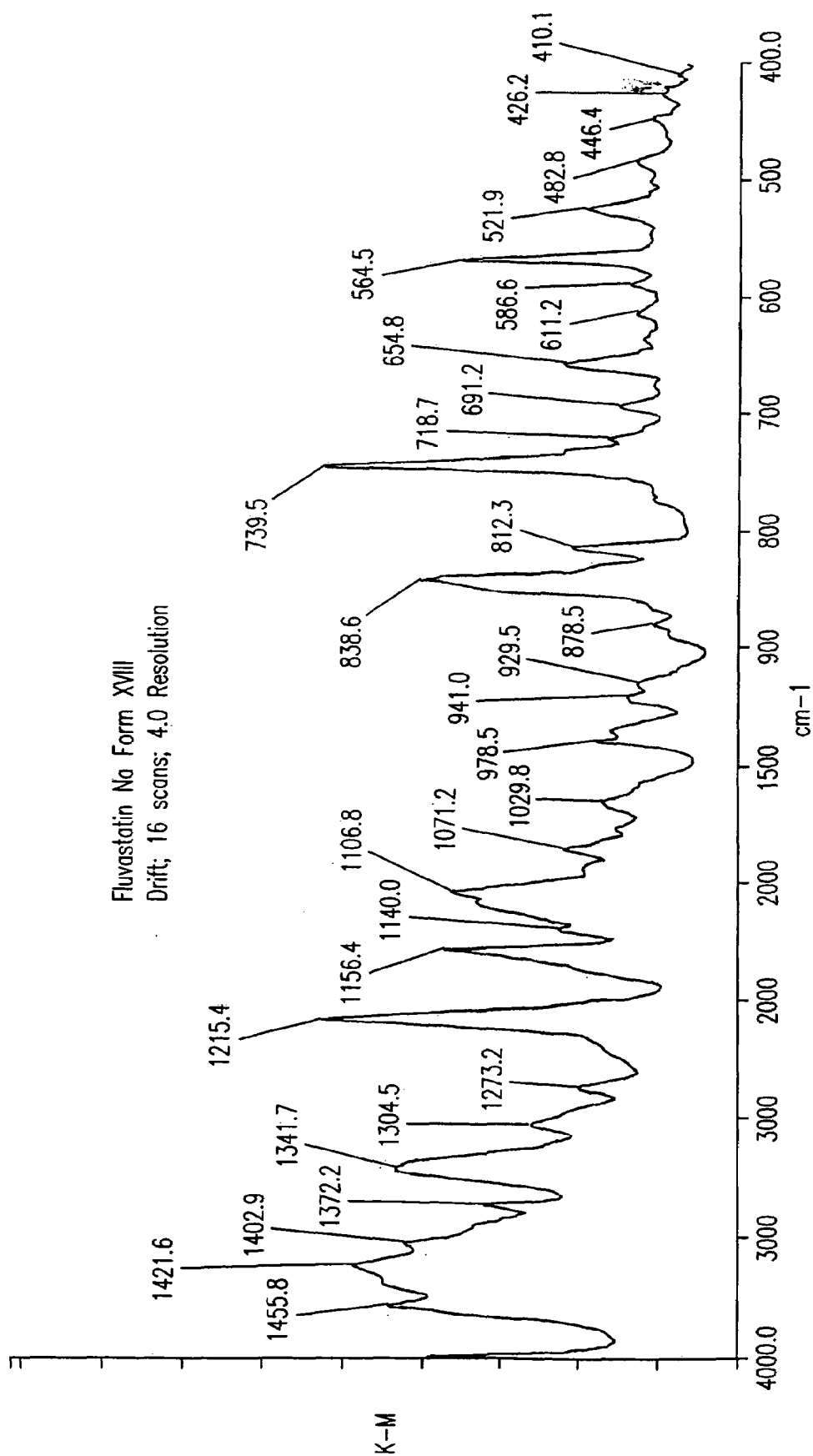

Fluvastatin sodium Form XVIII produces a PXRD diffractogram with characteristic peaks at 3.4, 8.4, 10.0 and 10.9±0.2 degrees two-theta and other peaks at 11.7, 12.6, 15.8, 17.4, 18.0, 18.8, 20.0, 20.7 and 21.3±0.2 degrees two-theta. (FIG. 36). Fluvastatin sodium Form XVIII produced the DSC thermogram shown in FIG. 37, in which two endothermic peaks can be seen below 70° C. and at about 180° C. The water content of the sample is about 4 wt. %. The loss on drying shown by TGA is about 4 wt. %. Fluvastatin sodium form XVIII is a monohydrate. The IR spectrum of fluvastatin sodium Form XVIII is shown in FIGS. 38, 38a and 38b.

Fluvastatin sodium Form XVIII can be prepared by suspending fluvastatin sodium in refluxing methylethyl ketone (MEK). The mixture may be maintained at reflux temperature for any amount of time necessary to achieve the desired yield of Form XVIII. Afterwards, the mixture is allowed to cool to room temperature and Form XVIII can be isolated by a known method of isolation such as filtering, decanting, centrifuging, distilling and the like, preferably filtering under a nitrogen stream or distillation.

Fluvastatin Sodium Crystal Form XIX

Figure 40:
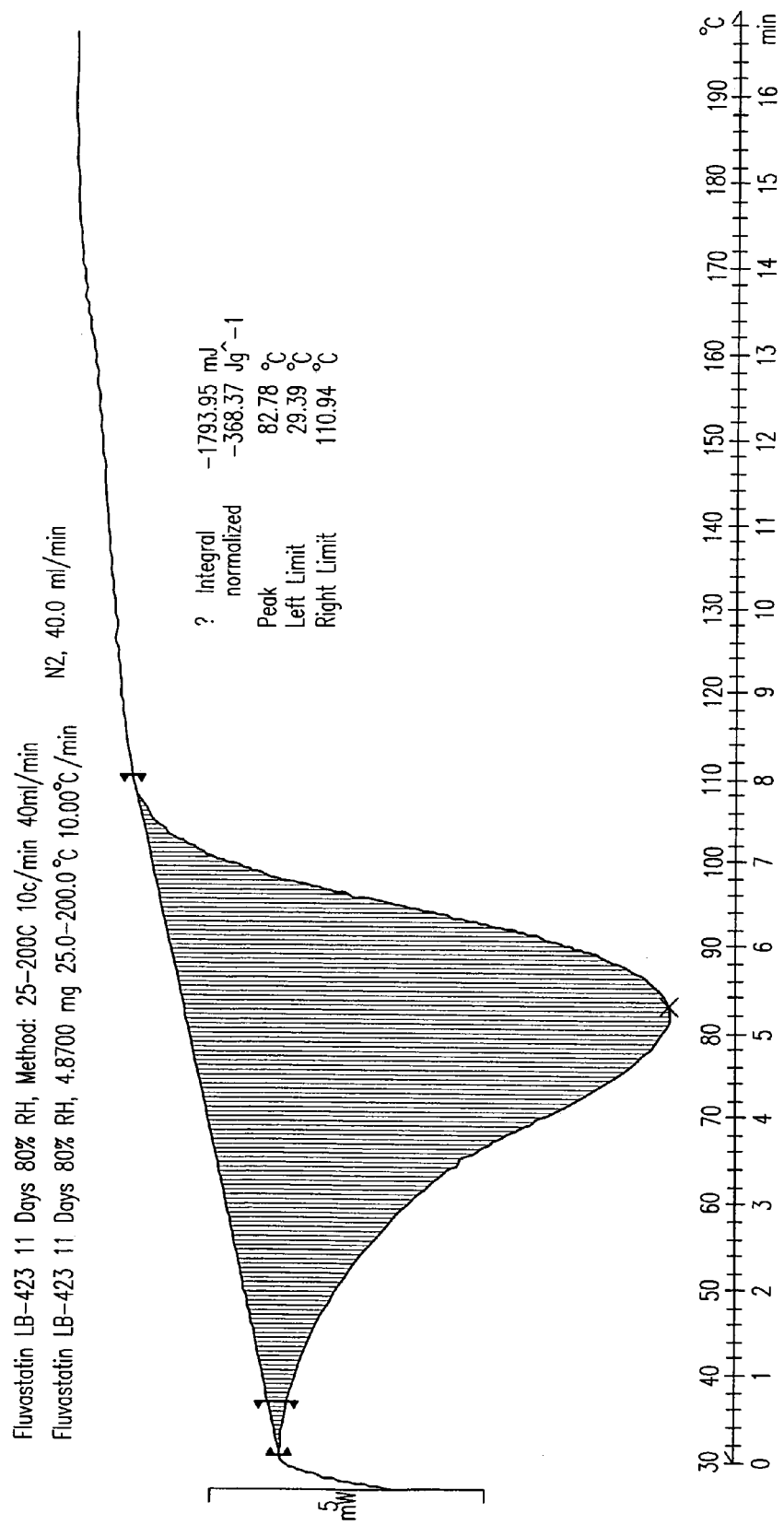
FIG. 40 depicts a DSC thermogram of fluvastatin sodium Form XIX.
Figure 41:
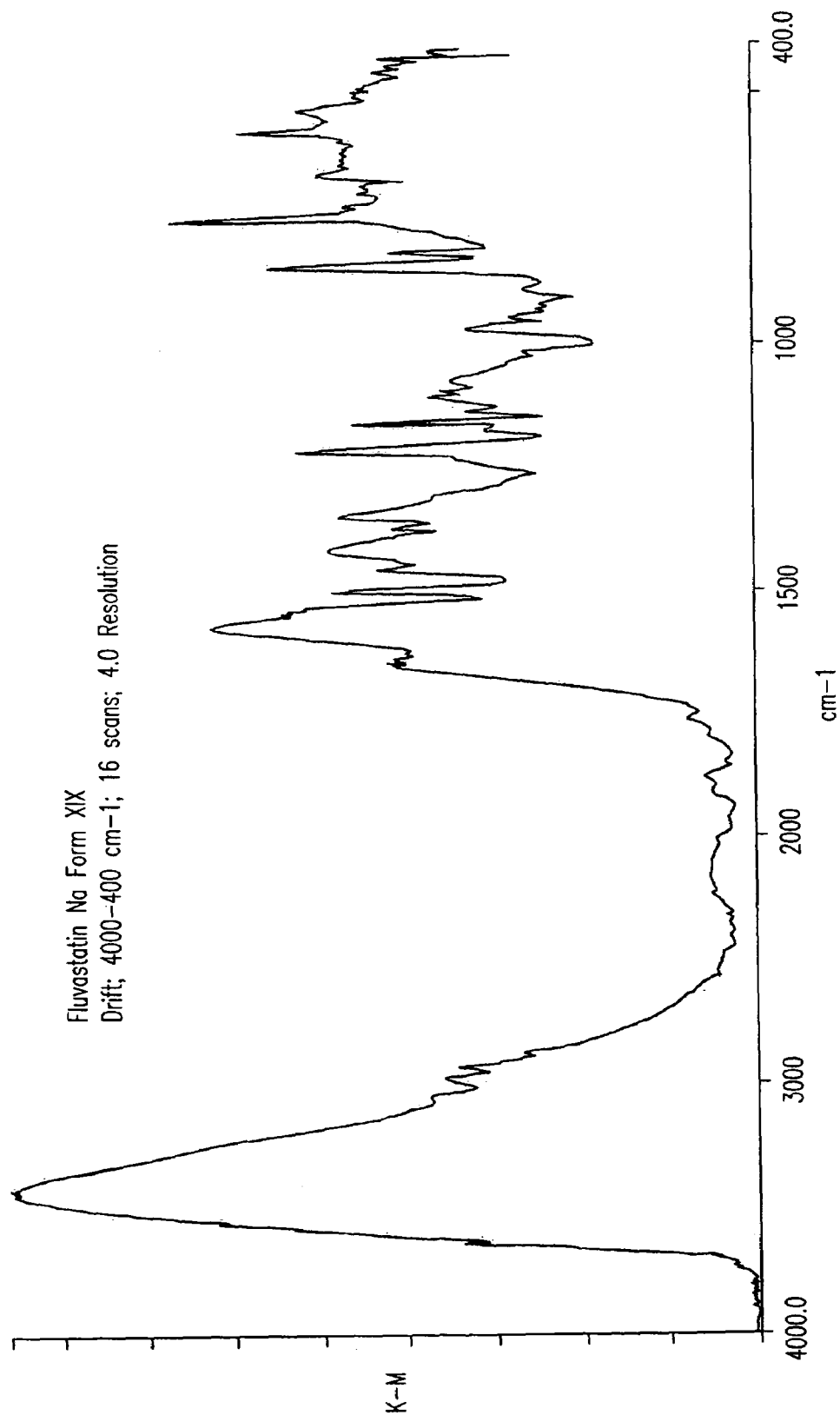
FIG. 41 depicts an IR spectrum of fluvastatin sodium Form XIX scanned from 4000 to 400 cm$^{-1}$, while FIG. 41a expands the 4000-1500 cm$^{-1}$ region of the spectrum and FIG. 41b expands the 1500-400 cm$^{-1}$ region of the spectrum.
Figure 41A:
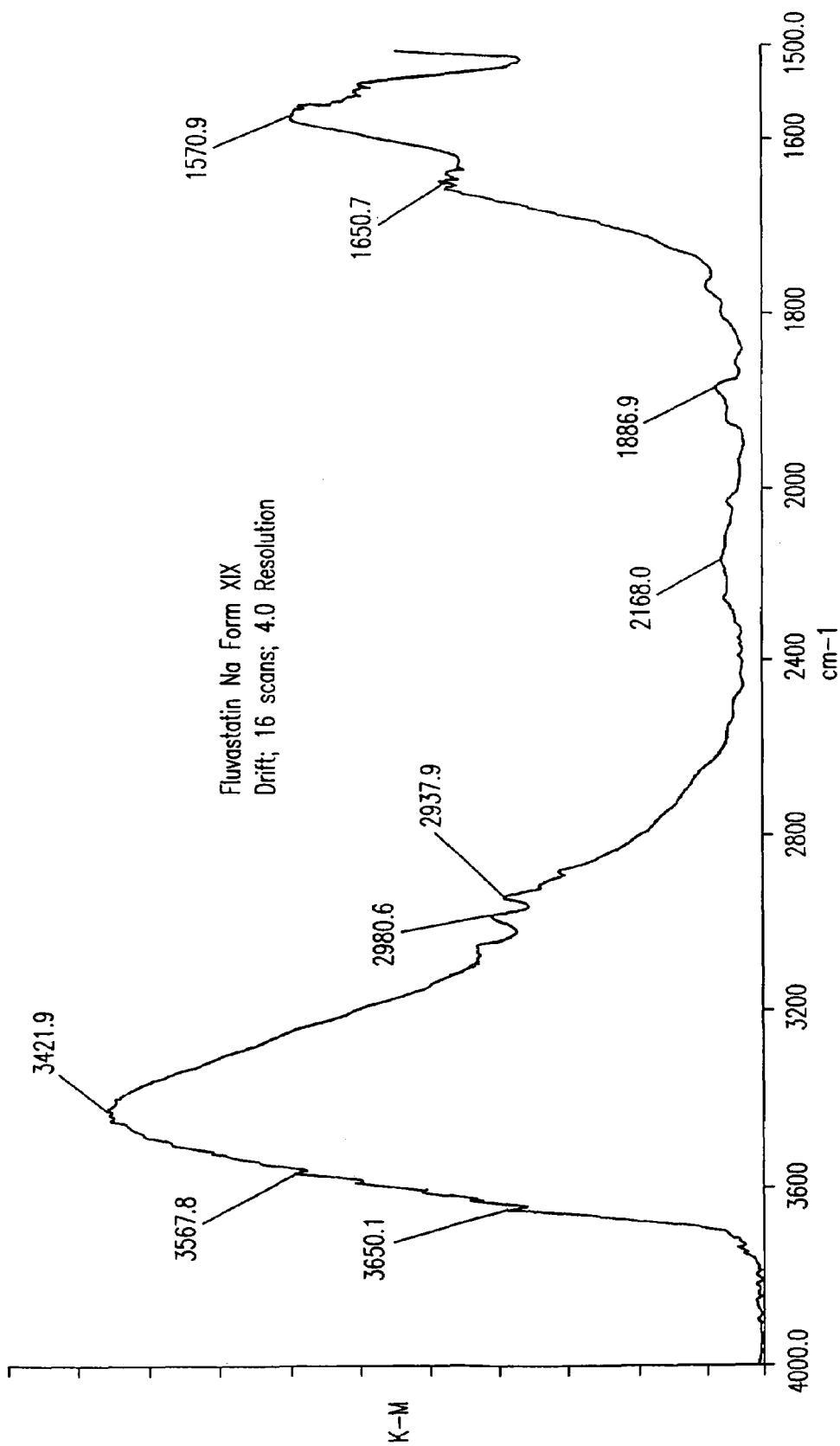
Figure 41B:
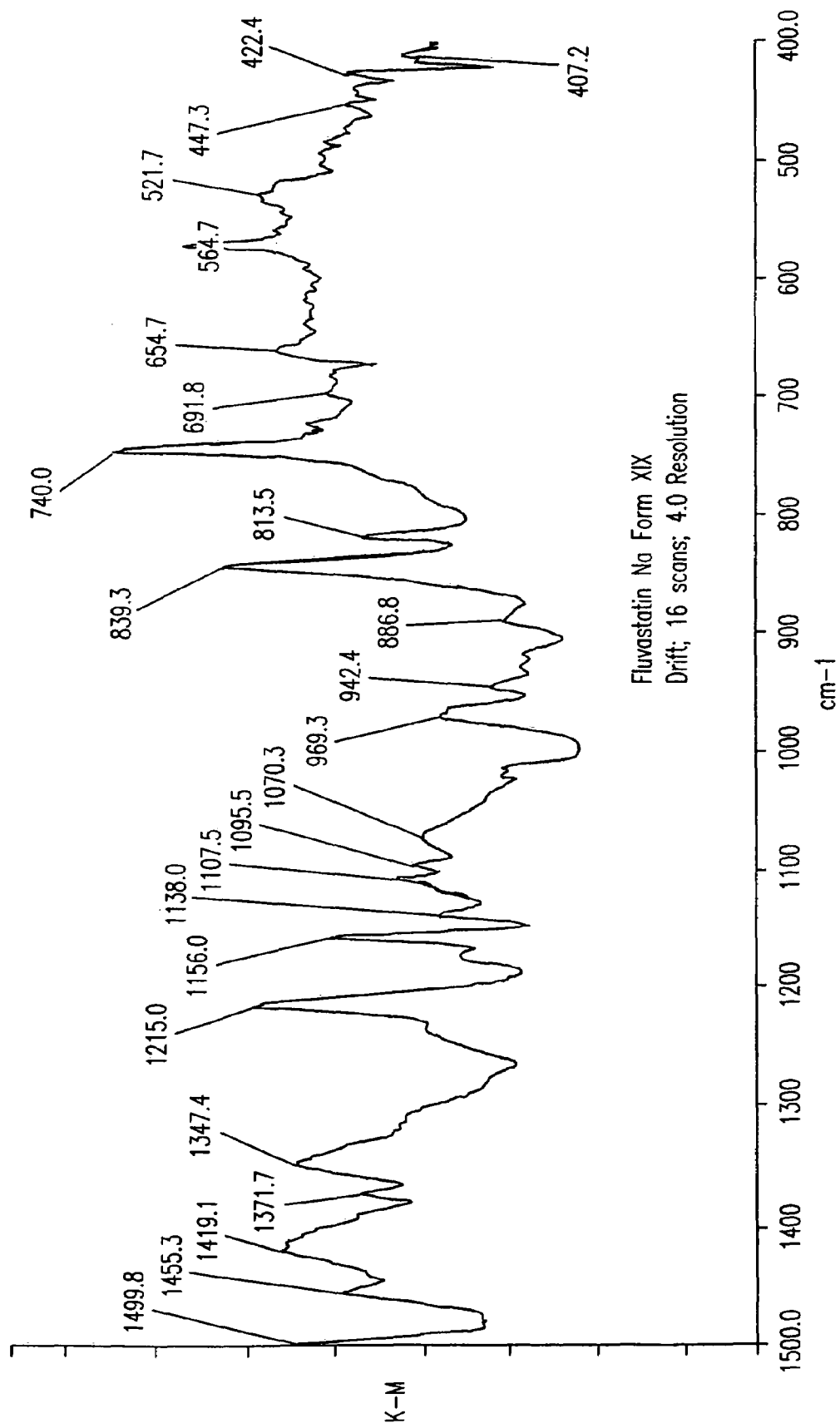

Fluvastatin sodium Form XIX produces a PXRD diffractogram with characteristic peaks at 3.4, 10.1, 13.5 and 18.0±0.2 degrees two-theta and other peaks at 6.8, 20.1, 21.8 and 25.6±0.2 degrees two-theta. (FIG. 39). Fluvastatin sodium Form XIX produced the DSC thermogram shown in FIG. 40, in which one main endothermic peak can be seen at about 80° C. The water content of the sample is 19-28 wt. %. The weight loss by TGA is 22-26 wt. %. Fluvastatin sodium Form XIX is in hexahydrate, 8-hydrate, and 9-hydrate forms. The IR spectrum of fluvastatin sodium Form XIX is shown in FIGS. 41, 41a and 41b.

Fluvastatin sodium Form XIX can be prepared by exposing Form XI, IV-1 or XVI to an atmosphere of elevated humidity ranging of about 60% to about 100% RH.

Fluvastatin Sodium Crystal Form XIX-1

Fluvastatin sodium Form XIX-1 produces a PXRD diffractogram (FIG. 42) with characteristic peaks at 3.5, 10.4, 11.9, 14.0, 22.5±0.2 degrees two-theta and other peaks at 17.5, 17.8, 18.0, 18.3, 25.4±0.2 degrees two-theta. The water content of fluvastatin Form XIX-1 measured by Karl Fisher analysis is about 8% by weight. The weight loss by TGA is about 7% by weight. Fluvastatin sodium Form XIV is a dihydrate.

Fluvastatin sodium Form XIX-1 can be prepared by forming a heterogeneous mixture of fluvastatin sodium Form XI and water and maintaining the mixture for a period of time sufficient to achieve the desired yield of Form XIX-1. The mixture may be stirred and preferably is stirred for about 2 hours to about 15 hours, with about 5 hours being especially preferred. The product may then be recovered from the mixture by conventional techniques such as filtration.

The recovered wet product may then be optionally dried. Drying may be carried out at a preferred temperature range of from about 40EC to about 60EC, for about 12 to about 48 hours.

Fluvastatin Sodium Crystal Form XX

Figure 44:
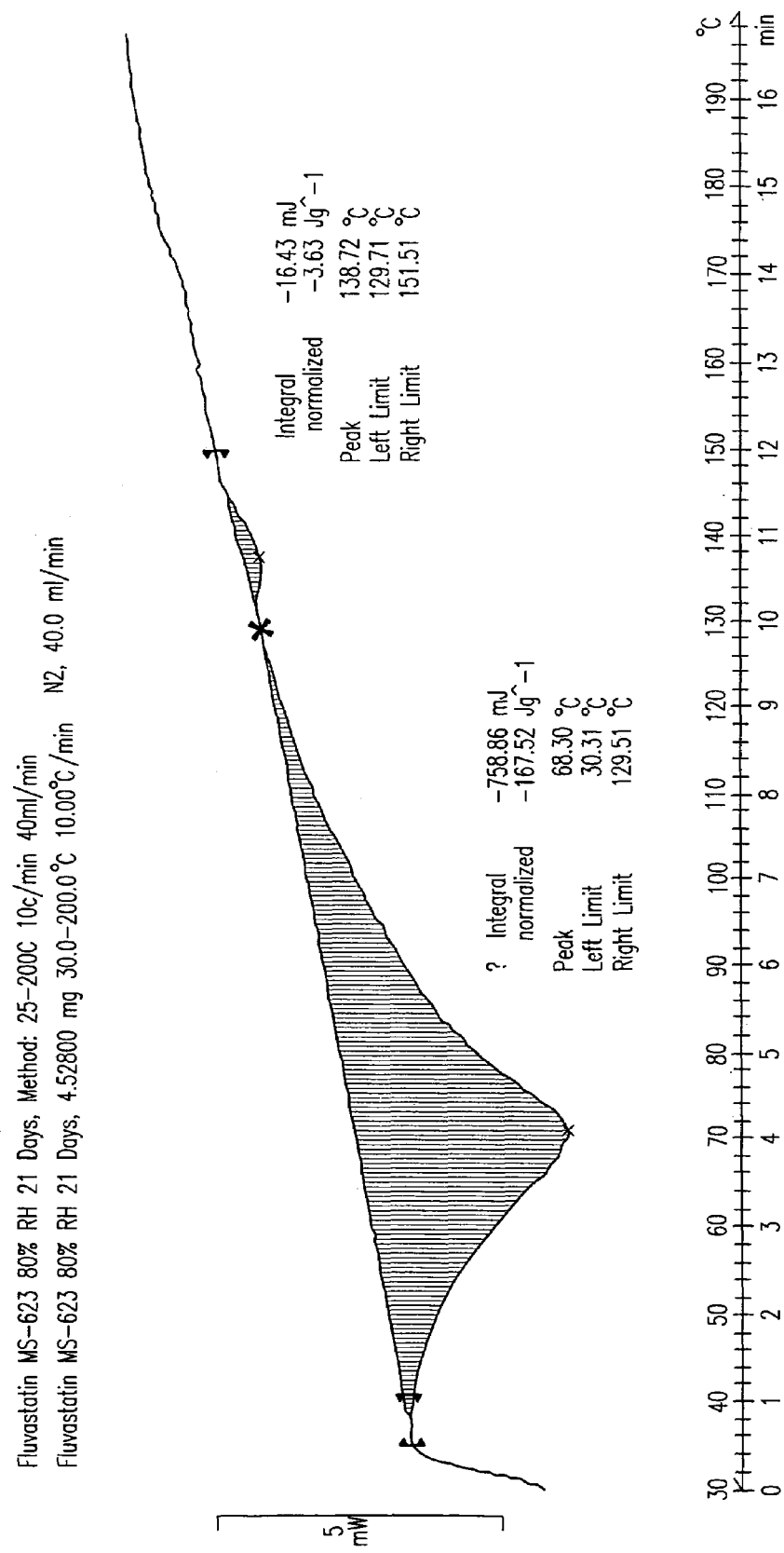
FIG. 44 depicts a DSC thermogram of fluvastatin sodium Form XX.
Figure 45:
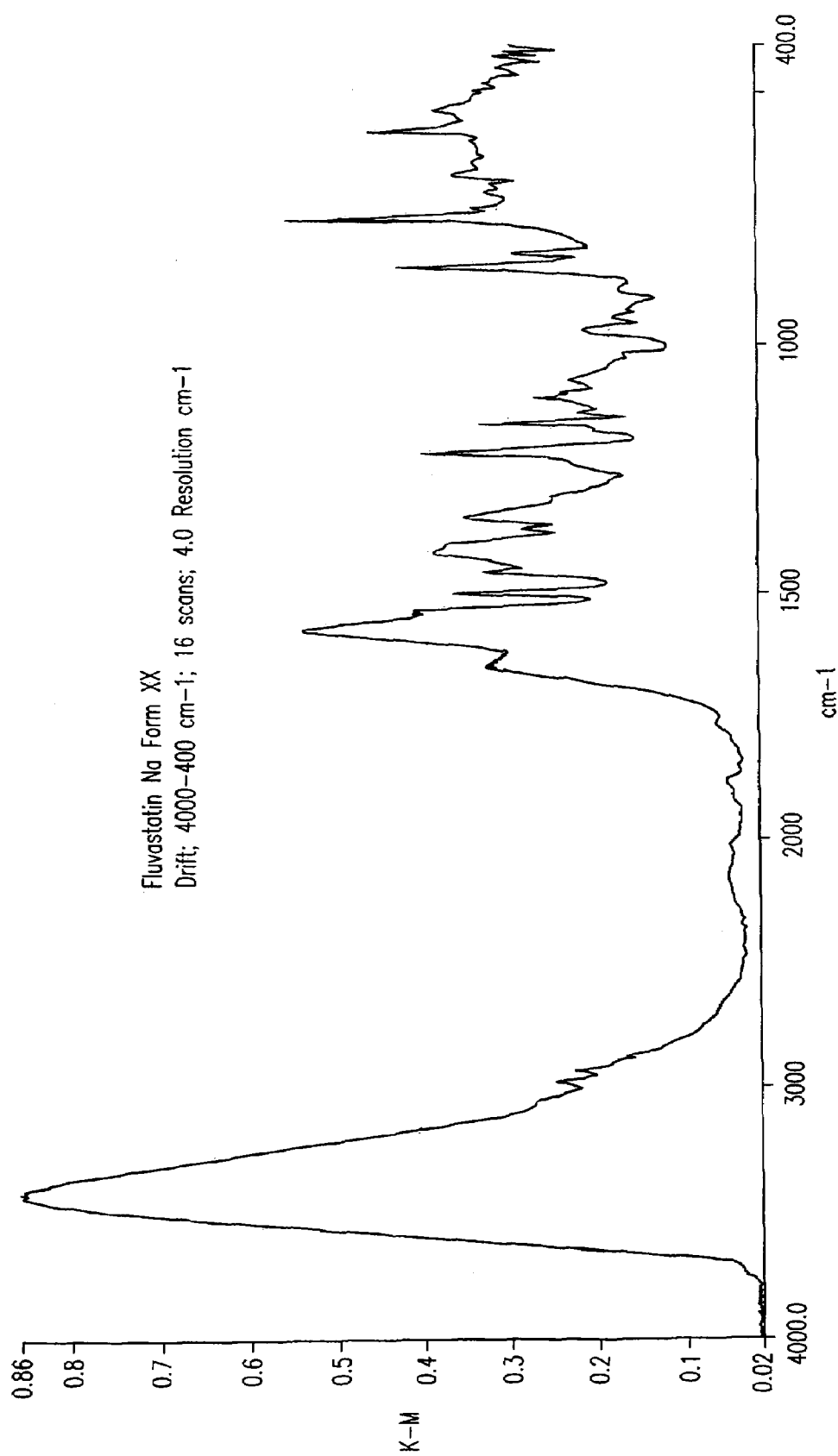
FIG. 45 depicts an IR spectrum of fluvastatin sodium Form XX scanned from 4000 to 400 cm$^{-1}$, while FIG. 45a expands the 4000-1500 cm$^{-1}$ region of the spectrum and FIG. 45b expands the 1500-400 cm$^{-1}$ region of the spectrum.
Figure 45A:
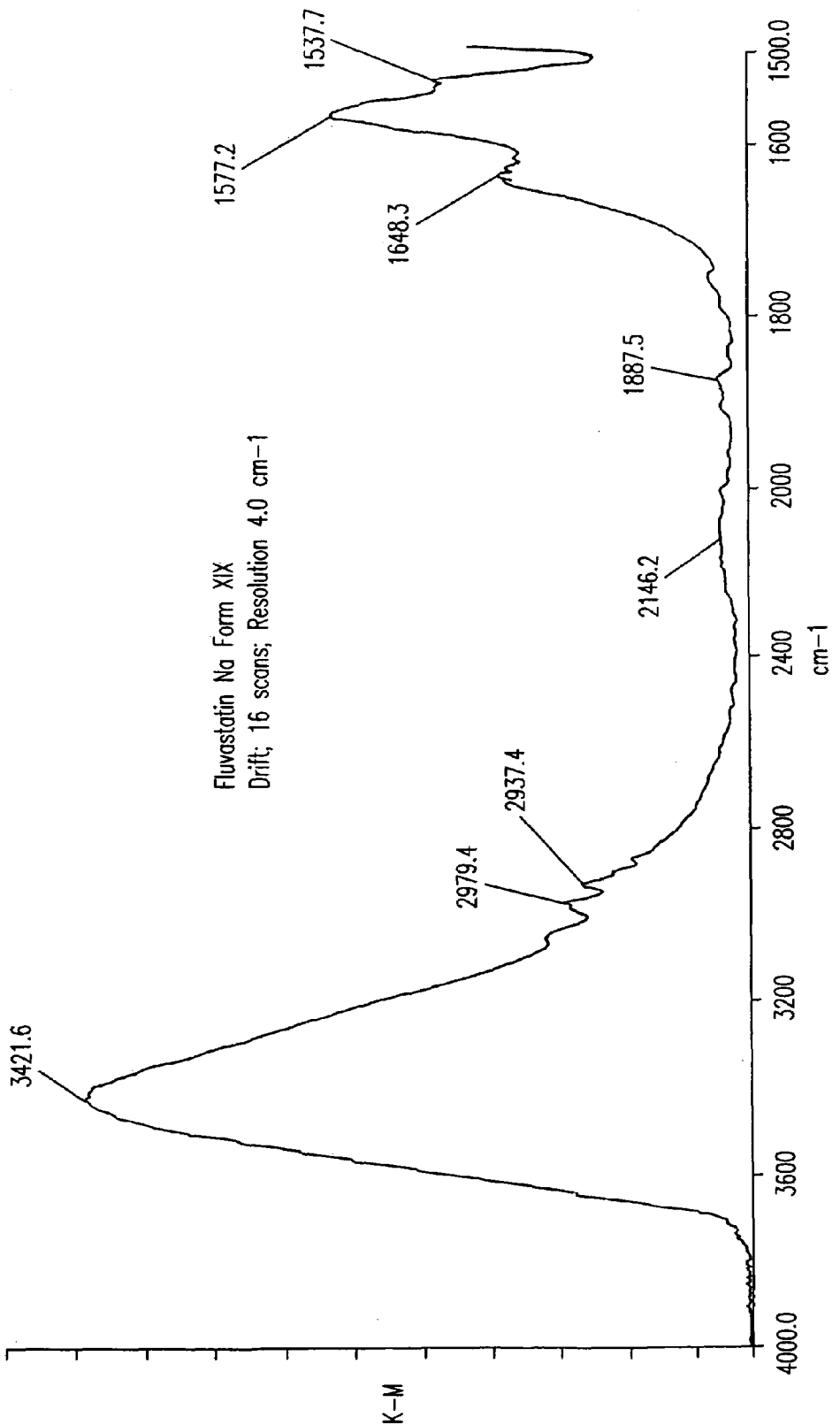
Figure 45B:
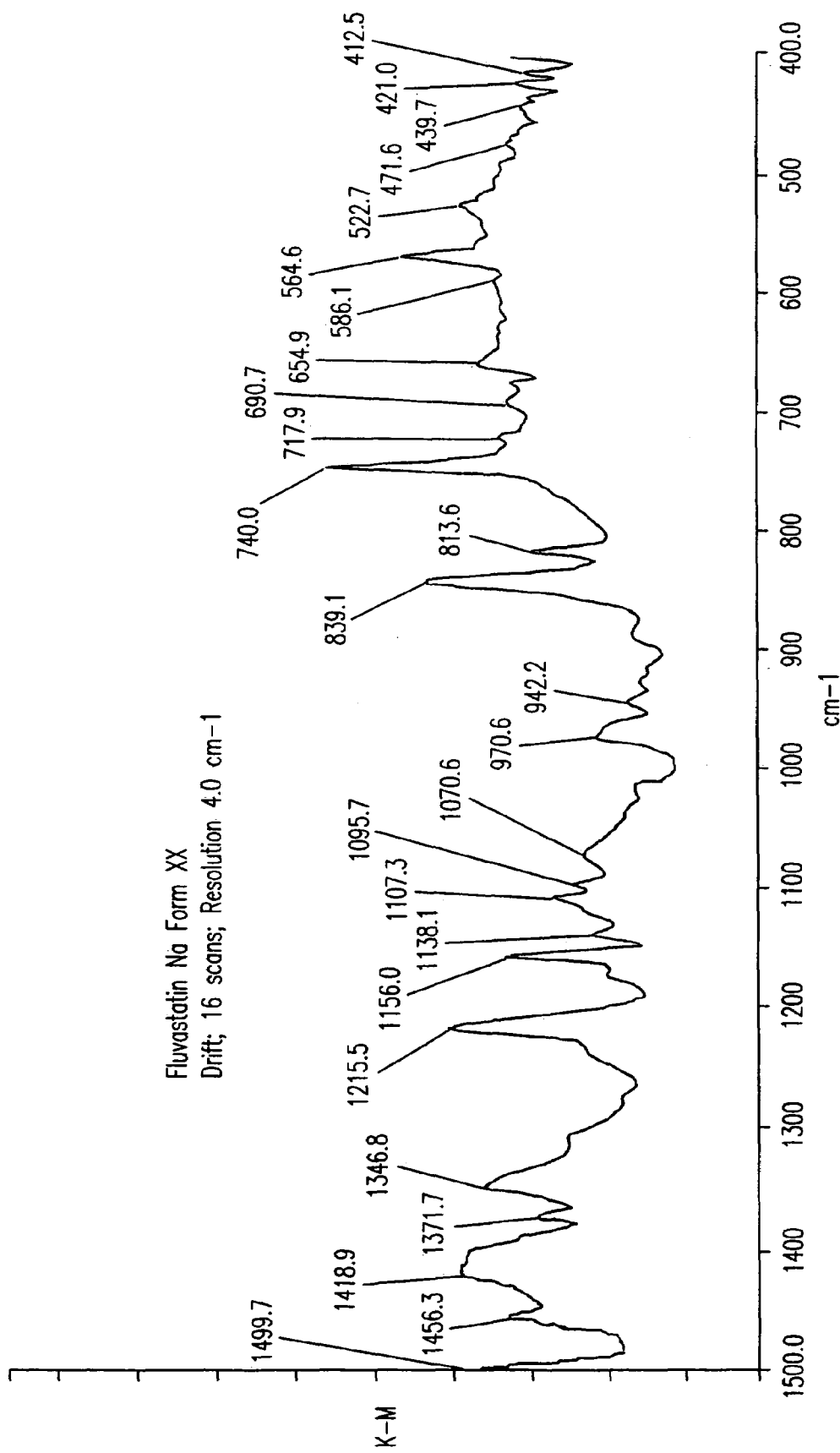

Fluvastatin sodium Form XX produces a PXRD diffractogram with characteristic peaks at 3.5, 10.1, 13.5, 18.0 and 20.8±0.2 degrees two-theta and other peaks at 5.9 and 12.4 degrees two-theta. (FIG. 43). Fluvastatin sodium Form XX produced the DSC thermogram shown in FIG. 44, in which one main endothermic peak is seen below about 130° C. The water content of the sample is about 19 wt. %. The loss on drying by TGA is about 19 wt. %. Fluvastatin sodium Form XX is a hexahydrate. The IR spectrum of fluvastatin sodium Form XX is shown in FIGS. 45, 45a and 45b.

Fluvastatin Form XX can be prepared by exposing fluvastatin sodium Form VII to an atmosphere of relative humidity of 80% or higher for a period of time sufficient to effect the conversion of Form XX.

In the case of fluvastatin sodium Forms XI, XIV, XVIII, XIX and XX, the TGA and Karl Fisher analyses were in close agreement, which is taken as an indication that those samples are mainly hydrated forms.

In fluvastatin sodium Forms IV, IV-1, VI, VII and XI-2, the TGA analysis exceeded that of Karl Fisher, which is taken as an indication that a considerable quantity of organic solvent was present. After exposure at 60% relative humidity for 11 days, the gap between TGA and KF results decreased (see below Forms VII and XI stored at different relative humidities), indicating that the level of organic solvent decreased. As a consequence, exposure to humidity is a useful method minimize the organic solvent present in fluvastatin sodium.

Fluvastatin Sodium Crystal Form XXII

Fluvastatin sodium Form XXII produces a PXRD diffractogram (FIG. 46) with characteristic peaks at 3.2, 12.4, and 18.3±0.2 degrees two-theta and other peaks at 6.4, 9.5, 15.6 and 21.4 degrees two-theta.

Form XXII can be prepared by exposing fluvastatin sodium Form XV to water vapor. Preferably, Form XV is maintained under an atmosphere of 100% relative humidity at ambient temperature. Substantially complete conversion is achieved over a period of weeks, typically about two weeks.

Fluvastatin Sodium Crystal Form XXIII

Fluvastatin sodium Form XXIII produces a PXRD diffractogram (FIG. 47) with characteristic peaks at 3.6, 4.0, 4.4, 17.1 and 19.3±0.2 degrees two-theta and other peaks at 6.2, 7.2, 9.3, 10.2 and 18.6 degrees two-theta.

Form XXIII can be prepared by dissolving about 1:20 (w/v) of fluvastatin sodium Form B in refluxing propan-1-ol. In a matter of hours after complete dissolution, fluvastatin sodium should begin to precipitate in Form XXIII. After the initial crystals form, the mixture can be cooled or allowed to cool to ambient temperature to complete the crystallization yielding Form XXIII. Form XXIII can be separated from the propan-1-ol by conventional techniques such as filtering, decanting, centrifuging and the like, preferably filtering under an inert atmosphere like nitrogen. The separated Form XXIII may be dried. A suitable drying condition is 50EC under vacuum.

Fluvastatin Sodium Crystal Form XXIV

Fluvastatin sodium Form XXIV produces a PXRD diffractogram (FIG. 48) with characteristic peaks at 3.4, 10.2, 13.6, 17.9 and 18.7±0.2 degrees two-theta and other peaks at 6.9, 10.7, 12.0, 22.5 and 25.4 degrees two-theta.

Form XXIV can be prepared from fluvastatin sodium Form B and fluvastatin Form XV. Form XXIV can be obtained from these forms by crystallization from water. When starting from Form XV, the starting material is dissolved in refluxing water. After a period of hours to a few days following cooling of the solution to ambient temperature, Form XXIV crystallizes out of solution. Form XXIV can be separated from the water by conventional techniques such as filtering, decanting, centrifuging and the like, preferably filtering under an inert atmosphere like nitrogen. The separated Form XXIV may be dried. A suitable drying condition is 50EC under vacuum. When starting from Form B, the starting material can be dissolved in the water at ambient temperature. If Form XXIV does not crystallize, the procedure can be modified as follows. Diethyl ether is added to the vessel containing the solution and contacted with the solution for several minutes. Then, the phases are separated and the aqueous phase is lyophilized to obtain a residue that is fluvastatin sodium Form XXIV.

Fluvastatin Sodium Crystal Form XXVI

Fluvastatin sodium Form XXVI produces a PXRD diffractogram (FIG. 49) with characteristic peaks at 3.8, 15.0, 18.5, 21.6 and 25.8±0.2 degrees two-theta and other peaks at 11.7, 15.9, 16.2, 24.3 and 35.2 degrees two-theta.

Form XXVI can be prepared by dissolving about 1:7 (w/v) of fluvastatin sodium Form B in a 20:1 mixture of 1,4-dioxane:water. The mixture is refluxed until a clear solution is obtained. Then the mixture is cooled or allowed to cool to induce precipitation of fluvastatin sodium in Form XXVI. Form XXVI can be separated from the water and 1,4-dioxane by conventional techniques such as filtering, decanting, centrifuging and the like, preferably filtering under an inert atmosphere like nitrogen. The separated Form XXVI may be dried. A suitable drying condition is 50EC under vacuum.

Fluvastatin Sodium Crystal Form XXVII

Fluvastatin sodium Form XXVII produces a PXRD diffractogram (FIG. 50) with characteristic peaks at 3.3, 3.9, 15.9, 18.4 and 21.6±0.2 degrees two-theta and other peaks at 8.4, 15.0, 17.9, 24.3 and 25.7±0.2 degrees two-theta.

The initial steps for preparing Form XXVII are the same as for preparing Form XXVI. Form B is dissolved in a refluxing 20:1 mixture of 1,4-dioxane:water. However, at reflux temperature 1.5 volumes of hexanes is slowly added to the solution. Thereafter, the mixture is cooled to ambient temperature after which fluvastatin sodium crystallizes in Form XXVII from the mixture. Form XXVII can be separated from the solution by conventional techniques such as filtering, decanting, centrifuging and the like, preferably filtering under an inert atmosphere like nitrogen. The separated Form XXVII may be dried. A suitable drying condition is 50EC under vacuum.

Fluvastatin Sodium Crystal Form XXIX

Fluvastatin sodium Form XXIX produces a PXRD diffractogram with characteristic peaks at 4.4, 5.9, 6.8, 7.9, 10.8±0.2 degrees two-theta and other peaks at 14.3, 15.6, 17.5, 19.7, 21.3, 22.7±0.2 degrees two-theta (FIG. 51).

Fluvastatin sodium Form XXIX can be prepared by forming a heterogeneous mixture of fluvastatin sodium Form XV and 1,4-dioxane and maintaining the heterogeneous mixture until substantially all of the Form XV is converted into Form XXIX. Preferably, the conversion is accelerated by heating the heterogeneous mixture.

Under an especially preferred set of conditions, the heterogeneous mixture is heated to the reflux temperature of 1,4-dioxane and maintained at reflux for about 16 hours. Then, Form XXIX is separated from the 1,4 dioxane by cooling the mixture and filtering the mixture under a nitrogen flow. Thereafter, Form XXIX may be conventionally dried.

Fluvastatin Sodium Crystal Form XXX

Fluvastatin sodium Form XXX produces a PXRD diffractogram with characteristic peaks at 5.4, 5.8, 10.8, 13.8, 14.8±0.2 degrees two-theta and other peaks at 16.4, 19.0, 19.5, 20.2, 20.8, 21.5, 22.7±0.2 degrees two-theta (FIG. 52). The water content of the sample, measured by Karl Fisher, is about 4% by weight. The weight loss by TGA is about 10%.

Fluvastatin sodium Form XXX can be prepared by forming a heterogeneous mixture of fluvastatin sodium Form XV and one or a mixture of certain selected organic liquids. Liquids that have been found suitable include methylethylketone ("MEK"), tetrahydrofuran ("THF"), acetone, butan-2-ol and butan-1-ol. The heterogeneous mixture is maintained until substantially all of the Form XV is converted into Form XXX. Preferably, the conversion is accelerated by heating the heterogeneous mixture.

Under an especially preferred set of conditions, the heterogeneous mixture is heated to the reflux temperature of organic liquid used and maintained at reflux for about 16 hours. Then, Form XXX is separated from the organic liquid by cooling the mixture and filtering the mixture under a nitrogen flow. Thereafter, Form XXX may be conventionally dried.

Fluvastatin sodium Form XXX also can be prepared directly from a lower alkyl ester of fluvastatin by precipitation from a solution containing an excess of sodium. The preferred excess of sodium is about 1.5 molar equivalents. According to a preferred procedure, the starting material is added to a solution of sodium hydroxide in mixture containing water as a minor component and methanol as a major component and the resulting mixture is heated, e.g. to the reflux temperature of the solvent, until a clear solution is obtained. Acetone is then added to the solution at elevated temperature to induce precipitation of Form XXX. After cooling to ambient temperature. Form XXX can be separated from the methanol and water by conventional techniques such as filtering, decanting, centrifuging and the like. Preferably, the water is separated by vacuum filtration under an inert gas like nitrogen. A suitable condition for drying the separated product is 50EC under vacuum.

Fluvastatin Sodium Crystal Form XXXI

Fluvastatin sodium Form XXXI produces a PXRD diffractogram with characteristic peaks at 5.3, 6.1, 6.5, 11.9, 13.2±0.2 degrees two-theta, and other peaks at 8.0, 8.5, 9.3, 16.3, 18.3, 20.2, 20.6, 21.1±0.2 degrees two-theta (FIG. 53).

The water content of fluvastatin sodium Form XXXI measured by Karl Fisher analysis is about 16% by weight. The weight loss by TGA is about 10% by weight. Fluvastatin sodium Form XXXI is a tetrahydrate.

Fluvastatin sodium Form XXXI can be prepared by forming a heterogeneous mixture of fluvastatin sodium Form XV and ethanol and maintaining the heterogeneous mixture until substantially all of the Form XV is converted into Form XXXI. Preferably, the conversion is accelerated by heating the heterogeneous mixture.

Under an especially preferred set of conditions, the heterogeneous mixture is heated to the reflux temperature of ethanol and maintained at reflux for about 23 hours. Then, Form XXXI is separated from the ethanol by cooling the mixture and filtering the mixture under a nitrogen flow. Thereafter, Form XXXI may be conventionally dried.

Fluvastatin Sodium Crystal Form XXXIII

Fluvastatin sodium Form XXXIII produces a PXRD diffractogram (FIG. 54) with characteristic peaks at 4.0, 5.5, 8.0, 9.1, 13.4, 16.6, 21.2±0.2 degrees two-theta and other peaks at 6.6, 8.8, 10.4, 11.6, 12.0, 14.1, 14.8, 16.1, 17.9, 18.5, 19.7, 20.3, 24.3, 24.9, 26.7±0.2 degrees two-theta. The water content of the sample measured by Karl Fisher is about 7% by weight. The weight loss by TGA is about 7%. The water content measured may reach about 10% by weight. Fluvastatin sodium Form XXXIII is in dihydrate and hemipentahydrate form.

Fluvastatin sodium Form XXXIII can be prepared by forming a heterogeneous mixture of fluvastatin sodium Form XV or Form B and ethanol, preferably absolute ethanol and maintaining the mixture for a period of time sufficient to achieve the desired yield of Form XXXIII. The mixture preferably is stirred for about 5 hours to about 48 hours and heated to reflux temperature while stirring. The product may then be recovered from the mixture by conventional techniques such as filtering, decanting, centrifuging and the like. The recovered wet product may then be optionally dried. Drying may be carried out at a preferred temperature range of from about 40EC to about 60EC, for about 12 to about 48 hours.

Fluvastatin Sodium Form XXXIV

Fluvastatin sodium Form XXXIV produces a PXRD diffractogram (FIG. 55) with characteristic peaks at 5.4, 6.1, 7.6, 18.5, 21.1±0.2 degrees two-theta and other peaks at 8.8, 9.3, 12.4, 13.1, 14.3, 15.2, 15.9, 17.2, 17.6, 20.5, 22.2, 24.1, 25.4, 26.2±0.2 degrees two-theta. The water content of Form XXXIV as measured by Karl Fisher analysis is about 10% by weight. The weight loss by TGA is about 20%.

Fluvastatin sodium Form XXXIV can be prepared by forming a heterogeneous mixture of fluvastatin Form XV and dimethyl sulfoxide ("DMSO") and maintaining the mixture for a period of time sufficient to achieve the desired yield of Form XXXIV. The mixture preferably is stirred about 5 hours to about 48 hours and heated while stirring, yet more preferably heated to about 80EC or higher temperature. The product may then be recovered from the slurry by conventional techniques such as filtering, decanting, centrifuging and the like. The recovered wet product may then be optionally dried. Drying may be carried out at a preferred temperature range of from about 40EC to about 60EC, for about 12 to about 48 hours.

Fluvastatin Sodium Form XXXV

Fluvastatin sodium Form XXXV produces a PXRD diffractogram (FIG. 56) with characteristic peaks at 5.4, 6.0, 9.9, 14.8, 21.0±0.2 degrees 2 theta and other peaks at 16.7, 18.6, 19.8, 22.6±0.2 degrees two-theta. The water content of this sample measured by Karl Fisher is about 15% by weight. The weight loss by TGA is about 31% by weight. Fluvastatin sodium Form XXXVII is a hemipentahydrate.

Fluvastatin sodium Form XXXV may be prepared by forming a heterogeneous mixture of fluvastatin sodium Form XV in N,N dimethyl formamide ("DMF") and maintaining the mixture for a period of time sufficient to achieve the desired yield of Form XXXV. The mixture preferably is stirred for about 5 hours to about 48 hours. The mixture is preferably heated while stirring. Yet more preferably, the stirred mixture is heated to a temperature of about 80EC or higher. The product may then be recovered from the mixture by conventional techniques such as filtering, decanting, centrifuging and the like. The recovered wet product may then be optionally dried. Drying may be carried out at a preferred temperature range of from about 40EC to about 60EC, for about 12 to about 48 hours.

Fluvastatin Sodium Crystal Form XXXVI

Fluvastatin sodium Form XXXVI produces a PXRD diffractogram (FIG. 57) having characteristic peaks at 3.0, 9.2, 11.5, 14.4 and 20.2±0.2 degrees two-theta, and other peaks at 9.6, 12.3 and 12.8±0.2 degrees two-theta.

Form XXXVI can be prepared by suspending fluvastatin sodium Form XI-wet (obtained after filtration, but before drying) in water for a sufficient period time to effect the conversion (typically about 6 h). The product may then be recovered from the suspension by conventional techniques such as filtering, decanting, centrifuging and the like. The recovered wet product may then be optionally dried. A suitable condition for drying the separated product is 50EC under vacuum.

Fluvastatin Sodium Crystal Form XXXVII

Fluvastatin sodium Form XXXVII produces a PXRD diffractogram having characteristic peaks at 3.63, 10.36, 13.74, 17.93, 18.34±0.2 degrees two-theta, and other peaks at 11.26, 12.16, 12.91, 19.44, 20.57±0.2 degrees two-theta (FIG. 58). The water content of this sample measured by Karl Fisher is about 9% by weight. The weight loss by TGA is about 31% by weight.

Fluvastatin sodium Form XXXVII can be prepared by forming a heterogeneous mixture of fluvastatin sodium Form XI and water. The weight ratio of Form XI to water is preferably about 0.5:1. The mixture should be maintained at ambient temperature. The conversion takes about 5h, 45 min. at 22EC. Form XXXVII can then be separated from the water by conventional means such as filtering, decanting, centrifuging and the like. Preferably, the water is separated by vacuum filtration under an inert gas like nitrogen. A suitable condition for drying the separated product is 50EC under vacuum.

Fluvastatin Sodium Crystal Form XXXVIII

Fluvastatin sodium Form XXXVIII produces a PXRD diffractogram having characteristic peaks at 3.64, 4.66, 7.30, 8.84, 11.61±0.2 degrees two-theta, and other peaks at 19.08, 19.65, 21.15, 22.59, 24.20±0.2 degrees two-theta (FIG. 59). The water content of this sample measured by Karl Fisher is about 6-7% by weight. The weight loss by TGA is about 10-11% by weight.

Fluvastatin sodium Form XXXVIII can be prepared by forming a heterogeneous mixture of fluvastatin sodium Form XI and ethanol. To obtain a product of highest polymorphic purity it is preferable to use absolute ethanol. The ratio of Form XI to ethanol is preferably about 0.2 g ml$^{-1}$, more preferably about 0.19 g ml$^-$.

Under a particular preferred set of conditions the heterogeneous mixture is heated until the ethanol boils and is maintained at that temperature for several hours until the conversion of Form XI to Form XXXVIII is complete. The conversion can be monitored by powder X-ray diffractometry. If the conversion is still not complete after several hours (it took 16 hours in one of our experiments) then the mixture can be held at elevated or ambient temperature until the conversion is considered to be sufficiently complete.

Form XXXVIII can then be separated from the ethanol by conventional means such as filtering, decanting, centrifuging and the like. Preferably, the ethanol is separated by vacuum filtration under an inert gas like nitrogen. A suitable condition for drying the separated product is 50EC under vacuum.

Fluvastatin sodium Form XXXVIII also can be prepared from a lower alkyl ester of fluvastatin by taking it up in a solution of about one molar equivalent of sodium hydroxide in ethanol and then precipitating it by addition of ethyl acetate to the mixture. Thereafter, Form XXXVIII can then be separated from the ethanol and ethyl acetate by conventional means such as filtering, decanting, centrifuging and the like. Preferably, the ethanol and ethyl acetate are separated by vacuum filtration under an inert gas like nitrogen. A suitable condition for drying the separated product is 50EC under vacuum.

Yet further, Form XXXVIII can be prepared by suspending fluvastatin sodium Form XI-wet in refluxing absolute ethanol, preferably for about 16 h. Then the suspension is cooled to reduced temperature and the product is isolated by conventional means.

Fluvastatin Sodium Crystal Form XXXIX

Fluvastatin sodium Form XXXIX produces a PXRD diffractogram (FIG. 60) having characteristic peaks at 3.7, 4.5, 8.5, 17.8, 20.1±0.2 degrees two-theta and other peaks at 6.9, 11.2, 16.8, 19.6 and 21.6±0.2 degrees two-theta.

Form XXXIX can be prepared directly from a lower alkyl ester of fluvastatin such as fluvastatin methyl ester. The ester is dissolved in a solution of about one molar equivalent of sodium in ethanol. The sodium can be conveniently provided by dissolving the appropriate quantity of sodium hydroxide pellets in water, while exercising caution since the dissolution in water is highly exothermic. The solution is heated for a sufficient period of time to hydrolyze the ester, typically several hours. Then, a large excess (e.g. 8×v/v) of propan-2-ol is added to the solution. The mixture is then cooled to ambient temperature and maintained until a precipitate forms in the flask.

Form XXXIX can then be separated from the solution by conventional means. Form XXXIX unlike Form IX is obtained without use of water.

Fluvastatin Sodium Crystal Form XLI

Fluvastatin sodium Form XLI produces a PXRD diffractogram having characteristic peaks at 3.75, 4.31, 9.10, 11.00±0.2 degrees two-theta and other peaks at 5.60, 7.30, 7.55, 14.50, 18.04±0.2 degrees two-theta (FIG. 61). The water content of this sample measured by Karl Fisher is about 9% by weight. The weight loss by TGA is about 9% by weight. Fluvastatin sodium Form XLI is a hemipentahydrate.

Fluvastatin sodium Form XLI can be prepared by precipitating fluvastatin sodium from a mixture of water and acetonitrile. Fluvastatin sodium should first be dissolved in water. The water may be heated in order to produce a more concentrated solution and maximized recovery of Form XLI. Fluvastatin sodium can be dissolved to produce a solution of 0.375 g ml$^{-1}$ or greater in water at 100EC. Of course, if all of the fluvastatin sodium does not go into solution or reprecipitates, additional water should be added. Once a homogeneous solution has been formed, acetonitrile is added to the solution to induce precipitation of the fluvastatin sodium. The addition is done at whatever elevated temperature was used to dissolve the starting material or at higher temperature. The addition is dropwise and will generally require adding a excess of acetonitrile over the amount of water that was used. For example, we used a little less than four volumes of acetonitrile. The resulting heterogeneous mixture is then allowed to cool. Before isolating the fluvastatin sodium Form XLI that precipitates. The recovery can be improved by adding an addition portion of acetonitrile after cooling.

Form XLI can then be separated from the water and acetonitrile by conventional means such as filtering, decanting, centrifuging and the like. Preferably, the liquids are separated by vacuum filtration under an inert gas like nitrogen and washed with acetonitrile. A suitable condition for drying the separated product is 50EC under vacuum.

Fluvastatin Sodium Crystal Form XLII

Fluvastatin sodium Form XLII produces a PXRD diffractogram having characteristic peaks at 3.4, 9.7, 11.0, 18.9±0.2 degrees two-theta and other peaks at 5.7, 14.8, 16.1, 17.0, 22.6±0.2 degrees two-theta (FIG. 62). The water content of this sample measured by Karl Fisher is about 4% by weight. The weight loss by TGA is about 5% by weight. Fluvastatin sodium Form XLII is a monohydrate.

Form XLII can be prepared from a fluvastatin-diol by dissolving fluvastatin-diol in methyl ethyl ketone and then filtering the solution. Sodium hydroxide dissolved in methanol is then added to the solution and the solution is stirred at room temperature to obtain a gelatinous precipitate. The product is recovered by any conventional means such as filtering, decanting, centrifuging and the like. Preferably, the liquids are separated by vacuum filtration under an inert gas like nitrogen. A suitable condition for drying the separated product is 50EC under vacuum.

According to another process for preparing fluvastatin sodium Form XLII, fluvastatin diol is dissolved in methanol at reflux temperature and solid sodium hydroxide is added to the solution. The solution is stirred at room temperature to obtain a precipitate having a paste-like consistency. Ethyl acetate is added dropwise to the stirred solution. Then, the solution is cooled to form a slurry. The product is separated from the solution by any conventional means such as filtering, decanting, centrifuging and the like. Preferably, the liquids are separated by vacuum filtration under an inert gas like nitrogen. A suitable condition for drying the separated product is 50EC under vacuum.

According to yet another process for preparing fluvastatin sodium form XLII, fluvastatin-diol is completely dissolved in dichloromethane and the solution is filtered. An ethanolic or methanolic solution of NaOH is added to the solution. The solution is stirred at room temperature to obtain a precipitate and the product is separated by any conventional means such as filtering, decanting, centrifuging and the like. Preferably, the liquids are separated by vacuum filtration under an inert gas like nitrogen. A suitable condition for drying the separated product is 50EC under vacuum.

Fluvastatin Sodium Crystal Form XLIII

Fluvastatin sodium Form XLIII produces a PXRD diffractogram having characteristic peaks at 4.25, 5.29, 6.59, 8.60±0.2 degrees two-theta and other peaks at 12.75, 14.26±0.2 degrees two-theta (FIG. 63). The water content of this sample measured by Karl Fisher is about 9-11% by weight. The weight loss by TGA is about 12% by weight.

We have discovered two ways of making Form XLIII. It can be made by inducing precipitation from an aqueous solution by dropwise addition of propan-2-ol at elevated temperature. The preferred procedure is similar to that used to prepare Form XLI, except that propan-2-ol is used instead of acetonitrile. We prepared an aqueous solution with a three fold excess of water to fluvastatin sodium (ml g$^{-1}$). After obtaining a homogenous solution, a three-fold excess of propan-2-ol to water (ml ml$^{-1}$) was added to it at elevated temperature. The initial addition of propan-2-ol at elevated temperature causes crystals of Form XLIII to form. However, addition of another portion of propan-2-ol of about the same amount after the mixture has cooled should be done to maximize recovery of Form XLIII.

According to another process for preparing fluvastatin sodium Form XLIII, a lower alkyl ester of fluvastatin is dissolved in a solution containing about one molar equivalent of sodium hydroxide in water. Once a homogeneous solution of fluvastatin sodium is obtained, precipitation of the sodium salt is induced by addition of propan-2-ol. Formation of the salt and the initial addition of propan-2-ol are preferably conducted at elevated temperature, e.g. 70EC. After cooling the solution to ambient temperature, additional portions of propan-2-ol can be added to increase recovery of Form XLIII. There is a tendency for the solution to gel. As described in the examples, the gel can be broken by reheating the mixture and then cooling again.

Form XLIII can then be separated from the water and propan-2-ol in either of the processes just described by conventional means such as filtering, decanting, centrifuging and the like. Preferably, the liquids are separated by vacuum filtration under an inert gas like nitrogen. A suitable condition for drying the separated product is 50EC under vacuum.

Fluvastatin Sodium Crystal Form XLIV

Fluvastatin sodium Form XLIV produces a PXRD diffractogram having characteristic peaks at 3.46, 4.05, 9.19, 10.14, 20.56±0.2 degrees two-theta and other peaks at 6.26, 10.91, 11.12, 11.38, 15.98, 20.02, 22.21, 23.52, 25.45±0.2 degrees two-theta (FIG. 64). The water content of this sample measured by Karl Fisher is about 4-6% by weight. The weight loss by TGA is about 8-10% by weight.

Fluvastatin sodium Form XLIV can be prepared by forming a heterogeneous mixture of amorphous fluvastatin sodium in propan-2-ol. Preferably the two are used in a ratio of about 20 ml g$^{-1}$. The suspension should be heated to accelerate conversion. After cooling, Form XLIV can be separated from the propan-2-ol by conventional means such as filtering, decanting, centrifuging and the like. Preferably, the propan-2-ol is separated by vacuum filtration under an inert gas like nitrogen. A suitable condition for drying the separated product is 50EC under vacuum.

Alternatively Form XLIV can be prepared directly from fluvastatin free acid. According to a preferred embodiment of this method, the free acid is dissolved in acetone and a molar equivalent of ethanolic sodium (preferably prepared by dissolving an equivalent of sodium hydroxide in ethanol) is added to the solution and the resulting mixture is maintained until fluvastatin sodium Form XLIV precipitates. Form XLIV may then be separated from the acetone and ethanol by conventional means and dried. A suitable condition for drying the separated product is 50EC under vacuum.

Fluvastatin Sodium Crystal Form XLV

Fluvastatin sodium Form XLV produces a PXRD pattern (FIG. 65) having characteristic peaks at 3.7, 5.1, 10.7, 17.8 and 20.3±0.2 degrees two-theta, and other peaks at 6.2, 14.5, 21.6, 22.6 and 25.2±0.2 degrees two-theta.

Form XLV can be prepared by suspending amorphous fluvastatin sodium in propan-2-ol at room temperature for a period of time sufficient to effect the conversion to Form XLV, which typically requires about 25 h. Form XLV can then be separated from propan-2-ol by conventional means such as filtering, decanting, centrifuging and the like. Preferably, the liquids are separated by vacuum filtration under an inert gas like nitrogen. After optionally washing with for example propan-2-ol, the crystals can be dried. A suitable condition for drying the separated product is 50EC under vacuum.

Fluvastatin Sodium Crystal Form XLVI

Fluvastatin sodium Form XLVI produces a PXRD pattern (FIG. 66) having characteristic peaks at 3.3, 3.5, 10.2, 11.2 and 21.1±0.2 degrees two-theta, and other peaks at 9.7, 12.1, 17.2 and 19.0±0.2 degrees two-theta.

Form XLVI can be prepared directly from a lower alkyl ester of fluvastatin such as fluvastatin methyl ester. The ester is dissolved in a solution of about one molar equivalent of sodium in ethanol. The sodium can be conveniently provided by dissolving the appropriate quantity of sodium hydroxide pellets in water, while exercising caution since the dissolution in water is highly exothermic. The solution is heated for a sufficient period of time to hydrolyze the ester, typically several hours. Then, a large excess (e.g. 10×v/v) of acetonitrile is added to the solution to induce precipitation of Form XLVI. The resulting slurry is then cooled to ambient temperature and Form XLVI is separated from the ethanol and acetonitrile by conventional means such as filtering, decanting, centrifuging and the like. Preferably, the liquids are separated by vacuum filtration under an inert gas like nitrogen. A suitable condition for drying the separated product is 50EC under vacuum.

Fluvastatin Sodium Crystal Form XLVII

Fluvastatin sodium Form XLVII produces a PXRD (FIG. 67) pattern having characteristic peaks at 3.3, 10.2 and 18.0±0.2 degrees two-theta, and other peaks at 8.3, 10.8, 13.6, 20.7 and 21.3±0.2 degrees two-theta.

Fluvastatin sodium Form XLVII can be prepared by exposing fluvastatin sodium Form XVIII to water vapor. Preferably, Form XVIII is maintained under an atmosphere of 80% relative humidity at ambient temperature. Substantially complete conversion is achieved over a period of weeks, typically about three and a half weeks.

Fluvastatin Sodium Crystal Form XLVIII

Fluvastatin sodium Form XLVIII produces a PXRD pattern having characteristic peaks at 4.5, 6.7, 7.0, 10.9, 19.1, 21.7±0.2 degrees two-theta, and other peaks at 8.9, 12.9, 13.1, 13.5, 15.2, 16.8, 17.6, 18.3, 19.7, 20.6±0.2 degrees two-theta. The water content of this sample measured by Karl Fisher is about 6-8% by weight. The weight loss by TGA is about 8% by weight. Fluvastatin sodium Form XLII is a dihydrate.

Fluvastatin sodium Form XLVIII can be made by dissolving a lower alkyl ester of fluvastatin in a solution containing about one molar equivalent of sodium hydroxide in methanol. Once a homogeneous solution of fluvastatin sodium is obtained, precipitation of the sodium salt is induced by addition of acetonitrile. Formation of the salt and the addition of acetonitrile are preferably conducted at elevated temperature. After cooling and being allowed to stand for a sufficient time for crystallization to go substantially to completion, Form XLIII can then be separated from the methanol and acetonitrile by conventional means such as filtering, decanting, centrifuging and the like. Preferably, the liquids are separated by vacuum filtration under an inert gas like nitrogen. A suitable condition for drying the separated product is 50EC under vacuum.

Fluvatastin sodium Form XLVIII can also be prepared from fluvastatin sodium Form B. Fluvastatin sodium Form B is slurried in methanol at elevated temperature for a period of time sufficient to effect the conversion to Form XLVIII. The slurry is then cooled to ambient temperature and Form XLVIII is separated by conventional means known to one of skill in the art such as filtering, decanting, centrifuging, and the like. Preferably, the liquids are separated by vacuum filtration under an inert gas like nitrogen. A suitable condition for drying the separated product is 50EC under vacuum.

In another process for preparing fluvastatin sodium Form XLVIII, fluvastatin sodium Form B is dissolved in methanol at room temperature and the solution is heated to reflux temperature to obtain a precipitate. The methanol stays in solution for a short amount of time. The resulting slurry is cooled and stirred at room temperature and Form XLVIII is separated by conventional means known to one of skill in the art such as filtering, decanting, centrifuging, and the like. Preferably, the liquids are separated by vacuum filtration under an inert gas like nitrogen. A suitable condition for drying the separated product is 50EC under vacuum.

In another process for preparing fluvastatin sodium Form XLVIII, fluvastatin diol is completely dissolved in methanol at reflux temperature and the solution is filtered to obtain a clear solution and heated to reflux again. Solid NaOH is added to the solution at reflux temperature to obtain a precipitate. The resulting slurry is cooled to room temperature to obtain a mixture having a paste-like consistency. Acetone is added dropwise to the mixture at room temperature. The solution is stirred at room temperature to obtain Form XLVIII as a precipitate. Form XLVIII is separated by conventional means known to one of skill in the art such as filtering, decanting, centrifuging, and the like. Preferably, the liquids are separated by vacuum filtration under an inert gas like nitrogen. A suitable condition for drying the separated product is 50EC under vacuum.

Fluvastatin Sodium Crystal Form XLIX

Fluvastatin sodium Form XLIX produces a PXRD pattern (FIG. 69) having characteristic peaks at 3.5, 5.0, 12.1, 13.5 and 20.2±0.2 degrees two-theta and other peaks at 6.3, 10.1 and 17.1±0.2 degrees two-theta.

Form XLIX can be prepared from fluvastatin sodium Form B. According to a preferred process, about 1:8 (w/v) of Form B is dissolved in methanol at ambient temperature. After dissolution, the solution is heated to reflux and then MTBE is slowly added (dropwise on a bench scale) to the refluxing solution. The addition causes fluvastatin Form XLIX to precipitate from solution. After precipitation, the suspension can be cooled to ambient temperature and Form XLIX can be separated from the methanol and MTBE by conventional means known to one of skill in the art such as filtering, decanting, centrifuging, and the like. Preferably, the liquids are separated by vacuum filtration under an inert gas like nitrogen. After optional washing, for example with MTBE, the crystals can be dried. A suitable condition for drying the separated product is 50EC under vacuum.

Fluvastatin Sodium Crystal Form L

Fluvastatin sodium Form L (50) produces a PXRD pattern (FIG. 70) having characteristic peaks at 6.48, 6.92, 9.72, 12.64, 21.49±0.2 degrees two-theta and other peaks at 4.53, 12.06, 13.50, 14.79, 15.79, 16.32, 19.15, 23.19±0.2 degrees two-theta. The water content of this sample measured by Karl Fisher is about 5-6% by weight. The weight loss by TGA is about 7% by weight. Fluvastatin sodium Form L is a sesquihydrate.

Fluvastatin sodium Form L can be prepared by precipitation from a mixture of methanol and ethyl acetate. The fluvastatin sodium starting material, in any crystalline form or amorphous, should first be dissolved in the methanol. One gram of fluvastatin sodium will dissolve in 7 ml of methanol or more at room temperature. The starting material can be dissolved either at ambient or elevated temperature, e.g. the boiling point of methanol. Once dissolved, precipitation of Form L is induced by dropwise addition of ethyl acetate to the solution at elevated temperature. The amount of ethyl acetate used is preferably about three times the volume of methanol. Once precipitation has started, the mixture can then be allowed to cool and after an optional period of time for further crystallization at ambient temperature, Form L can be separated from the methanol and ethyl acetate by conventional means such as such as filtering, decanting, centrifuging and the like. Preferably, the liquids are separated by vacuum filtration under an inert gas like nitrogen. A suitable condition for drying the separated product is 50EC under vacuum.

Fluvastatin Sodium Crystal Form LI

Fluvastatin sodium Form XLIX produces a PXRD pattern (FIG. 71) having characteristic peaks at 6.2, 10.8, 14.5 and 20.7±0.2 degrees two-theta and other peaks at 8.9, 11.5 and 23.1±0.2 degrees two-theta.

Form LI can be prepared from fluvastatin sodium Form B by a procedure analogous to the one used to prepare Form XLIX, but substituting acetonitrile for MTBE.

Fluvastatin Sodium Crystal Form LIII

Fluvastatin sodium Form XLIX produces a PXRD pattern (FIG. 72) having characteristic peaks at 5.6, 6.3, 10.5, 20.9±0.2 degrees two-theta and other peaks at 14.3, 15.1, 15.6 and 17.1±0.2 degrees two-theta.

Form LIII can be prepared from fluvastatin sodium Form B by a procedure analogous to the one used to prepare Form XLIX, but substituting ethyl acetate for MTBE.

Fluvastatin Sodium Crystal Form LIII

Fluvastatin sodium Form LIV produces a PXRD pattern (FIG. 73) having characteristic peaks at 3.4, 10.4, 18.2, 19.6, 21.3±0.2 degrees two-theta and other peaks at 6.9, 12.1, 13.8, 17.7, 19.0±0.2 degrees two-theta. The water content of a sample of Form LIV measured by Karl Fisher was about 11% by weight. The weight loss by TGA is about 11% by weight. Fluvastatin sodium Form LIV is a trihydrate.

Fluvastatin sodium Form LIV can be prepared fromby mixing fluvastatin in an aqueous solution of sodium hydroxide to obtain a suspension having a mud-like consistency. The suspension is stirred at room temperature and the product can be separated by conventional means such as filtering, decanting, centrifuging and the like. Preferably, the liquids are separated by vacuum filtration under an inert gas like nitrogen. A suitable condition for drying the separated product is 50EC under vacuum.

Fluvastatin Sodium Crystal Form LV

Fluvastatin sodium Form LV produces a PXRD pattern having characteristic peaks at 3.7, 5.0, 5.9, 12.2±0.2 degrees two-theta and other peaks at 5.6, 8.7, 10.1, 11.2±0.2 degrees two-theta. The water content of this sample measured by Karl Fisher is about 7% by weight. The weight loss by TGA is about 7% by weight. Fluvastatin sodium Form LV is a dihydrate.

Fluvastatin sodium Form LV can be prepared by precipitation from a mixture of methanol and acetonitrile. Preferred mixtures contain from about 10% to about 12%, more preferably about 12.5% by volume (methanol volume/acetonitrile volume×100).

A preferred procedure starts with a lower alkyl ester of fluvastatin. The fluvastatin ester is added to acetonitrile and the mixture is heated until the ester dissolves. The solution is then cooled and a solution of sodium hydroxide in methanol is added to it. Form LV can be separated from the methanol and acetonitrile by conventional means such as filtering, decanting, centrifuging and the like. Preferably, the liquids are separated by vacuum filtration under an inert gas like nitrogen. A suitable condition for drying the separated product is 50EC under vacuum.

Fluvastatin Sodium Crystal Form LVI

Fluvastatin sodium Form LVI produces a PXRD pattern (FIG. 75) having characteristic peaks at 3.4, 22.1 and 27.4±0.2 degrees two-theta and other peaks at 6.8, 10.2, 13.6, 18.5 and 20.0±0.2 degrees two-theta.

Form LVI can be prepared directly from a lower alkyl ester derivative of fluvastatin having a ketal protecting group on the ∃ and * hydroxyl groups, such as an acetonide protected fluvastatin methyl ester. The starting material is taken up in THF and the acetonide is hydrolyzed with HCl, preferably 1.5% (aq.) HCl. The time required will be dependent upon the concentration of the starting material and acid concentration used, but can be readily determined by reaction-monitoring techniques such as thin layer chromatography. Thereafter, a sufficient excess of NaOH is added to neutralize the HCl. The THF is then evaporated and the residue is taken up in acetone. About a molar equivalent of sodium hydroxide is added to the solution. Over time, fluvastatin sodium precipitates as Form LVI. Form LVI can be separated by conventional means such as filtering, decanting, centrifuging and the like. Preferably, the acetone is separated by vacuum filtration under an inert gas like nitrogen. After optional washing, for example with acetone, the crystals can be dried. A suitable condition for drying is 50EC under vacuum.

Fluvastatin Sodium Crystal Form LVII

Fluvastatin sodium Form LVII produces a PXRD pattern (FIG. 76) having characteristic peaks at 3.7, 5.0, 5.5, 10.1, 12.1±0.2 degrees two-theta and other peaks at 8.6, 11.1, 14.9, 21.7, 22.8±0.2 degrees two-theta. The water content of this sample measured by Karl Fisher is about 2% by weight. The weight loss by TGA is about 2% by weight. Fluvastatin sodium Form LVII is a hemihydrate.

Fluvastatin sodium Form LVII can be prepared by forming a heterogeneous mixture of fluvastatin sodium Form VII and ethanol and maintaining the heterogeneous mixture until substantially all of the Form VII is converted into Form LVII. Preferably, the ethanol is anhydrous ("absolute") and the suspension is maintained under dry conditions. Form LVII can be separated from the ethanol by conventional means such as filtering, decanting, centrifuging and the like. Preferably, the ethanol separated by vacuum filtration under an inert gas like nitrogen. A suitable condition for drying the separated product is 50EC under vacuum.

Fluvastatin Sodium Crystal Form LVIII

Fluvastatin sodium Form LVIII produces a PXRD pattern (FIG. 77) having characteristic peaks at 3.4, 3.8, 5.4, 5.7, 10.3±0.2 degrees two-theta and other peaks at 4.7, 7.2, 8.4, 11.5, 17.5, 20.4, 21.4, 23.1±0.2 degrees two-theta. The water content of this sample measured by Karl Fisher is about 4-5% by weight. The weight loss by TGA is about 6-7% by weight.

Fluvastatin sodium Form LVIII can be prepared by forming a heterogeneous mixture of fluvastatin sodium and propan-2-ol and maintaining the heterogeneous mixture for a period of time sufficient to substantially convert the fluvastatin sodium into Form LVIII. A preferred starting material is fluvastatin sodium Form B. The conversion can be accelerated by heating the suspension, preferably to reflux temperature of the diluent. Form LVIII can be separated from the propan-2-ol by conventional means such as filtering, decanting, centrifuging and the like. Preferably, the liquids are separated by vacuum filtration under an inert gas like nitrogen. A suitable condition for drying the separated product is 50EC under vacuum.

Fluvastatin Sodium Crystal Form LX

Figure 78:
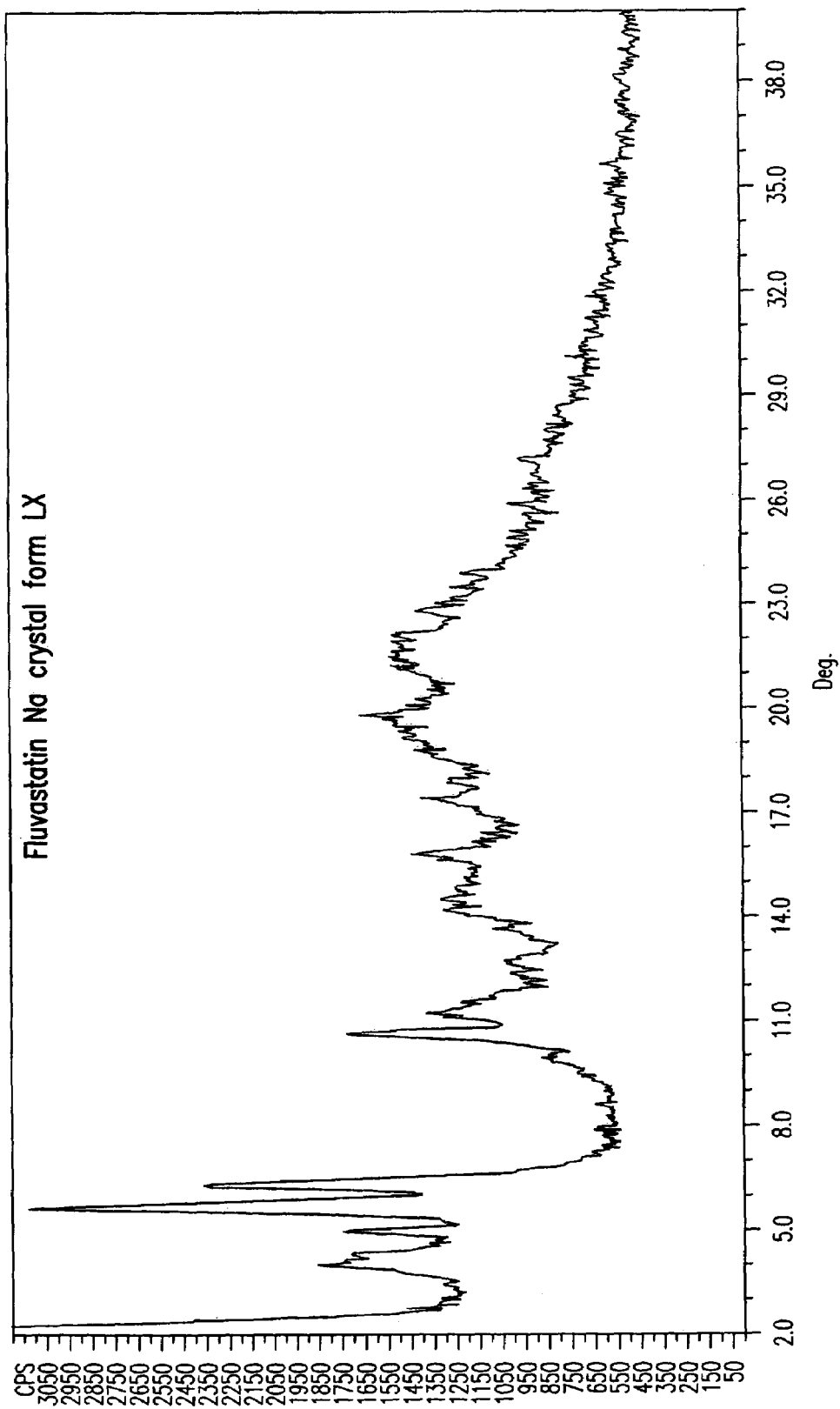
FIG. 78 depicts a powder X-ray diffractogram of fluvastatin sodium Form LX.

Fluvastatin sodium Form LX produces a PXRD pattern (FIG. 78) having characteristic peaks at 5.6, 6.3 and 10.5±0.2 degrees two-theta and other peaks at 4.1, 5.0, 11.0, 15.7, 17.2 and 19.6±0.2 degrees two-theta. Form LX may be prepared by adding ethyl acetate to solution of fluvastatin sodium in methanol. In the exemplified embodiment, the solution is heated, followed by portion-wise addition of ethyl acetate. Form LX then precipitates, and is stirred and recovered by conventional techniques.

Fluvastatin Sodium Crystal Form LXIV

Figure 79:
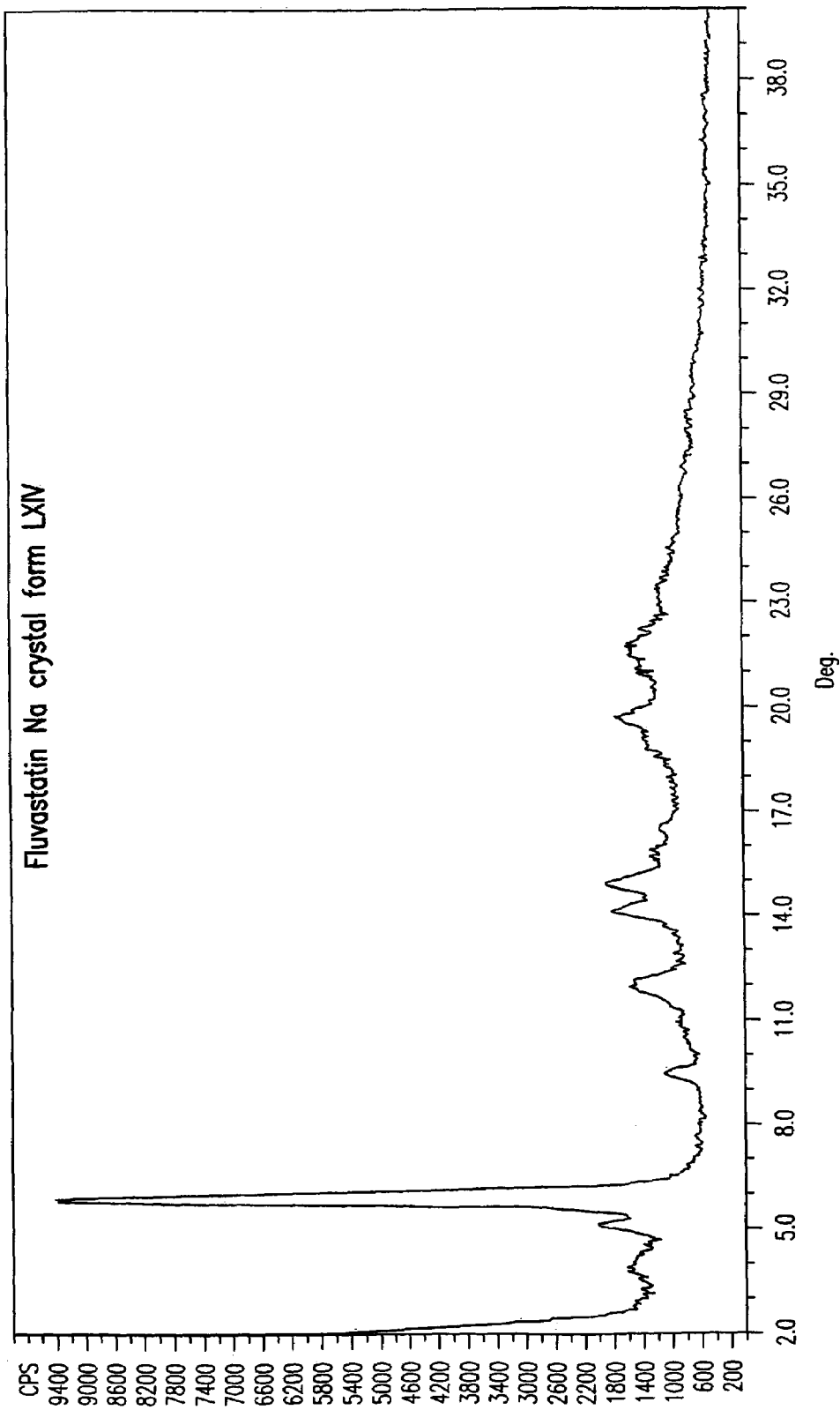
FIG. 79 depicts a powder X-ray diffractogram of fluvastatin sodium Form LXIV.

Fluvastatin sodium Form LXIV produces a PXRD pattern (FIG. 79) having characteristic peaks at 5.8, 13.9 and 14.7±0.2 degrees two-theta and other peaks at 5.1, 9.3, 11.7 and 19.4±0.2 degrees two-theta.

Form LXIV can be prepared directly from a lower alkyl ester of fluvastatin such as fluvastatin methyl ester. Two different processes have been discovered. According to a preferred embodiment of one process, about 0.1:1 (w/v) of the starting material is dissolved in methanol while heating the mixture to reflux. About one equivalent of sodium hydroxide is then added to the refluxing solution. During hydrolysis, fluvastatin sodium begins to precipitate. After the hydrolysis is complete, which can be determined by thin layer chromatography, the slurry is cooled to ambient temperature. Cooling causes the precipitate to redissolve. Acetone is then added to the solution to reprecipitate fluvastatin sodium in Form LXIV. Thereafter Form LXIV can be separated from the methanol and acetone by conventional means such as filtering, decanting, centrifuging and the like. Preferably, the liquids are separated by vacuum filtration under an inert gas like nitrogen. A suitable condition for drying the separated product is 50EC under vacuum.

According to an alternative process for making Form LXIV, about 1:15 (w/v) of the starting lower alkyl ester of fluvastatin is dissolved in acetone. Then an excess of sodium hydroxide dissolved in methanol is added to the solution. Over time, fluvastatin sodium precipitates from the solution as Form LXIV. Form LXIV can be separated from the acetone and methanol by conventional techniques such as filtering, decanting, centrifuging and the like, preferably filtering under an inert atmosphere like nitrogen. After optional washing, for example with acetone, the separated Form LXIV may be dried. A suitable drying condition is 50EC under vacuum.

Fluvastatin Sodium Crystal Form LXV

Figure 80:
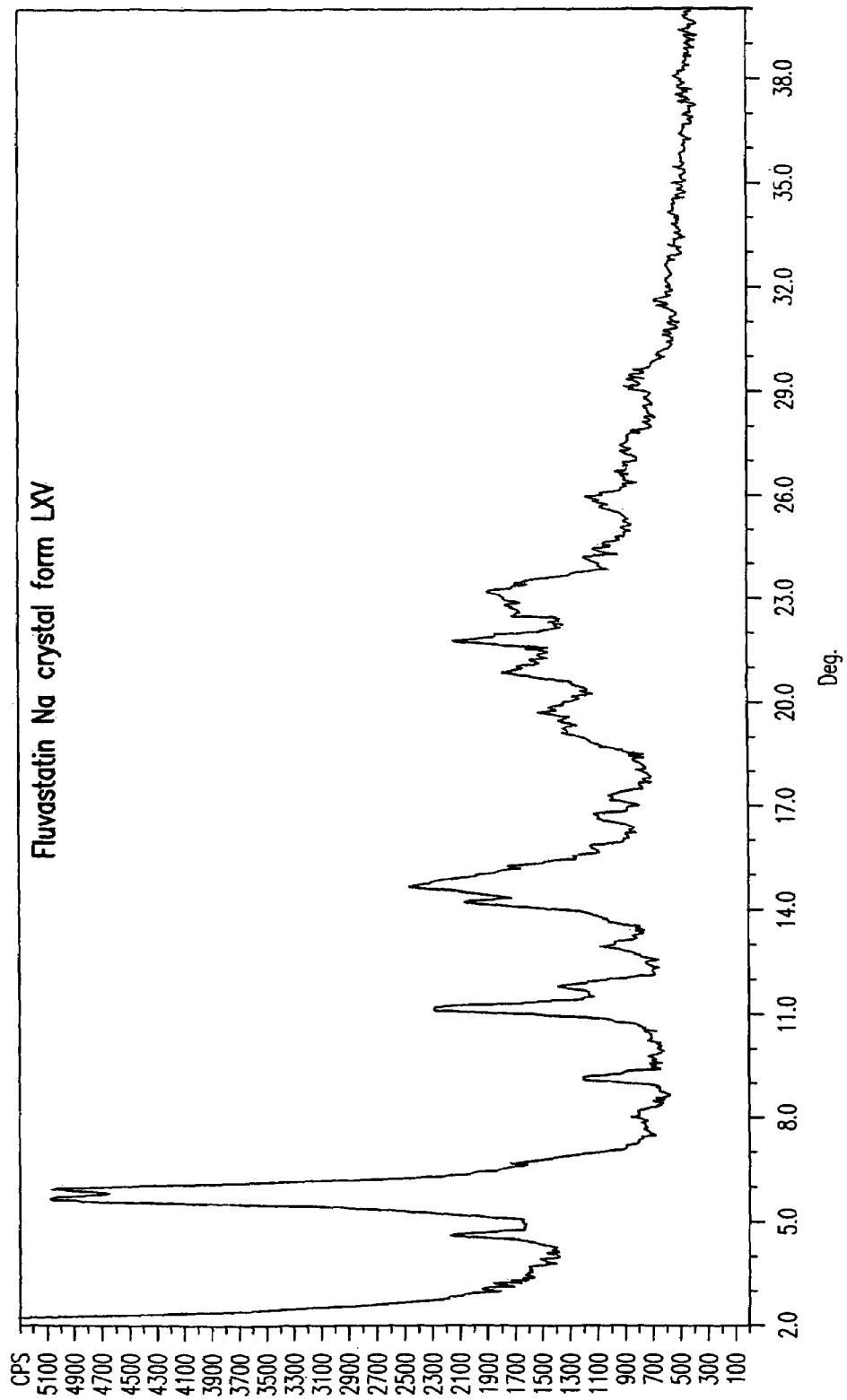
FIG. 80 depicts a powder X-ray diffractogram of fluvastatin sodium Form LXV.

Fluvastatin sodium Form LXV produces a PXRD pattern (FIG. 80) having characteristic peaks at 5.8, 13.9 and 14.7±0.2 degrees two-theta and other peaks at 5.1, 9.3, 11.7 and 19.4±0.2 degrees two-theta.

Form LXV can be prepared directly from a lower alkyl ester of fluvastatin such as fluvastatin methyl ester. According to a preferred process, about 1:7 (w/v) of the starting material is dissolved in methanol containing about one equivalent of sodium at ambient temperature. After the mixture becomes clear, about six volumes of propan-2-ol is added to induce precipitation of fluvastatin sodium in Form LXV. Thereafter Form LXV can be separated from the methanol and propan-2-ol by conventional means such as filtering, decanting, centrifuging and the like. Preferably, the liquids are separated by vacuum filtration under an inert gas like nitrogen. After optional washing, for example with acetone, the crystals can be dried. A suitable condition for drying the separated product is 50EC under vacuum. In the process, five volumes of acetone can be substituted for the six volumes of propan-2-ol.

Fluvastatin Sodium Crystal Form LXVI

Figure 81:
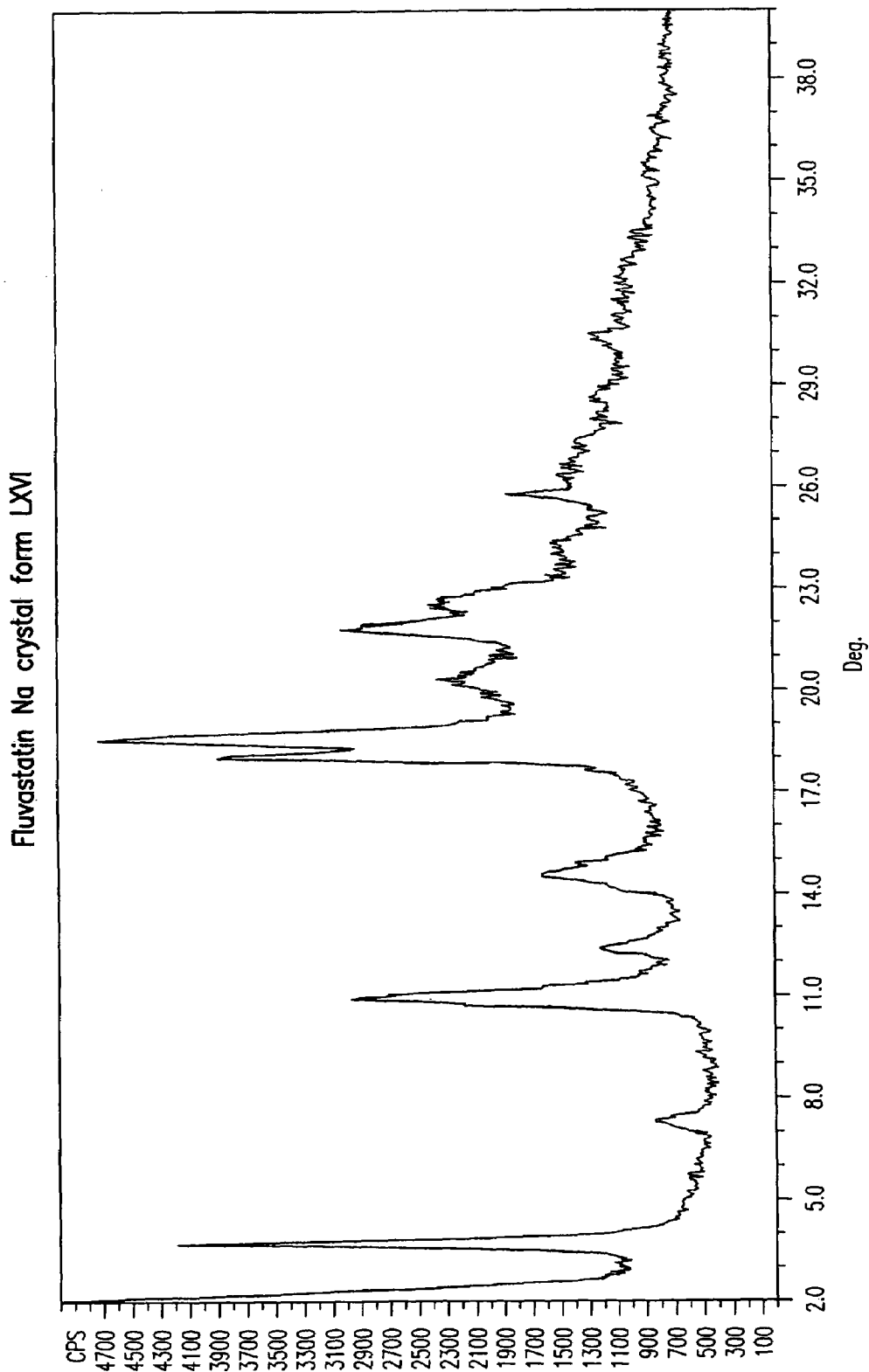
FIG. 81 depicts a powder X-ray diffractogram of fluvastatin sodium Form LXVI.

Fluvastatin sodium Form LXVI produces a PXRD pattern (FIG. 81) having characteristic peaks at 3.6, 10.8, 17.8, 18.3 and 21.6±0.2 degrees two-theta and other peaks at 7.2, 12.2, 14.4 and 25.5±0.2 degrees two-theta.

We have been able to produce Form LXVI from several other crystal forms of fluvastatin sodium by similar processes. In general terms either fluvastatin sodium Form VI, B or XV is dissolved in water either at ambient temperature or elevated temperature to obtain a clear solution. The solution is refluxed, preferably for one to two hours and then is cooled or allowed to cool to ambient temperature. After a period of time, Form LXVI precipitates from the solution. Form LXVI can be separated from the water by conventional means such as by filtering, decanting, centrifuging and the like. Preferably, the water is separated by vacuum filtration under an inert gas like nitrogen. After optional washing, for example with water, the crystals can be dried. A suitable condition for drying the separated product is 50EC under vacuum.

Fluvastatin Sodium Crystal Form LXVII

Figure 82:
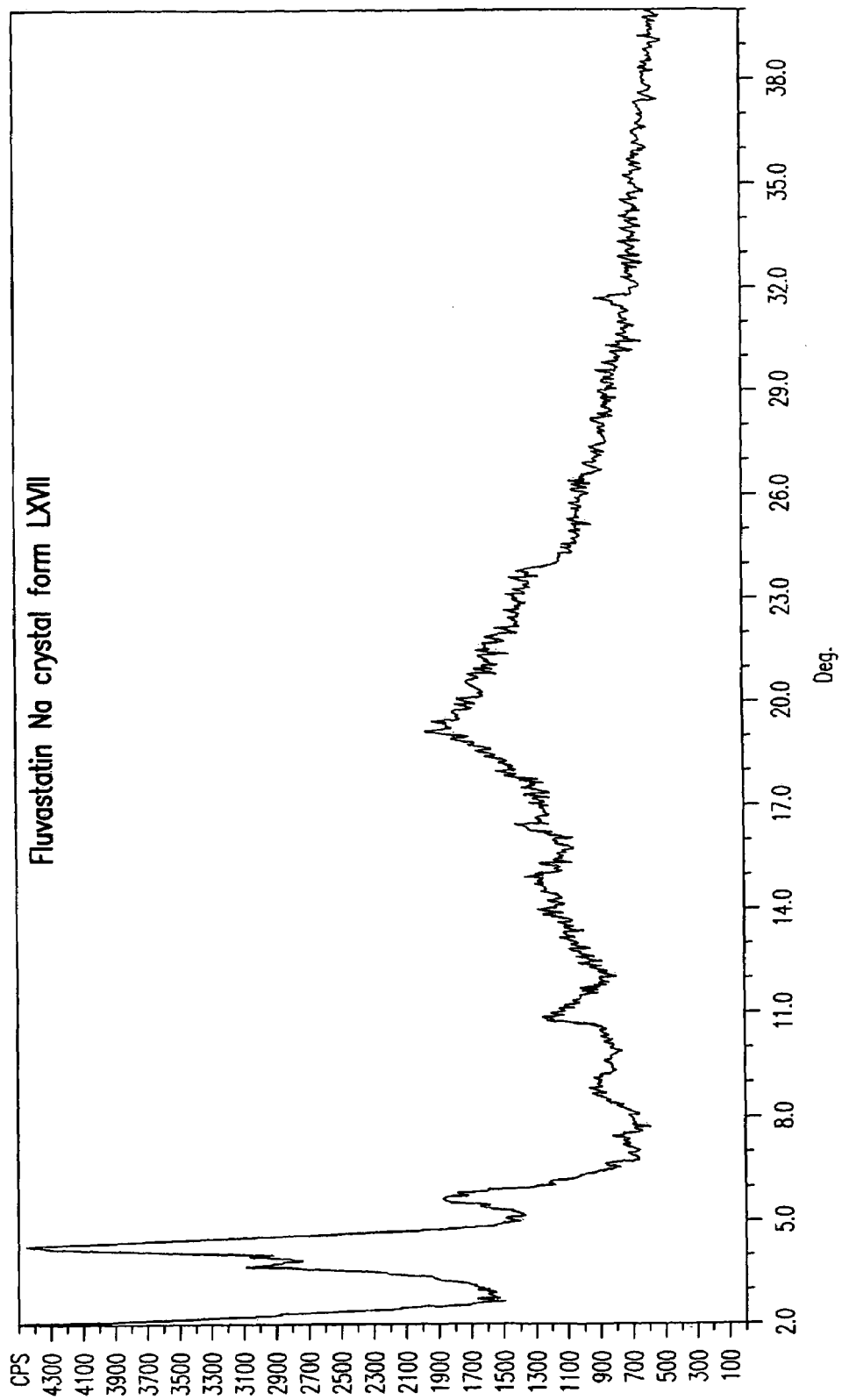
FIG. 82 depicts a powder X-ray diffractogram of fluvastatin sodium Form LXVII.

Fluvastatin sodium Form LXVII produces a PXRD pattern (FIG. 82) having characteristic peaks at 3.7 and 4.4±0.2 degrees two-theta and other peaks at 5.6 and 10.8±0.2 degrees two-theta.

Form LXVII can be prepared directly from a lower alkyl ester of fluvastatin such as fluvastatin methyl ester. According to a preferred process, 1:15 (w/v) of the starting material is dissolved in acetone. An excess of sodium hydroxide in methanol is added and the mixture is maintained at ambient temperature until hydrolysis of the ester is complete. Thereafter, fluvastatin sodium precipitates in Form LXVII. Thereafter Form LXVII can be separated from the methanol and acetone by conventional means such as by filtering, decanting, centrifuging and the like. Preferably, the methanol and acetone is separated by vacuum filtration under an inert gas like nitrogen. After optional washing, for example with acetone, the crystals can be dried. A suitable condition for drying the separated product is 50EC under vacuum.

Fluvastatin Sodium Crystal Form LXVIII

Figure 83:
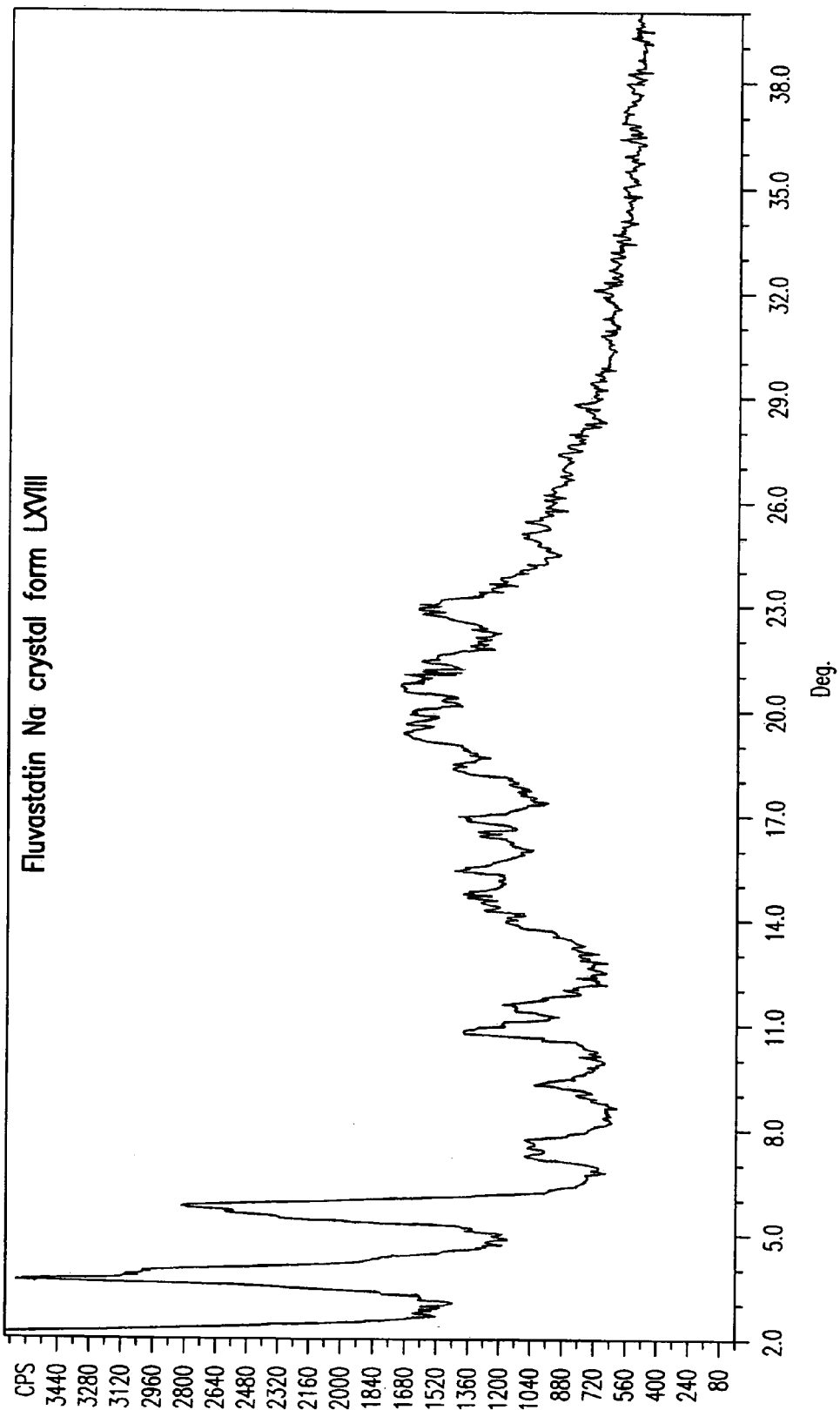
FIG. 83 depicts a powder X-ray diffractogram of fluvastatin sodium Form LXVIII.

Fluvastatin sodium Form LXVIII produces a PXRD pattern (FIG. 83) having characteristic peaks at 3.6, 5.9, 10.8 and 11.6±0.2 degrees two-theta and other peaks at 9.3, 15.4, 17.0, 18.4 and 23.0±0.2 degrees two-theta.

Form LXVIII can be prepared directly from a lower alkyl ester of fluvastatin such as fluvastatin methyl ester. According to a preferred process, 1:15 (w/v) of the starting material is dissolved in acetone. An excess of sodium hydroxide in methanol as added to the solution. The solution is maintained at ambient temperature for a period of time sufficient to hydrolyze the ester, which can be determined by thin layer chromatography. Thereafter, Form LXVIII crystallizes either spontaneously or with cooling and can be separated from the methanol and acetone by conventional means such as by filtering, decanting, centrifuging and the like. Preferably, the methanol and acetone are separated by vacuum filtration under an inert gas like nitrogen. After optional washing, for example with acetone, the crystals can be dried. A suitable condition for drying the separated product is 50EC under vacuum.

Fluvastatin Sodium Crystal Form LXIX

Fluvastatin sodium Form LXIX produces a PXRD pattern (FIG. 84) having characteristic peaks at 3.5, 5.7, 10.8, 18.2 and 21.6±0.2 degrees two-theta and other peaks at 12.4, 14.7, 20.4, 22.4 and 25.4±0.2 degrees two-theta.

Form LXIX can be prepared by slurrying fluvastatin sodium Form VI in propan-2-ol at reflux temperature for a period of time sufficient to effect the conversion. After cooling the solution, Form LXIX can be separated from the propan-2-ol by conventional means such as filtering, decanting, centrifuging and the like. Preferably, the propan-2-ol is separated by vacuum filtration under an inert gas like nitrogen. After optional washing, for example with propan-2-ol, the crystals can be dried. A suitable condition for drying the separated product is 50EC under vacuum.

Fluvastatin Sodium Crystal Form LXX

Fluvastatin sodium Form LXX produces a PXRD pattern (FIG. 85) having characteristic peaks at 3.0, 3.4, 5.9, and 13.8±0.2 degrees two-theta and other peaks at 8.2, 8.9, 18.6, 21.1 and 22.4±0.2 degrees two-theta.

Form LXX can be prepared from fluvastatin sodium such as Form LXVII by dissolving in water at reflux temperature and adding a ten fold excess of acetone to induce precipitation of fluvastatin sodium in Form LXX. After cooling the resulting mixture to ambient temperature, Form LXX can be separated from the water and acetone by conventional means such as by filtering, decanting, centrifuging and the like. Preferably, the water and acetone are separated by vacuum filtration under an inert gas like nitrogen. After optional washing, for example with acetone, the crystals can be dried. A suitable condition for drying the separated product is 50EC under vacuum.

Fluvastatin Sodium Crystal Form LXXI

Fluvastatin sodium Form LXXI produces a PXRD pattern (FIG. 86) having characteristic peaks at 3.9, 7.8, 11.6 and 15.5±0.2 degrees two-theta and other peaks at 9.2, 13.3, 19.0 and 23.2±0.2 degrees two-theta.

Form LXXI can be prepared by refluxing a 1:1 (w/v) mixture of fluvastatin sodium Form LXVII and water and then adding a large excess of acetone and maintaining the mixture for a period of time sufficient to effect the conversion to Form LXXI. After cooling the resulting mixture to ambient temperature, Form LXXI can be separated from the water and acetone by conventional means such as by filtering, decanting, centrifuging and the like. Preferably, the water and acetone are separated by vacuum filtration under an inert gas like nitrogen. After optional washing, for example with acetone, the crystals can be dried. A suitable condition for drying the separated product is 50EC under vacuum.

Fluvastatin Sodium Crystal Form LXXII

Fluvastatin sodium Form LXXII produces a PXRD pattern (FIG. 87) having characteristic peaks at 3.7, 5.7 and 12.1±0.2 degrees two-theta and other peaks at 5.0, 10.8, 16.8 and 20.1±0.2 degrees two-theta.

Form LXXII can be prepared from fluvastatin sodium Form VI. According to one preferred procedure, the starting material is suspended in an about 40:1 mixture of acetone and water and heated to reflux for a period of time sufficient to effect the conversion to Form LXXII. After the mixture has cooled to ambient temperature, Form LXXII can be separated from the water and acetone by conventional means such as by filtering, decanting, centrifuging and the like. Preferably, the water and acetone are separated by vacuum filtration under an inert gas like nitrogen. After optional washing, for example with acetone, the crystals can be dried. A suitable condition for drying the separated product is 50EC under vacuum.

According to another preferred procedure, Form VI is suspended in acetonitrile and heated to reflux for a period of time sufficient to effect the conversion. After the mixture has cooled to ambient temperature, Form LXXII can be separated from the acetonitrile by conventional means such as filtering, decanting, centrifuging and the like. Preferably, the acetonitrile is separated by vacuum filtration under an inert gas like nitrogen. After optional washing, for example with acetonitrile, the crystals can be dried. A suitable condition for drying the separated product is 50EC under vacuum.

Fluvastatin Sodium Crystal Form LXXIV

Fluvastatin sodium Form LXXIV produces a PXRD pattern (FIG. 89) having characteristic peaks at 4.0, 12.8, 19.0, 19.9 and 25.8±0.2 degrees two-theta and other peaks at 5.4, 11.8, 13.4, 18.0 and 24.6±0.2 degrees two-theta.

Form LXXIV can be prepared from fluvastatin sodium Form B by suspending Form B in a refluxing about 10:1 mixture of propan-2-ol and water for a sufficient period to effect the conversion. After cooling the solution, Form LXXIV can be separated from the propan-2-ol and water by conventional means such as filtering, decanting, centrifuging and the like. Preferably, the propan-2-ol and water are separated by vacuum filtration under an inert gas like nitrogen. After optional washing, for example with propan-2-ol, the crystals can be dried. A suitable condition for drying the separated product is 50EC under vacuum.

Fluvastatin Sodium Crystal Form LXXV

Fluvastatin sodium Form LXXV produces a PXRD pattern (FIG. 90) having characteristic peaks at 4.4, 6.6, 10.8, 14.3 and 22.2±0.2 degrees two-theta and other peaks at 7.8, 15.0, 19.8, 20.4 and 21.4±0.2 degrees two-theta.

Form LXXV can be prepared from fluvastatin sodium Form XXX by refluxing Form XXX in methanol for a period of time sufficient to effect the conversion. After cooling the solution, Form LXXV can be separated from the methanol by conventional means such as filtering, decanting, centrifuging and the like. Preferably, the methanol is separated by vacuum filtration under an inert gas like nitrogen. After optional washing, for example with methanol, the crystals can be dried. A suitable condition for drying the separated product is 50EC under vacuum.

Fluvastatin Sodium Crystal Form LXXVI

Fluvastatin sodium Form LXXVI produces a PXRD pattern (FIG. 91) having characteristic peaks at 3.5, 7.0, 10.5 and 13.0±0.2 degrees two-theta.

LXXVI can be prepared directly from a lower alkyl ester of fluvastatin such as fluvastatin methyl ester. According to a preferred process, the starting material is dissolved in an about 5:3 ethanol:water mixture containing about one equivalent of sodium hydroxide. After the hydrolysis is complete, the mixture is partially concentrated and additional water is added. The mixture is then extracted with a water immiscible solvent such as ethyl acetate. The aqueous phase is then distilled off leaving a residue that is fluvastatin sodium Form LXXVI.

Fluvastatin Sodium Crystal Form LXXVII

Fluvastatin sodium Form LXXVII produces a PXRD pattern (FIG. 92) having characteristic peaks at 3.6, 8.8, 11.0, 12.8 and 17.8±0.2 degrees two-theta and other peaks at 7.3, 20.2 and 31.0±0.2 degrees two-theta.

Form LXXVII can be prepared directly from a lower alkyl ester of fluvastatin such as fluvastatin methyl ester. According to a preferred process, 1:30 (w/v) of the starting material is dissolved in ethyl acetate. An excess of sodium hydroxide in water is added to the solution. The solution is maintained at ambient temperature for a period of time sufficient to hydrolyze the ester, which can be determined by thin layer chromatography. Thereafter, Form LXXVII crystallizes and can be separated from the ethyl acetate and water by conventional means such as filtering, decanting, centrifuging and the like. Preferably, the ethyl acetate and water are separated by vacuum filtration under an inert gas like nitrogen. After optional washing, for example with ethyl acetate, the crystals can be dried. A suitable condition for drying the separated product is 50EC under vacuum.

Fluvastatin Sodium Crystal Form LXXVIII

Fluvastatin sodium Form LXXVIII produces a PXRD pattern (FIG. 93) having characteristic peaks at 8.8, 19.1, 27.2, 29.6 and 30.9±0.2 degrees two-theta and other peaks at 3.4, 11.3, 17.7, 22.5 and 32.2±0.2 degrees two-theta.

Form LXXVIII can be prepared directly from a lower alkyl ester of fluvastatin such as fluvastatin methyl ester. The starting material is hydrolyzed with sodium hydroxide in water. Then, the reaction mixture is extracted with ethyl acetate. The aqueous phase is concentrated. The residue is then contacted with either propan-2-ol or acetonitrile for one or two days. After conventional separation of the propan-2-ol or acetonitrile, the fluvastatin sodium is in Form LXXVIII. After optional washing, for example with acetonitrile, the crystals can be dried. A suitable condition for drying the separated product is 50EC under vacuum.

Summary of Distinctive Physical Properties of Fluvastatin Sodium Crystal Forms
A summary of the water content of Forms IV, IV-1, VI, VII, XI, XI-2, XVI-XVIII, XIX, XIX-1, XX, XXIX, XXX, XXXI, XXXIII, XXXIV, XXXV, XXXVII, XXXVIII, XLI, XLII, XLIII, XLVIII, L, LIV, LV, LIV, LV, LVII, and LVIII is provided in the table below.

| Form | Water Content | Weight Loss | Water Content | Hydration |
|---|---|---|---|---|
| IV | 4% KF | 8.3% TGA | 4 | — |
| IV-1 | 2.1-2.6% KF | 10.5% TGA | 2-3 | — |
| VI | 5.0-5.6% KF | 12% TGA | 5-6% | — |
| VII | 4.1%-4.5% KF | 13-14% TGA + hygroscopicity | 1-9 | — |
| XI | 4-6% KF | 6-8% TGA + hygroscopicity | 1-6 | — |
| XI-2 | 1.9-3.2% KF | 7.7% TGA | 2-3 | — |
| XVI | 3-4% KF | 8.7% TGA | 3-4 | — |
| XVII | | 8.4% TGA | 8 | — |
| XVIII | 4% KF | 4% TGA | 4 | monohydrate |
| XIX | 19-28% KF | 22-26% TGA | 19-28 | Hexahydrate 8-hydrate 9-hydrate |
| XIX-1 | 8% KF | 7% TGA | | Dihydrate |
| XX | 19% KF | 19% TGA | 19 | hexahydrate |
| XXIX | — | — | — | — |
| XXX | 4% KF | 10% TGA | | — |
| XXXI | 16% KF | 16% TGA | | Tetrahydrate |
| XXXIII | 7% KF 9.5% KF | 7% TGA 10.7% TGA | | Dihydrate hemipentahydrate |
| XXXIV | 10% KF | 20.1% TGA | | — |
| XXXV | 15% KF | 31% TGA | | — |
| XXXVII | 9% KF | 9% TGA | | Hemipentahydrate |
| XXXVIII | 6-7% KF | 10-11% TGA | | — |
| XLI | 9% KF | 9% TGA | | monohydrate |
| XLII | 4% KF | 5% TGA | | monohydrate |
| XLIII | 9-11% KF | 12% TGA | | — |
| XLIV | 4-6% KF | 8-10% TGA | | — |
| XLVIII | 6-8% KF | 8% TGA | | Dihydrate |
| L | 5-6% KF | 7% TGA | | Sesquihydrate |
| LIV | 11% KF | 11% TGA | | Trihydrate |

-continued

Summary of Distinctive Physical Properties
of Fluvastatin Sodium Crystal Forms
A summary of the water content of Forms IV, IV-1, VI, VII, XI,
XI-2, XVI-XVIII, XIX, XIX-1, XX, XXIX, XXX, XXXI, XXXIII,
XXXIV, XXXV, XXXVII, XXXVIII, XLI, XLII, XLIII, XLVIII, L,
LIV, LV, LIV, LV, LVII, and LVIII is provided in the table
below.

| Form Form | Water Content | Weight Loss | Water Content | Hydration |
|---|---|---|---|---|
| LV | 7% KF | 7% TGA | | Dihydrate |
| LVII | 2% KF | 2% TGA | | hemihydrate |
| LVIII | 4.6% KF | 6.4% TGA | | — |

In addition to the crystalline polymorphic forms of fluvastatin sodium previously described, we have discovered a number of semi-crystalline solid forms of fluvastatin that can be reproducibly obtained by following certain procedures set forth below.

Fluvastatin Sodium Form XC

Fluvastatin sodium Form XC produces a PXRD pattern (FIG. 97) having characteristic peaks at 3.2 and 9.6±0.2 degrees two-theta and other peaks at 11.8 and 19.8±0.2 degrees two-theta.

Fluvastatin sodium Form XC can be prepared from fluvastatin sodium Form B by dissolving it in ethanol at ambient temperature and then adding cyclohexane to induce precipitation. Afterwards, Form XC can be separated from the ethanol and cyclohexane by conventional means such as by filtering, decanting, centrifuging and the like. Preferably, the liquids are separated by vacuum filtration under an inert gas like nitrogen. A suitable condition for drying the separated product is 50EC under vacuum.

Fluvastatin Sodium Form XCI

Fluvastatin sodium Form XCI produces a PXRD pattern (FIG. 98) having characteristic peaks at 4.7, 5.6 and 13.8±0.2 degrees two-theta and other peaks at 7.3, 9.6, 10.8, 16.4, 17.6, 19.8, 20.8 and 23.1±0.2 degrees two-theta.

Fluvastatin sodium Form XCI can be prepared from fluvastatin sodium Form XV by suspending Form XV in ethyl acetate and maintaining the suspension at elevated temperature for a sufficient period of time to convert Form XV into Form XCI. After cooling the suspension to ambient temperature, Form XCI can be separated from the ethyl acetate by conventional means such as filtering, decanting, centrifuging and the like. Preferably, the ethyl acetate is separated by vacuum filtration under an inert gas like nitrogen. A suitable condition for drying the separated product is 50EC under vacuum.

Fluvastatin Sodium Form XCII

Fluvastatin sodium Form XCII produces a PXRD pattern (FIG. 99) having characteristic peaks at 3.4, 10.1 and 11.8±0.2 degrees two-theta and other peaks at 4.1, 17.8, 20.1, 21.7, 23.4 and 25.3±0.2 degrees two-theta.

Fluvastatin sodium Form XCII can be prepared from fluvastatin sodium Form B by dissolving it in a 10:1 ethanol: methanol at reflux temperature and then adding hexanes to induce precipitation. Afterwards, Form XCII can be separated from the ethanol, methanol and cyclohexane by conventional means such as filtering, decanting, centrifuging and the like. Preferably, the liquids are separated by vacuum filtration under an inert gas like nitrogen. A suitable condition for drying the separated product is 50EC under vacuum.

Fluvastatin Sodium Form XCIII

Figure 100:
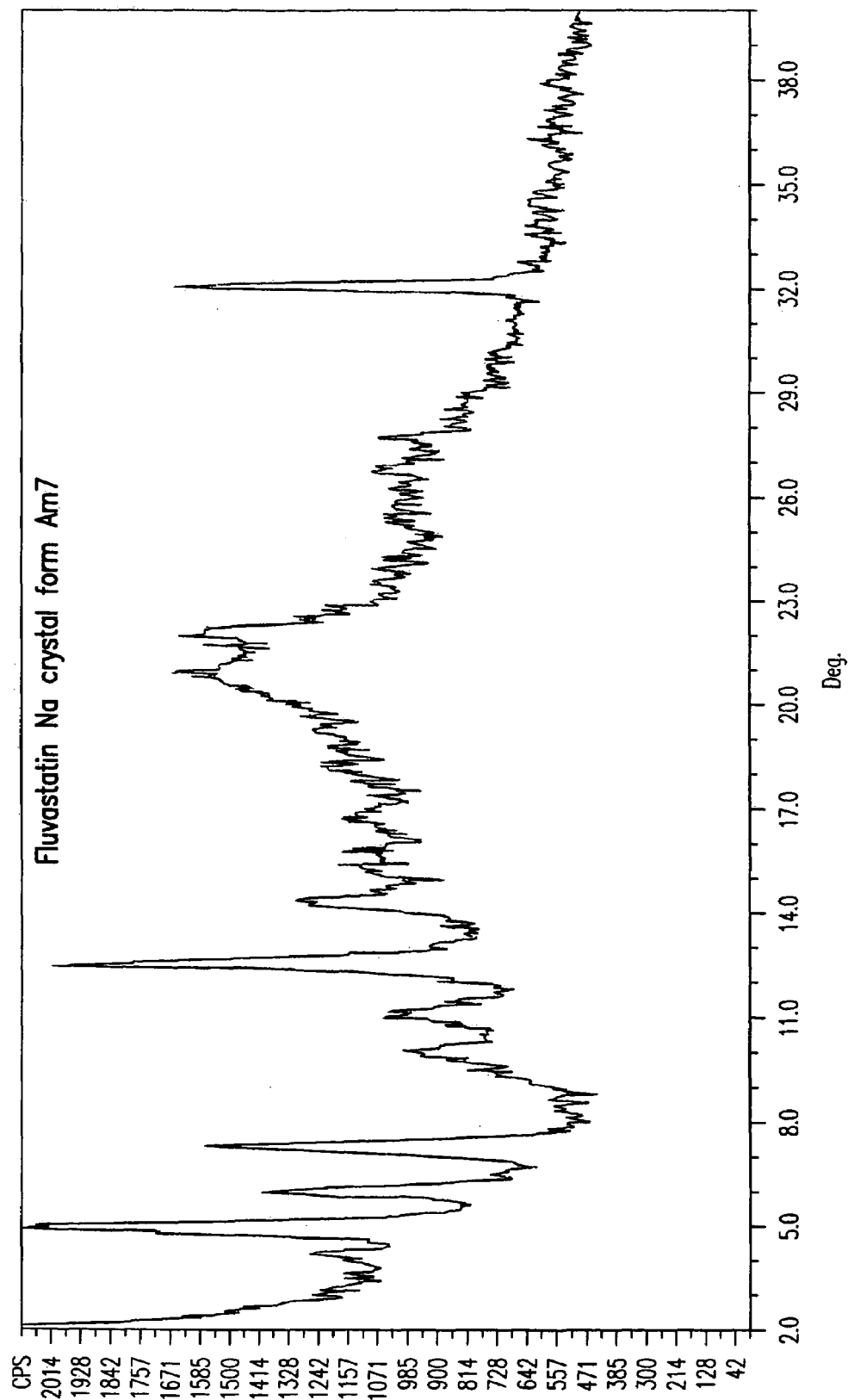
FIG. 100 depicts a powder X-ray diffractogram of fluvastatin sodium Form XCIII.

Fluvastatin sodium Form XCIII produces a PXRD pattern (FIG. 100) having characteristic peaks at 4.9, 5.9, 7.2 and 12.3±0.2 degrees two-theta and other peaks at 9.7, 10.9 and 13.9±0.2 degrees two-theta.

Fluvastatin sodium Form XCIII can be prepared from fluvastatin sodium Form XV by suspending it in propan-1-ol at ambient temperature and maintaining the suspension at ambient temperature for a sufficient period of time to convert Form XV into Form XCIII. Form XCIII can be separated from the propan-1-ol by conventional means such as filtering, decanting, centrifuging and the like. Preferably, the propan-1-ol is separated by vacuum filtration under an inert gas like nitrogen. A suitable condition for drying the separated product is 50EC under vacuum.

Fluvastatin Sodium Form XCIV

Fluvastatin sodium Form XCIV produces a PXRD pattern (FIG. 101) having characteristic peaks at 4.6, 9.2 and 20.3±0.2 degrees two-theta and other peaks at 4.1, 6.7, 13.0, 15.8, 17.7, 21.7 and 23.0±0.2 degrees two-theta.

Fluvastatin sodium Form XCIV can be prepared from fluvastatin sodium Form XV by suspending it in butan-1-ol at ambient temperature and maintaining the suspension at ambient temperature for a sufficient period to convert Form XV into Form XCIII. Form XCIII can be separated from the butan-1-ol by conventional means such as by filtering, decanting, centrifuging and the like. Preferably, the butan-1-ol is separated by vacuum filtration under an inert gas like nitrogen. A suitable condition for drying the separated product is 50EC under vacuum.

Fluvastatin Sodium Form XCV

Fluvastatin sodium Form XCV produces a PXRD pattern (FIG. 102) having characteristic peaks at 5.7, 13.0, 19.8 and 20.5±0.2 degrees two-theta and other peaks at 4.2, 4.7, 12.3 and 15.9±0.2 degrees two-theta.

Fluvastatin sodium Form XCV can be prepared from fluvastatin sodium Form XV by suspending it in either ethyl acetate, acetone, 1,4-dioxane or MEK at ambient temperature and maintaining the suspension at ambient temperature for a sufficient period of time to convert Form XV into Form XCV. Form XCV can be separated from the diluent by conventional means such as filtering, decanting, centrifuging and the like. Preferably, the diluent is separated by vacuum filtration under an inert gas like nitrogen. A suitable condition for drying the separated product is 50EC under vacuum.

Fluvastatin Sodium Form XCVI

Fluvastatin sodium Form XCVI produces a PXRD pattern (FIG. 103) having characteristic peaks at 3.7, 11.0, 12.9 and 18.2±0.2 degrees two-theta and other peaks at 5.2, 8.3, 17.7, 21.5 and 25.5±0.2 degrees two-theta.

Fluvastatin sodium Form XCVI can be prepared from fluvastatin sodium Form XV by suspending it in THF at ambient temperature and maintaining the suspension at ambient temperature for a sufficient period of time to convert Form XV into Form XCVI. Form XCV can be separated from the THF by conventional means such as filtering, decanting, centrifuging and the like. Preferably, the THF is separated by vacuum filtration under an inert gas like nitrogen. A suitable condition for drying the separated product is 50EC under vacuum.

Fluvastatin Sodium Form XCVII

Fluvastatin sodium Form XCVII produces a PXRD pattern (FIG. 104) having a characteristic peak at 3.5±0.2 degrees two-theta and other peaks at 9.4, 18.4, 20.0, 21.2 and 22.0±0.2 degrees two-theta.

Form XCVII can be prepared directly from a lower alkyl ester of fluvastatin such as fluvastatin methyl ester. The starting material is hydrolyzed with sodium hydroxide in cyclohexane. According to a preferred procedure, the sodium hydroxide is added as a methanolic solution. Over time, fluvastatin sodium Form XCVII precipitates from the mixture. Form XCVII can be separated from the cyclohexane by conventional means such as filtering, decanting, centrifuging and the like. Preferably, the cyclohexane is separated by vacuum filtration under an inert gas like nitrogen. A suitable condition for drying the separated product is 50EC under vacuum.

Fluvastatin Sodium Form XCVIII

Fluvastatin sodium Form XCVIII produces a PXRD pattern (FIG. 105) having characteristic peaks at 3.8 and 10.8±0.2 degrees two-theta and other peaks at 6.4 and 14.4±0.2 degrees two-theta.

Form XCVIII can be prepared directly from a lower alkyl ester of fluvastatin such as fluvastatin methyl ester. The starting material is hydrolyzed with sodium hydroxide in a concentrated methanol solution at elevated temperature. After completion of the hydrolysis, a large excess of acetonitrile (e.g. ~7×) is added to the methanol at elevated temperature. The hot solution is then cooled or allowed to cool to ambient temperature and held until Form XCVIII precipitates from the solution. Form XCVIII can be separated from the methanol and acetonitrile by conventional means such as by filtering, decanting, centrifuging and the like. Preferably, the methanol and acetonitrile are separated by vacuum filtration under an inert gas like nitrogen. A suitable condition for drying the separated product is 50EC under vacuum.

Fluvastatin Sodium Form XCIX

Fluvastatin sodium Form XCIX produces a PXRD pattern (FIG. 106) having characteristic peaks at 3.6, 5.3, 8.7 and 10.4±0.2 degrees two-theta and other peaks at 17.9 and 21.5±0.2 degrees two-theta.

Fluvastatin sodium Form XCIX can be prepared from fluvastatin sodium Form VI by suspending it in ethanol at ambient temperature and maintaining the suspension at ambient temperature for a sufficient period to convert Form VI into Form XCIX. Form XCIX can be separated from the ethanol by conventional means such as filtering, decanting, centrifuging and the like. Preferably, the ethanol is separated by vacuum filtration under an inert gas like nitrogen. A suitable condition for drying the separated product is 50EC under vacuum.

Fluvastatin Sodium Form C

Fluvastatin sodium Form C (100) produces a PXRD pattern (FIG. 107) having characteristic peaks at 3.3, 9.8, 11.0, 19.0 and 22.7±0.2 degrees two-theta and other peaks at 6.2, 17.2 and 21.3±0.2 degrees two-theta.

Form C can be prepared directly from a lower alkyl ester of fluvastatin such as fluvastatin methyl ester. The starting material is hydrolyzed with sodium hydroxide in dichloromethane at room temperature. Over time, fluvastatin sodium precipitates from the reaction mixture as Form C. Form C can be separated from the dichloromethane by conventional means such as filtering, decanting, centrifuging and the like. Preferably, the dichloromethane is separated by vacuum filtration under an inert gas like nitrogen. A suitable condition for drying the separated product is 50EC under vacuum.

Fluvastatin Sodium Form CI

Fluvastatin sodium Form CI produces a PXRD pattern (FIG. 108) having characteristic peaks at 4.5 and 11.2±0.2 degrees two-theta and other peaks at 5.7 and 19.3±0.2 degrees two-theta.

Form CI can be prepared directly from a lower alkyl ester of fluvastatin such as fluvastatin methyl ester. The starting material is hydrolyzed with sodium hydroxide in a mixture of acetone and methanol. After completion of the hydrolysis and, where applicable, cooling to ambient temperature, Form CI precipitates from the reaction mixture. Form CI can be separated from the methanol and acetone by conventional means such as filtering, decanting, centrifuging and the like. Preferably, the methanol and acetone are separated by vacuum filtration under an inert gas like nitrogen. A suitable condition for drying the separated product is 50EC under vacuum.

Fluvastatin Sodium Form CII

Fluvastatin sodium Form CII produces a PXRD pattern (FIG. 109) having a characteristic peak at 4.3±0.2 degrees two-theta and other peaks at 8.7, 11.0 and 19.2±0.2 degrees two-theta.

Form CII can be prepared directly from a lower alkyl ester of fluvastatin such as fluvastatin methyl ester. The starting material is hydrolyzed with sodium hydroxide in a mixture of acetone and methanol. After completion of the hydrolysis and, where applicable, cooling to ambient temperature, Form CI precipitates from the reaction mixture. Form CII can be separated from the methanol and acetone by conventional means such as filtering, decanting, centrifuging and the like. Preferably, the methanol and acetone are separated by vacuum filtration under an inert gas like nitrogen. A suitable condition for drying the separated product is 50EC under vacuum.

Fluvastatin Sodium Form CIII

Fluvastatin sodium Form CIII produces a PXRD pattern (FIG. 110) having characteristic peaks at 4.5, 20.4, 25.9 and 30.6±0.2 degrees two-theta and other peaks at 5.6, 10.1, 12.5, 19.0 and 19.7±0.2 degrees two-theta.

Form CIII can be prepared directly from a lower alkyl ester of fluvastatin such as fluvastatin methyl ester. The starting material is hydrolyzed with sodium hydroxide in a mixture of acetone and water. After completion of the hydrolysis and, where applicable, cooling to ambient temperature, Form CIII precipitates from the reaction mixture. Form CIII can be separated from the water and acetone by conventional means such as filtering, decanting, centrifuging and the like. Preferably, the water and acetone are separated by vacuum filtration under an inert gas like nitrogen. A suitable condition for drying the separated product is 50EC under vacuum.

Fluvastatin Sodium Form CIV

Fluvastatin sodium Form CIV produces a PXRD pattern (FIG. 111) having characteristic peaks at 3.7, 9.7, 18.3, 19.9, 21.8±0.2 degrees two-theta and other peaks at 5.6, 11.3, 14.8, 22.6±0.2 degrees two-theta. Form CIV can be prepared directly from a lower alkyl ester of fluvastatin such as fluvastatin methyl ester. The starting material is hydrolyzed with sodium hydroxide in THF. After completion of the hydrolysis, hexanes is added to the reaction mixture to induce precipitation of Form CIV. Form CIV can be separated from the THF by conventional means such as filtering, decanting, centrifuging and the like. Preferably, the THF is separated by vacuum filtration under an inert gas like nitrogen. A suitable condition for drying the separated product is 50EC under vacuum.

Fluvastatin Sodium Form CV

Fluvastatin sodium Form CV produces a PXRD pattern (FIG. 112) having characteristic peaks at 3.7, 8.9, 19.1, 22.5, 29.7±0.2 degrees two-theta and other peaks at 11.5, 17.0, 25.1, 26.9, 28.2±0.2 degrees two-theta. Form CV can be prepared directly from a lower alkyl ester of fluvastatin such as fluvastatin methyl ester. The starting material is hydrolyzed with sodium hydroxide in acetonitrile at elevated temperature. After completion of the hydrolysis, the reaction mixture is cooled or allowed to cool. Over time, fluvastatin sodium precipitates as Form CV. Form CV can be separated from the acetonitrile by conventional means such as filtering, decanting, centrifuging and the like. Preferably, the acetonitrile is separated by vacuum filtration under an inert gas like nitrogen. A suitable condition for drying the separated product is 50EC under vacuum.

Process for Preparing Amorphous Fluvastatin Sodium

We have discovered that fluvastatin sodium precipitates in an amorphous state from 1,4-dioxane and cyclohexane. Accordingly, one preferred process for making amorphous fluvastatin sodium of the present invention is to dissolve fluvastatin sodium in 1,4-dioxane, more preferably at elevated temperature, yet more preferably at about 85EC, and cooling the resulting solution to induce precipitation of amorphous fluvastatin sodium.

In another preferred process, a lower alkyl ester of fluvastatin is suspended in cyclohexane. Then, about one molar equivalent of sodium hydroxide dissolved in a minimum of protic solvent like methanol, is added to the suspension. The addition should cause the suspension to clarify. Upon standing, fluvastatin sodium may precipitate from the solution in amorphous form. Otherwise, additional cyclohexane can be added to induce precipitation.

In each of the foregoing processes, the precipitate is then separated from the 1,4-dioxane or cyclohexane by conventional means such as filtering, decanting, centrifuging and the like. Preferably, the 1,4-dioxane is separated by vacuum filtration under an inert gas like nitrogen. A suitable condition for drying the separated product is 50EC under vacuum.

Pharmaceutical Compositions and Dosage Forms Containing—and Methods of Medical Treatment Using the Novel Fluvastatin Sodium Forms Fluvastatin exerts an antihypercholesterolemia and antihyperlipidemia effect in mammals, especially humans. Accordingly, fluvastatin sodium Forms I, II, III, IV, IV-1, V, VI, VII, IX, IX-1, XI, XI-2, XII, XIII, XVI, XVII, XVIII, XIX, XIX-1, XX, XXII, XXIII, XXIV, XXVI, XXVII, XXIX, XXX, XXXI, XXXIII, XXXIV, XXXV, XXXVI, XXXVII, XXXVIII, XXXIX, XLI, XLII, XLIII, XLIV, XLV, XLVI, XLVII, XLVIII, XLIX, L, LI, LIII, LIV, LV, LVI, LVII, LVIII, LX, LXIV, LXV, LXVI, LXVII, LXVIII, LXIX, LXX, LXXI, LXXII, LXXIV, LXXV, LXXVI, LXXVII, LXXVIII, XC, XCI, XCII, XCIII, XCIV, XCV, XCVI, XCVII, XCVIII, XCIX, C, CI, CII, CIII, CIV, CV and mixtures thereof with each other as well as with other crystalline forms of fluvastatin sodium are useful for delivering fluvastatin to the gastrointestinal tract, bloodstream and liver of humans and other mammals suffering from or at risk of atherosclerosis. In particular, they are useful as active ingredients in pharmaceutical compositions and dosage forms. For this purpose, they may be formulated into a variety of compositions and dosage forms for administration to humans and animals.

Pharmaceutical compositions of the present invention contain fluvastatin sodium Form I, II, III, IV, IV-1, V, VI, VII, IX, IX-1, XI, XI-2, XII, XIII, XVI, XVII, XVIII, XIX, XIX-1, XX, XXII, XXIII, XXIV, XXVI, XXVII, XXIX, XXX, XXXI, XXXIII, XXXIV, XXXV, XXXVI, XXXVII, XXXVIII, XXXIX, XLI, XLII, XLIII, XLIV, XLV, XLVI, XLVII, XLVIII, XLIX, L, LI, LIII, LIV, LV, LVI, LVII, LVIII, LX, LXIV, LXV, LXVI, LXVII, LXVIII, LXIX, LXX, LXXI, LXXII, LXXIV, LXXV, LXXVI, LXXVII, LXXVIII; XC, XCI, XCII, XCIII, XCIV, XCV, XCVI, XCVII, XCVIII, XCIX, C, CI, CII, CIII, CIV, CV or mixtures thereof with each other or other crystalline forms of fluvastatin sodium, optionally in mixtures with one or more other active ingredient(s). In addition to the active ingredient(s), the pharmaceutical compositions of the present invention may contain one or more excipients. Excipients are added to the composition for a variety of purposes.

Diluents increase the bulk of a solid pharmaceutical composition and may make a pharmaceutical dosage form containing the composition easier for the patient and care giver to handle. Diluents for solid compositions include, for example, microcrystalline cellulose (e.g. Avicel®), microfine cellulose, lactose, starch, pregelitinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol and talc.

Solid pharmaceutical compositions that are compacted into a dosage form like a tablet may include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate and starch.

The dissolution rate of a compacted solid pharmaceutical composition in the patient's stomach may be increased by the addition of a disintegrant to the composition. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®) and starch.

Glidants can be added to improve the flow properties of non-compacted solid composition and improve the accuracy of dosing. Excipients that may function as glidants include colloidal silicon dioxide, magnesium trisilicate, powdered cellulose, starch, talc and tribasic calcium phosphate.

When a dosage form such as a tablet is made by compaction of a powdered composition, the composition is subjected to pressure from a punch and die. Some excipients and active ingredients have a tendency to adhere to the surfaces of the punch and die, which can cause the product to have pitting and other surface irregularities. A lubricant can be added to the composition to reduce adhesion and ease release of the product from the die. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

Flavoring agents and flavor enhancers make the dosage form more palatable to the patient. Common flavoring agents and flavor enhancers for pharmaceutical products that may be included in the composition of the present invention include maltol, vanillin, ethyl vanillin, menthol, citric acid, fumaric acid, ethyl maltol, and tartaric acid.

Solid and liquid compositions may also be dyed using any pharmaceutically acceptable colorant to improve their appearance and/or facilitate patient identification of the product and unit dosage level.

In liquid pharmaceutical compositions of the present invention, fluvastatin sodium Form I, II, III, IV, IV-1, V, VI, VII, IX, IX-1, XI, XI-2, XII, XIII, XVI, XVII, XVIII, XIX, XIX-1, XX, XXII, XXIII, XXIV, XXVI, XXVII, XXIX, XXX, XXXI, XXXIII, XXXIV, XXXV, XXXVI, XXXVII, XXXVIII, XXXIX, XLI, XLII, XLIII, XLIV, XLV, XLVI, XLVII, XLVIII, XLIX, L, LI, LIII, LIV, LV, LVI, LVII, LVIII, LX, LXIV, LXV, LXVI, LXVII, LXVIII, LXIX, LXX, LXXI, LXXII, LXXIV, LXXV, LXXVI, LXXVII, LXXVIII and any other solid excipients are dissolved or suspended in a liquid carrier such as water, vegetable oil, alcohol, polyethylene glycol, propylene glycol or glycerin.

Liquid pharmaceutical compositions may contain emulsifying agents to disperse uniformly throughout the composition an active ingredient or other excipient that is not soluble in the liquid carrier. Emulsifying agents that may be useful in liquid compositions of the present invention include, for example, gelatin, egg yolk, casein, cholesterol, acacia, tragacanth, chondrus, pectin, methyl cellulose, carbomer, cetostearyl alcohol and cetyl alcohol.

Liquid pharmaceutical compositions of the present invention may also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum.

Sweetening agents such as sorbitol, saccharin, sodium saccharin, sucrose, aspartame, fructose, mannitol and invert sugar may be added to improve the taste.

Preservatives and chelating agents such as alcohol, sodium benzoate, butylated hydroxy toluene, butylated hydroxyanisole and ethylenediamine tetraacetic acid may be added at levels safe for ingestion to improve storage stability.

A liquid composition according to the present invention may also contain a buffer such as guconic acid, lactic acid, citric acid or acetic acid, sodium guconate, sodium lactate, sodium citrate or sodium acetate.

Selection of excipients and the amounts to use may be readily determined by the formulation scientist based upon experience and consideration of standard procedures and reference works in the field.

The solid compositions of the present invention include powders, granulates, aggregates and compacted compositions. The dosage forms include dosage forms suitable for oral, buccal, rectal, parenteral (including subcutaneous, intramuscular, and intravenous), inhalant and ophthalmic administration. Although the most suitable route in any given case will depend on the nature and severity of the condition being treated, the most preferred route of the present invention is oral. The dosages may be conveniently presented in unit dosage form and prepared by any of the methods well-known in the pharmaceutical arts.

Dosage forms include solid dosage forms like tablets, powders, capsules, suppositories, sachets, troches and lozenges as well as liquid syrups, suspensions and elixirs.

An especially preferred dosage form of the present invention is a capsule containing the composition, preferably a powdered or granulated solid composition of the invention, within either a hard or soft shell. The shell may be made from gelatin and optionally contain a plasticizer such as glycerin and sorbitol, and an opacifying agent or colorant. An especially preferred capsule filling contains, in addition to one or more of the fluvastatin sodium crystalline forms of this invention, the excipients magnesium stearate, microcrystalline cellulose, pregelatinized starch, sodium lauryl sulfate and talc.

Another especially preferred dosage form of this invention is a compressed tablet that contains, in addition to one or more of the fluvastatin sodium crystalline forms of this invention, the excipients microcrystalline cellulose, hydroxypropyl cellulose, hydroxypropylmethyl cellulose, potassium bicarbonate, povidone, magnesium stearate, iron oxide yellow, titanium dioxide and polyethylene glycol 8000.

The active ingredient and excipients may be formulated into compositions and dosage forms according to methods known in the art.

A composition for tableting or capsule filing may be prepared by wet granulation. In wet granulation some or all of the active ingredients and excipients in powder form are blended and then further mixed in the presence of a liquid, typically water, that causes the powders to clump up into granules. The granulate is screened and/or milled, dried and then screened and/or milled to the desired particle size. The granulate may then be tableted or other excipients may be added prior to tableting such as a glidant and or lubricant.

A tableting composition may be prepared conventionally by dry blending. For instance, the blended composition of the actives and excipients may be compacted into a slug or a sheet and then comminuted into compacted granules. The compacted granules may be compressed subsequently into a tablet.

As an alternative to dry granulation, a blended composition may be compressed directly into a compacted dosage form using direct compression techniques. Direct compression produces a more uniform tablet without granules. Excipients that are particularly well suited to direct compression tableting include microcrystalline cellulose, spray dried lactose, dicalcium phosphate dihydrate and colloidal silica. The proper use of these and other excipients in direct compression tableting is known to those in the art with experience and skill in the particular formulation challenges of direct compression tableting.

A capsule filling of the present invention may comprise any of the aforementioned blends and granulates that were described with reference to tableting, only they are not subjected to a final tableting step.

Capsules, tablets and lozenges and other unit dosage forms preferably contain a dosage equivalent to from about 10 to about 100 mg fluvastatin. Preferably the dosage is equivalent to from about 20 to about 80 mg of fluvastatin. More particularly, immediate or uncontrolled release dosage forms preferably contain the equivalent of from abut 20 to about 40 mg of fluvastatin and extended release dosage forms preferably contain the equivalent of from about 60 to about 100 mg of fluvastatin, more preferably about 80 mg of fluvastatin.

Process for Preparing Fluvastatin Sodium Crystal Form B

In another aspect, the present invention provides a process for preparing known fluvastatin Form B. In the process, the free acid of fluvastatin, fluvastatin lactone or a mixture of the two, is dissolved in a solution containing about one molar equivalent of sodium hydroxide in a mixture of water and methanol. The most preferred solvent is a 10:1 mixture of methanol:water. Conversion of any lactone that may be present in the starting material can be monitored by HPLC. Once a homogeneous solution of fluvastatin sodium is obtained, precipitation of the sodium salt is induced by addition of methyl tert-butyl ether ("MTBE"). Formation of the salt and the initial addition of MTBE are preferably conducted at elevated temperature, e.g. the reflux temperature of the solvent system. Form B can be separated from the methanol, water and MTBE by conventional means such as filtering, decanting, centrifuging and the like. Preferably, the liquids are separated by vacuum filtration under an inert gas like nitrogen. A suitable condition for drying the separated product is 50EC under vacuum.

Having thus described the present invention with reference to certain preferred embodiments, the processes for producing fluvastatin sodium I, II, III, IV, IV-1, V, VI, VII, IX, IX-1, XI, XI-2, XII, XIII, XVI, XVII, XVIII, XIX, XIX-1, XX, XXII, XXIII, XXIV, XXVI, XXVII, XXIX, XXX, XXXI, XXXIII, XXXIV, XXXV, XXXVI, XXXVII, XXXVIII, XXXIX, XLI, XLII, XLIII, XLIV, XLV, XLVI, XLVII, XLVIII, XLIX, L, LI, LIII, LIV, LV, LVI, LVII, LVIII, LX, LXIV, LXV, LXVI, LXVII, LXVIII, LXIX, LXX, LXXI, LXXII, LXXIV, LXXV, LXXVI, LXXVII, LXXVIII, XC, XCI, XCII, XCIII, XCIV, XCV, XCVI, XCVII, XCVIII, XCIX, C, CI, CII, CIII, CIV, CV and B of the present invention and techniques suitable for identifying them are further illustrated by the examples which follow. These examples are provided for illustrative purposes only and are not intended to limit the invention in any way.

EXAMPLES

General

Powder X-ray diffraction data were obtained using methods known in the art on a SCINTAG powder X-ray diffractometer model X'TRA equipped with a solid state detector. Copper radiation of 1.5418 Å was used. A round aluminum sample holder with zero background was used.

DSC analysis was done on a Mettler 821 Star e. The weight of the samples was about 5 mg; the samples were scanned at a rate of 10° C./min from 30° C. to 200° C. The oven was constantly purged with nitrogen gas at a flow rate of 40 ml/min. Standard 40 μl aluminum crucibles covered by lids with 3 holes were used.

TGA analysis was done using a Mettler M3 meter. The weight of the samples was about 10 mg; the samples were scanned at a rate of 10° C./min from 25° C. to 200° C. The oven was constantly purged with nitrogen gas at a flow rate of 40 ml/min. Standard 70 μl alumina crucibles covered by lids with 1 hole were used.

IR analysis was done using a Perkin Elmer "Spectrum One" FT-IR spectrometer in DRIFTt mode. The samples in the 4000-400 cm−1 interval were scanned 16 times with 4.0 cm−1 resolution.

The water content of fluvastatin sodium is measured by the methods known in the art like Karl Fisher or thermogravimetric analysis.

Those skilled in the art will recognize the abbreviations used in the disclosure, as they are in widespread use in the fields of medicinal and organic chemistry. The abbreviations used include the following:

| ACN | acetonitrile |
| DMF | N,N-dimethyl formamide |
| DMSO | dimethyl sulfoxide |
| EtOH | ethanol |
| Et$_2$O | diethyl ether |
| EtOAc | ethyl acetate |
| IPA | isopropyl alcohol |
| MeOH | methanol |
| MTBE | methyl tert-butyl ether |
| MEK | methyl ethyl ketone |
| THF | tetrahydrofuran |

Preparative

All the preparations described below were carried out on fluvastatin sodium Form B except where indicated otherwise. Fluvastatin sodium Forms XIX-1, XXXIII, XXXIV, XXXV were prepared using as starting material fluvastatin sodium Form XV which was purchased from Zhejiang Hisun Pharmaceutical Company Limited; 46 Waisha Road, Jiaojiang District, Taizhou City, Zhejiang Province, China.

1) Preparation of Fluvastatin Sodium Crystal Form I

Example 1

Fluvastatin methyl ester (3.0 g) was dissolved in acetone (30 ml) and NaOH (0.29 g) partially dissolved in acetone (0.75 ml) was added. The mixture was stirred at room temperature overnight. The product was isolated by filtration under nitrogen, washed with acetone (40 ml) and dried at 50EC in a vacuum oven for 24 h to obtain 2.31 g (76.2%) of fluvastatin sodium crystal Form I.

Example 2

Fluvastatin methyl ester (3.01 g) was dissolved in acetonitrile (60 ml) by heating and NaOH (0.28 g) was added. The mixture was stirred at about 60EC for 1 h, cooled to room temperature, heated again to about 75EC for 2 h, then cooled to room temperature and stirred overnight. The product was isolated by filtration under nitrogen, washed with acetonitrile (40 ml) and dried at 50EC in a vacuum oven for 24 h to obtain 1.07 g (34.9%) of fluvastatin sodium crystal Form I.

Example 3

Fluvastatin methyl ester (3.01 g) was dissolved in acetonitrile (60 ml) by heating and a solution of NaOH (0.28 g) in water (0.75 ml) was added at about 50EC. The mixture was stirred at about 40EC for 2 h, cooled to room temperature and stirred for another h. The product was isolated by filtration under nitrogen, washed with acetonitrile (40 ml) and dried at 50EC in a vacuum oven for 24 h to obtain 2.52 g (82.2%) of fluvastatin sodium crystal Form I.

Example 4

Fluvastatin sodium crystal Form B (3.0 g) was dissolved in acetone (600 ml) at reflux temperature. The obtained solution was filtered and MTBE (200 ml) was added at reflux temperature. The solution was cooled to room temperature and MTBE (100 ml) was added. The mixture was concentrated under reduced pressure to obtain precipitate. The product was then filtered, washed with MTBE (2×18 ml) and dried at 50EC in a vacuum oven for 24 h to obtain 1.7 g (58%) of fluvastatin sodium crystal Form I.

Example 5

Fluvastatin sodium crystal Form B (3.0 g) was dissolved in butan-2-ol (60 ml) and water (6 ml) at reflux temperature. The solution was cooled to 15EC for 2 h to obtain a precipitate. The product was then filtered under nitrogen flow, washed with butan-2-ol (1×5 ml) and dried at 50EC in a vacuum oven for 24 h to obtain 0.05 g (2%) of fluvastatin sodium crystal Form I.

2) Preparation of Fluvastatin Sodium Crystal Form II

Example 6

Fluvastatin sodium crystal Form B (3.0 g) was almost completely dissolved in butan-1-ol (90 ml) at reflux temperature. The mixture was stirred at reflux temperature for 2.5 h. Then, it was cooled to room temperature and stirred at this temperature for 16 h. The product was filtered, washed with butan-1-ol (1×5 ml) and dried at 50EC in a vacuum oven for 52 h to obtain 1.7 g (56%) of fluvastatin sodium crystal Form II.

3) Preparation of Fluvastatin Sodium Crystal Form III

Example 7

Fluvastatin sodium crystal Form B (3.0 g) was dissolved in butan-1-ol (70 ml) at reflux temperature. MTBE (70 ml) was added dropwise and the mixture was stirred at reflux temperature for 3 h. The solution was cooled to room temperature and MTBE (70 ml) was added to obtain a massive precipitate after 2 h. The product was filtered, washed with MTBE (3×10 ml) and dried at 50EC in a vacuum oven for 24 h to obtain 1.5 g (49%) of fluvastatin sodium crystal Form III.

Example 8

Fluvastatin sodium crystal Form B (3.0 g) was dissolved in butan-1-ol (70 ml) at reflux temperature. The solution was filtered and n-hexane (70 ml) was added dropwise. The mixture was stirred at reflux temperature for 3.5 h. The solution was cooled to room temperature to obtain precipitate. The product was filtered, washed with n-hexane (2×20 ml) and dried at 50EC in a vacuum oven for 23 h to obtain 1.0 g (34%) of fluvastatin sodium crystal Form III.

Example 9

Fluvastatin sodium crystal Form B (3.0 g) was dissolved in 1,4-dioxane (75 ml) at reflux temperature. The solution was cooled to room temperature to obtain precipitate. The product was filtered, washed with 1,4-dioxane (1×25 ml) and dried at 50EC in a vacuum oven for 24 h to obtain 2.2 g (75%) of fluvastatin sodium crystal Form III.

Example 10

A suspension of fluvastatin sodium crystal Form B (3.0 g) in ethyl acetate (150 ml) was stirred at reflux temperature. Hexanes (150 ml) were added dropwise at reflux temperature. The mixture was stirred at reflux temperature for 3 h. The suspension was cooled to room temperature. The product was filtered under nitrogen flow, washed with hexanes (1×20 ml) and dried at 50EC in a vacuum oven for 22 h to obtain 2.7 g (91%) of fluvastatin sodium crystal Form III.

Example 11

Amorphous fluvastatin sodium (1.7 g) was dissolved in ethanol (10 ml) at reflux temperature. After 0.5 h the product was recrystallized at reflux temperature. The suspension was stirred at reflux temperature for additional 1 h. Then, the suspension was cooled to room temperature and additional amount of ethanol (10 ml) was added. The product was filtered under nitrogen flow, washed with ethanol (2×10 ml) and dried at 50EC in a vacuum oven for 24 h to obtain 0.9 g (53%) of fluvastatin sodium crystal Form III.

Example 12

Fluvastatin sodium crystal Form B (3.0 g) was dissolved in THF (50 ml) at reflux temperature. Cyclohexane (65 ml) was added dropwise at reflux temperature to obtain a precipitate. The mixture was cooled to room temperature. The product was filtered, washed with cyclohexane (2×20 ml) and dried at 50EC in a vacuum oven for 19.5 h to obtain 2.7 g (91%) of fluvastatin sodium crystal Form III.

Example 13

A suspension of fluvastatin sodium crystal Form XIV (3.0 g) was stirred in ethanol (20 ml) at reflux temperature for 7 h. The suspension was cooled to room temperature. The product was filtered under nitrogen flow, washed with ethanol (2×25 ml) and dried at 50EC in a vacuum oven for 21 h to obtain 2.3 g (77%) of fluvastatin sodium crystal Form III.

4) Preparation of Fluvastatin Sodium Crystal Form IV

Example 14

Fluvastatin sodium (3.0 g) was dissolved in tetrahydrofuran (THF) (50 ml) at reflux temperature. Chloroform (50 ml) was added dropwise at reflux temperature and the resulting mixture was stirred at this temperature for 40 minutes. A precipitate was obtained during reflux. Then, the mixture was cooled to room temperature. The product was isolated by filtration under nitrogen, washed with Chloroform (2×20 ml) and dried at 50EC in a vacuum oven for 19 h to obtain 2.7 g (89%) of fluvastatin sodium crystal Form IV.

Example 15

Fluvastatin sodium (3.0 g) was dissolved in THF (50 ml) at reflux temperature. Dichloromethane (65 ml) was added dropwise at reflux temperature and the resulting mixture was stirred at this temperature for 1 h. Then, the mixture was cooled to room temperature. The product was isolated by filtration under nitrogen, washed with dichloromethane (2×20 ml) and dried at 50EC in a vacuum oven for 20 h to obtain 2.6 g (87%) of fluvastatin sodium crystal Form IV.

Example 16

Fluvastatin sodium (3.0 g) was dissolved in THF (50 ml) at reflux temperature. 1,2-Dichloroethane (50 ml) was added dropwise at reflux temperature and the resulting mixture was stirred at this temperature for 1 h. A precipitate was obtained during the reflux. Then, the mixture was cooled to room temperature. The product was isolated by filtration under nitrogen and dried at 50EC in a vacuum oven for 24 h to obtain 0.7 g (24%) of fluvastatin sodium crystal Form IV.

Example 17

Fluvastatin sodium (3.0 g) was dissolved in THF (50 ml) at reflux temperature. Diethyl ether (50 ml) was added dropwise at reflux temperature and the resulting mixture was stirred at this temperature for 1 h. A precipitate was obtained during the reflux. Then, the mixture was cooled to room temperature. The product was isolated by filtration under nitrogen, washed with diethyl ether (2×25 ml) and dried at 50EC in a vacuum oven for 24.5 h to obtain 2.1 g (69%) of fluvastatin sodium crystal Form IV.

Example 18

Fluvastatin sodium (3.0 g) was dissolved in THF (50 ml) at reflux temperature. n-Pentane (50 ml) was added dropwise at reflux temperature and the resulting mixture was stirred at this temperature for 8 minutes. A massive precipitate was obtained during reflux. Then, the mixture was cooled to room temperature. The product was isolated by filtration under nitrogen, washed with n-pentane (2×25 ml) and dried at 50EC in a vacuum oven for 25 h to obtain 2.8 g (93%) of fluvastatin sodium crystal Form IV.

Example 19

Fluvastatin sodium (3.0 g) was dissolved in butan-1-ol (70 ml) at reflux temperature. Cyclohexane (70 ml) was added at reflux temperature and the resulting mixture was stirred at this temperature for 3 h. Then, the mixture was cooled to room temperature. The product was isolated by filtration, washed with cyclohexane (2×20 ml) and dried at 50EC in a vacuum oven for 25.5 h to obtain 2.1 g (69%) of fluvastatin sodium crystal Form IV.

Example 20

Fluvastatin sodium (3.0 g) was dissolved in 1,4-dioxane (75 ml) at reflux temperature. Cyclohexane (70 ml) was added at reflux temperature and the resulting mixture was stirred at this temperature for 3.5 h. A precipitate was obtained during the reflux. Then, the mixture was cooled to room temperature. The product was isolated by filtration, washed with cyclohexane (2×10 ml) and dried at 50EC in a vacuum oven for 22.5 h to obtain 2.7 g (89%) of fluvastatin sodium crystal Form IV.

Example 21

Fluvastatin sodium (3.0 g) was dissolved in propan-2-ol (70 ml) at reflux temperature. MTBE (70 ml) was added dropwise at reflux temperature and the resulting mixture was stirred at this temperature for 15 minutes. A precipitate was obtained during the reflux. Then, the mixture was cooled to room temperature. The product was isolated by filtration under nitrogen, washed with MTBE (3×20 ml) and dried at 50EC in a vacuum oven for 25.5 h to obtain 2.4 g (81%) of fluvastatin sodium crystal Form IV.

5) Preparation of Fluvastatin Sodium Crystal Form IV-1

Example 22

Fluvastatin sodium (3.0 g) was dissolved in THF (50 ml) at reflux temperature. n-Heptane (50 ml) was added dropwise at reflux temperature and the resulting mixture was stirred at this temperature for 1 h. A massive precipitate was obtained during reflux. Then, the mixture was cooled to room temperature. The product was isolated by filtration under nitrogen, washed with n-heptane (2×50 ml) and dried at 50EC in a vacuum oven for 24 h to obtain 2.9 g (97%) of fluvastatin sodium crystal Form IV-1.

Example 23

Fluvastatin sodium (3.0 g) was almost completely dissolved in butan-2-ol (70 ml) at reflux temperature. During this time the material was recrystallized. Cyclohexane (70 ml) was added at reflux temperature and the resulting mixture was stirred at this temperature for 5 h. Then, the mixture was cooled to room temperature. The product was isolated by filtration, washed with cyclohexane (1×20 ml) and dried at 50EC in a vacuum oven for 24 h to obtain 3.0 g (100%) of fluvastatin sodium crystal Form IV-1.

Example 24

Fluvastatin sodium (3.0 g) was dissolved in 1,4-dioxane (75 ml) at reflux temperature. MTBE (75 ml) was added dropwise at reflux temperature and the resulting mixture was stirred at this temperature for 4 h. A massive precipitate was obtained during the reflux. Then, the mixture was cooled to room temperature. The product was isolated by filtration, washed with MTBE (2×10 ml) and dried at 50EC in a vacuum oven for 22 h to obtain 2.7 g (89%) of fluvastatin sodium crystal Form IV-1.

6) Preparation of Fluvastatin Sodium Crystal Form V

Example 25

Fluvastatin sodium crystal Form B (3.0 g) was dissolved in butan-1-ol (70 ml) at reflux temperature. The solution was filtered and n-heptane (70 ml) was added dropwise at reflux temperature. The mixture was stirred at reflux temperature for additional 3 h. The mixture was cooled to room temperature and stirred at this temperature for 25 h. The product was filtered, washed with n-Heptane (1×20 ml) and dried at 50EC in a vacuum oven for 24 h to obtain 1.8 g (61%) of fluvastatin sodium crystal Form V.

Example 26

Fluvastatin sodium crystal Form B (3.0 g) was dissolved in a mixture of ethanol (50 ml), ethyl acetate (20 ml) and propan-1-ol (10 ml) at reflux temperature. The solution was filtered and n-hexane (200 ml) was added dropwise. The mixture was cooled to room temperature and stirred at this temperature for 16 h. The product was filtered under nitrogen flow, washed with n-hexane (2×25 ml) and dried at 50EC in a vacuum oven for 24 h to obtain 2.3 g (77%) of fluvastatin sodium crystal Form V.

7) Preparation of Fluvastatin Sodium Crystal Form VI

Example 27

Fluvastatin sodium (3.0 g) was dissolved in DMF (83 ml) at room temperature. Diethyl ether (100 ml) was added gradually at room temperature and the resulting mixture was stirred at this temperature for 1 h. Then, the mixture was cooled using an ice-bath. The product was isolated by filtration under nitrogen and dried at 50EC in a vacuum oven for 24 h to obtain 1.7 g (55%) of fluvastatin sodium crystal Form VI.

Example 28

Fluvastatin sodium (3.0 g) was dissolved in DMF (120 ml) at room temperature. Then, hexanes (10 ml) were added. The solvent and the anti-solvent were evaporated to dryness and the obtained solid was suspended in DMF (80 ml) at room temperature for 16 h. The mixture was cooled using an ice-bath. The product was isolated by filtration under nitrogen and dried at 50EC in a vacuum oven for 24 h to obtain 1.3 g (42%) of a mixture of fluvastatin sodium crystal Forms VI and VII.

Example 29

Fluvastatin methyl ester (3.0 g) was added to a solution of NaOH (1 eq.) in water (0.75 ml) and methanol (7.5 ml). The mixture was stirred at about 60EC for 4 hr, after which the starting material was no longer detectable by HPLC. Then, acetonitrile (58 ml) was dripped into the solution over 1.5 h. Turbidity appeared in the solution which as it was allowed to cool slowly to room temperature. The mixture was stirred overnight. The product was isolated by filtration under nitrogen, washed with acetonitrile (50 ml) and dried at 50EC in a vacuum oven for 24 h to obtain 2.23 g (73%) of fluvastatin sodium Form VI.

Example 30

Fluvastatin methyl ester (2.0 g) was added to a solution of NaOH (1 eq.) in methanol (5 ml). The mixture was heated to reflux and stirred for 2.25 h after which the starting material was not longer detected by HPLC. Then, acetonitrile (40 ml) was dripped into the solution in two portions over 1.5 h. The mixture was cooled slowly to room temperature and stirred for another 1.75 h. The product was isolated by filtration under nitrogen, washed with acetonitrile (20 ml) and dried at 50EC in a vacuum oven for 23 h to obtain 1.7 g (83.4%) of fluvastatin sodium Form VI.

Example 31

Fluvastatin methyl ester (2.0 g) was added to a solution of NaOH (1 eq.) in ethanol (15 ml). The mixture was stirred at about 70EC for 1.75 h, after which the starting material was not detected by HPLC. Then, acetone (40 ml) was dripped into the solution and the mixture was cooled slowly to room temperature and stirred overnight. The product was isolated by filtration under nitrogen, washed with acetone (20 ml) and dried at 50EC in a vacuum oven for 24 h to obtain 1.54 g (75.6%) of fluvastatin sodium Form VI.

Example 32

Fluvastatin methyl ester (2.0 g) was added to a solution of NaOH (1 eq.) in water (0.5 ml) and butan-1-ol (8 ml). The mixture was stirred at about 80EC for 4 h, after which the starting material was not detected by HPLC. Then, acetonitrile (40 ml) was dripped into the solution and the mixture was cooled slowly to room temperature and stirred overnight. The product was isolated by filtration under nitrogen, washed with acetonitrile (15 ml) and dried at 50EC in a vacuum oven for 24 h to obtain fluvastatin sodium Form VI (1.65 g, 81%).

8) Preparation of Fluvastatin Sodium Crystal Form VII

Example 33

Fluvastatin sodium (3.0 g) was dissolved in DMF (83 ml) at room temperature. Chloroform (100 ml) was added gradually at room temperature and the resulting mixture was stirred at this temperature for 4 days. Then, the mixture was cooled using an ice-bath. The product was isolated by filtration under nitrogen, washed with dichloromethane (1×35 ml) and dried at 50EC in a vacuum oven for 24 h to obtain 2.0 g (65%) of fluvastatin sodium crystal Form VII.

Example 34

Fluvastatin sodium (3.0 g) was dissolved in DMF (80 ml) at room temperature. MTBE (100 ml) was added gradually at room temperature and the resulting mixture was stirred at this temperature for 5 h. Then, the mixture was cooled using an ice-bath. The product was isolated by filtration under nitrogen and dried at 50EC in a vacuum oven for 22 h to obtain 1.8 g (59%) of fluvastatin sodium crystal Form VII.

Example 35

Fluvastatin sodium (3.0 g) was dissolved in DMF (80 ml) at room temperature. Dichloromethane (100 ml) was added gradually at room temperature and the resulting mixture was stirred at this temperature for 16 h. Then, the mixture was cooled using an ice-bath. The product was isolated by filtration under nitrogen and dried at 50EC in a vacuum oven for 23 h to obtain 2.4 g (79%) of fluvastatin sodium crystal Form VII.

Example 36

Fluvastatin sodium (3.0 g) was dissolved in DMF (120 ml) at room temperature. Then, cyclohexane (20 ml) was added. The solvent and the anti-solvent were evaporated to dryness and the obtained solid was suspended in DMF (80 ml) at room temperature for 16 h. The mixture was cooled using an ice-bath. The product was isolated by filtration under nitrogen and dried at 50EC in a vacuum oven for 23 h to obtain 1.9 g (64%) of fluvastatin sodium crystal Form VII.

Example 37

Fluvastatin sodium (3.0 g) was dissolved in DMF (80 ml) at room temperature. 1,2-Dichloroethane (100 ml) was added at room temperature and the resulting mixture was stirred at this temperature for 5 h. Then, the mixture was cooled using an ice-bath. The product was isolated by filtration under nitrogen and dried at 50EC in a vacuum oven for 21 h to obtain 1.8 g (60%) of fluvastatin sodium crystal Form VII.

Example 38

Fluvastatin sodium (3.0 g) was suspended in DMF (40 ml) at room temperature for 16h. The product was isolated by filtration under nitrogen, washed with DMF (1×20 ml) and dried at 50EC in a vacuum oven for 28 h to obtain 1.1 g (37%) of fluvastatin sodium crystal Form VII.

Example 39

Fluvastatin methyl ester (2.0 g) was added to a mixture of NaOH (1 eq.) and butan-1-ol (15 ml). The mixture was stirred at about 80EC for 1.5 h, after which the starting material was not detected by HPLC. Then, 40 ml of acetone was dripped into the solution and the mixture was cooled slowly to room temperature and stirred overnight. The product was isolated by filtration under nitrogen, washed with acetone (20 ml) and dried at 50EC in a vacuum oven for 24 h to obtain 1.09 g (53.5%) of fluvastatin sodium Form VII.

Example 40

Fluvastatin methyl ester (2.0 g) was added to a mixture of NaOH (1 eq.) and butan-1-ol (15 ml). The mixture was stirred at about 80EC for 2.5 h, after which the starting material was not detected by HPLC. Then, 40 ml of acetonitrile was dripped into the solution. The mixture was then cooled slowly to room temperature and stirred overnight. The product was isolated by filtration under nitrogen, washed with acetonitrile (45 ml) and dried at 50EC in a vacuum oven for 24 h to obtain 1.96 g (96.2%) of fluvastatin sodium Form VII.

Example 41

Fluvastatin methyl ester (3.0 g) was added to a solution of NaOH (1 eq.) in water (0.75 ml) and propan-2-ol (7.5 ml). The mixture was heated to reflux and 1 ml of propan-2-ol was added. After 2 h the mixture was cooled to room temperature and stirred for 2 h. MTBE (60 ml) was dripped into the solution over 20 min and it was stirred for another 1.5 h. The product was isolated by filtration under nitrogen, washed with MTBE and dried at 50EC in a vacuum oven for 24 h to obtain 1.9 g (62%) of fluvastatin sodium Form VII.

Example 42

Fluvastatin methyl ester (3.0 g) was added to a solution of NaOH (1 eq.) in MeOH (30 ml). The mixture was stirred at room temperature for 4.5 h. Then, it was filtered and concentration by vacuum distillation until a solid appeared. The concentrated solution was heated to reflux and 60 ml of acetonitrile was dripped into the mixture over 50 min. Turbidity was observed and the mixture was cooled slowly to room temperature and stirred over night. The product was isolated by filtration under nitrogen, washed with acetonitrile (60 ml) and dried at 50EC in a vacuum oven for 24 h to obtain fluvastatin sodium Form VII (2.54 g, 83.1%).

Example 43

Fluvastatin methyl ester (3.0 g) was added to acetonitrile (60 ml) and the mixture was heating to about 40EC for dissolution. A solution of NaOH (1 eq.) in EtOH (7.5 ml) was added and turbidity was immediately observed. The mixture then was heated to about 65EC. The mixture was cooled slowly to room temperature and stirred overnight. The product was isolated by filtration under nitrogen, washed with acetonitrile (40 ml) and dried at 50EC in a vacuum oven for 24 h to obtain fluvastatin sodium Form VII (1.99 g, 64.9%).

9) Preparation of Fluvastatin Sodium Crystal Form IX

Example 44

Into a 100 ml flask were placed fluvastatin methyl ester (3.0 g), EtOH (7.5 ml) and a solution of NaOH (0.28 g) in water (0.75 ml). The mixture was heated to reflux for two h, propan-2-ol was added (58 ml) and the mixture was cooled to room temperature and stirred over night. The product was isolated by filtration under nitrogen, washed with propan-2-ol (50 ml) and dried at 50EC in a vacuum oven for 24 h to obtain 1.92 g (62.8%) of fluvastatin sodium crystal Form IX.

Example 45

Fluvastatin sodium crystal Form B (3.0 g) was dissolved in 1,4-dioxane (75 ml) at reflux temperature. Dichloromethane (75 ml) was added dropwise to obtain a precipitate and the mixture was stirred at reflux temperature for 2.5 h. The suspension was cooled to room temperature and stirred at this temperature for 20 h. The product was filtered, washed with Dichloromethane (1×20 ml) and dried at 50EC in a vacuum oven for 24 h to obtain 1.5 g (51%) of fluvastatin sodium crystal Form IX.

Example 46

A suspension of fluvastatin sodium crystal Form B (3.0 g) in ethyl acetate (100 ml) was stirred at reflux temperature for 2.5 h. The suspension was cooled to room temperature. The product was filtered, washed with ethyl acetate (1×20 ml) and dried at 50EC in a vacuum oven for 23 h to obtain 2.0 g (66%) of fluvastatin sodium crystal Form IX.

Example 47

Fluvastatin sodium crystal Form B (5.0 g) was almost completely dissolved in ethanol (100 ml) at 45EC. The solution was filtered and cooled to room temperature. ethyl acetate (250 ml) was added and the mixture was stirred at room temperature for 63 h to obtain precipitate. The product was filtered under nitrogen flow, washed with ethyl acetate (1×20 ml) and dried at 50EC in a vacuum oven for 23 h to obtain 2.2 g (44%) of fluvastatin sodium crystal Form IX.

Example 48

Fluvastatin sodium crystal Form B (3.0 g) was dissolved in ethanol (130 ml) at room temperature. The solution was filtered and Diethyl ether (260 ml) was added. The mixture was stirred at room temperature for 16 h to obtain precipitate. The product was filtered and dried at 50EC in a vacuum oven for 22 h to obtain 1.7 g (56%) of fluvastatin sodium crystal Form IX.

Example 49

Fluvastatin sodium crystal Form B (3.0 g) was dissolved in ethanol (130 ml) at room temperature. The solution was filtered and n-pentane (260 ml) was added. The mixture was stirred at room temperature for 17 h to obtain precipitate. The product was filtered, washed with n-pentane (2×35 ml) and dried at 50EC in a vacuum oven for 24 h to obtain 1.9 g (63%) of fluvastatin sodium crystal Form IX.

Example 50

Fluvastatin sodium crystal Form B (5.0 g) was almost completely dissolved in a mixture of ethanol (130 ml) and methanol (5 ml) at room temperature. The solution was filtered and hexanes (200 ml) were added dropwise. The mixture was stirred at room temperature for 19 h to obtain precipitate. The product was filtered under nitrogen flow and dried at 50EC in a vacuum oven for 22 h to obtain 3.6 g (73%) of fluvastatin sodium crystal Form IX.

10) Preparation of Fluvastatin Sodium Crystal Form IX-1

Example 51

Fluvastatin sodium crystal Form B (3.0 g) was dissolved in butan-1-ol (70 ml) at reflux temperature. The solution was filtered and n-pentane (70 ml) was added dropwise at reflux temperature. The mixture was stirred at reflux temperature for 1.5 h. The mixture was cooled to room temperature. The product was filtered, washed with n-pentane (2×10 ml) and dried at 50EC in a vacuum oven for 21 h to obtain 2.2 g (73%) of fluvastatin sodium crystal Form IX-1.

Example 52

Fluvastatin sodium crystal Form B (3.0 g) was dissolved in butan-1-ol (70 ml) at reflux temperature. The solution was filtered and Diethyl ether (70 ml) was added dropwise at reflux temperature. The mixture was stirred at reflux temperature for 0.5 h. The mixture was cooled to room temperature. The product was filtered, washed with Diethyl ether (2×5 ml) and dried at 50EC in a vacuum oven for 24 h to obtain 2.0 g (65%) of fluvastatin sodium crystal Form IX-1.

Example 53

A slurry of fluvastatin sodium crystal Form B (3.0 g) in ethyl acetate (240 ml) was heated to reflux temperature. Additional amount of ethyl acetate (80 ml) was added at reflux temperature. The material was recrystallized during reflux and the mixture was stirred at reflux temperature for 2.5 h to obtain a massive precipitate. The mixture was cooled to room temperature. The product was filtered under nitrogen flow, washed with ethyl acetate (2×10 ml) and dried at 50EC in a vacuum oven for 23 h to obtain 2.7 g (89%) of fluvastatin sodium crystal Form IX-1.

Example 54

A slurry of fluvastatin sodium crystal Form B (3.0 g) in isobutyl acetate (70 ml) was heated to reflux temperature. The material was recrystallized during reflux and MTBE (70 ml) was added dropwise to obtain a massive precipitate. The mixture was stirred at reflux temperature for additional 0.5 h. The mixture was cooled to room temperature. The product was filtered under nitrogen flow, washed with MTBE (2×10 ml) and dried at 50EC in a vacuum oven for 22 h to obtain 2.74 g (91%) of fluvastatin sodium crystal Form IX-1.

Example 55

Fluvastatin sodium crystal Form B (3.0 g) was almost completely dissolved in isobutyl acetate (70 ml) at reflux temperature. Dichloromethane (70 ml) was added dropwise to obtain precipitate. The mixture was cooled to room temperature. The product was filtered, washed with Dichloromethane (2×10 ml) and dried at 50EC in a vacuum oven for 25 h to obtain 2.5 g (82%) of fluvastatin sodium crystal Form IX-1.

Example 56

Fluvastatin sodium crystal Form B (3.0 g) was dissolved in ethanol (130 ml) at room temperature. The solution was filtered and hexanes (200 ml) were added dropwise. The mixture was stirred at room temperature for 19 h. The product was filtered under nitrogen flow, washed with hexanes (2×25 ml) and dried at 50EC in a vacuum oven for 24 h to obtain 1.2 g (41%) of amorphous fluvastatin sodium. A precipitate was observed in the mother-liquid after 20 days. The precipitate was dried at 50EC in a vacuum oven for 26 h to obtain fluvastatin sodium crystal Form IX-1.

Example 57

A slurry of fluvastatin sodium crystal Form B (3.0 g) in toluene (60 ml) and Cyclohexane (60 ml) was heated to reflux temperature for 22 h. The mixture was cooled to room temperature. The product was filtered under nitrogen flow and dried at 50EC in a vacuum oven for 24 h to obtain 2.6 g (85%) of fluvastatin sodium crystal Form IX-1.

Example 58

Fluvastatin sodium crystal Form B (3.0 g) was dissolved in THF (100 ml) at reflux temperature. The solution was filtered and hexanes (100 ml) were added dropwise at reflux temperature. The mixture was stirred at reflux temperature for 1 h and then was cooled to room temperature. The product was filtered under nitrogen flow, washed with hexanes (2×20 ml) and dried at 50EC in a vacuum oven for 19 h to obtain 2.5 g (83%) of fluvastatin sodium crystal Form IX-1.

Example 59

Fluvastatin sodium crystal Form B (3.0 g) was dissolved in THF (60 ml) at reflux temperature. The solution was filtered and MTBE (60 ml) was added dropwise at reflux temperature. The mixture was stirred at reflux temperature for 1 h and then was cooled to room temperature. The product was filtered under nitrogen flow, washed with MTBE (2×20 ml) and dried at 50EC in a vacuum oven for 18 h to obtain 1.9 g (63%) of fluvastatin sodium crystal Form IX-1.

Example 60

Fluvastatin sodium. crystal Form B (3.0 g) was dissolved in MEK (70 ml) at reflux temperature. MTBE (70 ml) was added dropwise at reflux temperature. The mixture was cooled to room temperature. The product was filtered under nitrogen flow and dried at 50EC in a vacuum oven for 29 h to obtain 0.7 g (24%) of fluvastatin sodium crystal Form IX-1.

11) Preparation of Fluvastatin Sodium Crystal Form XI

Example 61

Fluvastatin sodium (3.0 g) was almost completely dissolved in butan-2-ol (70 ml) at reflux temperature. During this time the material was recrystallized. Hexanes (70 ml) were added at reflux temperature to obtain a massive precipitate. The resulting suspension was stirred at reflux temperature for 4.5 h. Then, the mixture was cooled to room temperature. The product was isolated by filtration, washed with hexanes (2×15 ml) and dried at 50EC in a vacuum oven for 23.5 h to obtain 2.8 g (93%) of fluvastatin sodium crystal Form XI.

Example 62

Fluvastatin sodium (3.0 g) was almost completely dissolved in butan-2-ol (70 ml) at reflux temperature. During this time the material was recrystallized. n-pentane (70 ml) was added at reflux temperature to obtain a massive precipitate. The resulting suspension was stirred at reflux temperature for 4 h. Then, the mixture was cooled to room temperature. The product was isolated by filtration, washed with n-pentane (2×10 ml) and dried at 50EC in a vacuum oven for 23.5 h to obtain 2.76 g (92%) of fluvastatin sodium crystal Form XI.

Example 63

Fluvastatin sodium (3.0 g) was dissolved in butan-2-ol (70 ml) at reflux temperature. MTBE (70 ml) was added at reflux temperature to obtain a massive precipitate. The resulting suspension was stirred at reflux temperature for 5 h. Then, the mixture was cooled to room temperature. The product was isolated by filtration, washed with MTBE (2×10 ml) and dried at 50EC in a vacuum oven for 21 h to obtain 2.7 g (90%) of fluvastatin sodium crystal Form XI.

Example 64

Fluvastatin sodium (3.0 g) was almost completely dissolved in butan-2-ol (70 ml) at reflux temperature. During this time the material was recrystallized. Diethyl ether (70 ml) was added at reflux temperature to obtain a massive precipitate. The resulting suspension was stirred at reflux temperature for 4.5 h. Then, the mixture was cooled to room temperature. The product was isolated by filtration, washed with diethyl ether (2×10 ml) and dried at 50EC in a vacuum oven for 24 h to obtain 2.8 g (94%) of fluvastatin sodium crystal Form XI.

Example 65

Fluvastatin sodium (3.0 g) was almost completely dissolved in butan-2-ol (70 ml) at reflux temperature. During this time the material was recrystallized. n-heptane (70 ml) was added at reflux temperature to obtain a massive precipitate. The resulting suspension was stirred at reflux temperature for 4.5 h. Then, the mixture was cooled to room temperature. The product was isolated by filtration, washed with n-heptane (2×10 ml) and dried at 50EC in a vacuum oven for 24 h to obtain 2.8 g (94%) of fluvastatin sodium crystal Form XI.

Example 66

Fluvastatin sodium (3.0 g) was almost completely dissolved in butan-2-ol (70 ml) at reflux temperature. During this time the material was recrystallized. Chloroform (70 ml) was added dropwise at reflux temperature to obtain a massive precipitate. The resulting suspension was stirred at reflux temperature for 4 h. Then, the mixture was cooled to room temperature. The product was isolated by filtration, washed with Chloroform (2×10 ml) and dried at 50EC in a vacuum oven for 24 h to obtain 1.7 g (57%) of fluvastatin sodium crystal Form XI.

12) Preparation of Fluvastatin Sodium Crystal Form XI-2

Example 67

Fluvastatin sodium (3.0 g) was dissolved in propan-1-ol (60 ml) at reflux temperature. Hexanes (60 ml) were added dropwise at reflux temperature and the resulting mixture was stirred at this temperature for 1.5 h. Then, the mixture was cooled to room temperature. The product was isolated by filtration under nitrogen, washed with hexanes (2×20 ml) and dried at 50EC in a vacuum oven for 28 h to obtain 2.3 g (78%) of fluvastatin sodium crystal Form XI-2.

Example 68

Fluvastatin sodium (3.0 g) was dissolved in propan-1-ol (60 ml) at reflux temperature. MTBE (60 ml) was added dropwise at reflux temperature and the resulting mixture was stirred at this temperature for 40 minutes. Then, the mixture was cooled to room temperature. The product was isolated by filtration under nitrogen, washed with MTBE (2×30 ml) and dried at 50EC in a vacuum oven for 28 h to obtain 2.5 g (82%) of fluvastatin sodium crystal Form XI-2.

Example 69

Fluvastatin sodium (3.0 g) was dissolved in propan-1-ol (60 ml) at reflux temperature. Dichloromethane (60 ml) was added dropwise at reflux temperature and the resulting mixture was stirred at this temperature for 30 minutes. Then, the mixture was cooled to room temperature. The product was isolated by filtration under nitrogen, washed with dichloromethane (2×20 ml) and dried at 50EC in a vacuum oven for 24 h to obtain 0.3 g (11%) of fluvastatin sodium crystal Form XI-2.

13) Preparation of Fluvastatin Sodium Crystal Form XII

Example 70

Fluvastatin sodium crystal Form B (3.0 g) was dissolved in butan-1-ol (70 ml) at reflux temperature. 1,4-dioxane (140 ml) was added in two portions (2×70 ml) at reflux temperature during 18 h. Then, the turbid solution was cooled to room temperature and another portion of 1,4-dioxane (70 ml) was added. The mixture was stirred at room temperature for 23 h. Then, it was concentrated under reduced pressure and was stirred at room temperature for 9.5 h to obtain a precipitate. The product was filtered under nitrogen flow, washed with 1,4-dioxane (2×15 ml) and dried at 50EC in a vacuum oven for 20 h to obtain 0.35 g (12%) of fluvastatin sodium crystal Form XII.

14) Preparation of Fluvastatin Sodium Crystal Form XIII

Example 71

A suspension of fluvastatin sodium crystal Form B (3.0 g) in acetonitrile (600 ml) was stirred at reflux temperature for 2 h. The suspension was then cooled to 10EC using an ice-bath.

The product was filtered under nitrogen flow and dried at 50EC in a vacuum oven for 24 h to obtain 2.1 g (70%) of fluvastatin sodium crystal Form XIII.

15) Preparation of Fluvastatin Sodium Crystal form XVI

Example 72

Fluvastatin sodium (3.0 g) was almost completely dissolved in propan-2-ol (70 ml) at reflux temperature. Dichloromethane (70 ml) was added dropwise at reflux temperature. The resulting solution was stirred at reflux temperature for 3 h. Then, the mixture was cooled to room temperature and stirred at this temperature for 16 h. The product was isolated by filtration, washed with dichloromethane (2×10 ml) and dried at 50EC in a vacuum oven for 22 h to obtain 1.3 g (44%) of fluvastatin sodium crystal Form XVI.

16) Preparation of Fluvastatin Sodium Crystal Form XVII

Example 73

Fluvastatin sodium (3.0 g) was dissolved in propan-1-ol (60 ml) at reflux temperature. The resulting solution was stirred at reflux temperature for 3 h. During this time the material was recrystallized. Then, the mixture was cooled to room temperature. The product was isolated by filtration under nitrogen, washed with propan-1-ol (1×10 ml) and dried at 50EC in a vacuum oven for 21 h to obtain 0.2 g (7%) of fluvastatin sodium crystal Form XVII.

17) Preparation of Fluvastatin Sodium Crystal Form XVIII

Example 74

Fluvastatin sodium (3.0 g) was suspended in MEK (30 ml) at reflux temperature for 16 h. Then, the solvent was distilled out and the residue was dried in a vacuum oven for 24 h to obtain 2.7 g (90%) of fluvastatin sodium crystal Form XVIII.

Example 75

Fluvastatin sodium (3.0 g) was suspended in MEK (30 ml) at reflux temperature for 2.5 h. Then, the mixture was cooled to room temperature. The product was isolated by filtration under nitrogen, washed with MEK (2×15 ml) and dried at 50EC in a vacuum oven for 25.5 h to obtain 2.6 g (86%) of fluvastatin sodium crystal Form XVIII.

18) Preparation of Fluvastatin Sodium Crystal Form XIX

Example 76

Fluvastatin sodium Form XI (~300 mg) was placed on flat dishes with a diameter of 35 mm and introduced in a chamber with controlled relative humidity of about 80% for 11 days. Fluvastatin sodium Form XIX was recovered.

Example 77

Fluvastatin sodium Form XI (~300 mg) was placed on flat dishes with a diameter of 35 mm and introduced in a chamberwith controlled relative humidity of about 100% for 11 days. Fluvastatin sodium Form XIX was recovered.

Example 78

Fluvastatin sodium Form IV-1 (~300 mg) was placed on flat dishes with a diameter of 35 mm and introduced in a chamber with controlled relative humidity of about 80% for 11 days. Fluvastatin sodium Form XIX was recovered.

Example 79

Fluvastatin sodium Form IV-11(~300 mg) was placed on flat dishes with a diameter of 35 mm and introduced in a chamber with controlled relative humidity of about 100% for 11 days. Fluvastatin sodium Form XIX was recovered.

Example 80

Fluvastatin sodium Form XVI (~300 mg) was placed on flat dishes with a diameter of 35 mm and introduced in a chamber with controlled relative humidity of about 80% for 24 days. Fluvastatin sodium Form XIX was recovered.

Example 81

Fluvastatin sodium Form XVI (~300 mg) was placed on flat dishes with a diameter of 35 mm and introduced in a chamber with controlled relative humidity of about 100% for 24 days. Fluvastatin sodium Form XIX was recovered.

19) Preparation of Fluvastatin Sodium Crystal Form XIX-1

Example 82

Wet fluvastatin sodium crystal form XI (10.0 g) was stirred in water (10 ml) at room temperature for 6 h. Then, the product was filtered under nitrogen flow, washed with water (2 ml) and dried at 50EC in a vacuum oven for 21.5 h to obtain 3.8 g of fluvastatin sodium crystal form XIX-1.

20) Preparation of Fluvastatin Sodium Crystal Form XX

Example 83

Fluvastatin sodium Form XVI (~300 mg) was placed on flat dishes with a diameter of 35 mm and introduced in a chamber with controlled relative humidity of about 80% for 1 days. Fluvastatin sodium Form XX was recovered.

21) Preparation of Fluvastatin Sodium Crystal Form XXII

Example 84

About 300 mg fluvastatin sodium Form XV was placed on flat dishes with a diameter of 35 mm and introduced in a chamber with controlled relative humidity of about 100% for 14 days, and fluvastatin sodium Form XXII was recovered.

22) Preparation of Fluvastatin Sodium Crystal Form XXIII

Example 85

Fluvastatin sodium crystal Form B (5.0 g) was dissolved in propan-1-ol (100 ml) at reflux temperature. The material was recrystallized at reflux temperature after 1 h. The suspension was stirred at reflux temperature for additional 2 h. Then, the mixture was cooled to room temperature and stirred at this temperature for 16 h to obtain a massive precipitation. The product was filtered under nitrogen flow, washed with propan-1-ol (2×25 ml) and dried at 50EC in a vacuum oven for 72 h to obtain 3.3 g (66%) of fluvastatin sodium crystal Form XXIII.

23) Preparation of Fluvastatin Sodium Crystal Form XXIV

Example 86

Fluvastatin sodium crystal Form XV (5.0 g) was dissolved in water (14 ml) at reflux temperature. The mixture was stirred at reflux temperature for 1.5 h and then was cooled to room temperature. The mixture was stirred at room temperature for 16 h to obtain a massive precipitate. The product was filtered under nitrogen flow, washed with water (2×3 ml) and dried at 50EC in a vacuum oven for 22 h to obtain 4.5 g (90%) of fluvastatin sodium crystal Form XXIV.

Example 87

Fluvastatin sodium crystal Form XV (5.0 g) was dissolved in water (9 ml) at reflux temperature. The mixture was stirred at reflux temperature for 1.5 h and then was cooled to room temperature. The mixture was stirred at room temperature for 16 h to obtain a massive precipitate. The product was filtered under nitrogen flow, washed with water (1×5 ml) and dried at 50EC in a vacuum oven for 24 h to obtain 4.2 g (84%) of fluvastatin sodium crystal Form XXIV.

Example 88

Fluvastatin sodium crystal Form B (5.0 g) was dissolved in water (5 ml) at reflux temperature. The mixture was stirred at reflux temperature for 2 h and then was cooled to room temperature. The product was dried (without filtration) at 50EC in a vacuum oven for 24 h to obtain 4.4 g (88%) of fluvastatin sodium crystal Form XXIV.

Example 89

A slurry of fluvastatin sodium crystal Form B (8.0 g) in water (200 ml) was stirred at room temperature for 1 h. Diethyl ether (100 ml) was added and the mixture was stirred for 5 minutes. The organic and aqueous phases were separated. Traces of diethyl ether were removed from the aqueous phase under reduced pressure. The aqueous solution was lyophilized for 72 h to obtain fluvastatin sodium crystal Form XXIV.

Example 90

A slurry of fluvastatin sodium crystal Form B (8.0 g) in water (200 ml) was stirred at room temperature for 1 h. Diethyl ether (100 ml) was added and the mixture was stirred for 15 minutes. The organic and aqueous phases were separated. Traces of Diethyl ether were removed from the aqueous phase under reduced pressure. The aqueous solution was lyophilized for 96 h to obtain fluvastatin sodium crystal Form XXIV.

24) Preparation of Fluvastatin Sodium Crystal Form XXVI

Example 91

Fluvastatin sodium crystal Form B (3.0 g) was dissolved in 1,4-dioxane (20 ml) and water (1 ml) at reflux temperature. The solution was stirred at reflux temperature for 1 h. Then, the mixture was cooled to room temperature and stirred at this temperature for 1.5 h to obtain a massive precipitation. The product was dried at 50EC in a vacuum oven (without isolation by filtration) for 22 h to obtain 3.2 g (107%) of fluvastatin sodium crystal Form XXVI.

25) Preparation of Fluvastatin Sodium Crystal Form XXVII

Example 92

Fluvastatin sodium crystal Form B (3.0 g) was dissolved in 1,4-dioxane (20 ml) and water (1 ml) at reflux temperature. Hexanes (30 ml) were added dropwise at reflux temperature and the obtained mixture was stirred at this temperature for additional 1 h. Then, the mixture was cooled to room temperature and stirred at this temperature for 1 h to obtain a massive precipitation. The product was isolated by filtration, washed with hexanes (3×20 ml) and dried at 50EC in a vacuum oven for 22 h to obtain 2.5 g (82%) of fluvastatin sodium crystal Form XXVII.

26) Preparation of Fluvastatin Sodium Crystal Form XXIX

Example 93

Fluvastatin sodium crystal Form XV (5.0 g) was stirred in 1,4-dioxane (80 ml) at reflux temperature for 16 h. Then, the suspension was cooled to room temperature. The product was filtered under nitrogen flow, washed with 1,4-dioxane (4×25 ml) and dried at 50EC in a vacuum oven for 24 h to obtain 3.8 g (76%) of fluvastatin sodium crystal Form XXIX.

27) Preparation of Fluvastatin Sodium Crystal Form XXX

Example 94 fluvastatin sodium crystal Form XV (5.0 g) was stirred in methylethylketone (MEK) (70 ml) at reflux temperature for 16 h. Then, the suspension was cooled to room temperature. The product was filtered under nitrogen flow, washed with MEK (4×15 ml) and dried at 50EC in a vacuum oven for 22 h to obtain 4.2 g (84%) of fluvastatin sodium crystal Form XXX.

Example 95

Fluvastatin sodium crystal Form XV (5.0 g) was stirred in tetrahydrofuran (THF) (50 ml) at reflux temperature for 16 h. Then, the suspension was cooled to room temperature. The product was filtered under nitrogen flow, washed with THF (2×15 ml) and dried at 50EC in a vacuum oven for 21 h to obtain 3.9 g (78%) of fluvastatin sodium crystal Form XXX.

Example 96

Fluvastatin sodium crystal Form XV (5.0 g) was stirred in acetone (75 ml) at reflux temperature for 16 h. Then, the suspension was cooled to room temperature. The product was filtered under nitrogen flow, washed with acetone (3×25 ml) and dried at 50EC in a vacuum oven for 24 h to obtain 4.0 g (80%) of fluvastatin sodium crystal Form XXX.

Example 97

Fluvastatin sodium crystal Form XV (5.0 g) was stirred butan-2-ol (60 ml) at reflux temperature for 16 h. Then, the suspension was cooled to room temperature. The product was filtered under nitrogen flow, washed with butan-2-ol (3×25 ml) and dried at 50EC in a vacuum oven for 25 h to obtain 4.2 g (84%) of fluvastatin sodium crystal Form XXX.

Example 98

Fluvastatin sodium crystal Form XV (5.0 g) was stirred butan-1-ol (60 ml) at reflux temperature for 16 h. Then, the suspension was cooled to room temperature. The product was filtered under nitrogen flow, washed with butan-2-ol (4×25 ml) and dried at 50EC in a vacuum oven for 24 h to obtain 4.2 g (84%) of fluvastatin sodium Form XXX.

Example 99

Fluvastatin methyl ester (3.0 g) was added to a solution of NaOH (1 eq.) in water (0.75 ml) and methanol (7.5 ml). The mixture was stirred at about 65EC for 3.5 h. Then, another portion of NaOH (0.5 eq.) in water (0.4 ml) was added. After another 40 min the starting material was no longer detectable by HPLC. Acetone (58 ml) was dripped into the solution over 25 min. Turbidity appeared in the solution. The mixture was cooled slowly to room temperature and stirred overnight. The product was isolated by filtration under nitrogen, washed with acetone (20 ml) and dried at 50EC in a vacuum oven for 24 h to obtain 0.25 g (8.2%) of fluvastatin sodium Form XXX.

28) Preparation of Fluvastatin Sodium Crystal Form XXXI

Example 100

Fluvastatin sodium crystal Form XV (5.0 g) was stirred ethanol (100 ml) at reflux temperature for 23 h. Then, the suspension was cooled to room temperature. The product was filtered under nitrogen flow, washed with ethanol (2×10 ml) and dried at 50EC in a vacuum oven for 21 h to obtain 4.4 g (88%) of fluvastatin sodium crystal Form XXXI.

29) Preparation of Fluvastatin Sodium Crystal Form XXXIII

Example 101

Fluvastatin sodium crystal Form XV (5.0 g) was stirred in absolute ethanol (40 ml) at reflux temperature for 16 h. Then, the suspension was cooled to room temperature. The product was filtered under nitrogen flow, washed with absolute ethanol (4×20 ml) and dried at 50EC in a vacuum oven for 24 h to obtain 4.2 g (84%) of fluvastatin sodium crystal Form XXXIII.

Example 102

Absolute ethanol was added in 4 portions (1×60 ml, 3×20 ml) to fluvastatin sodium Form B (5.0 g). The heterogeneous mixture was at reflux temperature for 1.25 h. Then, the suspension was cooled to room temperature and stirred at this temperature for 23 h. The product was filtered under nitrogen flow, washed with absolute ethanol (2×20 ml) and dried at 50EC in a vacuum oven for 22 h to obtain 2.3 g (45%) of fluvastatin sodium Form XXXIII.

Example 103

Absolute ethanol was added in two portions (2×100 ml) to fluvastatin sodium Form B (5.0 g). The heterogeneous mixture was at reflux temperature for 3 h. Then, the suspension was cooled to room temperature and stirred at this temperature for 18 h. The product was filtered under nitrogen flow, washed with absolute ethanol (1×20 ml) and dried at 50EC in a vacuum oven for 24 h to obtain 0.8 g (16%) of Fluvastatin sodium Form XXXIII.

30) Preparation of Fluvastatin Sodium Crystal Form XXXIV

Example 104

Fluvastatin sodium crystal Form XV (5.0 g) was stirred in DMSO (50 ml) at 100EC for 16 h. Then, the suspension was cooled to room temperature. The product was filtered under nitrogen flow, washed with DMSO (2×25 ml) and dried at 50EC in a vacuum oven for 24 h to obtain 3.6 g (71%) of fluvastatin sodium crystal Form XXXIV.

31) Preparation of Fluvastatin Sodium Crystal Form XXXV

Example 105

Fluvastatin sodium crystal Form XV (5.0 g) was stirred in DMF (50 ml) at 95EC for 16h. Then, the suspension was cooled to room temperature. The product was filtered under nitrogen flow, washed with DMF (2×25 ml) and dried at 50EC in a vacuum oven for 24 h to obtain 4.9 g (98%) of fluvastatin sodium crystal form XXXV.

32) Preparation of Fluvastatin Sodium Crystal Form XXXVI

Example 106

A suspension of fluvastatin sodium crystal Form XI wet (10.0 g) in water (10 ml) was stirred at room temperature for 6 h. The product was then filtered under nitrogen flow and washed with water (1×2 ml) to obtain 9.6 g (88%) of wet fluvastatin sodium crystal Form XXXVI.

33) Preparation of Fluvastatin Sodium Crystal Form XXXVII

Example 107

Fluvastatin sodium Form XI (6.0 g) was suspended in water (12 ml) at room temperature for 5.75 h. Then, the product was filtered under nitrogen flow and dried at 50EC in a vacuum oven for 23 h to obtain 4.1 g (68%) of fluvastatin sodium crystal Form XXXVII.

34) Preparation of Fluvastatin Sodium Crystal Form XXXVIII

Example 108

Fluvastatin sodium Form XI (2.5 g) was suspended in absolute ethanol (13.5 ml) at reflux temperature for 16 h. Then, the suspension was cooled to room temperature and stirred at this temperature for 3 h. The product was filtered under nitrogen flow, washed with absolute ethanol (2×10 ml) and dried at 50EC in a vacuum oven for 23 h to obtain 2.0 g (79%) of fluvastatin sodium crystal Form XXXVIII.

Example 109

Fluvastatin methyl ester (2.0 g) was added to a solution of NaOH (1 eq.) in EtOH (15 ml). The mixture was stirred at about 70EC for 4 h (it became clear and turned to a slurry), after which the starting material was not detected by HPLC. Then, 40 ml of ethyl acetate was dripped into the mixture and it was cooled slowly to room temperature and stirred overnight. The product was isolated by filtration under nitrogen, washed with ethyl acetate (10 ml) and dried at 50EC in a vacuum oven for 24 h to obtain fluvastatin sodium Form XXXVIII (1.78 g, 87.4%).

Example 110

Fluvastatin sodium crystal Form XI (2.5 g) was suspended in absolute ethanol (13.5 ml) at reflux temperature for 16 h. The suspension was cooled to room temperature and stirred at this temperature for 3 h. The product was filtered under nitrogen flow, washed with absolute ethanol (2×10 ml) and dried at 50EC in a vacuum oven for 23 h to obtain 2.0 g (79%) of fluvastatin sodium crystal Form XXXVIII.

35) Preparation of Fluvastatin Sodium Crystal Form XXXIX

Example 111

In a 100 ml flask were placed Fluvastatin methyl ester (2.0 g) and a solution of NaOH (0.19 g) in EtOH (5 ml). The mixture was stirred at reflux for 3.5 h and propan-2-ol (40 ml) was added. The slurry was cooled to room temperature and stirred over night. The product was isolated by filtration under nitrogen, washed with propan-2-ol (20 ml) and dried at 50EC in a vacuum oven for 24 h to obtain 1.93 g (95%) of fluvastatin sodium crystal Form XXXIX.

36) Preparation of Fluvastatin Sodium Crystal Form XLI

Example 112

Fluvastatin sodium Form XV (6.0 g) was dissolved in water (16 ml) at reflux temperature. Acetonitrile (60 ml) was added dropwise and the mixture was stirred at reflux temperature for 1 h. Then, the mixture was cooled to room temperature and stirred at this temperature for 16 h. Another portion of acetonitrile (70 ml) was added to obtain precipitation. After 3.5 h, the product was isolated by filtration under nitrogen, washed with acetonitrile (2×20 ml) and dried at 50EC in a vacuum oven for 25 h to obtain 2.96 g (49%) of fluvastatin sodium crystal Form XLI.

37) Preparation of Fluvastatin Sodium Crystal Form XLII

Example 113

Fluvastatin (3.0 g) was completely dissolved in MEK (40 ml) at room temperature. The solution was filtered to obtain a clear solution and 97% NaOH (0.29 g) dissolved in MeOH (3 ml) was added to the solution. The solution was stirred at room temperature for 94 h to obtain a gelatinous precipitate. The product was filtered under nitrogen flow washed with MEK (2×11 ml) and dried at 50EC is a vacuum oven for 25.5 h to obtain 2.6 (g) (85.5%) of fluvastatin sodium crystal Form XLII.

Example 114

Fluvastatin (2.0 g) was completely dissolved in MeOH (5 ml) at reflux temperature and NaOH (s) (0.19 g) was added. The solution was stirred at reflux temperature for 3 h to obtain a precipitate having a paste-like consistency. ethyl acetate (40 ml) was added dropwise at reflux temperature and then the solution was cooled to room temperature and the slurry was stirred for 3 h. The product was filtered under nitrogen flow, washed with ethyl acetate (2×10 ml) and dried at 50EC in a vacuum oven for 23 h to obtain 1.58 g (77.5%) of fluvastatin-sodium form XLII.

Example 115

Fluvastatin (3.0 g) was completely dissolved in dichloromethane (35 ml) at room temperature and the solution was filtered to obtain clear solution. NaOH (s) (0.29 g) dissolved in MeOH (3 ml) was added to the solution and the solution was then stirred at room temperature for 23 h to obtain a precipitate. The product was filtered under nitrogen flow, washed with dichloromethane (2×10 ml) and dried at 50° C. in a vacuum oven for 42 h to obtain 2.3 g (75%) of Fluvastatin-sodium form XLII.

Example 116

Fluvastatin-diol (3.0 g) was completely dissolved in dichloromethane (35 ml) at room temperature and the solution was filtered to obtain clear solution. NaOH (s) (0.29 g) dissolved in EtOH (5 ml) was added to the solution and the solution was then stirred at room temperature for 23 h to obtain a precipitate. The product was filtered under nitrogen flow, washed with dichloromethane (2×10 ml) and dried at 50° C. in a vacuum oven for 42 h to obtain 1.88 g (61.5%) of fluvastatin-sodium form XLII.

38) Preparation of Fluvastatin Sodium Crystal Form XLIII

Example 117

Fluvastatin sodium Form B (5.0 g) was dissolved in water (15 ml) at reflux temperature. Propan-2-ol (45 ml) was added dropwise and the mixture was stirred at reflux temperature for 2 h. Then, the mixture was cooled to room temperature and stirred at this temperature for 16 h. Another portion of propan-2-ol (50 ml) was added to obtain a massive precipitation. After 7.5 h, the product was isolated by filtration under nitrogen, washed with propan-2-ol (2×25 ml) and dried at 50EC in a vacuum oven for 24 h to obtain 0.74 g (15%) of fluvastatin sodium Form XLIII.

Example 118

Fluvastatin methyl ester (2.0 g) was added to a solution of NaOH (1 eq.) in water. The mixture was stirred at about 70EC for 2 h until the raw material wasn't observed by HPLC. After this time, propan-2-ol (10 ml) was dripped and the solution was cooled slowly to room temperature. Another 40 ml of propan-2-ol (in 3 portions) were added at room temperature to the solution but no precipitation was ECcurred. The solution was stirred overnight and a gel-like precipitate formed. The mixture was heated to reflux to dissolve the gel. The mixture was then allowed to cool to room temperature. A yellow slurry was obtained. After stirring overnight, another 15 ml of propan-2-ol were added dropwise. The product was isolated by filtration under nitrogen, washed with propan-2-ol (25 ml) and dried at 50EC in a vacuum oven for 24 h to obtain 0.46 g (22.6%) of fluvastatin sodium Form XLIII.

39) Preparation of Fluvastatin Sodium Crystal Form XLIV

Example 119

Amorphous fluvastatin sodium (1.5 g) was suspended in propan-2-ol (31 ml) at reflux temperature for 4.25 h. Then, the suspension was cooled to room temperature and stirred at this temperature for 1 h. The product was filtered under nitrogen flow, washed with propan-2-ol (2×35 ml) and dried at 50EC in a vacuum oven for 23 h to obtain 0.4 g (25%) of fluvastatin sodium Form XLIV.

Example 120

Fluvastatin methyl ester (3.0 g) was added to acetone (30 ml) and the solution was stirred at room temperature. NaOH (1 eq.) in EtOH (3 ml) was added to the solution. The mixture was stirred overnight. The product that precipitated was isolated by filtration under nitrogen, washed with acetone (100 ml) and dried at 50EC in a vacuum oven for 24 h to obtain 2.45 g (80.8%) of fluvastatin sodium Form XLIV.

40) Preparation of Fluvastatin Sodium Crystal Form XLV

Example 121

A suspension of fluvastatin sodium Form Am1 (2.6 g) in propan-2-ol (36 ml) was stirred at room temperature for 25 h. The product was then filtered under nitrogen flow, washed with propan-2-ol (2×20 ml) and dried at 50EC in a vacuum oven for 20.5 h to obtain 2.4 g (92%) of fluvastatin sodium crystal Form XLV.

Preparation of Form Am1

Fluvastatin-diol-methyl ester (FDME) (3.0 g) was added to cyclohexane (60 ml) and the mixture was heated to reflux. NaOH (1 eq.) dissolved in MeOH (3 ml) was added to the slurry solution which became clear. After 15 min precipitant was appeared. After another hour the mixture was cooled to rt, cyclohexane (40 ml) was added and it was stirred overnight. The product was isolated by filtration under nitrogen, washed with cyclohexane (90 ml) and dried at 50° C. in a vacuum over for 24 hours to obtain 2.73 gr (90%) of Fluvastatin sodium Am1.

41) Preparation of Fluvastatin Sodium Crystal Form XLVI

Example 122

In a 100 ml flask were placed fluvastatin methyl ester (2.42 g), EtOH (5 ml) and a solution of NaOH (0.23 g) in EtOH (7 ml). The mixture was stirred at reflux for 2.5 h and acetonitrile (50 ml) was added. The slurry was stirred at reflux for another 3 h then cooled to room temperature and stirred over night. The product was isolated by filtration under nitrogen and dried at 50EC in a vacuum oven for 24 h to obtain 2.02 g (83%) of fluvastatin sodium crystal Form XLVI.

42) Preparation of Fluvastatin Sodium Crystal Form XLVII

Example 123

About 300 mg fluvastatin sodium Form XVIII was placed on flat dishes with a diameter of 35 mm and introduced in a chamber with controlled relative humidity of about 80% for 25 days, and fluvastatin sodium form XLVII was recovered.

43) Preparation of Fluvastatin Sodium Crystal Form XLVIII

Example 124

To a three necked flask was added fluvastatin methyl ester (3.0 g) and NaOH (1 eq.) dissolved in MeOH (7.5 ml). The mixture refluxed for 6.5 h. Then, acetonitrile (50 ml) was added dropwise to the refluxing solution over 10 min. The mixture was then cooled to room temperature and stirred for 46 h. The product was isolated by filtration under nitrogen, washed with acetonitrile (50 ml) and dried at 50EC in a vacuum oven for 24 h to obtain 1.84 g (60.7%) of fluvastatin sodium Form XLVIII.

Example 125

Fluvastatin sodium Form B (5.0 g) was stirred in MeOH (40 ml) at reflux for 5 h. The slurry was cooled to room temperature and stirred at room temperature for 17 h. The product was filtered under nitrogen flow, washed with MeOH (2×20 ml) and dried at 50° C. in a vacuum oven for 21.5 h to obtain 0.28 g (5.6%) of fluvastatin sodium Form XLVIII.

Example 126

Fluvastatin sodium Form B (5.0 g) was dissolved in MeOH (24 ml) at room temperature. The solution was heated to reflux temperature to obtain a precipitate. The slurry formed was cooled to room temperature and stirred at room temperature for 19.5 h. The product was filtered under nitrogen flow, and dried at 50° C. in a vacuum oven for 24 h to obtain 0.53 g (10.6%) of fluvastatin sodium Form XLVIII.

Example 127

Fluvastatin (3 g) was completely dissolved in MeOH (15 ml) at reflux temperature. Then, the solution was filtered to obtain a clear solution and heated to reflux again. NaOH (s) (0.29 g) was added at reflux temperature to obtain a precipitate. The slurry was cooled to room temperature to obtain a paste-like mixture. Acetone (30 g) was added dropwise at room temperature and the solution stirred at room temperature for 21 h to obtain a massive precipitate. The product was filtered under nitrogen flow, washed with acetone (2×15 ml) and dried at 50° C. in a vacuum oven for 22.5 h to obtain 1.89 g (62%) of fluvastatin sodium Form XLVIII.

44) Preparation of Fluvastatin Sodium Crystal Form XLIX

Example 128

Fluvastatin sodium crystal Form B (5.0 g) was dissolved in methanol (40 ml) at room temperature. The solution was heated to reflux temperature and MTBE (100 ml) was added dropwise to obtain a precipitate. The obtained suspension was stirred at reflux temperature for 1 h. Then, the mixture was cooled to room temperature and stirred at this temperature for 16 h. The product was filtered under nitrogen flow, washed with MTBE (2×10 ml) and dried at 50EC in a vacuum oven for 24 h to obtain 3.2 g (64%) of fluvastatin sodium crystal Form XLIX.

45) Preparation of Fluvastatin Sodium Crystal Form L

Example 129

Fluvastatin sodium (5.0 g) was dissolved in methanol (35 ml) at room temperature. The solution was heated to reflux temperature and ethyl acetate (100 ml) was added dropwise. A precipitation was obtained during addition of ethyl acetate. The mixture was stirred at reflux temperature for 1.5 h. Then, the suspension was cooled to room temperature and stirred at this temperature for 16 h. The product was filtered under nitrogen flow and dried at 50EC in a vacuum oven for 24 h to obtain 0.7 g (14%) of Fluvastatin sodium Form L.

46) Preparation of Fluvastatin Sodium Crystal Form LI

Example 130

Fluvastatin sodium crystal Form B (5.0 g) was dissolved in methanol (50 ml) at room temperature. The solution was heated to reflux temperature and acetonitrile (100 ml) was added dropwise to obtain a precipitate. The obtained suspension was stirred at reflux temperature for 1 h. Then, the mixture was cooled to room temperature and stirred at this temperature for 16 h. The product was filtered under nitrogen flow, washed with acetonitrile (2×115 ml) and dried at 50EC in a vacuum oven for 23 h to obtain 0.73 g (15%) of fluvastatin sodium crystal Form LI.

47) Preparation of Fluvastatin Sodium Crystal Form LIII

Example 131

Fluvastatin sodium crystal Form B (16.0 g) was dissolved in methanol (112 ml) at room temperature. The solution was heated to reflux temperature and ethyl acetate (320 ml) was added dropwise to obtain a precipitate. The obtained suspension was stirred at reflux temperature for 1.5 h. Then, the mixture was cooled to room temperature and stirred at this temperature for 16 h. The product was filtered under nitrogen flow, washed with ethyl acetate (1×25 ml) and dried at 50EC in a vacuum oven for 23.5 h to obtain 2.1 g (13%) of fluvastatin sodium crystal Form LIII.

48) Preparation of Fluvastatin Sodium Crystal Form LIV

Example 132

Fluvastatin (3.52 g) was stirred in a solution of $H_2O$ (9.9 ml) and NaOH (s) (0.32 g) at room temperature to obtain a mud-like suspension. The suspension was stirred at room temperature over night. The product was filtered under nitrogen flow, washed with $H_2O$ (2×3 ml) and dried at 50° C. in a vacuum oven for 24 h to obtain 3.36 g (65.8%) of fluvastatin sodium Form LIV.

49) Preparation of Fluvastatin Sodium Crystal Form LV

Example 133

Fluvastatin methyl ester (3.0 g) was added to acetonitrile (60 ml) and dissolved by heating the mixture to reflux. The solution was then cooled to about 40EC and NaOH (1 eq.) dissolved in MeOH (7.5 ml) was added. Turbidity appeared immediately. After 30 minutes an oil residue separated from the mixture. The mixture was heated again to about 55EC for 3 h to dissolve the oil. The product was isolated by filtration under nitrogen, washed with acetonitrile (40 ml) and dried at 50EC in a vacuum oven for 24 h to obtain 2.48 g (81.1%) of fluvastatin sodium Form LV.

50) Preparation of Fluvastatin Sodium Crystal Form LVI

Example 134

In a 250 ml flask were placed Fluvastatin-acetonide-methylester (4.4 g), THF (44 ml) and 1.5% HCl solution (0.67 ml). The mixture was stirred at room temperature for 10 h, then NaOH (0.25 g) was added and the solvents were evaporated. The residue was dissolved in acetone (80 ml), NaOH (0.43 g) was added and the mixture was stirred at room temperature over night. The product was isolated by filtration under nitrogen, washed with acetone (50 ml) and dried at 50EC in a vacuum oven for 24 h to obtain 1.37 g of fluvastatin sodium crystal Form LVI.

51) Preparation of Fluvastatin Sodium Crystal Form LVII

Example 135

Fluvastatin sodium Form VII (20.5 g) was suspended in absolute ethanol (246 ml) at room temperature for 21 h. The product was then filtered under nitrogen flow, washed with absolute ethanol (2×40 ml) and dried at 50EC in a vacuum oven for 24 h to obtain 11.8 g (58%) of fluvastatin sodium Form LVII.

52) Preparation of Fluvastatin-Sodium Crystal Form LVIII

Example 136

Propan-2-ol (120 ml) was heated to reflux temperature. Fluvastatin sodium (5.0 g) was added to the boiled solvent. The mixture was stirred at reflux temperature for 3 h. Then, the suspension was cooled to room temperature and stirred at this temperature for 16 h. The product was filtered under nitrogen flow, washed with propan-2-ol (2×25 ml) and dried at 50EC in a vacuum oven for 22 h to obtain 4.7 g (95%) of fluvastatin sodium Form LVIII.

53) Preparation of Fluvastatin-Sodium Crystal Form LX

Example 137

Fluvastatin sodium crystal Form B (16.0 g) was dissolved in methanol (112 ml) at room temperature. The solution was heated to reflux temperature and ethyl acetate (320 ml) was added dropwise to obtain a precipitate. The obtained suspension was stirred at reflux temperature for 1.5 h. Then, the mixture was cooled to room temperature and stirred at this temperature for 16 h. The product was filtered under nitrogen flow, washed with ethyl acetate (1×20 ml) and dried at 50EC in a vacuum oven for 24 h to obtain 2.3 g (14%) of fluvastatin sodium crystal Form LX.

54) Preparation of Fluvastatin-Sodium Crystal Form LXIV

Example 138

In a 3 neck flask were placed fluvastatin methyl ester (3.0 g) and MeOH (30 ml). The mixture was heated to reflux for dissolution and NaOH (0.42) was added in two portions. Precipitant was appeared at reflux temperature and wasn't dissolved after addition of another 45 ml of MeOH during 4 h. The slurry mixture was cooled to room temperature and stirred over night. The precipitant was dissolved, acetone (150 ml) was added and the mixture was stirred at room temperature for 22 h. The product was isolated by filtration under nitrogen, washed with acetone (35 ml) and dried at 50EC in a vacuum oven for 22.5 h to obtain 1.68 g of fluvastatin sodium crystal Form LXIV.

Example 139

Fluvastatin methyl ester (15.0 g) was dissolved in acetone (225 ml) and filtered. A solution of NaOH (1.46 g) in MeOH (15 ml) was added and the solution was stirred at room temperature. After 2 h a solution of NaOH (0.73 g) in MeOH (15 ml) was added and the mixture was stirred over night. The product was isolated by filtration under nitrogen, washed with acetone and dried at 50EC in a vacuum oven for 24 h to obtain fluvastatin sodium form LXIV.

Example 140

Fluvastatin methyl ester (15.0 g) was dissolved in acetone (225 ml) and filtered. A solution of NaOH (1.46 g) in MeOH (15 ml) was added and the solution was stirred at room temperature. After 2 h a solution of NaOH (0.73 g) in MeOH (15 ml) was added. After 2 h the mixture was cooled to 14EC and stirred at this temperature over night. The product was isolated by filtration under nitrogen, washed with acetone and dried at 50EC in a vacuum oven for 24 h to obtain fluvastatin sodium form LXIV.

55) Preparation of Fluvastatin-Sodium Crystal Form LXV

Example 141

In a 100 ml flask were placed Fluvastatin methyl ester (3.0 g), MeOH (20 ml) and NaOH (0.29 g). After a clear solution was obtained propan-2-ol (80 ml) was added and the solution was stirred at room temperature over night. A little precipitation occurred, propan-2-ol (40 ml) was added and the solution was stirred at room temperature for another night. The product was isolated by filtration under nitrogen, washed with acetone (35 ml) and dried at 50EC in a vacuum oven for 22.5 h to obtain 0.92 g of fluvastatin sodium crystal Form LXV.

Example 142

Fluvastatin methyl ester (3.0 g) was dissolved in MeOH (15 ml) by heating to reflux. NaOH (0.29 g) was added and the clear solution was stirred at reflux for 30 min, then acetone (75 ml) was added. The solution was cooled to room temperature and stirred over night. The product was isolated by filtration under nitrogen, washed with acetone (35 ml) and dried at 50EC in a vacuum oven for 21.5 h to obtain 1.34 g of fluvastatin sodium crystal Form LXV.

56) Preparation of Fluvastatin-Sodium Crystal Form LXVI

Example 143

In a 50 ml flask were placed fluvastatin sodium crystal Form VI (1.98 g) and water (4 ml), then the mixture was heated to reflux for dissolution. After 2 h the solution was cooled to room temperature and stirred over night. The product was isolated by filtration under nitrogen, washed with water (3 ml) and dried at 50EC in a vacuum oven for 24 h to obtain 1.25 g (63%) of fluvastatin sodium crystal Form LXVI.

Example 144

Fluvastatin sodium crystal Form B (5.0 g) was dissolved in water (10 ml) at reflux temperature. The solution was stirred at reflux temperature for 2 h. Then, the solution was cooled to room temperature and stirred at this temperature for 16 h to obtain a precipitate. The product was filtered under nitrogen flow, washed with water (2×2 ml) and dried at 50EC in a vacuum oven for 24.5 h to obtain 4.4 g (89%) of fluvastatin sodium crystal Form LXVI.

Example 145

Fluvastatin sodium crystal Form XV (5.0 g) was dissolved in water (14 ml) at reflux temperature. The solution was stirred at reflux temperature for 1.25 h. Then, the solution was cooled to room temperature and stirred at this temperature for 16 h to obtain a precipitate. The product was filtered under nitrogen flow, washed with water (2×3 ml) and dried at 50EC in a vacuum oven for 24 h to obtain 4.2 g (84%) of fluvastatin sodium crystal Form LXVI.

57) Preparation of Fluvastatin-Sodium Crystal Form LXVII

Example 146

Fluvastatin methyl ester (3.0 g) was dissolved in acetone (45 ml) and a solution of NaOH (0.36 g) in MeOH (5 ml) was added. After 3 h NaOH (0.072 g) was added and the mixture was stirred at room temperature for another 21 h. NaOH (0.073 g) was added and the mixture was stirred for another 4 h. The product was isolated by filtration under nitrogen, washed with acetone (55 ml) and dried at 50EC in a vacuum oven for 24 h to obtain 2.64 g of fluvastatin sodium crystal Form LXVII.

Example 147

Fluvastatin methyl ester (3.0 g) was dissolved in acetone (45 ml), a solution of NaOH (0.58 g) in MeOH (8 ml) was added and the mixture was stirred at room temperature for another 3.75 h. The product was isolated by filtration under nitrogen, washed with acetone (40 ml) and dried at 50EC in a vacuum oven for 21 h to obtain 2.54 g of fluvastatin sodium crystal Form LXVII.

Example 148

Fluvastatin methyl ester (10.0 g) was dissolved in acetone (150 ml) and a solution of NaOH (0.94 g) in MeOH (10 ml) was added. After 26.5 h, NaOH (0.47 g) was added and the mixture was stirred at room temperature over night. The product was isolated by filtration under nitrogen, washed with acetone (20 ml) and dried at 50EC in a vacuum oven for 23 h to obtain 8.01 g of fluvastatin sodium crystal Form LXVII.

58) Preparation of Fluvastatin-Sodium Crystal Form LVIII

Example 149

Fluvastatin methyl ester (3.0 g) was dissolved in acetone (45 ml) and a solution of NaOH (0.44 g) in MeOH (6 ml) was added. After 29 h, NaOH (0.14 g) was added and the mixture was stirred at room temperature for another 1 h, then it was cooled with ice bath for 30 min. The product was isolated by filtration under nitrogen, washed with acetone (38 ml) and dried at 50EC in a vacuum oven for 22 h to obtain 2.76 g of fluvastatin sodium crystal Form LXVIII.

Example 150

Fluvastatin methyl ester (15.0 g) was dissolved in acetone (225 ml) and filtered. A solution of NaOH (1.46 g) in MeOH (15 ml) was added and the solution was stirred at room temperature. After 27 h, a solution of NaOH (0.73 g) in MeOH (15 ml) was added and the mixture was stirred over night. The product was isolated by filtration under nitrogen, washed with acetone and dried at 50EC in a vacuum oven for 24 h to obtain fluvastatin sodium form LXVIII.

59) Preparation of Fluvastatin Sodium Crystal Form LXIX

Example 151

In a 50 ml flask were placed fluvastatin sodium crystal Form VI (1.63 g) and propan-2-ol (28 ml) then the mixture was heated to reflux. After 2 h, propan-2-ol (4 ml) was added, the slurry was stirred at reflux for another 20 min, cooled to room temperature and stirred over night. The product was isolated by filtration under nitrogen, washed with propan-2-ol (30 ml) and dried at 50EC in a vacuum oven for 24 h to obtain 1.52 g (93%) of fluvastatin sodium crystal Form LXIX.

60) Preparation of Fluvastatin Sodium Crystal Form LXX

Example 152

In a 100 ml flask were placed fluvastatin sodium crystal Form LXVII (2.0 g) and water (3.4 ml). The mixture was heated to reflux for dissolving and acetone (34 ml) was added. After 2 h, the mixture was cooled to room temperature and stirred over night. The product was isolated by filtration under nitrogen, washed with acetone (20 ml) and dried at 50EC in a vacuum oven for 24 h to obtain 1.69 g (84.5%) of fluvastatin sodium crystal Form LXX.

61) Preparation of Fluvastatin Sodium Crystal Form LXXI

Example 153

In a 100 ml flask were placed fluvastatin sodium crystal Form LXVII (2.0 g) and water (2 ml). The mixture was heated to reflux and acetone (74 ml) was added. After 2 h, the mixture was cooled to room temperature and stirred over night. The product was isolated by filtration under nitrogen, washed with acetone (20 ml) and dried at 50EC in a vacuum oven for 24 h to obtain 1.85 g (92.5%) of fluvastatin sodium crystal Form LXXI.

62) Preparation of Fluvastatin Sodium Crystal Form LXXII

Example 154

In a 100 ml flask were placed fluvastatin sodium crystal Form VI (1.33 g), acetone (28 ml) and water (0.7 ml). The mixture was heated to reflux for 2 h, then cooled to room temperature and stirred over night. The product was isolated by filtration under nitrogen, washed with acetone (20 ml) and dried at 50EC in a vacuum oven for 24 h to obtain 1.26 g (95%) of fluvastatin sodium crystal Form LXXII.

Example 155

In a 100 ml flask were placed fluvastatin sodium crystal Form VI (1.12 g) and acetonitrile (19 ml). The mixture was heated to reflux for 2 h, then cooled to room temperature and stirred over night. The product was isolated by filtration under nitrogen, washed with acetonitrile (20 ml) and dried at 50EC in a vacuum oven for 24 h to obtain 1.02 g (86%) of fluvastatin sodium crystal Form LXXII.

63) Preparation of Fluvastatin Sodium Crystal Form LXXIV

Example 156

A suspension of fluvastatin sodium crystal Form B (30.0 g) in a mixture of propan-2-ol (501 ml) and water (51 ml) was heated to reflux temperature for 16 h. The suspension was then cooled to room temperature. The product was filtered under nitrogen flow, washed with propan-2-ol (2×25 ml) and dried at 50EC in a vacuum oven for 21.5 h to obtain 4.7 g (16%) of fluvastatin sodium crystal Form LXXIV.

Example 157

A suspension of fluvastatin sodium crystal Form B (2.0 g) in a mixture of propan-2-ol (33.3 ml) and water (4.3 ml) was heated to reflux temperature for 4 h. The suspension was then cooled in an ice-bath. The product was filtered under nitrogen flow, washed with propan-2-ol (2×10 ml) and dried at 50EC in a vacuum oven for 17.5 h to obtain 0.4 g (20%) of fluvastatin sodium crystal Form LXXIV.

64) Preparation of Fluvastatin Sodium Crystal Form LXXV

Example 158

Fluvastatin sodium crystal Form XXX (2.0 g) was refluxed in MeOH (10 ml) for 15 h, cooled to room temperature and stirred for another 2 h. The product was isolated by filtration under nitrogen, washed with MeOH (15 ml) and dried at 50EC in a vacuum oven for 24 h to obtain 0.48 g (24%) of fluvastatin sodium crystal Form LXXV.

65) Preparation of Fluvastatin Sodium Crystal Form LXXVI

Example 159

A 250 round bottom flask was loaded with fluvastatin methyl ester (12.0 g), EtOH (60 ml), water (36 ml) and NaOH (1 eq.). After 2 h the ethanol was evaporated and the residue was divided to 4 fractions. Water was added (completing to 20 vol) and extracted twice with ethyl acetate. The product was isolated by distillation of water to obtain wet fluvastatin sodium crystal Form LXXVI. (the sample was kept at room temperature for 3 days).

66) Preparation of Fluvastatin Sodium Crystal Form LXXVII

Example 160

Fluvastatin methyl ester (3.0 g) was dissolved in ethyl acetate (90 ml), a solution of NaOH (0.2 g) in water (1 ml) was added and the mixture was stirred at room temperature over night. The product was isolated by filtration under nitrogen, washed with ethyl acetate (50 ml) and dried at 50EC in a vacuum oven for 24 h to obtain 1.52 g (49.7%) of fluvastatin sodium crystal Form LXXVII.

67) Preparation of Fluvastatin Sodium Crystal Form LXXVIII

Example 161

A 100 ml round bottom flask was loaded with fluvastatin methyl ester (4.0 g, 9.4 mmole), water (32 ml) and NaOH (0.39 g). The mixture was stirred for 3 days at room temperature then extracted with ethyl acetate (32 ml, 16 ml). The aqueous solution was evaporated, propan-2-ol (40 ml) was added and the mixture was stirred at room temperature over night. Precipitation occurred after scraping the mixture with spatula and stirring for another day. The product was isolated by filtration under nitrogen flow, washed with propan-2-ol (20 ml) and dried at 50EC in a vacuum oven for 24 h to obtain 1.28 g (31%) of fluvastatin sodium crystal Form LXXVIII.

Example 162

A 100 ml round bottom flask was loaded with Fluvastatin methyl ester (3.0 g, 7.08 mmole), water (30 ml) and NaOH (0.29 g). The mixture was stirred for 3 h at room temperature then extracted with ethyl acetate (30 ml). The aqueous solution was evaporated, acetonitrile (12 ml) was added and the mixture was stirred at room temperature over night. The product was isolated by filtration under nitrogen flow, washed with acetonitrile (20 ml) and dried at 40EC in a vacuum oven for 24 h to obtain 0.37 g (12%) of fluvastatin sodium crystal Form LXXVIII.

68) Preparation of Fluvastatin Sodium Form XC

Example 163

Fluvastatin sodium crystal Form B (3.0 g) was dissolved in ethanol (140 ml). The obtained solution was filtered and cyclohexane (2×140 ml) was added in two portions. The mixture was stirred at room temperature for 26 h to obtain a massive precipitate. Then, the product was filtered, washed with cyclohexane (2×25 ml) and dried at 50EC in a vacuum oven for 21.5 h to obtain 1.7 g (55%) of fluvastatin sodium Form XC.

69) Preparation of Fluvastatin Sodium Form XCI

Example 164

A suspension of fluvastatin sodium crystal Form XV (5.0 g) in ethyl acetate (75 ml) was stirred at reflux temperature for 16 h. Then, the suspension was cooled to room temperature. The product was filtered under nitrogen flow, washed with ethyl acetate (4×25 ml) and dried at 50EC in a vacuum oven for 21 h to obtain 3.9 g (78%) of fluvastatin sodium Form XCI.

70) Preparation of Fluvastatin Sodium Form XCII

Example 165

Fluvastatin sodium crystal Form B (1.0 g) was dissolved in ethanol (10 ml) and methanol (1 ml) at reflux temperature. Hexanes (10 ml) were added in one portion and the turbid solution was stirred at reflux temperature for 4 h. A precipitation was obtained during this time. Then, the suspension was cooled to room temperature and stirred at this temperature for 16 h. The product was filtered under nitrogen flow, washed with hexanes (3×7 ml) and dried at 50EC in a vacuum oven for 19 h to obtain 0.67 g (67%) of fluvastatin sodium Form XCII.

71) Preparation of Fluvastatin Sodium Form XCIII

Example 166

A suspension of fluvastatin sodium crystal Form XV (5.0 g) in propan-1-ol (50 ml) was stirred at room temperature for 25 h. The product was then filtered under nitrogen flow, washed with propan-1-ol (3×40 ml) and dried at 50EC in a vacuum oven for 24 h to obtain 3.8 g (76%) of fluvastatin sodium Form XCIII.

72) Preparation of Fluvastatin Sodium Form XCIV

Example 167

A suspension of fluvastatin sodium crystal Form XV (5.0 g) in butan-1-ol (50 ml) was stirred at room temperature for 24 h. The product was then filtered under nitrogen flow, washed with butan-1-ol (2×20 ml) and dried at 50EC in a vacuum oven for 24 h to obtain 6.0 g (120%) of fluvastatin sodium Form XCIV.

73) Preparation of Fluvastatin Sodium Form XCV

Example 168

A suspension of fluvastatin sodium crystal Form XV (5.0 g) in ethyl acetate (90 ml) was stirred at room temperature for 19 h. The product was then filtered under nitrogen flow, washed with ethyl acetate (2×20 ml) and dried at 50EC in a vacuum oven for 22 h to obtain 5.2 g (104%) of fluvastatin sodium Form XCV.

Example 169

A suspension of fluvastatin sodium crystal Form XV (5.0 g) in acetone (70 ml) was stirred at room temperature for 23 h. The product was then filtered under nitrogen flow, washed with acetone (2×15 ml) and dried at 50EC in a vacuum oven for 20 h to obtain 4.6 g (92%) of fluvastatin sodium Form XCV.

Example 170

A suspension of fluvastatin sodium crystal Form XV (5.0 g) in 1,4-dioxane (50 ml) was stirred at room temperature for 24 h. The product was then filtered under nitrogen flow, washed with 1,4-dioxane (2×30 ml) and dried at 50EC in a vacuum oven for 23 h to obtain 4.4 g (88%) of fluvastatin sodium Form XCV.

Example 171

A suspension of fluvastatin sodium crystal Form XV (5.0 g) in MEK (70 ml) was stirred at room temperature for 30 h. The product was then filtered under nitrogen flow, washed with MEK (2×20 ml) and dried at 50EC in a vacuum oven for 21 h to obtain 4.7 g (93%) of fluvastatin sodium Form XCV.

74) Preparation of Fluvastatin Sodium Form XCVI

Example 172

A suspension of fluvastatin sodium crystal Form XV (5.0 g) in THF (70 ml) was stirred at room temperature for 29 h. Then, the product was filtered under nitrogen flow, washed with THF (2×20 ml) and dried at 50EC in a vacuum oven for 20 h to obtain 4.1 g (82%) of fluvastatin sodium Form XCVI.

75) Preparation of Fluvastatin Sodium Form XCVII

Example 173

In a 3 neck flask were placed fluvastatin methyl ester (3.0 g) and cyclohexane (60 ml) then the mixture was heated to reflux. A solution of NaOH (0.29 g) in MeOH (3 ml) was added and the mixture was stirred at reflux for 1.6 h. The slurry was cooled to room temperature, cyclohexane (40 ml) was added and the mixture was stirred over night. The product was isolated by filtration under nitrogen, washed with cyclohexane (90 ml) and dried at 50EC in a vacuum oven for 24 h to obtain 2.81 g (93%) of fluvastatin sodium Form XCVII.

76) Preparation of Fluvastatin Sodium Form XCVIII

Example 174

Fluvastatin methyl ester (3.0 g) was dissolved in a solution of NaOH (0.29 g) in MeOH (7.5 ml) by heating to reflux. The clear solution was stirred at reflux for 85 min and acetonitrile (50 ml) was added. The solution was cooled to room temperature and stirred over night. The product was isolated by filtration under nitrogen, washed with acetonitrile (50 ml) and dried at 50EC in a vacuum oven for 25.5 h to obtain 0.97 g of fluvastatin sodium Form XCVIII.

77) Preparation of Fluvastatin Sodium Form XCIX

Example 175

In a 50 ml flask were placed fluvastatin sodium crystal Form VI (1.02 g) and EtOH (10 ml). After 2.5 h EtOH (15 ml) was added and the mixture was stirred at room temperature over night. The product was isolated by filtration under nitrogen, washed with EtOH (20 ml) and dried at 50EC in a vacuum oven for 24 h to obtain 0.14 g (14%) of fluvastatin sodium Form XCIX.

78) Preparation of Fluvastatin Sodium Form C

Example 176

Fluvastatin methyl ester (3.0 g) was dissolved in dichloromethane (35 ml). NaOH (0.29 g) was added and the mixture was stirred at room over night. The product was isolated by filtration under nitrogen, washed with dichloromethane (20 ml) and dried at 50EC in a vacuum oven for 24 h to obtain 1.89 g (62%) of fluvastatin sodium Form C.

79) Preparation of Fluvastatin Sodium Form CI

Example 177

Fluvastatin methyl ester (3.0 g) was dissolved in acetone (45 ml), a solution of NaOH (0.58 g) in MeOH (8 ml) was added and the mixture was stirred at room temperature for another 3.5 h. The product was isolated by filtration under nitrogen, washed with acetone (40 ml) and dried at 50EC in a vacuum oven for 22.5 h to obtain 2.37 g of fluvastatin sodium Form CI.

Example 178

Fluvastatin methyl ester (8.0 g) was dissolved in acetone (120 ml) and a solution of NaOH (0.75 g) in MeOH (8 ml) was added. The mixture was heated to 50EC for 4.25 h, cooled to room temperature and stirred over night. NaOH (0.2 g) was added and the mixture was heated again to 50EC. After 5.5 h a solution of NaOH (0.2 g) in MeOH (8 ml) was added and stirred for 1.5 h, then the mixture was cooled to room temperature and stirred for 1 h. The product was isolated by filtration under nitrogen, washed with acetone (100 ml) and dried at 50EC in a vacuum oven for 21.5 h to obtain 7.26 g of fluvastatin sodium Form CI.

80) Preparation of Fluvastatin Sodium Form CII

Example 179

Fluvastatin methyl ester (8.0 g) was dissolved in acetone (120 ml), filtered and cooled to 10EC. A solution of NaOH (0.75 g) in MeOH (8 ml) was added and the mixture was stirred at 10EC for 10 h. A solution of NaOH (0.4 g) in MeOH (4 ml) was added to the mixture in 3 portions during this time. The product was isolated by filtration under nitrogen, washed with acetone (120 ml) and dried at 50EC in a vacuum oven for 22.5 h to obtain 5.04 g of fluvastatin sodium Form CII.

81) Preparation of Fluvastatin Sodium Form CIII

Example 180

Fluvastatin methyl ester (3.0 g) was dissolved in acetone (30 ml) and filtered. A solution of NaOH (0.29 g) in water (1 ml) was added and the mixture was stirred at room temperature over night. The product was isolated by filtration under nitrogen, washed with acetone (40 ml) and dried at 50EC in a vacuum oven for 25.5 h to obtain 1.08 g of fluvastatin sodium Form CIII.

82) Preparation of Fluvastatin Sodium Form CIV

Example 181

Fluvastatin methyl ester (3.0 g) was dissolved in THF (30 ml) and the NaOH (1 eq.) was added. After 2.5 h hexanes (60 ml) was added and the slurry stirred at room temperature over night. The product was isolated by filtration under nitrogen, washed with hexanes (30 ml) and dried at 50EC in a vacuum oven for 24 h to obtain 1.2 g (39%) of fluvastatin sodium Form CIV.

83) Preparation of Fluvastatin Sodium Form CV

Example 182

Fluvastatin methyl ester (5.0 g) was dissolved in acetonitrile (100 ml) by heating. At 50EC a solution of NaOH (1 eq.) in water (1.25 ml) was added and the mixture was stirred at this temperature for 2 h, then cooled to room temperature and stirred over night. The product was isolated by filtration under nitrogen, washed with acetonitrile (30 ml) and dried at 50EC in a vacuum oven for 24 h to obtain 1.75 g (34.5%) of fluvastatin sodium Form CV.

84) Preparation of Fluvastatin Sodium Crystal Form B

Example 183

Fluvastatin methyl ester (3.0 g) was added to a solution of NaOH (1 eq.) in water (0.75 ml) and methanol (7.5 ml). The mixture was stirred at reflux temperature for 2 h. After this time the raw material was not observed by HPLC. MTBE (58 ml) was dripped into the solution over 2 h. The solution was cooled slowly to room temperature and was stirred overnight. The product was isolated by filtration under nitrogen, washed with MTBE (50 ml) and dried at 50EC in a vacuum oven for 24 h to obtain 2.78 g (91.3%) of fluvastatin sodium Form B.

85) Preparation of Amorphous Fluvastatin Sodium

Example 184

Fluvastatin sodium (3.0 g) was dissolved in 1,4-dioxane (40 ml) at 85EC. Then, the solution was cooled to room temperature and stirred at this temperature for 70 h. The product was filtered under nitrogen flow and dried at 50EC in a vacuum oven for 25 h to obtain 2.7 g (90%) of amorphous fluvastatin sodium.

Example 185

Fluvastatin methyl ester (3.0 g) was added to cyclohexane (60 ml) and the slurry was heated to reflux. A solution of NaOH (1 eq.) in MeOH (3 ml) was added to the slurry solution which became clear. After 15 min. a precipitate formed. After another hour, the mixture was cooled to room temperature and cyclohexane (40 ml) was added. The mixture was stirred over night. The product was isolated by filtration under nitrogen, washed with cyclohexane (90 ml) and dried at 50EC in a vacuum oven for 24 h to yield 2.73 g (90%) of amorphous fluvastatin sodium.

Example 186

A suspension of amorphous fluvastatin (5.0 g) in propan-2-ol (104 ml) was stirred at reflux temperature for 4.5 h. Then, the suspension was cooled to room temperature and stirred at this temperature for 16 h. The product was filtered under nitrogen flow, washed with propan-2-ol (2×10 ml) and dried at 50EC in a vacuum oven for 24 h to obtain 3.8 g (76%) of amorphous fluvastatin sodium.

Example 187

A 100 ml round bottom flask was loaded with Fluvastatin-diol-t-butyl ester (20.0 g, 43 mmole), MeOH (120 ml) and NaOH (1.82gr) in water (10 ml). The mixture was heated to 35° C. The solution became clear and water (50 ml) was added. The mixture was stirred for 3 hr then the MeOH was evaporated. The volume of the water was completed to 8 vol. and the mixture was extracted with MTBE (120 ml). The organic solvents residue was evaporated and solution was divided to two portions of 68 ml. NaCl (0.7gr) was added to one of the solutions and it was cooled to 4oC during 1 hr. The product was isolated after 1 hr by filtration under nitrogen and dried at 40° C. in a vacuum oven for 24 hours to obtain 6.04 gr (65%) of Fluvastatin sodium crystal form D.

Example 188

Fluvastatin-diol-methyl ester (FDME) (4.0 g) was dissolved in acetone (40 ml). A solution of NaOH (0.38gr) in MeOH (4 ml) was added and the mixture was stirred at room temperature for 20 hr. The product was isolated by filtration under nitrogen, washed with acetone (20 ml) and dried at 50° C. in a vacuum oven for 26 hours to obtain 3.35gr (82.2%) of Fluvastatin sodium crystal form VI.

Example 189

Fluvastatin-diol-methyl ester (FDME) (3.5 g) was dissolved in acetone (35 ml). A solution of NaOH (0.34 gr) in MeOH (4 ml) was added and the mixture was stirred at room temperature for 22.5 hr. The product was isolated by filtration under nitrogen, washed with acetone (20 ml×2) and dried at 50° C. in a vacuum oven for 26 hours to obtain 3.22 gr (90.3%) of Fluvastatin sodium crystal form VI.

What is claimed is:

1. A process for preparing amorphous fluvastatin sodium comprising:
   a) dissolving fluvastatin sodium in 1,4-dioxane to obtain a solution,
   b) cooling the solution to induce precipitation of amorphous fluvastatin sodium, and
   c) separating the amorphous fluvastatin sodium from the 1,4-dioxane.

2. The process of claim 1, wherein the dissolution is carried out at elevated temperature.

3. The process of claim 2, wherein the temperature is about 85° C.

4. The process of claim 1, wherein cooling is carried out to room temperature.

5. The process of claim 4, wherein the cooled solution is stirred at room temperature for 70 hours.

6. The process of claim 1, wherein separating is carried out by filtering under nitrogen flow.

7. The process of claim 1, wherein the separated product is dried at 50° C. in a vacuum oven.

8. A process for preparing amorphous fluvastatin sodium comprising:
   a) suspending an alkyl ester of fluvastatin in cyclohexane;
   b) combining the cyclohexane suspension with sodium hydroxide to obtain a solution of fluvastatin sodium;
   c) maintaining the reaction mixture to precipitate amorphous fluvastatin sodium; and
   d) separating the amorphous fluvastatin sodium from the cyclohexane.

9. The process of claim 8, wherein about one molar equivalent of sodium hydroxide is added.

10. The process of claim 9, wherein the sodium hydroxide is dissolved in a protic solvent.

11. The process of claim 10, wherein the protic solvent is methanol.

12. The process of claim 8, further comprising heating the suspension.

13. The process of claim 12, wherein heating is carried out to the reflux temperature.

14. The process of claim 12, further comprising cooling.

15. The process of claim 14, wherein cooling is carried out to room temperature.

16. The process of claim 13, further comprising adding an additional amount of cyclohexane.

17. The process of claim 12, further comprising stirring the mixture over night before separating.

18. The process of claim 8, wherein the product is separated by filtration under nitrogen.

19. The process of claim 8, wherein the product is dried at 50° C. in a vacuum oven.

Figure 113:
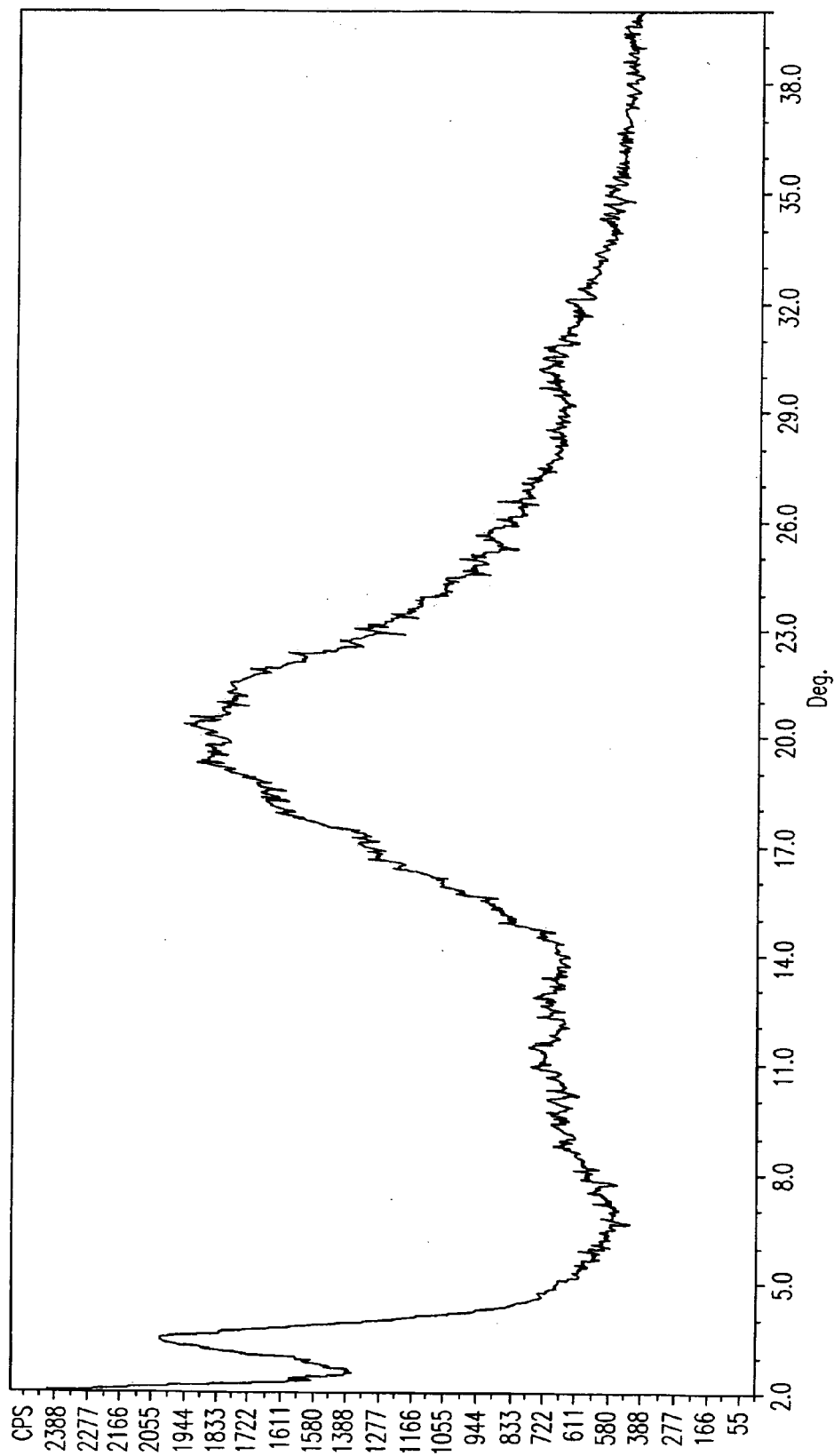
FIG. 113 depicts a powder X-ray diffractogram of the product of Example 184.

20. Amorphous fluvastatin sodium having a powder XRD pattern as substantially depicted in FIG. 113.

Figure 114:
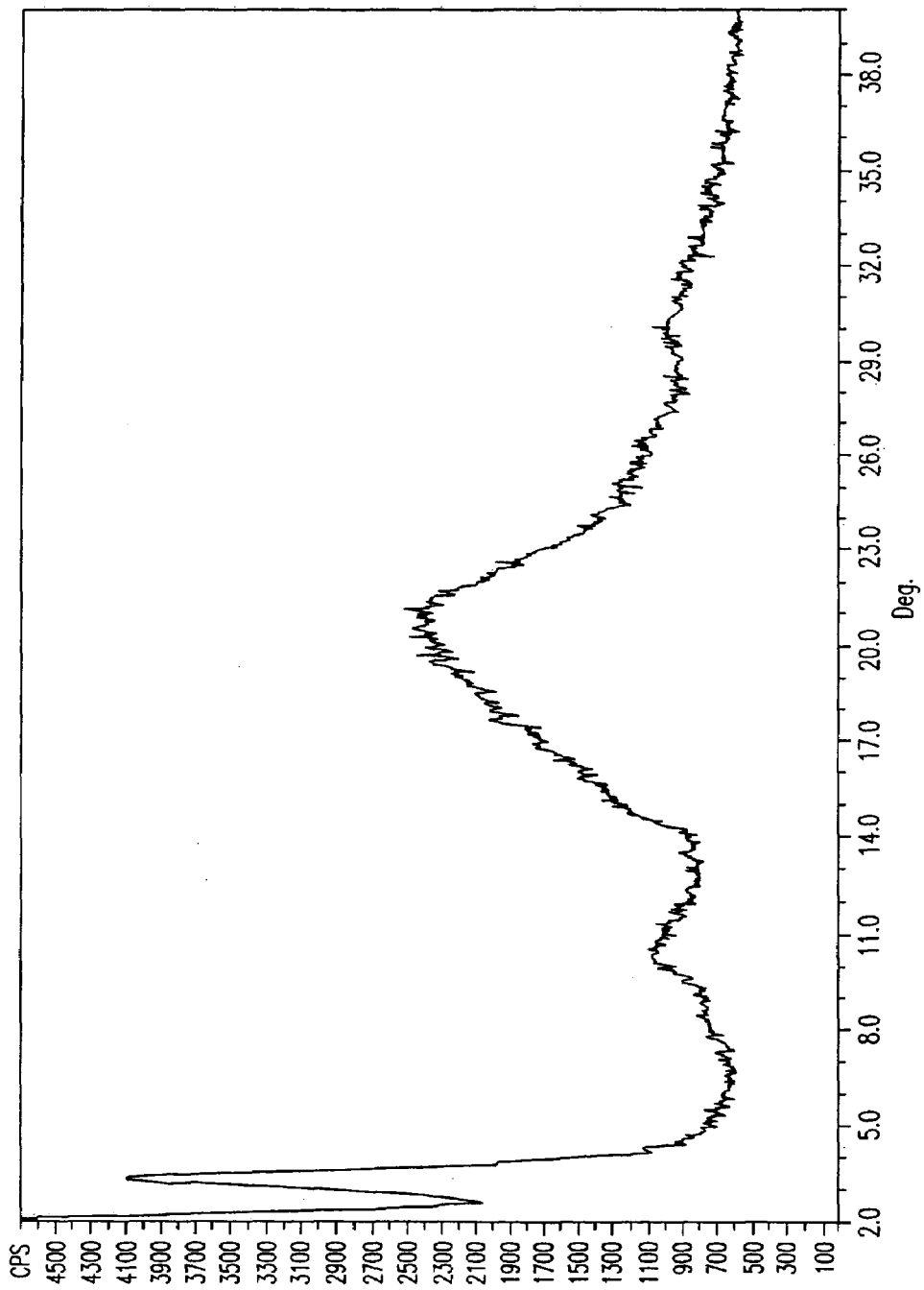
FIG. 114 depicts a powder X-ray diffractogram of the product of Example 185.

21. Amorphous fluvastatin sodium having a powder XRD pattern as substantially depicted in FIG. 114.

* * * * *